(12) United States Patent
Ackermann et al.

(10) Patent No.: US 8,329,904 B2
(45) Date of Patent: Dec. 11, 2012

(54) AZACYCLIC DERIVATIVES

(75) Inventors: Jean Ackermann, Riehen (CH); Aurelia Conte, Basel (CH); Daniel Hunziker, Moehlin (CH); Werner Neidhart, Hagenthal-le-Bas (FR); Matthias Nettekoven, Grenzach-Wyhlen (DE); Tanja Schulz-Gasch, Ziefen (CH); Stanley Wertheimer, Croton, NY (US)

(73) Assignee: Hoffmann-La Roche Inc., Nutley, NJ (US)

( * ) Notice: Subject to any disclaimer, the term of this patent is extended or adjusted under 35 U.S.C. 154(b) by 275 days.

(21) Appl. No.: 12/772,246

(22) Filed: May 3, 2010

(65) Prior Publication Data
US 2010/0292212 A1    Nov. 18, 2010

(30) Foreign Application Priority Data
May 12, 2009  (EP) .................... 09160026

(51) Int. Cl.
*C07D 215/00* (2006.01)
*C07D 273/00* (2006.01)
(52) U.S. Cl. .......................... 546/16; 544/70
(58) Field of Classification Search ............ 546/16; 544/70
See application file for complete search history.

(56) References Cited

U.S. PATENT DOCUMENTS
2007/0129345 A1* 6/2007 Zhuo et al. ............ 514/210.04

FOREIGN PATENT DOCUMENTS
| WO | 2004/035550 | 4/2004 |
| WO | 2005/084667 | 9/2005 |
| WO | 2007/067504 | 6/2007 |

OTHER PUBLICATIONS

Mehrotra et al. Journal of Medicinal Chemistry (2004), 47(8), 2037-2061.*
Wang et al., Chem. Biol. 2006, vol. 13 pp. 1019-1027.
Gregoire et al., Physiol. Rev. 1998, vol. 78 pp. 783-809.
Unger, R. H., Annu. Rev. Med. 2002, vol. 53 pp. 319-336.
Duncan et al., Annu. Rev. Nutr. vol. 27, 2007 pp. 79-101.
Jaworski et al., Am. J. Physiol. Gastrointest. Liver Physiol. 2007, vol. 293, G1-4.
Large et al., J. Lipid. Res. vol. 39, 1998, pp. 1688-1695.
Lewis et al., Dig. Dis. Sci. vol. 55, 2010, pp. 560-578.
Buchwald et al., JACS, 2002, vol. 124 p. 7421.
Shahespeare, W. Tetrahedron Lett. vol. 40, 1999, p. 2035.

* cited by examiner

*Primary Examiner* — Nizal Chandrakumar
(74) *Attorney, Agent, or Firm* — George W. Johnston; Patricia S. Rocha-Tramaloni; Gene J. Yao

(57) ABSTRACT

The present invention relates to compounds of formula (I)

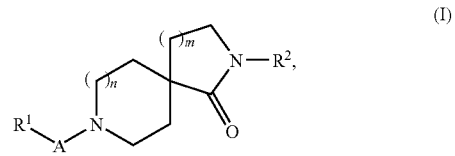

(I)

and pharmaceutically acceptable salts thereof, wherein n, m, A, $R^1$ and $R^2$ have the significance given in the description. The compounds are useful as HSL inhibitors and may be used in the treatment or prophylaxis of diabetes, dyslipidemia, atherosclerosis or obesity.

11 Claims, No Drawings

AZACYCLIC DERIVATIVES

PRIORITY TO RELATED APPLICATION(S)

This application claims the benefit of European Patent Application No. 09160026.2, filed May 12, 2009, which is hereby incorporated by reference in its entirety.

FIELD OF THE INVENTION

The present invention is concerned with novel azacyclic derivatives useful as HSL inhibitors.

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess (Wang M. et al., Chem. Biol., 2006, 13, 1019-10271; Gregoire F. M. et al., Physiol. Rev., 1998, 78, 783-809). However, unlike TAG synthesis that also occurs at high levels in liver for very low density lipoprotein (VLDL) production, lipolysis for the provision of fatty acids as an energy source for use by other organs is unique to adipocytes. The release of free fatty acids (FFA) from TAG proceeds in an orderly and regulated manner (Unger R. H, Annu. Rev. Med. 2002, 53, 319-336; Duncan R. E. et al, 2007, Annu Rev Nutr, 27, 79-101; Jaworski K. Et al, 2007, Am J Physiol Gastrointest Liver Physiol, 293, G1-4), stimulated by catecholamines and regulated by hormones such as insulin, glucagon and epinephrine.

The most important enzyme in WAT believed responsible for hormone regulated hydrolysis of triglyceride is hormone sensitive lipase (HSL). This enzyme is also present in the liver, skeletal muscle, pancreas and adrenal glands. In the basal state, it has minimal activity against its substrate. Stimulation of adipocytes by hormones activates protein kinase A resulting in the phosphorylation of HSL and the lipid droplet coating protein perilipin. Phosphorylation of perilipin leads to its removal from the lipid droplet and migration of phosphorylated HSL from the cytosol to the lipid droplet where it catalyzes the hydrolysis of triglycerides (Wang M. et al., Chem. Biol., 2006, 13, 1019-10271).

Dysregulation of adipocyte lipolysis, resulting in elevated circulating non-esterified fatty acids (NEFA) is associated with obesity and co-morbidities including the development of type 2 diabetes (Unger R. H, Annu. Rev. Med. 2002, 53, 319-336). Obese or insulin resistant subjects have increased visceral adipose tissue depots. These depots contain elevated levels of HSL protein (Large, V. et al., 1998, J. Lipid. Res. 39, 1688-1695) and exhibit enhanced lipolytic activity as they are resistant to the insulin-mediated suppression of lipolysis. This results in increased plasma levels of free fatty acids, which further exacerbates insulin resistance due to the accumulation of triglycerides in tissues other than WAT such as liver, pancreas and muscle. The ectopic deposition of triglycerides results in pathological effects such as increased glucose production in the liver, decreased insulin secretion from the pancreas, and reduced glucose uptake and fatty acid oxidation in skeletal muscle. Thus, the elevated plasma levels of FFA due to increased HSL activity contributes to and worsens insulin resistance in obese and type 2 diabetic individuals. Restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function.

As HSL is major hormone regulated lipase, it is know that during insulin resistant states, the ability of insulin to suppress lipolysis is reduced, and contributes to the increased FFA, ie. lipotoxicity. These fatty acids collect in the liver and lead to increased production of TAG, which are packaged into VLDLs which are secreted. There is also an accumulation of lipid in liver, leading to a fatty liver phenotype. Lipolysis is increased during diabetes and obesity which contributes to this phenotype. Therefore, reducing the activity of HSL would decrease the release of FFA to the blood, thus limiting the supply of FFA to the liver for TAG synthesis. Thus, HSL inhibitors could have beneficial effects as treatment of NAFLD (nonalkoholic fatty liver disease) and NASH (non-alkoholic steatohepatitis) (Jeffry R. Lewis et al, Dig Dis Sci 2010, 55: 560-578).

Objects of the present invention are the compounds of formula (I) and their aforementioned salts and esters per se and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of diabetes, dyslipidemia, atherosclerosis or obesity and the use of the said compounds, salts or esters for the production of medicaments for the treatment or prophylaxis of diabetes, dyslipidemia, atherosclerosis or obesity.

SUMMARY OF THE INVENTION

The invention is concerned particularly with compounds of formula (I)

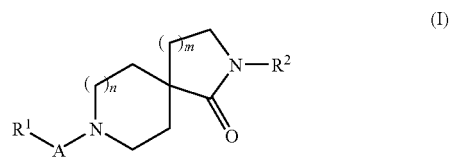

wherein m is 1 or 2;

n is zero, 1 or 2, wherein, when n is zero, m is 1;

A is $—S(O)_2—$ or carbonyl;

$R^1$ is selected from the group consisting of alkyl, aminoalkyl, cycloalkyl, cycloalkylalkyl, haloalkyl, haloalkylcycloalkyl, hydroxycycloalkylalkyl, (cycloalkyl)(hydroxy)alkyl, (cycloalkyl)(alkoxy)alkyl, alkoxycycloalkylalkyl, hydroxycycloalkyl, cycloalkoxyalkyl, hydroxyalkyl, alkoxyalkyl, benzyloxyalkyl, phenyloxyalkyl, dihydrofuranylidenemethyl, tetrahydro-furanylmethyl, dihydroisoindolyl, dihydro-quinolinyl, $—NR^4R^5$, azepanyl, morpholinyl, piperidinyl, pyrrolidinyl, pyrazolyl, imidazolyl, isoxazolyl, oxazolyl, thiophenyl, thiazolyl, pyridinyl, pyridinylalkyl, pyridazinyl, pyridazinylalkyl, pyrazinyl, pyrazinylalkyl, pyrimidyl, pyrimidylalkyl, phenyl, phenylalkyl, substituted piperidinyl, substituted pyrrolidinyl, substituted pyrazolyl, substituted imidazolyl, substituted isoxazolyl, substituted oxazolyl, substituted thiophenyl, substituted thiazolyl, substituted pyridinyl, substituted pyridinylalkyl, substituted pyridazinyl, substituted pyridazinylalkyl, substituted pyrazinyl, substituted pyrazinylalkyl, substituted pyrimidyl, substituted pyrimidylalkyl, substituted phenyl and substituted phenylalkyl, wherein said substituted piperidinyl, substituted pyrrolidinyl, substituted pyrazolyl, substituted imidazolyl, substituted isoxazolyl, substituted oxazolyl, substituted thiophenyl, substituted thiazolyl, substituted pyridinyl, substituted pyridinylalkyl, substituted pyridazinyl, substituted pyridazinylalkyl, substituted pyrazinyl, substituted pyrazinylalkyl, substituted pyrimidyl, substituted pyrimidylalkyl, substituted phenyl or substituted phenylalkyl is substituted with one to three substituents independently selected from the group consisting of: alkyl, haloalkyl, halogen, hydroxy, alkoxy, haloalkoxy, phenyloxy, alkylphenyloxy, alkylsulfonyl, oxopyrrolidinyl, alkoxycarbonyl, benzyloxy and —NR$^6$R$^7$;

$R^2$ is selected from the group consisting of imidazolyl, imidazolylalkyl, phenyl, phenylalkyl, pyridinyl, pyridinylalkyl, pyridazinyl, pyridazinylalkyl, pyrazolyl, pyrazolylalkyl, alkylindazolyl, alkylbenzothiazolyl, difluorobenzo[1,3]dioxolyl, pyrimidyl, pyrimidylalkyl, pyrazinyl, pyrazinylalkyl, substituted imidazolyl, substituted imidazolylalkyl, substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted pyrimidyl, substituted pyrimidylalkyl, substituted pyrazinyl and substituted pyrazinylalkyl, wherein said substituted imidazolyl, substituted imidazolylalkyl, substituted phenyl, substituted phenylalkyl, substituted pyridinyl, substituted pyridinylalkyl, substituted pyridazinyl, substituted pyridazinylalkyl, substituted pyrazolyl substituted pyrazolylalkyl, substituted pyrimidyl, substituted pyrimidylalkyl, substituted pyrazinyl or substituted pyrazinylalkyl is substituted with one to three substituents independently selected from the group consisting of: alkyl, haloalkyl, cycloalkyl, cycloalkylalkyl, halogen, haloalkoxy, alkoxy, hydroxy, alkoxyalkyl, hydroxyalkyl, alkylsulfonyl, alkylsulfonyloxy, alkylsulfanyl, cycloalkylsulfonyloxy, cycloalkoxy, alkenyl, cycloalkylalkoxy, alkoxyalkoxy, tetrahydrofuranyloxy, pyridinyloxy, alkoxycarbonylalkyl, cyanoalkyl, alkyloxazodiazolylalkyl, haloalkyloxazodiazolylalkyl, alkoxyalkenyl, cycloalkylalkenyl, cycloalkylalkoxyalkyl, alkoxycarbonyl, alkylcarbonyl, haloalkylhydroxyalkyl, alkylaminocarbonyl, dialkylaminocarbonyl, hydroxyoxetanyl, fluorooxetanyl and hydroxycycloalkyl;

one of $R^4$ and $R^5$ is hydrogen or alkyl and the other is selected from the group consisting of hydrogen, alkyl, hydroxyalkyl, alkoxyalkyl, cycloalkyl, phenyl, alkylphenyl, haloalkoxyphenyl, phenylalkyl, halophenyl, halophenylalkyl, haloalkylphenyl or pyridinylalkyl; and one of $R^6$ and $R^7$ is selected from the group consisting of hydrogen, alkyl, cycloalkyl and hydroxyalkyl and the other is selected from the group consisting of hydrogen, alkyl, cycloalkyl and hydroxyalkyl;

or a pharmaceutically acceptable salt thereof.

Another aspect of the invention is a process for preparing the compound described above.

A further aspect of the invention is a composition comprising a compound as described above and a therapeutically inert carrier.

A yet further aspect of the invention is a method for the treatment or prophylaxis of diabetes, dyslipidemia, atherosclerosis or obesity, said method comprising administering an effective amount of the compound described above.

DETAILED DESCRIPTION OF THE INVENTION

In the present description the term "alkyl", alone or in combination, signifies a straight-chain or branched-chain alkyl group with 1 to 8 carbon atoms, preferably with 1 to 6 carbon atoms and particularly preferred are alkyl groups with 1 to 4 carbon atoms. Examples of straight-chain and branched $C_1$-$C_8$ alkyl groups are methyl, ethyl, propyl, isopropyl, butyl, isobutyl, tert-butyl, the isomeric pentyls, the isomeric hexyls, the isomeric heptyls and the isomeric octyls, preferably methyl, ethyl, isopropyl, tert-butyl and isomeric pentyls and particularly preferred methyl, isopropyl and tert-butyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_s$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. A preferred cycloalkyl is cyclopropyl.

The term "alkoxy", alone or in combination, signifies a group of the formula alkyl-O— in which the term "alkyl" has the previously given significance. Examples are methoxy, ethoxy, n-propoxy, isopropoxy, n-butoxy, isobutoxy, sec-butoxy and tert-butoxy, preferably methoxy and isopropoxy. A particularly preferred alkoxy is isopropoxy.

The term "hydroxyalkyl", alone or in combination, signifies an alkyl group as defined before, wherein one or more hydrogen atoms is replaced by a hydroxy group. Examples of hydroxyalkyl are hydroxymethyl, hydroxyethyl, hydroxypropyl and dihydroxypropyl.

The terms "halogen" and "halo", alone or in combination, signify fluorine, chlorine, bromine or iodine and preferably fluorine or chlorine.

The term "carbonyl", alone or in combination, signifies the —C(O)— group.

The term "hydroxy", alone or in combination, signifies the —OH group.

The term "sulfonyl", alone or in combination, signifies the —S(O)$_2$— group.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —NH$_2$, methylamino, ethylamino, dimethylamino, diethylamino, methyl-ethylamino, pyrrolidin-1-yl or piperidino etc., preferably primary amino, dimethylamino and diethylamino and particularly preferred dimethylamino.

The term cycloalkoxy, alone or in combination, signifies a group of the formula cycloalkyl-O— in which the term "cycloalkyl" has the previously given significance. Example is cyclopentyloxy.

The term "hydroxycycloalkyl", alone or in combination, signifies a cycloalkyl group as defined before, wherein one or more hydrogen atoms is replaced by a hydroxy group. Example is 1-hydroxycyclopentyl.

The term "alkoxycycloalkyl", alone or in combination, signifies a cycloalkyl group as defined before, wherein one or more hydrogen atoms is replaced by a alkoxy group. Example is 1-alkoxycyclopentyl.

The term "(cycloalkyl)(hydroxy)alkyl", alone or in combination, signifies an alkyl group as defined before, wherein one or more hydrogen atoms of the alkyl group is replaced by a "cycloalkyl" and wherein one or more hydrogen atoms of the alkyl group is replaced by a "hydroxy", in which the terms "cycloalkyl" and "hydroxy" have the previously given significances. Example of (cycloalkyl)(hydroxy)alkyl is 2-cyclopropyl-2-hydroxyethyl.

The term "(cycloalkyl)(alkoxy)alkyl", alone or in combination, signifies an alkyl group as defined before, wherein one or more hydrogen atoms of the alkyl group is replaced by a cycloalkyl group and wherein one or more hydrogen atoms of the alkyl group is replaced by an alkoxy group, in which the terms "cycloalkyl" and "alkoxy" have the previously given significances. Example of (cycloalkyl)(alkoxy)alkyl is 2-cyclopropyl-2-methoxyethyl.

The term "alkenyl", alone or in combination, signifies an alkyl group as defined above, wherein one or more carbon-carbon single bond is replaced by a carbon-carbon double bond. Examples of alkenyl are ethenyl, n-propenyl, isopropenyl, n-butenyl or isobutenyl. Preferred alkenyl are ethenyl and n-propenyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particularly preferred pharmaceutically acceptable salts of compounds of formula (I) are the hydrochloride salts, methanesulfonic acid salts and citric acid salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. Preferred pharmaceutically acceptable esters of compounds of formula (I) are methyl and ethyl esters.

The present invention relates to compounds of formula (I)

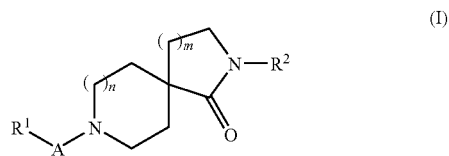

wherein
m is 1 or 2;
n is zero, 1 or 2, wherein, when n is zero, m is 1;
A is $-S(O)_2-$ or carbonyl;
$R^1$ is selected from the group consisting of alkyl, aminoalkyl, cycloalkyl, cycloalkylalkyl, haloalkyl, haloalkylcycloalkyl, hydroxycycloalkylalkyl, (cycloalkyl)(hydroxy)alkyl, (cycloalkyl)(alkoxy)alkyl, alkoxycycloalkylalkyl, hydroxycycloalkyl, cycloalkoxyalkyl, hydroxyalkyl, alkoxyalkyl, benzyloxyalkyl, phenyloxyalkyl, dihydro-furanylidenemethyl, tetrahydro-furanylmethyl, dihydro-isoindolyl, dihydro-quinolinyl, $-NR^4R^5$, azepanyl, morpholinyl, piperidinyl, pyrrolidinyl, pyrazolyl, imidazolyl, isoxazolyl, oxazolyl, thiophenyl, thiazolyl, pyridinyl, pyridinylalkyl, pyridazinyl, pyridazinylalkyl, pyrazinyl, pyrazinylalkyl, pyrimidyl, pyrimidylalkyl, phenyl, phenylalkyl, substituted piperidinyl, substituted pyrrolidinyl, substituted pyrazolyl, substituted imidazolyl, substituted isoxazolyl, substituted oxazolyl, substituted thiophenyl, substituted thiazolyl, substituted pyridinyl, substituted pyridinylalkyl, substituted pyridazinyl, substituted pyridazinylalkyl, substituted pyrazinyl, substituted pyrazinylalkyl, substituted pyrimidyl, substituted pyrimidylalkyl, substituted phenyl and substituted phenylalkyl, wherein said substituted piperidinyl, substituted pyrrolidinyl, substituted pyrazolyl, substituted imidazolyl, substituted isoxazolyl, substituted oxazolyl, substituted thiophenyl, substituted thiazolyl, substituted pyridinyl, substituted pyridinylalkyl, substituted pyridazinyl, substituted pyridazinylalkyl, substituted pyrazinyl, substituted pyrazinylalkyl, substituted pyrimidyl, substituted pyrimidylalkyl, substituted phenyl or substituted phenylalkyl is substituted with one to three substituents independently selected from the group consisting of: alkyl, haloalkyl, halogen, hydroxy, alkoxy, haloalkoxy, phenyloxy, alkylphenyloxy, alkylsulfonyl, oxopyrrolidinyl, alkoxycarbonyl, benzyloxy and $-NR^6R^7$;
$R^2$ is selected from the group consisting of imidazolyl, imidazolylalkyl, phenyl, phenylalkyl, pyridinyl, pyridinylalkyl, pyridazinyl, pyridazinylalkyl, pyrazolyl, pyrazolylalkyl, alkylindazolyl, alkylbenzothiazolyl, difluorobenzo[1,3]dioxolyl, pyrimidyl, pyrimidylalkyl, pyrazinyl, pyrazinylalkyl, substituted imidazolyl, substituted imidazolylalkyl, substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted pyrimidyl, substituted pyrimidylalkyl, substituted pyrazinyl and substituted pyrazinylalkyl, wherein said substituted imidazolyl, substituted imidazolylalkyl, substituted phenyl, substituted phenylalkyl, substituted pyridinyl, substituted pyridinylalkyl, substituted pyridazinyl, substituted pyridazinylalkyl, substituted pyrazolyl substituted pyrazolylalkyl, substituted pyrimidyl, substituted pyrimidylalkyl, substituted pyrazinyl or substituted pyrazinylalkyl is substituted with one to three substituents independently selected from the group consisting of: alkyl, haloalkyl, cycloalkyl, cycloalkylalkyl, halogen, haloalkoxy, alkoxy, hydroxy, alkoxyalkyl, hydroxyalkyl, alkylsulfonyl, alkylsulfonyloxy, alkylsulfanyl, cycloalkylsulfonyloxy, cycloalkyl, alkenyl, cycloalkylalkoxy, alkoxyalkoxy, tetrahydrofuranyloxy, pyridinyloxy, alkoxycarbonylalkyl, cyanoalkyl, alkyloxazodiazolylalkyl, haloalkyloxazodiazolylalkyl, alkoxyalkenyl, cycloalkylalkenyl, cycloalkylalkoxyalkyl, alkoxycarbonyl, alkylcarbonyl, haloalkylhydroxyalkyl, alkylaminocarbonyl, dialkylaminocarbonyl, hydroxyoxetanyl, fluorooxetanyl and hydroxycycloalkyl;

one of $R^4$ and $R^5$ is hydrogen or alkyl and the other is selected from the group consisting of hydrogen, alkyl, hydroxyalkyl, alkoxyalkyl, cycloalkyl, phenyl, alkylphenyl, haloalkoxyphenyl, phenylalkyl, halophenyl, halophenylalkyl, haloalkylphenyl or pyridinylalkyl; and one of $R^6$ and $R^7$ is selected from the group consisting of hydrogen, alkyl, cycloalkyl and hydroxyalkyl and the other is selected from the group consisting of hydrogen, alkyl, cycloalkyl and hydroxyalkyl;

or a pharmaceutically acceptable salt thereof.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Preferred are the compounds of formula (I) and pharmaceutically acceptable salts and esters thereof.

Preferred are the compounds of formula (I) and pharmaceutically acceptable salts thereof, particularly the compounds of formula (I).

Also preferred are compounds of formula (I), wherein
m is 1 or 2;
n is zero, 1 or 2, wherein, when n is zero, m is 1;
A is —S(O)$_2$— or carbonyl;
$R^1$ is selected from the group consisting of alkyl, aminoalkyl, alkylamino, cycloalkyl, cycloalkylalkyl, haloalkyl, morpholinyl, piperidinyl, pyrrolidinyl, pyrazolyl, imidazolyl, oxazolyl, thiophenyl, thiazolyl, pyridinyl, pyridinylalkyl, pyridazinyl, pyrazinyl, phenyl, phenylalkyl, substituted phenyl and substituted phenylalkyl, wherein said substituted phenyl or substituted phenylalkyl is substituted with one to three substituents independently selected from the group consisting of: alkyl, haloalkyl, halogen, hydroxy, alkoxy, haloalkoxy, phenyloxy and alkylphenyloxy; and
$R^2$ is selected from the group consisting of phenyl, phenylalkyl, pyridinyl, pyridinylalkyl, pyridazinyl, pyridazinylalkyl, pyrazolyl, pyrazolylalkyl, substituted phenyl, substituted phenylalkyl, substituted pyridinyl, substituted pyridinylalkyl, substituted pyridazinyl, substituted pyridazinylalkyl, substituted pyrazolyl and substituted pyrazolylalkyl, wherein said substituted phenyl, substituted phenylalkyl, substituted pyridinyl, substituted pyridinylalkyl, substituted pyridazinyl, substituted pyridazinylalkyl, substituted pyrazolyl or substituted pyrazolylalkyl is substituted with one to three substituents independently selected from the group consisting of: alkyl, haloalkyl, cycloalkyl, cycloalkylalkyl, halogen, haloalkoxy, alkoxy, hydroxy, alkoxyalkyl, hydroxyalkyl, alkylsulfonyl and alkylsulfonyloxy;
or a pharmaceutically acceptable salt thereof.

Further preferred are compounds of formula (I) wherein $R^1$ is selected from the group consisting of alkyl, cycloalkyl, cycloalkylalkyl, haloalkyl, morpholinyl, piperidinyl, phenyl and substituted phenyl, wherein said substituted phenyl is substituted with one to three substituents independently selected from the group consisting of: alkyl, haloalkyl, halogen, hydroxy, alkoxy and haloalkoxy. Also further preferred are compounds of formula (I) wherein $R^1$ is selected from the group consisting of aminoalkyl, alkylamino, pyrrolidinyl, pyrazolyl, imidazolyl, oxazolyl, thiophenyl, thyazolyl, pyridinyl, pyridinylalkyl, pyridazinyl, pyrazinyl, phenylalkyl and substituted phenylalkyl, wherein said substituted phenylalkyl is substituted with one to three substituents independently selected from the group consisting of: alkyl, haloalkyl, halogen, hydroxy, alkoxy, haloalkoxy, phenyloxy and alkylphenyloxy. More preferred are compounds of formula (I) wherein $R^1$ is selected from the group consisting of alkyl, cycloalkylalkyl, haloalkyl, morpholinyl, phenyl or substituted phenyl, wherein said substituted phenyl is substituted with one to three substituents, preferably one or two substituents, independently selected from the group consisting of: alkyl, haloalkyl, halogen, hydroxy, alkoxy and haloalkoxy. Particularly preferred are those compounds of formula (I) wherein $R^1$ is selected from the group consisting of alkyl, cycloalkylalkyl, haloalkyl and morpholinyl. Also particularly preferred are those compounds of formula (I) wherein $R^1$ is phenyl or substituted phenyl, wherein said substituted phenyl is substituted with one to three substituents, preferably one or two substituents, independently selected from the group consisting of: alkyl, haloalkyl, halogen, hydroxy, alkoxy and haloalkoxy. Moreover preferred are compounds of formula (I) wherein $R^1$ is phenyl. Furthermore preferred are those compounds of formula (I) wherein $R^1$ is chlorophenyl.

Also further preferred are those compounds of formula (I) wherein $R^1$ is selected from the group consisting of alkyl, cycloalkyl, cycloalkylalkyl, haloalkyl, haloalkylcycloalkyl, hydroxycycloalkylalkyl, (cycloalkyl)(hydroxy)alkyl, (cycloalkyl)(alkoxy)alkyl, alkoxycycloalkylalkyl, hydroxycycloalkyl, cycloalkoxyalkyl, hydroxyalkyl, alkoxyalkyl, benzyloxyalkyl, phenyloxyalkyl, dihydro-furanylidenemethyl, tetrahydro-furanylmethyl, dihydro-isoindolyl, dihydroquinolinyl, —NR$^4$R$^5$, azepanyl, morpholinyl, piperidinyl, pyrrolidinyl, thiophenyl, pyridinyl, alkoxypyridinyl, pyrimidyl, phenyl, phenylalkyl, substituted piperidinyl, substituted pyrrolidinyl, substituted pyrazolyl, substituted imidazolyl, substituted isoxazolyl, substituted thiophenyl, substituted thiazolyl, substituted pyridinyl, substituted pyridazinyl, substituted phenyl and substituted phenylalkyl, wherein said substituted piperidinyl, substituted pyrrolidinyl, substituted pyrazolyl, substituted imidazolyl, substituted isoxazolyl, substituted thiophenyl, substituted thiazolyl, substituted pyridinyl, substituted pyridazinyl, substituted phenyl or substituted phenylalkyl is substituted with one to three substituents independently selected from the group consisting of: alkyl, haloalkyl, halogen, hydroxy, haloalkoxy, alkylsulfonyl, oxopyrrolidinyl, alkoxycarbonyl, benzyloxy and —NR$^6$R$^7$.

Also particularly preferred are those compounds of formula (I) wherein $R^1$ is selected from the group consisting of alkyl, phenyl, substituted pyrazolyl, substituted isoxazolyl, substituted pyridinyl and substituted phenyl, wherein said substituted pyrazolyl, substituted isoxazolyl, substituted pyridinyl or substituted phenyl is substituted with one to three substituents independently selected from the group consisting of: alkyl, haloalkyl, halogen, hydroxy and haloalkoxy.

Also moreover preferred are compounds of formula (I) wherein $R^1$ is selected from the group consisting of: methylpropanyl, dimethylpropanyl, phenyl, trifluoromethoxyphenyl, trifluoromethylphenyl, dimethylisoxazolyl, chlorophenyl, methylpyrazolyl, chloropyridinyl and hydroxypyridinyl.

Also preferred are compounds of formula (I) wherein n is 1 or 2. Particularly preferred are those wherein n is 1.

Preferred are compounds of formula (I) wherein m is 2. Particularly preferred are compounds of formula (I) wherein m is 1.

Preferred are compounds of formula (I) wherein A is —S(O)$_2$—.

Another preferred embodiment of the present invention are the compounds according to formula (I) wherein R$^2$ is selected from the group consisting of phenyl, pyridinyl, pyridazinyl, pyrazolyl, substituted phenyl, substituted pyridinyl, substituted pyridazinyl and substituted pyrazolyl, wherein said substituted phenyl, substituted pyridinyl, substituted pyridazinyl or substituted pyrazolyl are substituted with one to three substituents, preferably one or two substituents, independently selected from the group consisting of: alkyl, haloalkyl, cycloalkyl, cycloalkylalkyl, halogen, haloalkoxy, alkoxy, hydroxy, alkoxyalkyl and hydroxyalkyl.

Also a preferred embodiment of the present invention are those compounds of formula (I) wherein R$^2$ is selected from the group consisting of phenylalkyl, alkylindazolyl, alkylbenzothiazolyl, difluorobenzo[1,3]dioxolyl, substituted phenyl, substituted phenylalkyl, substituted pyridinyl, substituted pyridazinyl and substituted pyrimidyl, wherein said substituted phenyl, substituted phenylalkyl, substituted pyridinyl, substituted pyridazinyl or substituted pyrimidyl is substituted with one to three substituents independently selected from the group consisting of: alkyl, haloalkyl, cycloalkyl, cycloalkylalkyl, halogen, haloalkoxy, alkoxy, alkoxyalkyl, hydroxyalkyl, alkylsulfonyl, alkylsulfonyloxy, alkylsulfanyl, cycloalkylsulfonyloxy, cycloalkoxy, alkenyl, cycloalkylalkoxy, alkoxyalkoxy, tetrahydrofuranyloxy, pyridinyloxy, alkoxycarbonylalkyl, cyanoalkyl, alkyloxazodiazolylalkyl, haloalkyloxazodiazolylalkyl, alkoxyalkenyl, cycloalkylalkenyl, cycloalkylalkoxyalkyl, alkoxycarbonyl, alkylcarbonyl, haloalkylhydroxyalkyl, alkylaminocarbonyl, dialkylaminocarbonyl, hydroxyoxetanyl, fluorooxetanyl and hydroxycycloalkyl.

Also a preferred embodiment of the present invention are those compounds of formula (I) wherein R$^2$ is selected from the group consisting of phenylalkyl, alkylindazolyl, alkylbenzothiazolyl, difluorobenzo[1,3]dioxolyl, substituted phenyl, substituted phenylalkyl, substituted pyridinyl and substituted pyrimidyl, wherein said substituted phenyl, substituted phenylalkyl, substituted pyridinyl or substituted pyrimidyl is substituted with one to three substituents independently selected from the group consisting of: alkyl, haloalkyl, cycloalkyl, cycloalkylalkyl, halogen, haloalkoxy, alkoxy, alkoxyalkyl, hydroxyalkyl, alkylsulfonyl, alkylsulfonyloxy, alkylsulfanyl, cycloalkylsulfonyloxy, cycloalkoxy, alkenyl, cycloalkylalkoxy, alkoxyalkoxy, tetrahydrofuranyloxy, pyridinyloxy, alkoxycarbonylalkyl, cyanoalkyl, alkyloxazodiazolylalkyl, haloalkyloxazodiazolylalkyl, alkoxyalkenyl, cycloalkylalkenyl, cycloalkylalkoxyalkyl, alkoxycarbonyl, alkylcarbonyl, haloalkylhydroxyalkyl, alkylaminocarbonyl, dialkylaminocarbonyl, hydroxyoxetanyl, fluorooxetanyl and hydroxycycloalkyl.

Particularly preferred are the compounds according to formula (I) wherein R$^2$ is selected from the group consisting of phenyl, pyridinyl, pyridazinyl, substituted phenyl, substituted pyridinyl and substituted pyridazinyl, wherein said substituted phenyl, substituted pyridinyl or substituted pyridazinyl is substituted with one to three substituents, preferably one or two substituents, independently selected from the group consisting of: alkyl, halogen, haloalkoxy and alkoxy. More preferred are the compounds according to formula (I) wherein R$^2$ is phenyl substituted with one to three substituents, preferably one or two, independently selected from the group consisting of: alkyl, haloalkoxy and alkoxy. Further preferred are the compounds according to formula (I) wherein R$^2$ is selected from the group consisting of: ethylphenyl, tert-butylphenyl, isopropyloxyphenyl, trifluoromethoxyphenyl, 2,2,2-trifluoroethoxyphenyl, 2,2,2-trifluoro-1-methylethoxyphenyl and 2,2,2-trifluoro-1,1-dimethylethoxyphenyl.

Also particularly preferred are those compounds of formula (I) wherein R$^2$ is substituted phenyl or substituted pydridinyl, wherein said substituted phenyl or substituted pydridinyl is substituted with one to three substituents independently selected from the group consisting of: alkyl, haloalkyl, cycloalkyl, haloalkoxy, alkoxy, haloalkylhydroxyalkyl and hydroxycycloalkyl.

Also moreover preferred are those compounds of formula (I) wherein R$^2$ is selected from the group consisting of: ethylphenyl, tert-butylphenyl, isopropyloxyphenyl, cyclopropylphenyl, 2,2,2-trifluoroethylphenyl, 2,2,2-trifluoro-1-hydroxyethylphenyl, (1-hydroxycyclobutyl)phenyl, trifluoromethoxyphenyl, 2,2,2-trifluoroethoxyphenyl, 2,2,2-trifluoro-1-methylethoxyphenyl, 2,2,2-trifluoro-1,1-dimethylethoxyphenyl and 2,2,2-trifluoroethoxypyridinyl.

Furthermore preferred are those compounds of formula (I) wherein R$^2$ is selected from the group consisting of: ethylphenyl, isopropyloxyphenyl, cyclopropylphenyl, 2,2,2-trifluoroethylphenyl, 2,2,2-trifluoro-1-hydroxyethylphenyl, (1-hydroxycyclobutyl)phenyl, trifluoromethoxyphenyl, 2,2,2-trifluoroethoxyphenyl, 2,2,2-trifluoro-1-methylethoxyphenyl and 2,2,2-trifluoroethoxypyridinyl.

Another preferred embodiment of the present invention are the compounds according to formula (I) wherein when one of R$^4$ and R$^5$ is hydrogen and the other is alkyl or cycloalkyl, —NR$^4$R$^5$ is "alkylamino" wherein "amino" signifies a secondary amino group as defined above. Preferred are compounds according to formula (I), wherein —NR$^4$R$^5$ is ethylamino, n-propylamino or isopropylamino.

Also preferred are compounds according to formula (I) wherein when one of R$^4$ and R$^5$ is alkyl and the other is alkyl or cycloalkyl, —NR$^4$R$^5$ is "alkylamino" wherein "amino" signifies a tertiary amino group as defined above. Preferred are compounds according to formula (I), wherein —NR$^4$R$^5$ is methyl-propylamino, diethylamino, ethyl-propylamino, butyl-methylamino, isobutyl-methylamino, butyl-ethylamino, ethyl-isopropylamino, methyl-pentylamino, cyclohexyl-methylamino or cyclohexyl-ethylamino.

Examples of preferred compounds of formula (I) are selected from:
1. 8-(2-Chloro-benzenesulfonyl)-2-(4-trifluoromethoxy-phenyl)-2,8-diaza-spiro[4.5]decan-1-one;
2. 8-Benzenesulfonyl-2-(4-trifluoromethoxy-phenyl)-2,8-diaza-spiro[4.5]decan-1-one;
3. 8-Benzenesulfonyl-2-(4-tert-butyl-phenyl)-2,8-diaza-spiro[4.5]decan-1-one;
4. (rac)-8-Benzenesulfonyl-2-[4-(2,2,2-trifluoro-1-methylethoxy)-phenyl]-2,8-diaza-piro[4.5]decan-1-one;
5. 8-Benzenesulfonyl-2-[4-(2,2,2-trifluoro-1,1-dimethylethoxy)-phenyl]-2,8-diaza-spiro[4.5]decan-1-one;
6. 8-Benzenesulfonyl-2-(4-isopropoxy-phenyl)-2,8-diaza-spiro[4.5]decan-1-one;
7. 8-(3,3-Dimethyl-butyryl)-2-(4-trifluoromethoxy-phenyl)-2,8-diaza-spiro[4.5]decan-1-one;
8. 8-(Morpholine-4-sulfonyl)-2-(4-trifluoromethoxy-phenyl)-2,8-diaza-spiro[4.5]decan-1-one;
9. 9-Benzenesulfonyl-2-(4-trifluoromethoxy-phenyl)-2,9-diaza-spiro[5.5]undecan-1-one;
10. 8-Benzenesulfonyl-2-(6-isopropyl-pyridin-3-yl)-2,8-diaza-spiro[4.5]decan-1-one;

11. 8-Benzenesulfonyl-2-(6-chloro-pyridin-3-yl)-2,8-diaza-spiro[4.5]decan-1-one;
12. 8-Benzenesulfonyl-2-pyridin-3-yl-2,8-diaza-spiro[4.5]decan-1-one;
13. 8-(3-Cyclopropyl-propionyl)-2-(4-trifluoromethoxy-phenyl)-2,8-diaza-spiro[4.5]decan-1-one;
14. 8-(4,4-Dimethyl-pentanoyl)-2-(4-trifluoromethoxy-phenyl)-2,8-diaza-spiro[4.5]decan-1-one;
15. 2-(4-Isopropoxy-phenyl)-8-(morpholine-4-sulfonyl)-2,8-diaza-spiro[4.5]decan-1-one;
16. 8-Benzenesulfonyl-2-(6-methoxy-pyridazin-3-yl)-2,8-diaza-spiro[4.5]decan-1-one;
17. 8-(2-Chloro-benzenesulfonyl)-2-(4-ethyl-phenyl)-2,8-diaza-spiro[4.5]decan-1-one;
18. 8-(2-Methyl-propane-1-sulfonyl)-2-(4-trifluoromethoxy-phenyl)-2,8-diaza-spiro[4.5]decan-1-one;
19. 8-(2,2-Dimethyl-propane-1-sulfonyl)-2-(4-trifluoromethoxy-phenyl)-2,8-diaza-spiro[4.5]decan-1-one;
20. 8-(3,3-Dimethyl-butyryl)-2-(4-ethyl-phenyl)-2,8-diaza-spiro[4.5]decan-1-one;
21. 2-(4-Ethyl-phenyl)-8-(morpholine-4-sulfonyl)-2,8-diaza-spiro[4.5]decan-1-one;
22. (rac)-8-(2,2-Dimethyl-propane-1-sulfonyl)-2-[4-(2,2,2-trifluoro-1-methyl-ethoxy)-phenyl]-2,8-diaza-spiro[4.5]decan-1-one;
23. 2-(4-Isopropoxy-phenyl)-8-(2-methyl-propane-1-sulfonyl)-2,8-diaza-spiro[4.5]decan-1-one;
24. 2-(4-Ethyl-phenyl)-8-(2-methyl-propane-1-sulfonyl)-2,8-diaza-spiro[4.5]decan-1-one;
25. (rac)-8-Benzenesulfonyl-2-[6-(2,2,2-trifluoro-1-methyl-ethoxy)-pyridin-3-yl]-2,8-diaza-spiro[4.5]decan-1-one; and
26. 8-Benzenesulfonyl-2-[4-(2,2,2-trifluoro-ethoxy)-phenyl]-2,8-diaza-spiro[4.5]decan-1-one.

Further examples of preferred compounds of formula (I) are selected from:

2-(4-Ethyl-phenyl)-8-(2-methyl-propane-1-sulfonyl)-2,8-diaza-spiro[4.5]decan-1-one;
8-(Thiophene-2-sulfonyl)-2-(4-trifluoromethoxy-phenyl)-2,8-diaza-spiro[4.5]decan-1-one;
2-(4-Ethyl-phenyl)-8-(thiophene-2-sulfonyl)-2,8-diaza-spiro[4.5]decan-1-one;
2-(4-Ethyl-phenyl)-8-(3,3,3-trifluoro-propane-1-sulfonyl)-2,8-diaza-spiro[4.5]decan-1-one;
8-(3,3-Dimethyl-butyryl)-2-(4-propyl-phenyl)-2,8-diaza-spiro[4.5]decan-1-one;
8-(2,2-Dimethyl-propane-1-sulfonyl)-2-(4-ethyl-phenyl)-2,8-diaza-spiro[4.5]decan-1-one;
8-(2-Chloro-benzenesulfonyl)-2-(4-cyclopropyl-phenyl)-2,8-diaza-spiro[4.5]decan-1-one;
8-(2-Chloro-benzenesulfonyl)-2-(4-methylsulfanyl-phenyl)-2,8-diaza-spiro[4.5]decan-1-one;
2-(4-Cyclopropyl-phenyl)-8-(3,3-dimethyl-butyryl)-2,8-diaza-spiro[4.5]decan-1-one;
2-(4-Cyclopropyl-phenyl)-8-(thiophene-2-sulfonyl)-2,8-diaza-spiro[4.5]decan-1-one;
8-(2-Cyclopentyl-acetyl)-2-(4-cyclopropyl-phenyl)-2,8-diaza-spiro[4.5]decan-1-one;
2-(4-Cyclopropyl-phenyl)-8-phenylmethanesulfonyl-2,8-diaza-spiro[4.5]decan-1-one;
2-(4-Cyclopropyl-phenyl)-8-(propane-1-sulfonyl)-2,8-diaza-spiro[4.5]decan-1-one;
8-(3,3-Dimethyl-butyryl)-2-[4-(2,2,2-trifluoro-ethyl)-phenyl]-2,8-diaza-spiro[4.5]decan-1-one;
2-(4-Ethyl-phenyl)-8-(5-methyl-thiophene-2-sulfonyl)-2,8-diaza-spiro[4.5]decan-1-one;
8-(5-Methyl-thiophene-2-sulfonyl)-2-(4-trifluoromethoxy-phenyl)-2,8-diaza-spiro[4.5]decan-1-one;
2-(4-sec-Butyl-phenyl)-8-(thiophene-2-sulfonyl)-2,8-diaza-spiro[4.5]decan-1-one;
2-(4-sec-Butyl-phenyl)-8-(morpholine-4-sulfonyl)-2,8-diaza-spiro[4.5]decan-1-one;
2-(4-sec-Butyl-phenyl)-8-(5-methyl-thiophene-2-sulfonyl)-2,8-diaza-spiro[4.5]decan-1-one;
2-(4-sec-Butyl-phenyl)-8-(3,3-dimethyl-butyryl)-2,8-diaza-spiro[4.5]decan-1-one;
8-(2-Chloro-benzenesulfonyl)-2-[2-(4-chloro-phenyl)-ethyl]-2,8-diaza-spiro[4.5]decan-1-one
Methanesulfonic acid 4-[8-(2-chloro-benzenesulfonyl)-1-oxo-2,8-diaza-spiro[4.5]dec-2-yl]-phenyl ester;
8-(2-Chloro-benzenesulfonyl)-2-(4-trifluoromethoxy-benzyl)-2,8-diaza-spiro[4.5]decan-1-one;
Methanesulfonic acid 4-[8-(5-methyl-thiophene-2-sulfonyl)-1-oxo-2,8-diaza-spiro[4.5]dec-2-yl]-phenyl ester;
8-(2-Methanesulfonyl-benzenesulfonyl)-2-(4-trifluoromethoxy-phenyl)-2,8-diaza-spiro[4.5]decan-1-one;
2-(4-Ethyl-phenyl)-8-(2-methanesulfonyl-benzenesulfonyl)-2,8-diaza-spiro[4.5]decan-1-one;
Methanesulfonic acid 4-[8-(2,2-dimethyl-propane-1-sulfonyl)-1-oxo-2,8-diaza-spiro[4.5]dec-2-yl]-phenyl ester;
2-(4-Ethyl-phenyl)-8-(2-trifluoromethoxy-benzenesulfonyl)-2,8-diaza-spiro[4.5]decan-1-one;
8-(2-Trifluoromethoxy-benzenesulfonyl)-2-(4-trifluoromethoxy-phenyl)-2,8-diaza-spiro[4.5]decan-1-one;
Methanesulfonic acid 4-[1-oxo-8-(2-trifluoromethoxy-benzenesulfonyl)-2,8-diaza-spiro[4.5]dec-2-yl]-phenyl ester;
8-(2-Methanesulfonyl-benzenesulfonyl)-2-(4-propyl-phenyl)-2,8-diaza-spiro[4.5]decan-1-one;
2-(4-Propyl-phenyl)-8-(2-trifluoromethoxy-benzenesulfonyl)-2,8-diaza-spiro[4.5]decan-1-one;
Methanesulfonic acid 4-[1-oxo-8-(thiophene-2-sulfonyl)-2,8-diaza-spiro[4.5]dec-2-yl]-phenyl ester;
8-(2-Methyl-propane-1-sulfonyl)-2-[4-(2,2,2-trifluoro-ethyl)-phenyl]-2,8-diaza-spiro[4.5]decan-1-one;
2-(4-sec-Butyl-phenyl)-8-(2-methyl-propane-1-sulfonyl)-2,8-diaza-spiro[4.5]decan-1-one;
Methanesulfonic acid 4-[8-(2-methyl-propane-1-sulfonyl)-1-oxo-2,8-diaza-spiro[4.5]dec-2-yl]-phenyl ester;
8-(2-Methyl-propane-1-sulfonyl)-2-[4-(2,2,2-trifluoro-ethoxy)-phenyl]-2,8-diaza-spiro[4.5]decan-1-one;
Cyclopropanesulfonic acid 4-[8-(2-methyl-propane-1-sulfonyl)-1-oxo-2,8-diaza-spiro[4.5]dec-2-yl]-phenyl ester;
2-(4-Cyclopropyl-phenyl)-8-(2-methyl-propane-1-sulfonyl)-2,8-diaza-spiro[4.5]decan-1-one;
2-(4-Cyclopentyloxy-phenyl)-8-(2-methyl-propane-1-sulfonyl)-2,8-diaza-spiro[4.5]decan-1-one;
2-(4-Ethyl-phenyl)-8-(2-trifluoromethyl-benzenesulfonyl)-2,8-diaza-spiro[4.5]decan-1-one;
2-(4-Trifluoromethoxy-phenyl)-8-(2-trifluoromethyl-benzenesulfonyl)-2,8-diaza-spiro[4.5]decan-1-one;
8-(2-Chloro-4-trifluoromethyl-benzenesulfonyl)-2-(4-ethyl-phenyl)-2,8-diaza-spiro[4.5]decan-1-one;
8-(2-Chloro-4-trifluoromethyl-benzenesulfonyl)-2-(4-trifluoromethoxy-phenyl)-2,8-diaza-spiro[4.5]decan-1-one;
2-(4-Cyclopropyl-phenyl)-8-(2-trifluoromethyl-benzenesulfonyl)-2,8-diaza-spiro[4.5]decan-1-one;
2-(4-Cyclopropyl-phenyl)-8-(4-fluoro-2-trifluoromethyl-benzenesulfonyl)-2,8-diaza-spiro[4.5]decan-1-one;
2-[4-(2,2,2-Trifluoro-ethyl)-phenyl]-8-(2-trifluoromethyl-benzenesulfonyl)-2,8-diaza-spiro[4.5]decan-1-one;
2-(4-Ethyl-phenyl)-8-(2-iodo-benzenesulfonyl)-2,8-diaza-spiro[4.5]decan-1-one;

2-(4-Ethyl-phenyl)-8-(4-fluoro-2-trifluoromethyl-benzenesulfonyl)-2,8-diaza-spiro[4.5]decan-1-one;
8-(4-Fluoro-2-trifluoromethyl-benzenesulfonyl)-2-(4-trifluoromethoxy-phenyl)-2,8-diaza-spiro[4.5]decan-1-one;
8-(2-Chloro-4-trifluoromethyl-benzenesulfonyl)-2-(4-cyclopropyl-phenyl)-2,8-diaza-spiro[4.5]decan-1-one;
2-[4-(2,2,2-Trifluoro-ethyl)-phenyl]-8-(2-trifluoromethoxy-benzenesulfonyl)-2,8-diaza-spiro[4.5]decan-1-one;
2-[4-(2,2,2-Trifluoro-ethoxy)-phenyl]-8-(2-trifluoromethoxy-benzenesulfonyl)-2,8-diaza-spiro[4.5]decan-1-one;
Cyclopropanesulfonic acid 4-[1-oxo-8-(2-trifluoromethoxy-benzenesulfonyl)-2,8-diaza-spiro[4.5]dec-2-yl]-phenyl ester;
8-(4-Fluoro-2-trifluoromethyl-benzenesulfonyl)-2-[4-(2,2,2-trifluoro-ethyl)-phenyl]-2,8-diaza-spiro[4.5]decan-1-one;
2-(4-Cyclopropyl-phenyl)-8-(2-trifluoromethoxy-benzenesulfonyl)-2,8-diaza-spiro[4.5]decan-1-one;
Methanesulfonic acid 4-[8-(4-fluoro-2-trifluoromethyl-benzenesulfonyl)-1-oxo-2,8-diaza-spiro[4.5]dec-2-yl]-phenyl ester;
2-(4-Butoxy-phenyl)-8-(2-methyl-propane-1-sulfonyl)-2,8-diaza-spiro[4.5]decan-1-one;
2-(4-sec-Butoxy-phenyl)-8-(2-methyl-propane-1-sulfonyl)-2,8-diaza-spiro[4.5]decan-1-one;
8-(2-Methyl-propane-1-sulfonyl)-2-[4-(2,2,2-trifluoro-1-methyl-ethoxy)-phenyl]-2,8-diaza-spiro[4.5]decan-1-one;
2-(4-Isopropoxy-phenyl)-8-(2-trifluoromethoxy-benzenesulfonyl)-2,8-diaza-spiro[4.5]decan-1-one;
2-(4-Butoxy-phenyl)-8-(2-trifluoromethoxy-benzenesulfonyl)-2,8-diaza-spiro[4.5]decan-1-one;
8-(2-Trifluoromethoxy-benzenesulfonyl)-2-[6-(2,2,2-trifluoro-1-methyl-ethoxy)-pyridin-3-yl]-2,8-diaza-spiro[4.5]decan-1-one;
2-(4-sec-Butoxy-phenyl)-8-(2-trifluoromethoxy-benzenesulfonyl)-2,8-diaza-spiro[4.5]decan-1-one;
8-(2-Chloro-benzenesulfonyl)-2-(4-vinyl-phenyl)-2,8-diaza-spiro[4.5]decan-1-one;
8-Cyclobutylmethanesulfonyl-2-(4-isopropoxy-phenyl)-2,8-diaza-spiro[4.5]decan-1-one;
8-Cyclobutylmethanesulfonyl-2-(4-trifluoromethoxy-phenyl)-2,8-diaza-spiro[4.5]decan-1-one;
2-(4-Cyclopropylmethoxy-phenyl)-8-(2-methyl-propane-1-sulfonyl)-2,8-diaza-spiro[4.5]decan-1-one;
8-Cyclopropanesulfonyl-2-(4-isopropoxy-phenyl)-2,8-diaza-spiro[4.5]decan-1-one;
8-Cyclopropanesulfonyl-2-(4-trifluoromethoxy-phenyl)-2,8-diaza-spiro[4.5]decan-1-one;
8-(3,5-Dimethyl-isoxazole-4-sulfonyl)-2-[4-(2,2,2-trifluoro-1-methyl-ethoxy)-phenyl]-2,8-diaza-spiro[4.5]decan-1-one;
8-Cyclopropanesulfonyl-2-[4-(2,2,2-trifluoro-1-methyl-ethoxy)-phenyl]-2,8-diaza-spiro[4.5]decan-1-one;
8-(2-Trifluoromethoxy-benzenesulfonyl)-2-[4-(2,2,2-trifluoro-1-methyl-ethoxy)-phenyl]-2,8-diaza-spiro[4.5]decan-1-one;
8-(2-Trifluoromethyl-benzenesulfonyl)-2-[4-(2,2,2-trifluoro-1-methyl-ethoxy)-phenyl]-2,8-diaza-spiro[4.5]decan-1-one;
2-(4-Isopropoxy-phenyl)-8-(2-trifluoromethyl-benzenesulfonyl)-2,8-diaza-spiro[4.5]decan-1-one;
8-(2-Methyl-propane-1-sulfonyl)-2-[4-(3,3,3-trifluoro-propoxy)-phenyl]-2,8-diaza-spiro[4.5]decan-1-one;
8-(2-Trifluoromethoxy-benzenesulfonyl)-2-[4-(3,3,3-trifluoro-propoxy)-phenyl]-2,8-diaza-spiro[4.5]decan-1-one;
2-(4-Iodo-phenyl)-8-(2-trifluoromethoxy-benzenesulfonyl)-2,8-diaza-spiro[4.5]decan-1-one;
2-[4-(2-Methoxy-ethyl)-phenyl]-8-(2-trifluoromethoxy-benzenesulfonyl)-2,8-diaza-spiro[4.5]decan-1-one;
2-[4-(2-Methoxy-ethoxy)-phenyl]-8-(2-trifluoromethoxy-benzenesulfonyl)-2,8-diaza-spiro[4.5]decan-1-one;
2-[4-(3-Methoxy-propoxy)-phenyl]-8-(2-methyl-propane-1-sulfonyl)-2,8-diaza-spiro[4.5]decan-1-one;
2-[4-(2-Methoxy-1,1-dimethyl-ethyl)-phenyl]-8-(2-methyl-propane-1-sulfonyl)-2,8-diaza-spiro[4.5]decan-1-one;
2-[4-(3-Methoxy-propoxy)-phenyl]-8-(2-trifluoromethoxy-benzenesulfonyl)-2,8-diaza-spiro[4.5]decan-1-one;
2-[4-(2-Methoxy-1,1-dimethyl-ethyl)-phenyl]-8-(2-trifluoromethoxy-benzenesulfonyl)-2,8-diaza-spiro[4.5]decan-1-one;
8-(3,5-Dimethyl-isoxazole-4-sulfonyl)-2-(4-isopropoxy-phenyl)-2,8-diaza-spiro[4.5]decan-1-one;
8-(3,5-Dimethyl-isoxazole-4-sulfonyl)-2-[4-(2-methoxy-1,1-dimethyl-ethyl)-phenyl]-2,8-diaza-spiro[4.5]decan-1-one;
8-(2,2-Dichloro-1-methyl-cyclopropanecarbonyl)-2-[4-(2,2,2-trifluoro-1-methyl-ethoxy)-phenyl]-2,8-diaza-spiro[4.5]decan-1-one;
8-(2-Chloro-benzenesulfonyl)-2-[6-(2,2,2-trifluoro-1-methyl-ethoxy)-pyridin-3-yl]-2,8-diaza-spiro[4.5]decan-1-one;
8-(2-Chloro-benzenesulfonyl)-2-[4-(2,2,2-trifluoro-ethoxy)-phenyl]-2,8-diaza-spiro[4.5]decan-1-one;
8-(2-Chloro-benzenesulfonyl)-2-[6-(3,3,3-trifluoro-propoxy)-pyridin-3-yl]-2,8-diaza-spiro[4.5]decan-1-one;
8-Benzenesulfonyl-2-[6-(2,2,2-trifluoro-ethoxy)-pyridin-3-yl]-2,8-diaza-spiro[4.5]decan-1-one;
8-Benzenesulfonyl-2-[2-(2,2,2-trifluoro-ethoxy)-pyrimidin-5-yl]-2,8-diaza-spiro[4.5]decan-1-one;
8-(2-Chloro-benzenesulfonyl)-2-[6-(2,2,2-trifluoro-ethoxy)-pyridin-3-yl]-2,8-diaza-spiro[4.5]decan-1-one;
8-(3,3-Dimethyl-butyryl)-2-[4-(2,2,2-trifluoro-ethoxy)-phenyl]-2,8-diaza-spiro[4.5]decan-1-one;
8-(2,2-Dichloro-1-methyl-cyclopropanecarbonyl)-2-[4-(2,2,2-trifluoro-ethoxy)-phenyl]-2,8-diaza-spiro[4.5]decan-1-one;
8-(3,3-Dimethyl-butyryl)-2-[6-(2,2,2-trifluoro-ethoxy)-pyridin-3-yl]-2,8-diaza-spiro[4.5]decan-1-one;
8-(3,3-Dimethyl-butyryl)-2-[4-(2,2,2-trifluoro-1-methyl-ethoxy)-phenyl]-2,8-diaza-spiro[4.5]decan-1-one;
8-(2-Chloro-benzenesulfonyl)-2-(2-ethyl-2H-indazol-5-yl)-2,8-diaza-spiro[4.5]decan-1-one;
8-(2-Chloro-benzenesulfonyl)-2-[4-(2,2,2-trifluoro-1-methyl-ethoxy)-phenyl]-2,8-diaza-spiro[4.5]decan-1-one;
8-(2-Chloro-benzenesulfonyl)-2-(1-ethyl-1H-indazol-5-yl)-2,8-diaza-spiro[4.5]decan-1-one;
8-(2-Chloro-benzenesulfonyl)-2-(2-methyl-benzothiazol-6-yl)-2,8-diaza-spiro[4.5]decan-1-one;
8-(2-Chloro-benzenesulfonyl)-2-(4-cyclopentyloxy-phenyl)-2,8-diaza-spiro[4.5]decan-1-one;
8-(2-Chloro-benzenesulfonyl)-2-[4-(tetrahydro-furan-3-yloxy)-phenyl]-2,8-diaza-spiro[4.5]decan-1-one;
8-(2-Chloro-benzenesulfonyl)-2-(1-methyl-1H-indazol-5-yl)-2,8-diaza-spiro[4.5]decan-1-one;
8-(2-Chloro-benzenesulfonyl)-2-(2-methyl-2H-indazol-5-yl)-2,8-diaza-spiro[4.5]decan-1-one;
8-(2-Chloro-benzenesulfonyl)-2-[4-(pyridin-3-yloxy)-phenyl]-2,8-diaza-spiro[4.5]decan-1-one;
8-(2-Chloro-benzenesulfonyl)-2-(4-cyclopentylmethoxy-phenyl)-2,8-diaza-spiro[4.5]decan-1-one;
{4-[8-(2-Chloro-benzenesulfonyl)-1-oxo-2,8-diaza-spiro[4.5]dec-2-yl]-phenyl}-acetic acid ethyl ester;

{4-[8-(2-Chloro-benzenesulfonyl)-1-oxo-2,8-diaza-spiro[4.5]dec-2-yl]-phenyl}-acetonitrile;
8-(2-Chloro-benzenesulfonyl)-2-[4-(5-methyl-[1,2,4]oxadiazol-3-ylmethyl)-phenyl]-2,8-diaza-spiro[4.5]decan-1-one;
8-(2-Chloro-benzenesulfonyl)-2-[4-(5-methyl-[1,3,4]oxadiazol-2-ylmethyl)-phenyl]-2,8-diaza-spiro[4.5]decan-1-one;
8-(2-Chloro-benzenesulfonyl)-2-[4-(5-trifluoromethyl-[1,3,4]oxadiazol-2-ylmethyl)-phenyl]-2,8-diaza-spiro[4.5]decan-1-one;
8-(neopentylsulfonyl)-2-(4-(3,3,3-trifluoropropoxy)phenyl)-2,8-diazaspiro[4.5]decan-1-one;
8-(2-Chloro-benzenesulfonyl)-2-(4-methanesulfonyl-phenyl)-2,8-diaza-spiro[4.5]decan-1-one;
8-(2-Chloro-benzenesulfonyl)-2-(4-hydroxymethyl-phenyl)-2,8-diaza-spiro[4.5]decan-1-one;
8-(2-Chloro-benzenesulfonyl)-2-(4-methoxymethyl-phenyl)-2,8-diaza-spiro[4.5]decan-1-one;
2-(4-Ethyl-phenyl)-8-[2-(2-oxo-pyrrolidin-1-yl)-benzenesulfonyl]-2,8-diaza-spiro[4.5]decan-1-one;
2-[4-((E)-3-Methoxy-propenyl)-phenyl]-8-(2-trifluoromethoxy-benzenesulfonyl)-2,8-diaza-spiro[4.5]decan-1-one;
2-[4-((E)-2-Cyclopropyl-vinyl)-phenyl]-8-(2-trifluoromethoxy-benzenesulfonyl)-2,8-diaza-spiro[4.5]decan-1-one;
2-[4-(3-Methoxy-propyl)-phenyl]-8-(2-trifluoromethoxy-benzenesulfonyl)-2,8-diaza-spiro[4.5]decan-1-one;
2-[4-(2-Cyclopropyl-ethyl)-phenyl]-8-(2-trifluoromethoxy-benzenesulfonyl)-2,8-diaza-spiro[4.5]decan-1-one;
8-(2-Chloro-benzenesulfonyl)-2-(4-cyclopropylmethoxymethyl-phenyl)-2,8-diaza-spiro[4.5]decan-1-one;
8-(2-Chloro-benzenesulfonyl)-2-(4-ethoxymethyl-phenyl)-2,8-diaza-spiro[4.5]decan-1-one;
4-[8-(2-Chloro-benzenesulfonyl)-1-oxo-2,8-diaza-spiro[4.5]dec-2-yl]-benzoic acid methyl ester;
2-(4-Acetyl-phenyl)-8-(2-chloro-benzenesulfonyl)-2,8-diaza-spiro[4.5]decan-1-one;
(rac)-8-(2-Chloro-benzenesulfonyl)-2-[4-(2,2,2-trifluoro-1-hydroxy-ethyl)-phenyl]-2,8-diaza-spiro[4.5]decan-1-one;
8-(2-Chloro-benzenesulfonyl)-2-[4-(1-hydroxy-ethyl)-phenyl]-2,8-diaza-spiro[4.5]decan-1-one;
8-(2-Chloro-benzenesulfonyl)-2-(2-chloro-5-trifluoromethyl-phenyl)-2,8-diaza-spiro[4.5]decan-1-one;
(rac)-8-(2-Chloro-benzenesulfonyl)-2-[4-(2,2,2-trifluoro-1-hydroxy-1-methyl-ethyl)-phenyl]-2,8-diaza-spiro[4.5]decan-1-one;
8-(2-Chloro-benzenesulfonyl)-2-(4-ethanesulfonyl-phenyl)-2,8-diaza-spiro[4.5]decan-1-one;
8-(2-Chloro-benzenesulfonyl)-2-[4-(2,2,2-trifluoro-1-hydroxy-1-trifluoromethyl-ethyl)-phenyl]-2,8-diaza-spiro[4.5]decan-1-one;
9-(2-Chloro-benzenesulfonyl)-2-(4-trifluoromethyl-phenyl)-2,9-diaza-spiro[5.5]undecan-1-one;
9-(2-Chloro-benzenesulfonyl)-2-(4-ethoxymethyl-phenyl)-2,9-diaza-spiro[5.5]undecan-1-one;
4-[8-(2-Chloro-benzenesulfonyl)-1-oxo-2,8-diaza-spiro[4.5]dec-2-yl]-N-isopropyl-benzamide;
4-[8-(2-Chloro-benzenesulfonyl)-1-oxo-2,8-diaza-spiro[4.5]dec-2-yl]-N-isopropyl-N-methyl-benzamide;
(rac)-8-(3,5-Dimethyl-isoxazole-4-sulfonyl)-2-[4-(2,2,2-trifluoro-1-hydroxy-ethyl)-phenyl]-2,8-diaza-spiro[4.5]decan-1-one;
(rac)-2-[4-(2,2,2-Trifluoro-1-hydroxy-ethyl)-phenyl]-8-(2-trifluoromethoxy-benzenesulfonyl)-2,8-diaza-spiro[4.5]decan-1-one;
8-(3,5-Dimethyl-isoxazole-4-sulfonyl)-2-(4-trifluoromethyl-phenyl)-2,8-diaza-spiro[4.5]decan-1-one;
(rac)-8-(3,3-Dimethyl-butyryl)-2-[4-(2,2,2-trifluoro-1-hydroxy-ethyl)-phenyl]-2,8-diaza-spiro[4.5]decan-1-one;
(rac)-2-(4-(2,2,2-trifluoro-1-hydroxyethyl)phenyl)-8-(2-(trifluoromethyl)phenylsulfonyl)-2,8-diazaspiro[4.5]decan-1-one;
(rac)-8-(isobutylsulfonyl)-2-(4-(2,2,2-trifluoro-1-hydroxyethyl)phenyl)-2,8-diazaspiro[4.5]decan-1-one;
(rac)-8-(isobutylsulfonyl)-2-(4-(1,1,1-trifluoro-2-hydroxypropan-2-yl)phenyl)-2,8-diazaspiro[4.5]decan-1-one;
(rac)-2-(4-(1,1,1-trifluoro-2-hydroxypropan-2-yl)phenyl)-8-(2-(trifluoromethyl)phenylsulfonyl)-2,8-diazaspiro[4.5]decan-1-one;
(rac)-8-(Cyclopropylsulfonyl)-2-(4-(2,2,2-trifluoro-1-hydroxyethyl)phenyl)-2,8-diazaspiro[4.5]decan-1-one;
(rac)-8-(Cyclopropylsulfonyl)-2-(4-(1,1,1-trifluoro-2-hydroxypropan-2-yl)phenyl)-2,8-diazaspiro[4.5]decan-1-one;
8-(2,2-Dimethyl-propane-1-sulfonyl)-2-(4-ethanesulfonyl-phenyl)-2,8-diaza-spiro[4.5]decan-1-one;
(rac)-2-(4-(2-fluoro-1-hydroxyethyl)phenyl)-8-(2-(trifluoromethyl)phenylsulfonyl)-2,8-diazaspiro[4.5]decan-1-one;
2-[4-(1-Hydroxy-1-methyl-ethyl)-phenyl]-8-(2-trifluoromethyl-benzenesulfonyl)-2,8-diaza-spiro[4.5]decan-1-one;
(rac)-2-(4-(2,2-difluoro-1-hydroxypropyl)phenyl)-8-(3,3-dimethylbutanoyl)-2,8-diazaspiro[4.5]decan-1-one;
(rac)-2-(4-(2,2-difluoro-1-hydroxyethyl)phenyl)-8-(2-(trifluoromethyl)phenylsulfonyl)-2,8-diazaspiro[4.5]decan-1-one;
(rac) 2-(4-(2,2-difluoro-1-hydroxyethyl)phenyl)-8-(isobutylsulfonyl)-2,8-diazaspiro[4.5]decan-1-one;
(rac)-2-(4-(2,2-difluoro-1-hydroxyethyl)phenyl)-8-(3,3-dimethylbutanoyl)-2,8-diazaspiro[4.5]decan-1-one;
8-(2-Chloro-benzenesulfonyl)-2-(4-trifluoromethyl-phenyl)-2,8-diaza-spiro[4.5]decan-1-one;
2-(4-Trifluoromethoxy-phenyl)-8-(1,3,5-trimethyl-1H-pyrazole-4-sulfonyl)-2,8-diaza-spiro[4.5]decan-1-one;
8-(1-Methyl-1H-imidazole-4-sulfonyl)-2-(4-trifluoromethoxy-phenyl)-2,8-diaza-spiro[4.5]decan-1-one;
8-(Pyrrolidine-1-sulfonyl)-2-(4-trifluoromethoxy-phenyl)-2,8-diaza-spiro[4.5]decan-1-one;
8-(2-Methyl-2H-pyrazole-3-sulfonyl)-2-(4-trifluoromethoxy-phenyl)-2,8-diaza-spiro[4.5]decan-1-one;
8-(1-Methyl-1H-pyrazole-3-sulfonyl)-2-(4-trifluoromethoxy-phenyl)-2,8-diaza-spiro[4.5]decan-1-one;
8-(5-Methyl-isoxazole-4-sulfonyl)-2-(4-trifluoromethoxy-phenyl)-2,8-diaza-spiro[4.5]decan-1-one;
8-(3,5-Dimethyl-isoxazole-4-sulfonyl)-2-(4-trifluoromethoxy-phenyl)-2,8-diaza-spiro[4.5]decan-1-one;
8-(Pyridine-3-sulfonyl)-2-(4-trifluoromethoxy-phenyl)-2,8-diaza-spiro[4.5]decan-1-one;
8-(2-Chloro-pyridine-3-sulfonyl)-2-(4-trifluoromethoxy-phenyl)-2,8-diaza-spiro[4.5]decan-1-one;
8-(2-Methylamino-pyridine-3-sulfonyl)-2-(4-trifluoromethoxy-phenyl)-2,8-diaza-spiro[4.5]decan-1-one;
8-(2-Dimethylamino-pyridine-3-sulfonyl)-2-(4-trifluoromethoxy-phenyl)-2,8-diaza-spiro[4.5]decan-1-one;
8-(2-Cyclopropylamino-pyridine-3-sulfonyl)-2-(4-trifluoromethoxy-phenyl)-2,8-diaza-spiro[4.5]decan-1-one;
8-[2-(2-Hydroxy-ethylamino)-pyridine-3-sulfonyl]-2-(4-trifluoromethoxy-phenyl)-2,8-diaza-spiro[4.5]decan-1-one;
8-[2-(2-Hydroxy-1-methyl-ethylamino)-pyridine-3-sulfonyl]-2-(4-trifluoromethoxy-phenyl)-2,8-diaza-spiro[4.5]decan-1-one;

8-(2-Methoxy-pyridine-3-sulfonyl)-2-(4-trifluoromethoxy-phenyl)-2,8-diaza-spiro[4.5]decan-1-one;
8-(2-Benzyloxy-pyridine-3-sulfonyl)-2-(4-trifluoromethoxy-phenyl)-2,8-diaza-spiro[4.5]decan-1-one;
8-(2-Hydroxy-pyridine-3-sulfonyl)-2-(4-trifluoromethoxy-phenyl)-2,8-diaza-spiro[4.5]decan-1-one;
8-(2-Amino-pyridine-3-sulfonyl)-2-(4-trifluoromethoxy-phenyl)-2,8-diaza-spiro[4.5]decan-1-one;
8-(6-Chloro-pyridine-3-sulfonyl)-2-(4-trifluoromethoxy-phenyl)-2,8-diaza-spiro[4.5]decan-1-one;
8-(4-Chloro-pyridine-3-sulfonyl)-2-(4-trifluoromethoxy-phenyl)-2,8-diaza-spiro[4.5]decan-1-one;
8-(4-Methoxy-pyridine-3-sulfonyl)-2-(4-trifluoromethoxy-phenyl)-2,8-diaza-spiro[4.5]decan-1-one;
8-(Pyridine-2-sulfonyl)-2-(4-trifluoromethoxy-phenyl)-2,8-diaza-spiro[4.5]decan-1-one;
8-(Pyrimidine-2-sulfonyl)-2-(4-trifluoromethoxy-phenyl)-2,8-diaza-spiro[4.5]decan-1-one;
8-(Pyridine-4-sulfonyl)-2-(4-trifluoromethoxy-phenyl)-2,8-diaza-spiro[4.5]decan-1-one;
8-(6-Methyl-pyridazine-3-sulfonyl)-2-(4-trifluoromethoxy-phenyl)-2,8-diaza-spiro[4.5]decan-1-one;
8-(Pyridine-3-sulfonyl)-2-[4-(2,2,2-trifluoro-ethoxy)-phenyl]-2,8-diaza-spiro[4.5]decan-1-one;
8-(2-Chloro-pyridine-3-sulfonyl)-2-[4-(2,2,2-trifluoro-ethoxy)-phenyl]-2,8-diaza-spiro[4.5]decan-1-one;
8-(2-Methylamino-pyridine-3-sulfonyl)-2-[4-(2,2,2-trifluoro-ethoxy)-phenyl]-2,8-diaza-spiro[4.5]decan-1-one;
8-(2-Cyclopropyl-2-hydroxy-ethanesulfonyl)-2-(4-trifluoromethoxy-phenyl)-2,8-diaza-spiro[4.5]decan-1-one;
8-(2-Cyclopropyl-2-methoxy-ethanesulfonyl)-2-(4-trifluoromethoxy-phenyl)-2,8-diaza-spiro[4.5]decan-1-one;
8-(1-Hydroxy-cyclopentylmethanesulfonyl)-2-(4-trifluoromethoxy-phenyl)-2,8-diaza-spiro[4.5]decan-1-one;
8-(1-Methoxy-cyclopentylmethanesulfonyl)-2-(4-trifluoromethoxy-phenyl)-2,8-diaza-spiro[4.5]decan-1-one;
8-(2-Hydroxy-2-methyl-propane-1-sulfonyl)-2-(4-trifluoromethoxy-phenyl)-2,8-diaza-spiro[4.5]decan-1-one;
8-[Dihydro-furan-(2Z)-ylidenemethanesulfonyl]-2-(4-trifluoromethoxy-phenyl)-2,8-diaza-spiro[4.5]decan-1-one;
8-(Tetrahydro-furan-2-ylmethanesulfonyl)-2-(4-trifluoromethoxy-phenyl)-2,8-diaza-spiro[4.5]decan-1-one;
8-(3-Hydroxy-3-methyl-pentanoyl)-2-(4-trifluoromethoxy-phenyl)-2,8-diaza-spiro[4.5]decan-1-one;
8-(2-Cyclobutyl-acetyl)-2-(4-trifluoromethoxy-phenyl)-2,8-diaza-spiro[4.5]decan-1-one;
8-(2-Isopropoxy-acetyl)-2-(4-trifluoromethoxy-phenyl)-2,8-diaza-spiro[4.5]decan-1-one;
8-(2-tert-Butoxy-acetyl)-2-(4-trifluoromethoxy-phenyl)-2,8-diaza-spiro[4.5]decan-1-one;
8-(1-Hydroxy-cyclopropanecarbonyl)-2-(4-trifluoromethoxy-phenyl)-2,8-diaza-spiro[4.5]decan-1-one;
8-(2-Benzyloxy-acetyl)-2-(4-trifluoromethoxy-phenyl)-2,8-diaza-spiro[4.5]decan-1-one;
8-(2-Phenoxy-acetyl)-2-(4-trifluoromethoxy-phenyl)-2,8-diaza-spiro[4.5]decan-1-one;
8-(2-Phenyl-propionyl)-2-(4-trifluoromethoxy-phenyl)-2,8-diaza-spiro[4.5]decan-1-one;
8-(2-Phenyl-butyryl)-2-(4-trifluoromethoxy-phenyl)-2,8-diaza-spiro[4.5]decan-1-one;
8-(2-Methyl-thiazole-4-carbonyl)-2-(4-trifluoromethoxy-phenyl)-2,8-diaza-spiro[4.5]decan-1-one;
8-(2-Chloro-acetyl)-2-(4-trifluoromethoxy-phenyl)-2,8-diaza-spiro[4.5]decan-1-one;
8-(2-Cyclopentyloxy-acetyl)-2-(4-trifluoromethoxy-phenyl)-2,8-diaza-spiro[4.5]decan-1-one;
8-(2-Chloro-benzenesulfonyl)-2-(3-chloro-4-trifluoromethyl-phenyl)-2,8-diaza-spiro[4.5]decan-1-one;
8-(2-Chloro-benzenesulfonyl)-2-(2,2-difluoro-benzo[1,3]dioxol-5-yl)-2,8-diaza-spiro[4.5]decan-1-one;
8-(2-Chloro-benzenesulfonyl)-2-[4-(3-hydroxy-oxetan-3-yl)-phenyl]-2,8-diaza-spiro[4.5]decan-1-one;
8-(2-Chloro-benzenesulfonyl)-2-[4-(3-fluoro-oxetan-3-yl)-phenyl]-2,8-diaza-spiro[4.5]decan-1-one;
8-(2-Chloro-benzenesulfonyl)-2-[4-(1-hydroxy-cyclobutyl)-phenyl]-2,8-diaza-spiro[4.5]decan-1-one;
8-(5-Methyl-isoxazol-3-ylmethanesulfonyl)-2-(4-trifluoromethoxy-phenyl)-2,8-diaza-spiro[4.5]decan-1-one;
8-(3-Isopropyl-isoxazol-5-ylmethanesulfonyl)-2-(4-trifluoromethoxy-phenyl)-2,8-diaza-spiro[4.5]decan-1-one;
3-Methyl-2-[1-oxo-2-(4-trifluoromethoxy-phenyl)-2,8-diaza-spiro[4.5]decane-8-sulfonyl]-benzoic acid methyl ester;
8-(2-Chloro-benzenesulfonyl)-2-(3-chloro-benzyl)-2,8-diaza-spiro[4.5]decan-1-one;
8-(2-Chloro-benzenesulfonyl)-2-phenethyl-2,8-diaza-spiro[4.5]decan-1-one;
8-(2-Chloro-benzenesulfonyl)-2-[2-(4-ethyl-phenyl)-ethyl]-2,8-diaza-piro[4.5]decan-1-one;
2-[2-(4-tert-Butyl-phenyl)-ethyl]-8-(2-chloro-benzenesulfonyl)-2,8-diaza-spiro[4.5]decan-1-one;
8-(2-Chloro-benzenesulfonyl)-2-[2-(4-fluoro-phenyl)-ethyl]-2,8-diaza-spiro[4.5]decan-1-one;
8-(2-Chloro-benzenesulfonyl)-2-[2-(4-methoxy-phenyl)-ethyl]-2,8-diaza-spiro[4.5]decan-1-one;
8-(2-Chloro-benzenesulfonyl)-2-(3-phenyl-propyl)-2,8-diaza-spiro[4.5]decan-1-one;
8-(2-Chloro-benzenesulfonyl)-2-[2-(2-chloro-phenyl)-ethyl]-2,8-diaza-spiro[4.5]decan-1-one;
8-(2-Chloro-benzenesulfonyl)-2-[2-(3-fluoro-phenyl)-ethyl]-2,8-diaza-spiro[4.5]decan-1-one;
8-(2-Chloro-benzenesulfonyl)-2-[2-(3-methoxy-phenyl)-ethyl]-2,8-diaza-spiro[4.5]decan-1-one;
8-(2-Chloro-benzenesulfonyl)-2-[2-(3-trifluoromethyl-phenyl)-ethyl]-2,8-diaza-spiro[4.5]decan-1-one;
8-(2-Chloro-benzenesulfonyl)-2-(4-phenyl-butyl)-2,8-diaza-spiro[4.5]decan-1-one;
8-(2-Chloro-benzenesulfonyl)-2-[2-(3-chloro-phenyl)-ethyl]-2,8-diaza-spiro[4.5]decan-1-one;
8-(2-Chloro-benzenesulfonyl)-2-[2-(3,4-dichloro-phenyl)-ethyl]-2,8-diaza-spiro[4.5]decan-1-one;
8-(2-Chloro-benzenesulfonyl)-2-[2-(4-fluoro-phenyl)-1-methyl-ethyl]-2,8-diaza-spiro[4.5]decan-1-one;
8-(2-Chloro-benzenesulfonyl)-2-(6-ethyl-pyridin-3-yl)-2,8-diaza-spiro[4.5]decan-1-one;
1-Oxo-2-(4-trifluoromethoxy-phenyl)-2,8-diaza-spiro[4.5]decane-8-carboxylic acid propylamide;
2-(4-Ethyl-phenyl)-1-oxo-2,8-diaza-spiro[4.5]decane-8-carboxylic acid methyl-propyl-amide;
1-Oxo-2-(4-trifluoromethoxy-phenyl)-2,8-diaza-spiro[4.5]decane-8-carboxylic acid methyl-propyl-amide;
1-Oxo-2-(4-trifluoromethoxy-phenyl)-2,8-diaza-spiro[4.5]decane-8-carboxylic acid isopropylamide;
2-(4-Ethyl-phenyl)-8-(piperidine-1-carbonyl)-2,8-diaza-spiro[4.5]decan-1-one;
8-(Piperidine-1-carbonyl)-2-(4-trifluoromethoxy-phenyl)-2,8-diaza-spiro[4.5]decan-1-one;
8-(Morpholine-4-carbonyl)-2-(4-trifluoromethoxy-phenyl)-2,8-diaza-spiro[4.5]decan-1-one;
2-(4-Ethyl-phenyl)-1-oxo-2,8-diaza-spiro[4.5]decane-8-carboxylic acid (4-fluoro-phenyl)-amide;
1-Oxo-2-(4-trifluoromethoxy-phenyl)-2,8-diaza-spiro[4.5]decane-8-carboxylic acid (4-fluoro-phenyl)-amide;

2-(4-Ethyl-phenyl)-1-oxo-2,8-diaza-spiro[4.5]decane-8-carboxylic acid 4-fluoro-benzylamide;
1-Oxo-2-(4-trifluoromethoxy-phenyl)-2,8-diaza-spiro[4.5]decane-8-carboxylic acid 4-fluoro-benzylamide;
1-Oxo-2-(4-trifluoromethoxy-phenyl)-2,8-diaza-spiro[4.5]decane-8-carboxylic acid 2-chloro-benzylamide;
2-(4-Ethyl-phenyl)-1-oxo-2,8-diaza-spiro[4.5]decane-8-carboxylic acid phenethyl-amide;
1-Oxo-2-(4-trifluoromethoxy-phenyl)-2,8-diaza-spiro[4.5]decane-8-carboxylic acid phenethyl-amide;
8-(Pyrrolidine-1-carbonyl)-2-(4-trifluoromethoxy-phenyl)-2,8-diaza-spiro[4.5]decan-1-one;
1-Oxo-2-(4-trifluoromethoxy-phenyl)-2,8-diaza-spiro[4.5]decane-8-carboxylic acid diethylamide;
8-(2-Methyl-pyrrolidine-1-carbonyl)-2-(4-trifluoromethoxy-phenyl)-2,8-diaza-spiro[4.5]decan-1-one;
1-Oxo-2-(4-trifluoromethoxy-phenyl)-2,8-diaza-spiro[4.5]decane-8-carboxylic acid ethyl-propyl-amide;
1-Oxo-2-(4-trifluoromethoxy-phenyl)-2,8-diaza-spiro[4.5]decane-8-carboxylic acid butyl-methyl-amide;
1-Oxo-2-(4-trifluoromethoxy-phenyl)-2,8-diaza-spiro[4.5]decane-8-carboxylic acid isobutyl-methyl-amide;
8-(Azepane-1-carbonyl)-2-(4-trifluoromethoxy-phenyl)-2,8-diaza-spiro[4.5]decan-1-one;
8-(2-Methyl-piperidine-1-carbonyl)-2-(4-trifluoromethoxy-phenyl)-2,8-diaza-spiro[4.5]decan-1-one;
1-Oxo-2-(4-trifluoromethoxy-phenyl)-2,8-diaza-spiro[4.5]decane-8-carboxylic acid methyl-pentyl-amide;
1-Oxo-2-(4-trifluoromethoxy-phenyl)-2,8-diaza-spiro[4.5]decane-8-carboxylic acid ethyl-(2-methoxy-ethyl)-amide;
1-Oxo-2-(4-trifluoromethoxy-phenyl)-2,8-diaza-spiro[4.5]decane-8-carboxylic acid methyl-phenyl-amide;
1-Oxo-2-(4-trifluoromethoxy-phenyl)-2,8-diaza-spiro[4.5]decane-8-carboxylic acid cyclohexyl-methyl-amide;
8-(1,3-Dihydro-isoindole-2-carbonyl)-2-(4-trifluoromethoxy-phenyl)-2,8-diaza-spiro[4.5]decan-1-one;
1-Oxo-2-(4-trifluoromethoxy-phenyl)-2,8-diaza-spiro[4.5]decane-8-carboxylic acid benzyl-methyl-amide;
1-Oxo-2-(4-trifluoromethoxy-phenyl)-2,8-diaza-spiro[4.5]decane-8-carboxylic acid ethyl-phenyl-amide;
1-Oxo-2-(4-trifluoromethoxy-phenyl)-2,8-diaza-spiro[4.5]decane-8-carboxylic acid (3-fluoro-phenyl)-methyl-amide;
8-(3,4-Dihydro-2H-quinoline-1-carbonyl)-2-(4-trifluoromethoxy-phenyl)-2,8-diaza-spiro[4.5]decan-1-one;
1-Oxo-2-(4-trifluoromethoxy-phenyl)-2,8-diaza-spiro[4.5]decane-8-carboxylic acid methyl-phenethyl-amide;
1-Oxo-2-(4-trifluoromethoxy-phenyl)-2,8-diaza-spiro[4.5]decane-8-carboxylic acid methyl-(2-pyridin-2-yl-ethyl)-amide;
1-Oxo-2-(4-trifluoromethoxy-phenyl)-2,8-diaza-spiro[4.5]decane-8-carboxylic acid ethyl-(2-pyridin-2-yl-ethyl)-amide;
1-Oxo-2-(4-trifluoromethoxy-phenyl)-2,8-diaza-spiro[4.5]decane-8-sulfonic acid isopropylamide;
1-Oxo-2-(4-trifluoromethoxy-phenyl)-2,8-diaza-spiro[4.5]decane-8-sulfonic acid .phenylamide;
1-Oxo-2-(4-trifluoromethoxy-phenyl)-2,8-diaza-spiro[4.5]decane-8-sulfonic acid benzylamide;
1-Oxo-2-(4-trifluoromethoxy-phenyl)-2,8-diaza-spiro[4.5]decane-8-sulfonic acid (2-phenyl-propyl)-amide;
1-Oxo-2-(4-trifluoromethoxy-phenyl)-2,8-diaza-spiro[4.5]decane-8-sulfonic acid (2-methoxy-ethyl)-amide;
1-Oxo-2-(4-trifluoromethoxy-phenyl)-2,8-diaza-spiro[4.5]decane-8-sulfonic acid ethylamide;
1-Oxo-2-(4-trifluoromethoxy-phenyl)-2,8-diaza-spiro[4.5]decane-8-sulfonic acid diethylamide;
1-Oxo-2-(4-trifluoromethoxy-phenyl)-2,8-diaza-spiro[4.5]decane-8-sulfonic acid (2-hydroxy-ethyl)-methyl-amide;
1-Oxo-2-(4-trifluoromethoxy-phenyl)-2,8-diaza-spiro[4.5]decane-8-sulfonic acid isobutyl-methyl-amide;
1-Oxo-2-(4-trifluoromethoxy-phenyl)-2,8-diaza-spiro[4.5]decane-8-sulfonic acid ethyl-(2-methoxy-ethyl)-amide;
1-Oxo-2-(4-trifluoromethoxy-phenyl)-2,8-diaza-spiro[4.5]decane-8-sulfonic acid methyl-phenyl-amide;
1-Oxo-2-(4-trifluoromethoxy-phenyl)-2,8-diaza-spiro[4.5]decane-8-sulfonic acid benzyl-methyl-amide;
1-Oxo-2-(4-trifluoromethoxy-phenyl)-2,8-diaza-spiro[4.5]decane-8-sulfonic acid methyl-phenethyl-amide;
1-Oxo-2-(4-trifluoromethoxy-phenyl)-2,8-diaza-spiro[4.5]decane-8-sulfonic acid methyl-(2-pyridin-2-yl-ethyl)-amide;
1-Oxo-2-(4-trifluoromethoxy-phenyl)-2,8-diaza-spiro[4.5]decane-8-carboxylic acid methyl-(4-trifluoromethyl-phenyl)-amide;
1-Oxo-2-(4-trifluoromethoxy-phenyl)-2,8-diaza-spiro[4.5]decane-8-carboxylic acid (4-chloro-phenyl)-methyl-amide;
1-Oxo-2-(4-trifluoromethoxy-phenyl)-2,8-diaza-spiro[4.5]decane-8-carboxylic acid (3,4-dichloro-phenyl)-methyl-amide;
1-Oxo-2-(4-trifluoromethoxy-phenyl)-2,8-diaza-spiro[4.5]decane-8-carboxylic acid (3-chloro-phenyl)-methyl-amide;
1-Oxo-2-(4-trifluoromethoxy-phenyl)-2,8-diaza-spiro[4.5]decane-8-carboxylic acid butyl-ethyl-amide;
1-Oxo-2-(4-trifluoromethoxy-phenyl)-2,8-diaza-spiro[4.5]decane-8-carboxylic acid ethyl-isopropyl-amide;
1-Oxo-2-(4-trifluoromethoxy-phenyl)-2,8-diaza-spiro[4.5]decane-8-carboxylic acid cyclohexyl-ethyl-amide;
1-Oxo-2-(4-trifluoromethoxy-phenyl)-2,8-diaza-spiro[4.5]decane-8-carboxylic acid ethyl-(2-fluoro-benzyl)-amide;
1-Oxo-2-(4-trifluoromethoxy-phenyl)-2,8-diaza-spiro[4.5]decane-8-carboxylic acid ethyl-pyridin-4-ylmethyl-amide;
1-Oxo-2-(4-trifluoromethoxy-phenyl)-2,8-diaza-spiro[4.5]decane-8-carboxylic acid ethyl-m-tolyl-amide;
1-Oxo-2-(4-trifluoromethoxy-phenyl)-2,8-diaza-spiro[4.5]decane-8-carboxylic acid (4-chloro-phenyl)-ethyl-amide;
1-Oxo-2-(4-trifluoromethoxy-phenyl)-2,8-diaza-spiro[4.5]decane-8-carboxylic acid benzyl-ethyl-amide;
1-Oxo-2-(4-trifluoromethoxy-phenyl)-2,8-diaza-spiro[4.5]decane-8-carboxylic acid ethyl-(4-trifluoromethoxy-phenyl)-amide;
8-(2-Chloro-6-methyl-benzenesulfonyl)-2-(4-trifluoromethoxy-phenyl)-2,8-diaza-spiro[4.5]decan-1-one;
2-(4-Cyclopropyl-phenyl)-1-oxo-2,8-diaza-spiro[4.5]decane-8-carboxylic acid isobutyl-methyl-amide; and
2-(4-Cyclopropyl-phenyl)-1-oxo-2,8-diaza-spiro[4.5]decane-8-carboxylic acid butyl-methyl-amide.
Examples of especially preferred compounds of formula (I) are selected from:
8-(2-Chloro-benzenesulfonyl)-2-(4-trifluoromethoxy-phenyl)-2,8-diaza-spiro[4.5]decan-1-one;
8-Benzenesulfonyl-2-(4-trifluoromethoxy-phenyl)-2,8-diaza-spiro[4.5]decan-1-one;
8-Benzenesulfonyl-2-(4-tert-butyl-phenyl)-2,8-diaza-spiro[4.5]decan-1-one;
(rac)-8-Benzenesulfonyl-2-[4-(2,2,2-trifluoro-1-methyl-ethoxy)-phenyl]-2,8-diaza-spiro[4.5]decan-1-one;
8-Benzenesulfonyl-2-[4-(2,2,2-trifluoro-1,1-dimethyl-ethoxy)-phenyl]-2,8-diaza-spiro[4.5]decan-1-one;
8-Benzenesulfonyl-2-(4-isopropoxy-phenyl)-2,8-diaza-spiro[4.5]decan-1-one;

8-(Morpholine-4-sulfonyl)-2-(4-trifluoromethoxy-phenyl)-2,8-diaza-spiro[4.5]decan-1-one;
8-Benzenesulfonyl-2-(6-isopropyl-pyridin-3-yl)-2,8-diaza-spiro[4.5]decan-1-one;
8-Benzenesulfonyl-2-(6-chloro-pyridin-3-yl)-2,8-diaza-spiro[4.5]decan-1-one;
8-Benzenesulfonyl-2-pyridin-3-yl-2,8-diaza-spiro[4.5]decan-1-one;
2-(4-Isopropoxy-phenyl)-8-(morpholine-4-sulfonyl)-2,8-diaza-spiro[4.5]decan-1-one;
8-Benzenesulfonyl-2-(6-methoxy-pyridazin-3-yl)-2,8-diaza-spiro[4.5]decan-1-one;
8-(2-Chloro-benzenesulfonyl)-2-(4-ethyl-phenyl)-2,8-diaza-spiro[4.5]decan-1-one;
8-(2-Methyl-propane-1-sulfonyl)-2-(4-trifluoromethoxy-phenyl)-2,8-diaza-spiro[4.5]decan-1-one;
8-(2,2-Dimethyl-propane-1-sulfonyl)-2-(4-trifluoromethoxy-phenyl)-2,8-diaza-spiro[4.5]decan-1-one;
2-(4-Ethyl-phenyl)-8-(morpholine-4-sulfonyl)-2,8-diaza-spiro[4.5]decan-1-one;
(rac)-8-(2,2-Dimethyl-propane-1-sulfonyl)-2-[4-(2,2,2-trifluoro-1-methyl-ethoxy)-phenyl]-2,8-diaza-spiro[4.5]decan-1-one;
2-(4-Isopropoxy-phenyl)-8-(2-methyl-propane-1-sulfonyl)-2,8-diaza-spiro[4.5]decan-1-one;
2-(4-Ethyl-phenyl)-8-(2-methyl-propane-1-sulfonyl)-2,8-diaza-spiro[4.5]decan-1-one;
(rac)-8-Benzenesulfonyl-2-[6-(2,2,2-trifluoro-1-methyl-ethoxy)-pyridin-3-yl]-2,8-diaza-spiro[4.5]decan-1-one; and
8-Benzenesulfonyl-2-[4-(2,2,2-trifluoro-ethoxy)-phenyl]-2,8-diaza-spiro[4.5]decan-1-one.

Further particularly preferred examples of compounds of formula (I) are selected from:
8-(2-Chloro-benzenesulfonyl)-2-(4-trifluoromethoxy-phenyl)-2,8-diaza-spiro[4.5]decan-1-one;
8-Benzenesulfonyl-2-(4-tert-butyl-phenyl)-2,8-diaza-spiro[4.5]decan-1-one;
(rac)-8-Benzenesulfonyl-2-[4-(2,2,2-trifluoro-1-methyl-ethoxy)-phenyl]-2,8-diaza-spiro[4.5]decan-1-one; and
8-Benzenesulfonyl-2-(4-isopropoxy-phenyl)-2,8-diaza-spiro[4.5]decan-1-one.

Also further particularly preferred examples of compounds of formula (I) are selected from:
2-(4-Ethyl-phenyl)-8-(2-methyl-propane-1-sulfonyl)-2,8-diaza-spiro[4.5]decan-1-one;
8-(2,2-Dimethyl-propane-1-sulfonyl)-2-(4-ethyl-phenyl)-2,8-diaza-spiro[4.5]decan-1-one;
8-(3,3-Dimethyl-butyryl)-2-[4-(2,2,2-trifluoro-ethyl)-phenyl]-2,8-diaza-spiro[4.5]decan-1-one;
8-(2-Trifluoromethoxy-benzenesulfonyl)-2-(4-trifluoromethoxy-phenyl)-2,8-diaza-spiro[4.5]decan-1-one;
2-(4-Cyclopropyl-phenyl)-8-(2-methyl-propane-1-sulfonyl)-2,8-diaza-spiro[4.5]decan-1-one;
2-(4-Trifluoromethoxy-phenyl)-8-(2-trifluoromethyl-benzenesulfonyl)-2,8-diaza-spiro[4.5]decan-1-one;
2-(4-Cyclopropyl-phenyl)-8-(2-trifluoromethyl-benzenesulfonyl)-2,8-diaza-spiro[4.5]decan-1-one;
2-[4-(2,2,2-Trifluoro-ethoxy)-phenyl]-8-(2-trifluoromethoxy-benzenesulfonyl)-2,8-diaza-spiro[4.5]decan-1-one;
8-(3,5-Dimethyl-isoxazole-4-sulfonyl)-2-[4-(2,2,2-trifluoro-1-methyl-ethoxy)-phenyl]-2,8-diaza-spiro[4.5]decan-1-one;
8-(2-Trifluoromethoxy-benzenesulfonyl)-2-[4-(2,2,2-trifluoro-1-methyl-ethoxy)-phenyl]-2,8-diaza-spiro[4.5]decan-1-one;
8-(3,5-Dimethyl-isoxazole-4-sulfonyl)-2-(4-isopropoxy-phenyl)-2,8-diaza-spiro[4.5]decan-1-one;
8-(2-Chloro-benzenesulfonyl)-2-[4-(2,2,2-trifluoro-ethoxy)-phenyl]-2,8-diaza-spiro[4.5]decan-1-one;
8-Benzenesulfonyl-2-[6-(2,2,2-trifluoro-ethoxy)-pyridin-3-yl]-2,8-diaza-spiro[4.5]decan-1-one;
8-(2-Chloro-benzenesulfonyl)-2-[6-(2,2,2-trifluoro-ethoxy)-pyridin-3-yl]-2,8-diaza-spiro[4.5]decan-1-one;
(rac)-8-(2-Chloro-benzenesulfonyl)-2-[4-(2,2,2-trifluoro-1-hydroxy-ethyl)-phenyl]-2,8-diaza-spiro[4.5]decan-1-one;
(rac)-8-(3,3-Dimethyl-butyryl)-2-[4-(2,2,2-trifluoro-1-hydroxy-ethyl)-phenyl]-2,8-diaza-spiro[4.5]decan-1-one;
8-(2-Methyl-2H-pyrazole-3-sulfonyl)-2-(4-trifluoromethoxy-phenyl)-2,8-diaza-spiro[4.5]decan-1-one;
8-(2-Chloro-pyridine-3-sulfonyl)-2-(4-trifluoromethoxy-phenyl)-2,8-diaza-spiro[4.5]decan-1-one;
8-(2-Hydroxy-pyridine-3-sulfonyl)-2-(4-trifluoromethoxy-phenyl)-2,8-diaza-spiro[4.5]decan-1-one;
8-(2-Chloro-pyridine-3-sulfonyl)-2-[4-(2,2,2-trifluoro-ethoxy)-phenyl]-2,8-diaza-spiro[4.5]decan-1-one; and
8-(2-Chloro-benzenesulfonyl)-2-[4-(1-hydroxy-cyclobutyl)-phenyl]-2,8-diaza-spiro[4.5]decan-1-one.

Processes for the manufacture of compounds of formula (I) are an object of the invention.

The preparation of compounds of formula (I) of the present invention may be carried out in sequential or convergent synthetic routes. Syntheses of the invention are shown in the following schemes. The skills required for carrying out the reaction and purification of the resulting products are known to those persons skilled in the art. The substituents and indices used in the following description of the processes have the significance given above.

Compounds of formula (I) are readily accessible as outlined in scheme 1 by heating compounds of formula (II) with an amine of general formula (III) and dimethylaluminium chloride in a solvent such as toluene at reflux temperature. Alternatively, dioxane can be used as solvent and trimethylaluminium as organometallic reagent. This transformation allows access to spirocyclic lactams of general formula (I) (scheme 1).

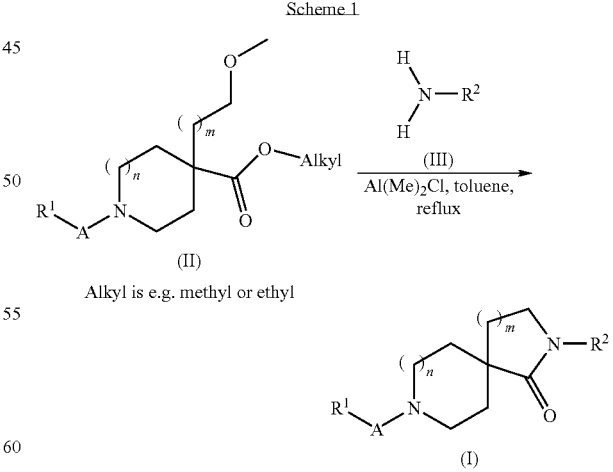

Scheme 1

Alkyl is e.g. methyl or ethyl

Alternatively, the synthesis of compounds of general formula (I) can be achieved in a stepwise process according to scheme 2, wherein compounds of formula (II) are first hydrolyzed under standard conditions on treatment with aqueous base such as 3M NaOH in a solvent such as methanol or ethanol at RT or reflux temperatures to give the corresponding acids (IV). These can then be condensed with the amines of formula (III) using standard condensation reagents such as EDC, BOP, TPTU, or CDMT in the presence of a base such as triethylamine, N-methyl-morpholine or Hunig's base in solvents such as acetonitril, THF or DMF, at RT or elevated temperatures to give the amides of formula (V). Alternatively, the acids of formula (IV) can first be converted to the corresponding acid chloride with, e.g. oxalyl chloride in methylene chloride and triethylamine as a base or with thionyl chloride and then reacted with the amines of formula (III) to give the amides of formula (V). The ring forming reaction is then conducted as already described above with dimethylaluminium chloride in toluene at reflux temperature or, alternatively, in dioxane as solvent or with trimethylaluminium as organometallic reagent.

under standard conditions in, for example, methylene chloride or THF as solvents and in the presence of a base such as triethylamine or DMAP or in pyridine. Compounds of formula (I), wherein A is carbonyl and $R^1$ is alkyamino, can be prepared from compounds of formula (Ib) and from the corresponding isocyanates of formula (VIII), wherein $R^3$ is alkyl. Carboxylic acids of formula (IX) can be used in the reaction together with an appropriate condensation reagent such as the EDC, BOP and the like in solvents such as THF, acetonitrile and a base e.g. Hunigs's base or trietylamine or DMAP to give the compounds of general formula (I), wherein A is carbonyl.

Alternatively, compounds of formula (I) wherein A is carbonyl, $R^1$ is —$NR^4R^5$ and $R^4$ is hydrogen, can also be prepared from compounds of formula (Ib) and from the corresponding isocyanates of formula (VIII), wherein $R^3$ is $R^5$.

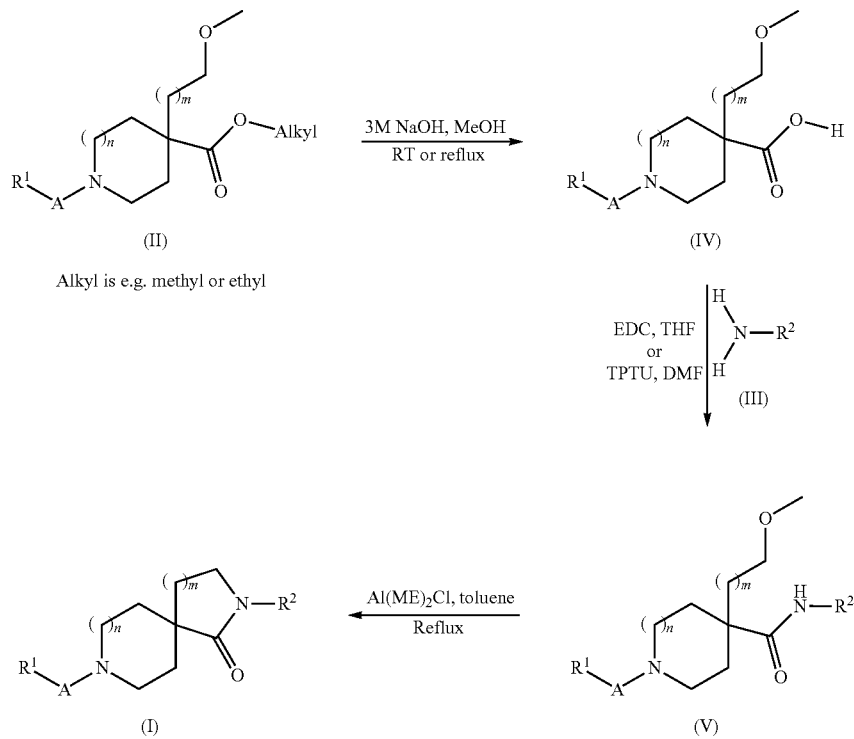

Scheme 2

A further alternative process to synthesize compounds of formula (I) is outlined in scheme 3.

Thus, starting form suitably protected compounds of formula (IIa), using a protecting group, e.g. benzyl, which is compatible with the spirocyclisation reaction conditions, these are subsequently converted to the spirocylic lactams of formula (Ia) with dimethylaluminium chloride in toluene at reflux temperature. The protecting group can then be removed by standard conditions e.g. hydrogenation to give the compounds of formula (Ib). Subsequent condensation with a corresponding sulfonyl or sulfamoyl chlorides of formula (VII), wherein A=S(O)$_2$, under standard conditions, in THF, methylene chloride, DMF or the like in the presence of a base such as DMAP, or triethylamine, or in pyridine gives then rise to compounds of formula (I). Compounds of formula (I), wherein A is carbonyl, can then be prepared from compounds of formula (Ib) and the corresponding acid chlorides, carbamoyl chlorides of formula (VII), wherein A is carbonyl, Alternatively, compounds of formula (I), wherein A=S(O)$_2$ and $R^1$ is —$NR^4R^5$, can be prepared from (Ib) stepwise by first conversion of (Ib) to the corresponding sulfonyl chloride intermediate by, for example treatment with sulfuryl chloride in a solvent such as chloroform and with triethylamine as base, followed by reaction with a compound of formula $R^4R^5NH$ in a solvent such as CH$_2$Cl$_2$ at RT or at elevated temperature to give compounds (I), wherein $R^1$ is —$NR^4R^5$.

Alternatively, compounds of formula (I), wherein A is carbonyl and $R^1$ is —$NR^4R^5$, can be prepared from (Ib) by first converting it to the corresponding carbonyl chloride intermediate on reaction with, for example, diphosgene in a solvent such as CH$_2$Cl$_2$ at RT or at elevated temperature and subsequent reaction with a compound of formula $R^4R^5NH$ to give compounds of formula (I) wherein R1 is —$NR^4R^5$.

Scheme 3

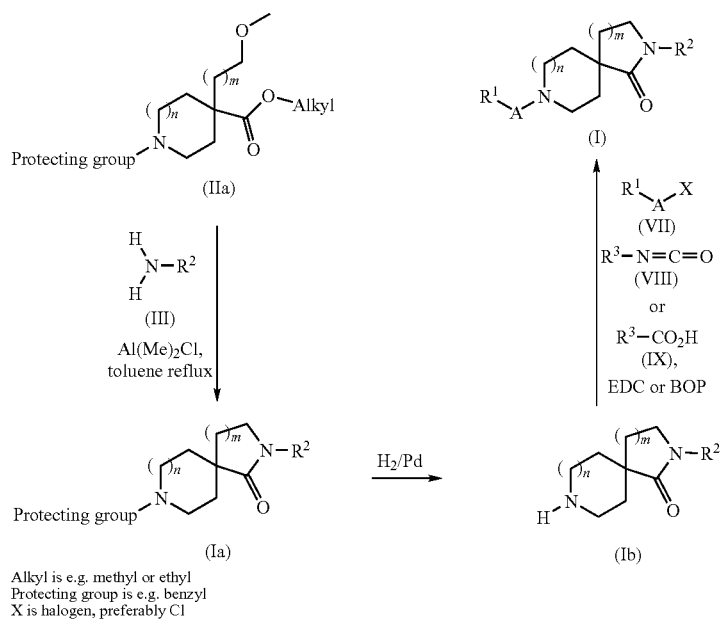

Alkyl is e.g. methyl or ethyl
Protecting group is e.g. benzyl
X is halogen, preferably Cl A further alternative to synthesize compounds of formula (I) is outlined below in scheme 3.1. Thus, compounds of formula (I) can be prepared from compounds of formula (Ic) by making use of a copper-catalysed coupling reaction with appropriately functionalized compounds of formula $R^2$—X in a Buchwald type reaction (for the general methodology: Buchwald et al. JACS, 2002, 124, p 7421). Thus, on reacting compounds of general formula (Ic) with a compounds of formula $R^2$—X, whereas X is halogen, e.g. iodo or bromo, in the presence of CuI and with, for example, N,N'-dimethylethylenediamine as ligand and $K_3PO_4$ as base, in a solvent such as in DMF at elevated temperature, there are obtained compounds of general formula (I). Alternatively, the transformation can be done by a palladium-catalysed coupling from corresponding aryl and heteroaryl halides with, for example, palladium(II) acetate as catalyst, DPPF, bis(diphenylphosphino)-ferrocene, as ligand, sodium tert-butoxide as a base and in a solvent such as toluene and at elevated temperatures to give compounds of formula (I). (For the general methodology: W. Shahespeare, Tetrahedron Lett., 40, 1999, p 2035).

Scheme 3.1

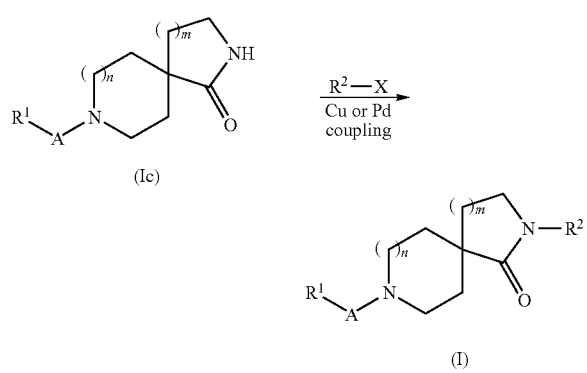

X is halogen, e.g. bromo or iodo

The starting materials that are used in schemes 1 to 3 can be prepared from commercial compounds or compounds described in the literature applying general reaction procedures known in the art and outlined in scheme 4.

The starting materials that are used in scheme 3.1 can be prepared from commercial compounds or compounds described in the literature applying general reaction procedures known in the art and outlined in scheme 4.

Thus, compounds of formula (VI) are reacted in the presence of a corresponding sulfonyl or sulfamoyl chlorides of formula (VII), wherein $A=S(O)_2$, under standard conditions, in THF, methylene chloride, DMF or the like in the presence of a base such as DMAP, or triethylamine, or in pyridine to give rise to compounds of formula (IV). Compounds of formula (IV) wherein A is carbonyl can then be prepared from compounds of formula (VI) and the corresponding acid chlorides, carbamoyl chlorides of formula (VII), wherein A is carbonyl, under standard condition in, for example, methylene chloride or THF as solvents and triethylamine or DMAP as base or in pyridine. Compounds of formula (IV), wherein A is carbonyl and $R^1$ is alkyamino, can then be prepared from compounds of formula (VI) and from the corresponding isocyanates of formula (VIII), wherein $R^3$ is alkyl, in THF or DMF in the presence of a base such as Hunig's base or without base at RT or elevated temperatures. Carboxylic acids of formula (IX) can be used in the reaction together with an appropriate condensation reagent such as the EDC, BOP or TPTU and the like in solvents such as THF, acetonitrile or DMF and a base such as Hunigs's base or triethylamine or DMAP to give the corresponding compounds of general formula (IV), wherein A is carbonyl.

Alternatively, compounds of formula (IV), $R^1$ is —$NR^4R^5$ and $R^4$ is hydrogen, can also be prepared from compounds of formula (VI) and from the corresponding isocyanates of formula (VIII), wherein $R^3$ is $R^5$, in THF or DMF in the presence of a base such as Hunig's base or without base at RT or elevated temperatures.

Compounds of formula (IV) can then be treated with a base such as LDA at low temperature in a solvent such as THF followed by addition of e.g. 1-bromo-2-methoxy-ethane or 1-bromo-3-methoxypropane to give compounds of formula (II) which are then further transformed to compounds of formula (I) as described above. Protected intermediates (VIa) wherein protecting group is e.g. benzyl, are either commercially available, known in the literature or can be prepared from compounds of formula (VI) by alkylation or reductive amination reactions applying reaction sequences essentially known in the art.

Alternatively, compounds of general formula (II) (scheme 4) and (IIa) (scheme 3) can also be prepared from compounds (VIa), with protecting groups such as benzyl or Boc, by changing the sequence of the reactions described in scheme 4: First alkylating (VIa) with e.g. 1-bromo-2-methoxy-ethane or 1-bromo-3-methoxypropane, gives rise to compounds (IIa) of scheme 3. This can then be followed by de-protection (e.g. treatment with trifluoroacetic acid at RT in the case of Boc as protecting group, or hydrogenation for benzyl as protecting group), followed by the subsequent fuctionalization step on reaction with compounds (VII), (VIII) or (IX), or the variations described above, to give compounds of general formula (II).

Starting material which are required to synthesize compounds of formula (Ic) of scheme 3.1. are either commercial, known in the literature or prepared as described in scheme 5.

Thus, alkylation of compound (VIa) with a base such as LDA in a solvent such as THF at low temperature such as −5° C. with a corresponding haloalkyl nitrile gives rise to compounds of formula (X). Subsequent removal of the protecting group, in the case of Boc protection by treatment with trifluoracetic acid in methylene chloride gives rise to compounds of general formula (XI), which are then further converted to compounds of formula (XII), as described and detailed in the schemes above. Compounds of formula (XII) can then be hydrogenated over, for example Pt in a solvent mixture of MeOH/AcOH at RT and at normal atmospheric pressure to give compounds of formula (XIII), which can then be ring-closed on heating with dimethylaluminium chloride, in a solvent such as toluene at reflux temperature to give compounds of general formula (Ic). Alternatively, dioxane can be used as solvent and trimethylaluminium as organometallic reagent in the spirocylic lactam formation step.

An alternative way to prepare compounds of formula (Ic) consists of functionalizing compounds (Id) as described above to give compounds of formula (Ic).

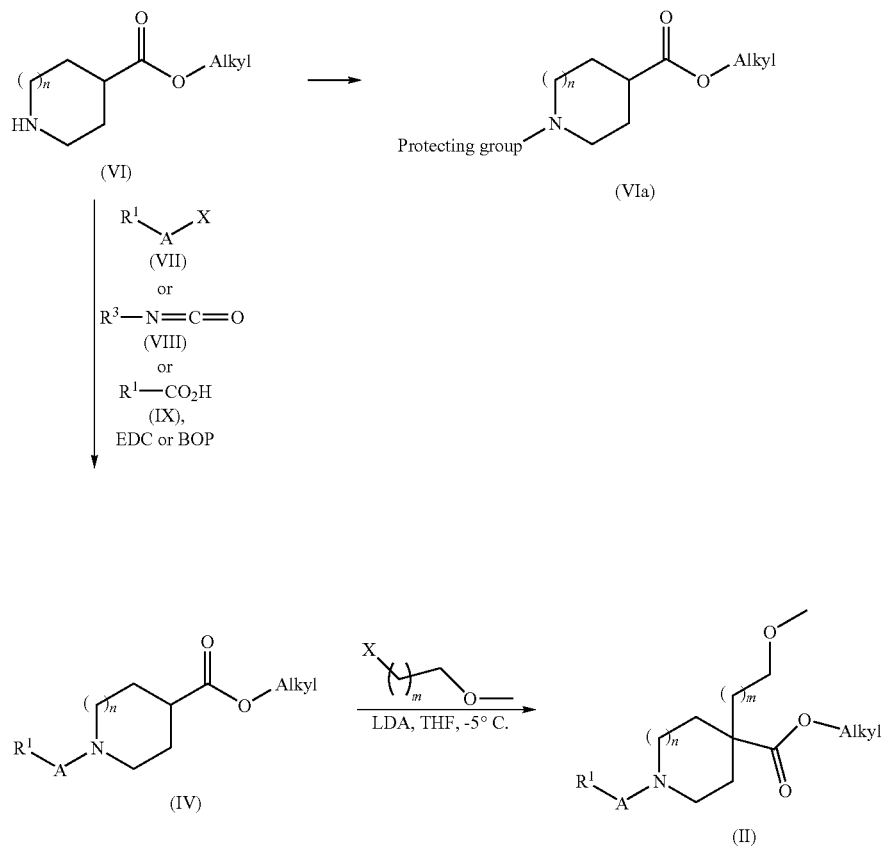

X is halogen, preferably Cl or Br
Alkyl is e.g. methyl or ethyl
Protecting group is e.g. benzyl Scheme 5

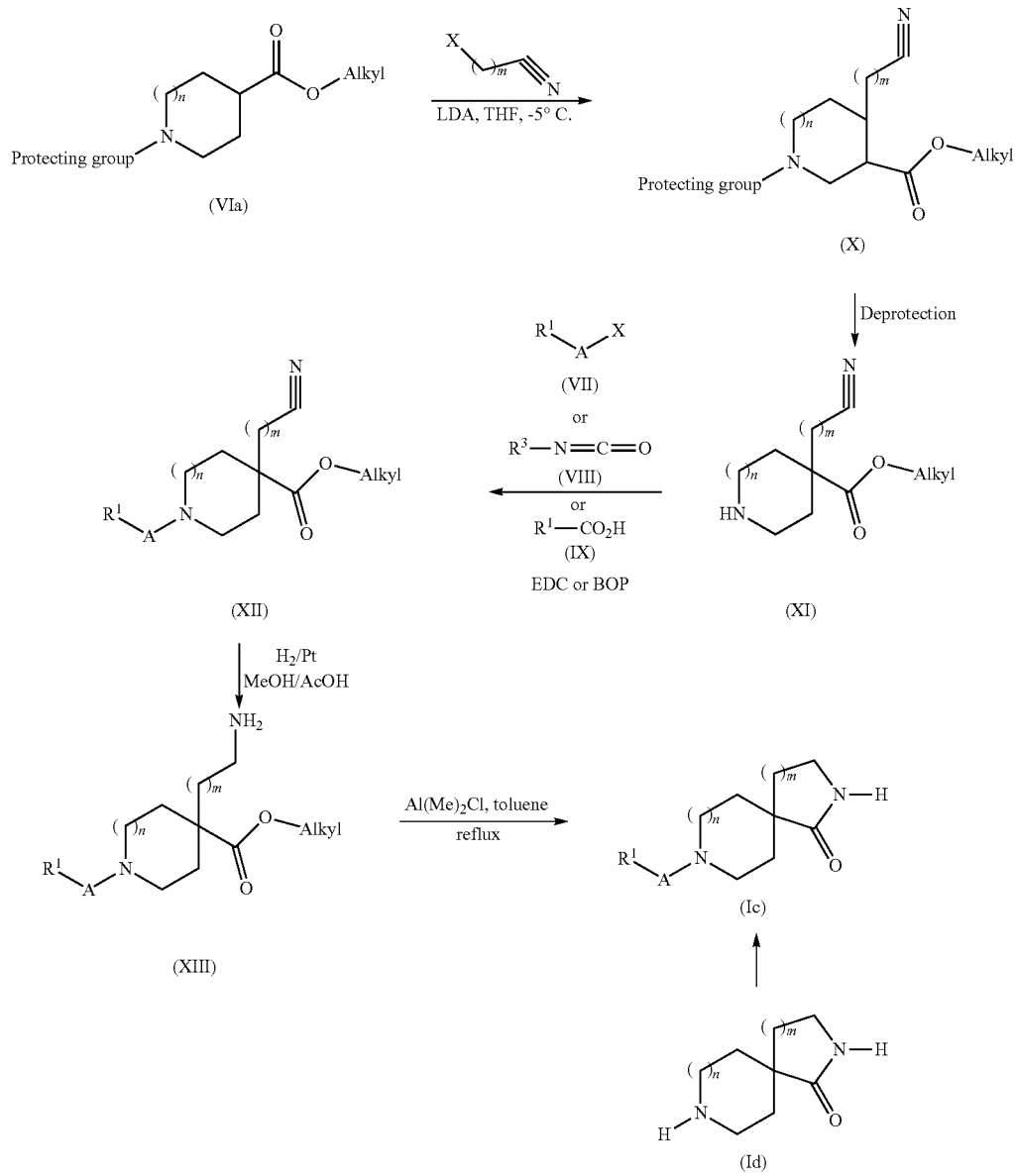

X is halogen, preferably chloro or bromo
Alkyl is e.g. methyl or ethyl
Protecting group is e.g., Boc An alternative way to prepare compounds of formula (Ib) is outlined in scheme 6. Thus, reacting compounds (Id) with a compound of formula $R^2$—X (in a copper or palladium catalysed coupling reaction as detailed above and outlined in scheme 3.1, gives compounds of formula (Ib) which can then be converted to compounds of formula (I) as described above.

Scheme 6

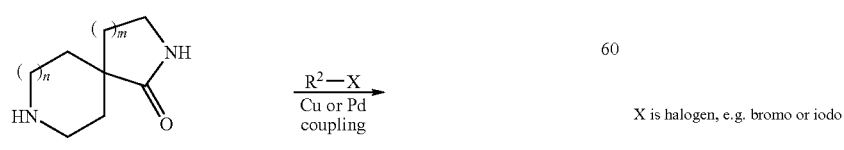

-continued

X is halogen, e.g. bromo or iodo

A preferred process for the preparation of a compound of formula (I)

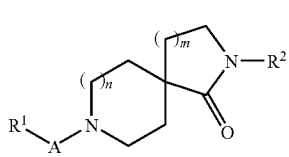

comprises one reaction selected from a) the reaction of a compound of formula (II) in the presence of a compound of formula (III) and an organoaluminium reagent of formula Al(Alkyl)$_3$ or Al(Alkyl)$_2$X, preferably dimethylaluminium chloride or trimethylaluminium, in a solvent, preferably toluene, preferably at reflux temperature of toluene, wherein n, m, A, $R^1$, $R^2$ and alkyl are as defined above and X is halogen, preferably chlorine;

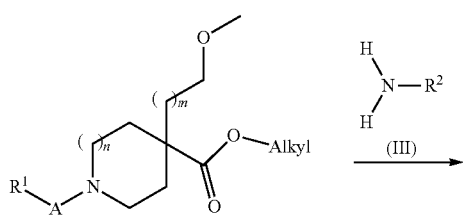

b) the reaction of a compound of formula (V) in the presence of an organoaluminium reagent of formula Al(Alkyl)$_3$ or Al(Alkyl)$_2$X, preferably dimethylaluminium chloride or trimethylaluminium, in a solvent, preferably toluene, preferably at reflux temperature of toluene, wherein n, m, A, $R^1$, $R^2$ and alkyl are as defined above and X is halogen, preferably chlorine;

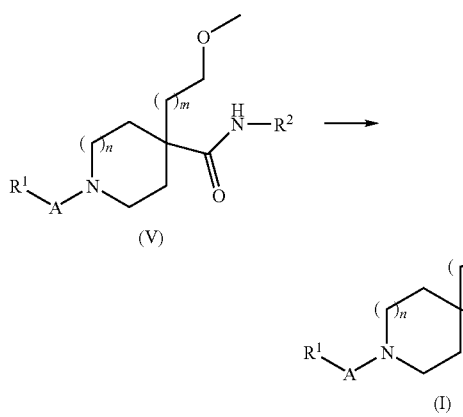

c) the reaction of a compound of formula (Ib) in the presence of a compound of formula (VII) and a base, preferably triethylamine or DMAP, in a solvent, preferably methylene chloride or pyridine, wherein A, $R^1$, $R^2$, n, m are as defined above and X is halogen, preferably chlorine;

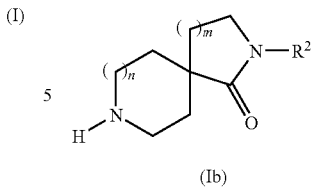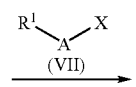

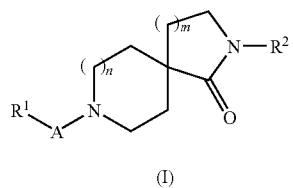

d) the reaction of a compound of formula (Ib) in the presence of a compound of formula (VIII) and a base, preferably Hunig's base, in a solvent, preferably THF or DMF, at a temperature comprised between RT and 160° C., wherein $R^2$, n, m are as defined above and A is carbonyl, $R^3$ is alkyl and $R^1$ is alkylamino;

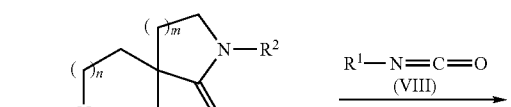

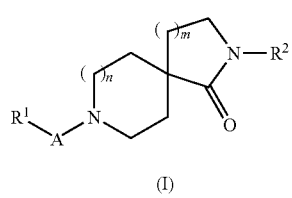

and e) the reaction of a compound of formula (Ib) in the presence of a compound of formula (IX) and a condensation reagent, preferably EDC or BOP, and a base, preferably DMAP or triethylamine, in a solvent, preferably THF or acetonitrile, wherein n, m, $R^1$ and $R^2$ are as defined above and A is carbonyl.

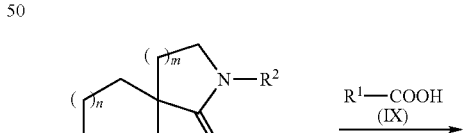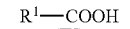

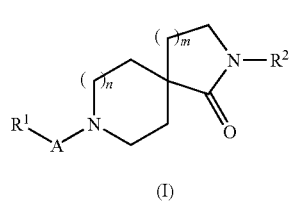

Another preferred process for the preparation of a compound of formula (I)

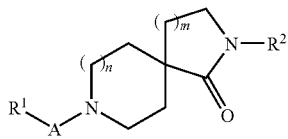

comprises one reaction selected from a) the reaction of a compound of formula (II) in the presence of a compound of formula (III) and an organoaluminium reagent of formula Al(Alkyl)$_3$ or Al(Alkyl)$_2$X, preferably dimethylaluminium chloride or trimethylaluminium, in a solvent, preferably toluene, preferably at reflux temperature of toluene, wherein n, m, A, $R^1$, $R^2$ and alkyl are as defined above and X is halogen, preferably chlorine;

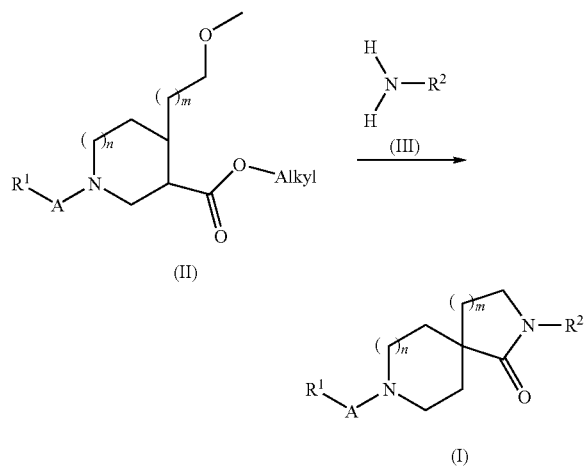

b) the reaction of a compound of formula (V) in the presence of an organoaluminium reagent of formula Al(Alkyl)$_3$ or Al(Alkyl)$_2$X, preferably dimethylaluminium chloride or trimethylaluminium, in a solvent, preferably toluene, preferably at reflux temperature of toluene, wherein n, m, A, $R^1$, $R^2$ and alkyl are as defined above and X is halogen, preferably chlorine;

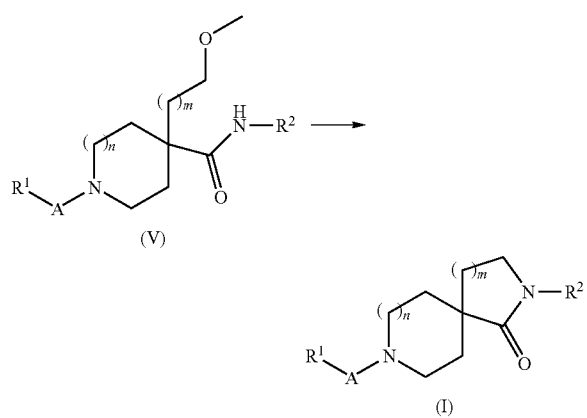

c) the reaction of a compound of formula (Ib) in the presence of a compound of formula (VII) and a base, preferably triethylamine or DMAP, in a solvent, preferably methylene chloride or pyridine, wherein A, $R^1$, $R^2$, n, m are as defined above and X is halogen, preferably chlorine;

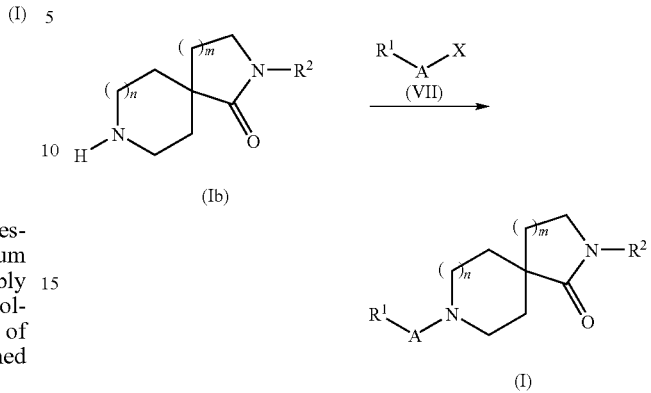

d) the reaction of a compound of formula (Ib) in the presence of a compound of formula (VIII) and a base, preferably Hunig's base, in a solvent, preferably THF or DMF, at a temperature comprised between RT and 160° C., wherein $R^2$, n, m are as defined above and A is carbonyl, $R^3$ is alkyl and $R^1$ is alkylamino;

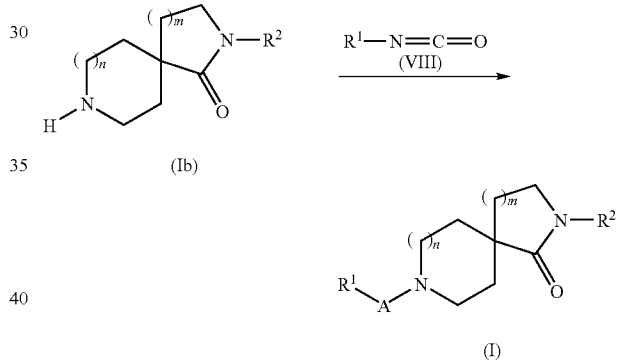

e) the reaction of a compound of formula (Ib) in the presence of a compound of formula (IX) and a condensation reagent, preferably EDC or BOP, and a base, preferably DMAP or triethylamine, in a solvent, preferably THF or acetonitrile, wherein n, m, $R^1$ and $R^2$ are as defined above and A is carbonyl;

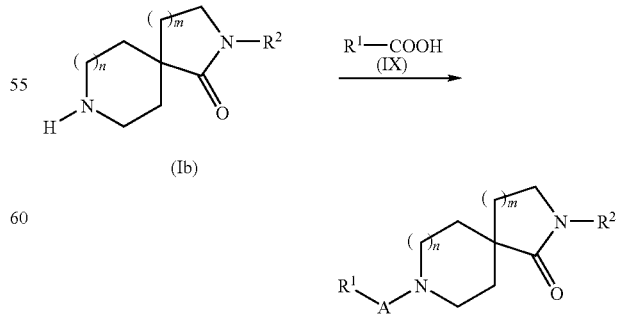

and f) the reaction of a compound of formula (Ic) in the presence of a compound of formula (X), a catalyst, preferably CuI or palladium (II) acetate, a ligand, preferably N,N'-dimethyl-ethylenediamine or bis(diphenylphosphino)-ferrocene, and a base, preferably K3PO4 or sodium tert-butoxide, in a solvent, preferably DMF or toluene, at a temperature comprised between RT and 160° C., wherein A, $R^1$, $R^2$, n, m are as defined above and X is halogen, preferably bromine or iodine.

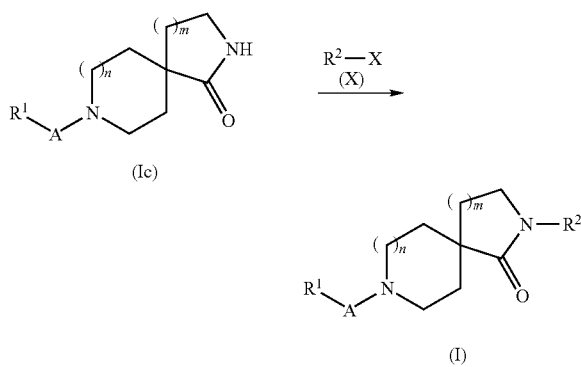

Preferred intermediates are selected from:
1-(2-Chloro-benzenesulfonyl)-4-(2-methoxy-ethyl)-piperidine-4-carboxylic acid ethyl ester;
1-Benzenesulfonyl-4-(2-methoxy-ethyl)-piperidine-4-carboxylic acid ethyl ester;
(rac)-4-(2,2,2-Trifluoro-1-methyl-ethoxy)-phenylamine;
4-(2,2,2-Trifluoro-1,1-dimethyl-ethoxy)-phenylamine;
1-(3,3-Dimethyl-butyryl)-4-(2-methoxy-ethyl)-piperidine-4-carboxylic acid ethyl ester;
4-(2-Methoxy-ethyl)-1-(morpholine-4-sulfonyl)-piperidine-4-carboxylic acid ethyl ester;
1-Benzenesulfonyl-4-(3-methoxy-propyl)-piperidine-4-carboxylic acid ethyl ester;
1-(3-Cyclopropyl-propionyl)-4-(2-methoxy-ethyl)-piperidine-4-carboxylic acid ethyl ester;
1-(4,4-Dimethyl-pentanoyl)-4-(2-methoxy-ethyl)-piperidine-4-carboxylic acid ethyl ester;
4-(2-Methoxy-ethyl)-1-(2-methyl-propane-1-sulfonyl)-piperidine-4-carboxylic acid ethyl ester;
1-(2,2-Dimethyl-propane-1-sulfonyl)-4-(2-methoxy-ethyl)-piperidine-4-carboxylic acid ethyl ester;
(rac)-6-(2,2,2-trifluoro-1-methyl-ethoxy)-pyridin-3-ylamine; and
4-(2,2,2-trifluoro-ethoxy)-phenylamine.
Preferred intermediates are also selected from:
4-(3,3,3-trifluoro-propoxy)-phenylamine;
6-(3,3,3-trifluoro-propoxy)-pyridin-3-ylamine;
(4-(tetrahydro-furan-3-yloxy)-phenylamine;
1-(2-Chloro-benzenesulfonyl)-4-(2-methoxy-ethyl)-piperidine-4-carboxylic acid;
(4-{[1-(2-Chloro-benzenesulfonyl)-4-(2-methoxy-ethyl)-piperidine-4-carbonyl]-amino}-phenyl)-acetic acid ethyl ester;
4-Cyanomethyl-piperidine-1,4-dicarboxylic acid 1-tert-butyl ester 4-ethyl ester;
4-Cyanomethyl-piperidine-4-carboxylic acid ethyl ester;
1-(2-Chloro-benzenesulfonyl)-4-cyanomethyl-piperidine-4-carboxylic acid ethyl ester;
4-(2-Amino-ethyl)-1-(2-chloro-benzenesulfonyl)-piperidine-4-carboxylic acid ethyl ester;
8-(2-Chloro-benzenesulfonyl)-2,8-diaza-spiro[4.5]decan-1-one;
9-(2-chloro-benzenesulfonyl)-2,9-diaza-spiro[5.5]undecan-1-one;
8-(3,5-Dimethyl-isoxazole-4-sulfonyl)-2,8-diaza-spiro[4.5]decan-1-one;
2-[4-(2,2,2-Trifluoro-1-hydroxy-ethyl)-phenyl]-2,8-diaza-spiro[4.5]decan-1-one;
8-(3,3-Dimethyl-butyryl)-2,8-diaza-spiro[4.5]decan-1-one;
8-(2-Trifluoromethyl-benzenesulfonyl)-2,8-diaza-spiro[4.5]decan-1-one;
8-(Isobutylsulfonyl)-2,8-diazaspiro[4.5]decan-1-one;
8-(Cyclopropylsulfonyl)-2,8-diazaspiro[4.5]decan-1-one;
2-fluoro-1-(4-iodo-phenyl)-ethanol;
1-(4-bromo-phenyl)-2,2-difluoro-ethanol;
Benzyl-4-(2-methoxy-ethyl)-piperidine-4-carboxylic acid ethyl ester;
8-Benzyl-2-(4-trifluoromethoxy-phenyl)-2,8-diaza-spiro[4.5]decan-1-one; and
2-(4-Trifluoromethoxy-phenyl)-2,8-diaza-spiro[4.5]decan-1-one.

Also an object of the present invention are compounds as described above for the preparation of a medicament for the treatment or prophylaxis of illnesses which are caused by disorders associated e.g. with the enzyme hormone-sensitive lipase.

Likewise an object of the present invention are pharmaceutical compositions comprising a compound of formula (I), or a pharmaceutically acceptable salt thereof, and a therapeutically inert carrier.

A further preferred embodiment of the present invention is the use of a compound of the formula (I) as described above, or a pharmaceutically acceptable salt thereof, for the preparation of a medicament for the treatment or prophylaxis of diabetes, dyslipidemia, atherosclerosis or obesity.

Particularly preferred is the use of a compound according to formula (I) as described above, or a pharmaceutically acceptable salt thereof, for the preparation of medicaments for the treatment or prophylaxis of diabetes.

Moreover preferred is the use of a compound according to formula (I) as described above, or a pharmaceutically acceptable salt thereof, for the preparation of medicaments for the treatment or prophylaxis of diabetes Type II.

A further preferred object of the present invention are compounds of the formula (I) as described above, or a pharmaceutically acceptable salt thereof, for the preparation of a medicament for the treatment or prophylaxis of diabetes, dyslipidemia, atherosclerosis or obesity.

Particularly preferred are compounds according to formula (I) as described above, or a pharmaceutically acceptable salt thereof, for the preparation of medicaments for the treatment or prophylaxis of diabetes.

Moreover preferred are compounds according to formula (I) as described above, or a pharmaceutically acceptable salt thereof, for the preparation of medicaments for the treatment or prophylaxis of diabetes Type II.

A further object of the present invention comprises a compound according to formula (I) as described above, or a pharmaceutically acceptable salt thereof, when manufactured according to any one of the described processes.

Also an object of the invention is a method for the treatment or prophylaxis of diabetes, dyslipidemia, atherosclerosis or obesity, which method comprises administering an effective amount of a compound of formula (I) as described above, or a pharmaceutically acceptable salt thereof.

Particularly preferred is a method for the treatment or prophylaxis of diabetes, which method comprises administering an effective amount of a compound according to formula (I) as described above, or a pharmaceutically acceptable salt thereof.

Moreover preferred is a method for the treatment or prophylaxis of diabetes Type II, which method comprises administering an effective amount of a compound according to formula (I) as described above, or a pharmaceutically acceptable salt thereof.

Also an object of the present invention is the use of a compound of the formula (I) as described above, or a pharmaceutically acceptable salt thereof, for the preparation of a medicament for the treatment or prophylaxis of nonalkoholic fatty liver disease or nonalkoholic steatohepatitis.

A further preferred object of the present invention are compounds of the formula (I) as described above, or a pharmaceutically acceptable salt thereof, for the preparation of a medicament for the treatment or prophylaxis of nonalkoholic fatty liver disease or nonalkoholic steatohepatitis.

Also an object of the invention is a method for the treatment or prophylaxis of nonalkoholic fatty liver disease or nonalkoholic steatohepatitis, which method comprises administering an effective amount of a compound of formula (I) as described above, or a pharmaceutically acceptable salt thereof.

Assay Procedures

Production of Human Full Length Hormone Sensitive Lipase-His[6]

1) Cloning: cDNA was prepared from commercial human brain polyA-+ RNA and used as a template in overlapping PCR to generate a full length human HSL ORF with a 3'-His6 tag. This full length insert was cloned into the pFast-BAC vector and the DNA-sequence of several single clones was verified. DNA from a correct full length clone with the 3'His6 tag was used to transform the E. coli strain DH10BAC. Resulting bacmid DNA was used to generate a titered baculovirus stock for protein generation. The sequence of the encoded HSL conforms to Swissprot entry Q05469, with the additional C-terminal His6-tag.

2) Protein purification: Culture: 5.5 L, High 5 cells expressing human full length HSL-His[6], 48 hr., containing 25 µM E-64. Cell count: $1.78 \times 10^{10}$ cells/ml, 90% viable.

Cells were thawed. On ice, cells were suspended in Base Buffer containing 10% glycerol, 25 mM Tris-Cl, 300 mM NaCl, 10 mM imidazole, 10 mM 2-mercaptoethanol, 2 µg pepstatin/ml, 2 µg leupeptin/ml, 2 µg antipain/ml, pH 8.0 at 4° C. in a final volume of 475 ml with $3.75 \times 10^7$ cells/ml. Sanitation was done at 3×30 sec., Lubrol PX was added to 0.2% final concentration followed by stirring for 15 min. at 4° C. and centrifugation at 25 k×g, 60 min., 4° C. Soluble proteins were mixed with 60 ml of pre-washed and equilibrated Ni-NTA Agarose (Qiagen 30210) followed by tumbling end-over-end, 45 min., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin wass poured onto a 0.8 µm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluated with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 µm membrane disposable filter unit (Millipore SCGP U02 RE) and the eluate collected in the reservoir. The eluate was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 µm disposable filter unit (Millipore SCGP00525). The protein concentration was calculated from absorbance at 280 nm, using 280=0.67 cm-1 mg-1. Yield was 235 mg, total. The protein was stored at −80° C.

Human Hormone-Sensitive Lipase (HSL) Enzyme Inhibition Assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

Cellular Assay

The following assay was used to measure the effect of the compounds to inhibit lipolysis in intact cells (adipocytes):

3T3-L1 pre-adipocyte cells were plated into 96-well plates at a density of 20,000 cells/well in 200 ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows. The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 pM). Each compound was then diluted 200-fold into KRBH/3% BSA (0.5% DMSO final). The resulting solutions range from 25 uM to 1.6 pM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

| Examples | HSL hum IC$_{50}$ (uM) | Examples | HSL hum IC$_{50}$ (uM) |
| --- | --- | --- | --- |
| 1 | 0.03 | 78 | 0.03 |
| 2 | 0.04 | 79 | 0.04 |
| 3 | 0.03 | 80 | 0.05 |
| 4 | 0.02 | 81 | 0.09 |
| 5 | 0.04 | 82 | 0.11 |
| 6 | 0.04 | 83 | 0.04 |
| 7 | 0.06 | 84 | 0.2 |
| 8 | 0.09 | 85 | 0.1 |
| 9 | 0.05 | 86 | 0.08 |
| 10 | 0.13 | 87 | 0.02 |
| 11 | 1.7 | 88 | 0.05 |
| 12 | 26 | 89 | 0.03 |
| 13 | 0.15 | 90 | 0.02 |
| 14 | 0.17 | 91 | 0.04 |
| 15 | 0.36 | 92 | 0.17 |
| 16 | 15 | 93 | 0.09 |
| 17 | 0.03 | 94 | 0.27 |
| 18 | 0.08 | 95 | 0.36 |
| 19 | 0.04 | 96 | 0.13 |
| 20 | 0.24 | 97 | 0.11 |
| 21 | 0.27 | 98 | 0.17 |
| 22 | 0.13 | 99 | 0.03 |
| 23 | 0.16 | 100 | 0.04 |
| 24 | 0.1 | 101 | 0.04 |
| 25 | 0.05 | 102 | 0.36 |
| 26 | 0.06 | 103 | 0.05 |
| 27 | 0.1 | 104 | 0.04 |
| 28 | 0.04 | 105 | 0.02 |
| 29 | 0.05 | 106 | 0.04 |
| 30 | 0.36 | 107 | 0.74 |
| 31 | 0.08 | 108 | 0.1 |
| 32 | 0.08 | 109 | 0.04 |
| 33 | 0.03 | 110 | 0.03 |
| 34 | 0.1 | 111 | 0.11 |
| 35 | 0.17 | 112 | 0.27 |
| 36 | 0.05 | 113 | 0.14 |
| 37 | 0.22 | 114 | 0.05 |
| 38 | 0.06 | 115 | 0.03 |
| 39 | 0.2 | 116 | 0.11 |
| 40 | 0.08 | 117 | 0.06 |
| 41 | 0.06 | 118 | 0.47 |
| 42 | 0.04 | 119 | 0.05 |
| 43 | 0.04 | 120 | 0.6 |
| 44 | 0.1 | 121 | 0.2 |
| 45 | 0.06 | 122 | 0.54 |
| 46 | 0.15 | 123 | 0.25 |
| 47 | 0.04 | 124 | 0.06 |
| 48 | 0.03 | 125 | 0.02 |
| 49 | 0.15 | 126 | 0.03 |
| 50 | 0.06 | 127 | 0.06 |
| 51 | 0.14 | 128 | 0.02 |
| 52 | 0.21 | 129 | 0.04 |
| 53 | 0.11 | 130 | 0.05 |
| 54 | 0.03 | 131 | 0.57 |
| 55 | 0.02 | 132 | 0.28 |
| 56 | 0.02 | 133 | 0.6 |
| 57 | 0.14 | 134 | 0.05 |
| 58 | 0.04 | 135 | 0.09 |
| 59 | 0.03 | 136 | 0.08 |
| 60 | 0.04 | 137 | 0.22 |
| 61 | 0.07 | 138 | 0.53 |
| 62 | 0.25 | 139 | 0.31 |
| 63 | 0.21 | 140 | 0.04 |
| 64 | 0.22 | 141 | 0.36 |
| 65 | 0.1 | 142 | 0.04 |
| 66 | 0.16 | 143 | 0.17 |
| 67 | 0.06 | 144 | 0.05 |
| 68 | 0.04 | 145 | 0.12 |
| 69 | 0.31 | 146 | 0.05 |
| 70 | 0.14 | 147 | 0.06 |
| 71 | 0.08 | 148 | 0.09 |
| 72 | 0.11 | 149 | 0.04 |
| 73 | 0.08 | 150 | 0.04 |
| 74 | 0.2 | 151 | 0.05 |
| 75 | 0.26 | 152 | 0.02 |
| 76 | 0.19 | 153 | 0.1 |
| 77 | 0.18 | 154 | 0.21 |

| Examples | HSL hum IC$_{50}$ (uM) | Examples | HSL hum IC$_{50}$ (uM) |
|---|---|---|---|
| 155 | 0.02 | 232 | 0.09 |
| 156 | 0.06 | 233 | 0.2 |
| 157 | 0.04 | 234 | 0.15 |
| 158 | 0.12 | 235 | 0.4 |
| 159 | 0.3 | 236 | 0.05 |
| 160 | 0.9 | 237 | 0.04 |
| 161 | 0.38 | 238 | 0.1 |
| 162 | 0.12 | 239 | 0.06 |
| 163 | 0.02 | 240 | 0.06 |
| 164 | 0.28 | 241 | 0.09 |
| 165 | 0.22 | 242 | 0.21 |
| 166 | 0.02 | 243 | 0.05 |
| 167 | 0.07 | 244 | 0.23 |
| 168 | 0.13 | 245 | 0.1 |
| 169 | 0.03 | 246 | 0.08 |
| 170 | 0.32 | 247 | 0.08 |
| 171 | 0.55 | 248 | 0.07 |
| 172 | 0.77 | 249 | 0.46 |
| 173 | 0.14 | 250 | 0.11 |
| 174 | 0.06 | 251 | 0.47 |
| 175 | 0.75 | 252 | 0.18 |
| 176 | 0.04 | 253 | 0.14 |
| 177 | 0.45 | 254 | 0.4 |
| 178 | 0.64 | 255 | 0.18 |
| 179 | 0.04 | 256 | 0.1 |
| 180 | 0.06 | 257 | 0.61 |
| 181 | 0.26 | 258 | 0.4 |
| 182 | 0.09 | 259 | 0.4 |
| 183 | 0.04 | 260 | 0.31 |
| 184 | 0.08 | 261 | 0.19 |
| 185 | 0.22 | 262 | 0.34 |
| 186 | 0.11 | 263 | 0.16 |
| 187 | 0.03 | 264 | 0.14 |
| 188 | 0.02 | 265 | 0.2 |
| 189 | 0.03 | 266 | 0.33 |
| 190 | 0.02 | 267 | 0.15 |
| 191 | 0.08 | 268 | 0.22 |
| 192 | 0.04 | 269 | 0.07 |
| 193 | 0.06 | 270 | 0.07 |
| 194 | 0.02 | 271 | 0.22 |
| 195 | 0.05 | 272 | 0.1 |
| 196 | 0.23 | 273 | 0.08 |
| 197 | 0.08 | 274 | 0.14 |
| 198 | 0.15 | 275 | 0.06 |
| 199 | 0.14 | 276 | 0.07 |
| 200 | 0.17 | 277 | 0.26 |
| 201 | 0.05 | 278 | 0.12 |
| 202 | 0.16 | 279 | 0.04 |
| 203 | 0.25 | 280 | 0.09 |
| 204 | 0.14 | 281 | 0.11 |
| 205 | 0.06 | 282 | 0.13 |
| 206 | 0.03 | 283 | 0.14 |
| 207 | 0.06 | 284 | 0.15 |
| 208 | 0.16 | 285 | 0.07 |
| 209 | 0.05 | 286 | 0.06 |
| 210 | 0.06 | 287 | 0.05 |
| 211 | 0.13 | 288 | 0.15 |
| 212 | 0.2 | 289 | 0.23 |
| 213 | 0.15 | 290 | 0.16 |
| 214 | 0.1 | 291 | 0.09 |
| 215 | 0.47 | 292 | 0.2 |
| 216 | 0.25 | 293 | 0.08 |
| 217 | 0.22 | 294 | 0.09 |
| 218 | 0.1 | 295 | 0.07 |
| 219 | 0.28 | 296 | 0.07 |
| 220 | 0.08 | 297 | 0.11 |
| 221 | 0.06 | 298 | 0.16 |
| 222 | 0.1 | 299 | 0.17 |
| 223 | 0.11 | 300 | 0.06 |
| 224 | 0.82 | 301 | 0.11 |
| 225 | 0.32 | 302 | 0.04 |
| 226 | 0.05 | 303 | 0.14 |
| 227 | 0.08 | 304 | 0.08 |
| 228 | 0.06 | 305 | 0.14 |
| 229 | 0.24 | 306 | 0.16 |
| 230 | 0.03 | 307 | 0.35 |
| 231 | 0.02 | 308 | 0.05 |

| Examples | HSL hum IC$_{50}$ (uM) |
|---|---|
| 309 | 0.12 |
| 310 | 0.17 |
| 311 | 0.06 |
| 312 | 0.08 |
| 313 | 0.09 |
| 314 | 0.13 |

Compounds as described above have IC$_{50}$ values below 1000 uM. In particular compounds as described above have IC$_{50}$ values below 100 uM.

Furthermore in particular, compounds as described above have IC$_{50}$ values between 50 uM and 0.005 uM, preferred compounds have IC$_{50}$ values between 5 uM and 0.01 uM, particularly preferred compounds have IC$_{50}$ values between 0.5 uM and 0.01 uM. These results have been obtained by using the foregoing HSL enzyme inhibition assay (uM means microMolar).

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula (I) and their pharmaceutically acceptable salts can be used for the prophylaxis or treatment of diabetes, dyslipidemia, atherosclerosis and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

8-(2-Chloro-benzenesulfonyl)-2-(4-trifluoromethoxy-phenyl)-2,8-diaza-spiro[4.5]decan-1-one

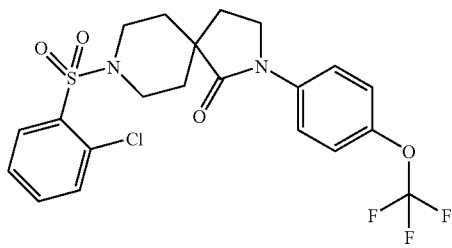

Step A): 4-(2-M ethoxy-ethyl)-piperidine-1,4-dicarboxylic acid 1-tert-butyl ester 4-ethyl ester LDA (2M solution in THF/heptane/ethylbenzene, 24.48 ml, 0.049 mol) was added under an argon atmosphere to THF (150 ml) at −5° C., piperidine-1,4-dicarboxylic acid 1-tert-butyl ester 4-ethyl ester (6.3 g, 6 ml) in THF (100 ml) was then added dropwise and the mixture was stirred for 2 hour at 0° C. Then 1-bromo-2-methoxy-ethane (6.8 g) was added at 0° C. and the mixture was stirred overnight at RT. The solvent was evaporated off, the residue partitioned between AcOEt and water. The layers were separated, the organic layer was washed with brine, dried over sodium sulphate and then concentrated to give 4-(2-methoxy-ethyl)-piperidine-1,4-dicarboxylic acid 1-tert-butyl ester 4-ethyl ester (8 g) as a brown oil which was essentially pure and used in the next step without further purification. MS (ESI): 216.3 [(M-Boc)H$^+$].

Step B): 4-(2-Methoxy-ethyl)-piperidine-4-carboxylic acid ethyl ester 4-(2-Methoxy-ethyl)-piperidine-1,4-dicarboxylic acid 1-tert-butyl ester 4-ethyl ester (8 g) was dissolved in methylene chloride (40 ml), trifluoroacetic acid (75.57 g, 50.72 ml) was added under an argon atmosphere at RT and the mixture was stirred for 2 hours until completion of the reaction. The reaction mixture was diluted with dichloromethane (500 ml), and then 3M NaOH (220.9 ml) was slowly added. The layers were separated, the organic layer washed with brine, dried over sodium sulphate and concentrated to give 4-(2-methoxyethyl)-piperidine-4-carboxylic acid ethyl ester a brown oil (3.76 g) which was essentially pure according to NMR and used in next reaction step without further purification. MS (ESI): 216.3 (MH$^+$).

Step C): 1-(2-Chloro-benzenesulfonyl)-4-(2-methoxy-ethyl)-piperidine-4-carboxylic acid ethyl ester 4-(2-Methoxy-ethyl)-piperidine-4-carboxylic acid ethyl ester (0.5 g) was dissolved in pyridine (20 ml) at RT and 2-chlorobenzenesulfonylchloride (0.49 g) was added and the mixture was stirred overnight at RT. The pyridine was evaporated off, the residue then dissolved in AcOEt and washed with 0.05M HCl and brine. The layers were separated, the organic layer dried over sodium sulphate and concentrated in vacuo. The residue was chromatographed over silica gel (AcOEt/heptane, gradient from 0 to 25%) to give the desired 1-(2-chloro-benzenesulfonyl)-4-(2-methoxy-ethyl)-piperidine-4-carboxylic acid ethyl ester (0.448 g) as light brown oil. MS (ESI): 390.11 (MH+).

Step D): 8-(2-Chloro-benzenesulfonyl)-2-(4-trifluoromethoxy-phenyl)-2,8-diaza-spiro[4.5]decan-1-one 1-(2-chloro-benzenesulfonyl)-4-(2-methoxy-ethyl)-piperidine-4-carboxylic acid ethyl ester (0.445 g) and 4-(trifluormethoxy)aniline (0.3 g) was dissolved in toluene (20 ml) under an argon atmosphere at RT, dimethylaluminium chloride in heptane (0.9 molar, 3.8 ml) was added and the mixture was refluxed for 3 hours. It was then cooled to RT, water (1 ml) was added and the reaction mixture was then stirred for 10 min. The solvent was evaporated off, the residue absorbed on silica gel and purified by flash chromatography (AcOEt/heptane, gradient from 0 to 25%) to give 8-(2-chloro-benzenesulfonyl)-2-(4-trifluoromethoxy-phenyl)-2,8-diaza-spiro[4.5]decan-1-one as a white solid. MS (ESI): 489.08 (MH+).

Example 2

8-Benzenesulfonyl-2-(4-trifluoromethoxy-phenyl)-2,8-diaza-spiro[4.5]decan-1-one

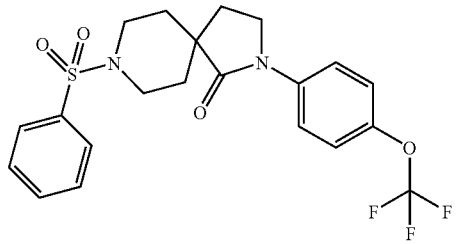

This material was obtained in analogy to example 1 step D) from 1-benzenesulfonyl-4-(2-methoxy-ethyl)-piperidine-4-carboxylic acid ethyl ester (0.16 g), dimethylaluminium chloride in heptane (0.9 molar, 0.55 ml) and 4-trifluoromethoxyaniline (0.087 g) to give the desired 8-benzenesulfonyl-2-(4-trifluoromethoxy-phenyl)-2,8-diaza-spiro[4.5]decan-1-one (0.11 g) as a brown solid. MS (ESI): 455.2 (MH+).

Preparation of the starting material, 1-benzenesulfonyl-4-(2-methoxy-ethyl)-piperidine-4-carboxylic acid ethyl ester:

This material was prepared in analogy to example 1 step C) from benzenesulfonyl chloride (0.115 g), 4-(2-methoxy-ethyl)-piperidine-4-carboxylic acid ethyl ester (0.14 g) as a brown oil (0.13 g). MS (ESI): 356.1 (MH+).

Example 3

8-Benzenesulfonyl-2-(4-tert-butyl-phenyl)-2,8-diaza-spiro[4.5]decan-1-one

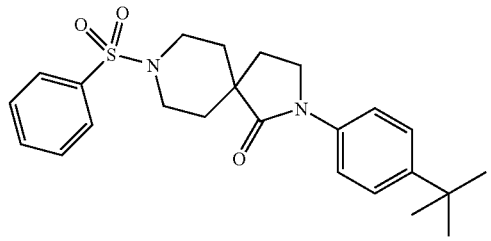

This material was obtained in analogy to example 1 step D) from 1-Benzenesulfonyl-4-(2-methoxy-ethyl)-piperidine-4-carboxylic acid ethyl ester (0.3 g), dimethylaluminium chloride in heptane (0.9 molar, 1.88 ml, and 4-tert butyl aniline (0.51 g) to give the desired 8-benzenesulfonyl-2-(4-tert-butyl-phenyl)-2,8-diaza-spiro[4.5]decan-1-one (0.19 g) as a white solid. MS (ESI): 427.2 (MH+).

Example 4

(rac)-8-Benzenesulfonyl-2-[4-(2,2,2-trifluoro-1-methylethoxy)-phenyl]-2,8-diaza-spiro[4.5]decan-1-one

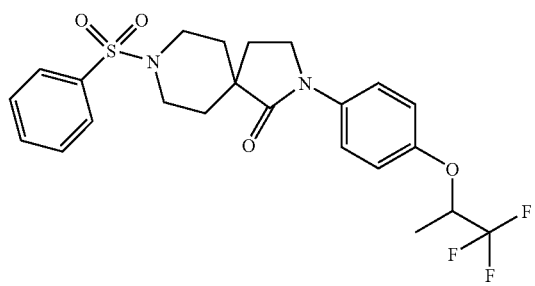

This material was obtained in analogy to example 1 step D) on from 1-benzenesulfonyl-4-(2-methoxy-ethyl)-piperidine-4-carboxylic acid ethyl ester (0.15 g), dimethylaluminium chloride in heptane (0.9 molar, 0.94 ml, and 4-(2,2,2-trifluoro-1-methyl-ethoxy)-phenylamine (0.104 g) to give the desired (rac)-8-benzenesulfonyl-2-[4-(2,2,2-trifluoro-1-methyl-ethoxy)-phenyl]-2,8-diaza-spiro[4.5]decan-1-one (0.1 g) as a white solid. MS (ESI): 483.15 (MH+).

Preparation of the starting material, (rac)-4-(2,2,2-Trifluoro-1-methyl-ethoxy)-phenylamine:

i) To a solution of 1-fluoro-4-nitro-benzene (4.24 g) and (rac)-1,1,1-trifluoro-propan-2-ol (4.563 g) in acetonitil (50 ml) under an argon atmosphere was added at RT Cs$_2$CO$_3$ (13.04 g) and the mixture was refluxed for 10 h. It was then acidified with diluted aqueous HCL and partitioned between AcOEt and water. The layers were separated, dried over Na$_2$SO$_4$ and the solvent was then evaporated off to give (rac)-1-nitro-4-(2,2,2-trifluoro-1-methyl-ethoxy)-benzene as brown oil (6.74 g) that was used without further purification.

ii) (rac)-1-nitro-4-(2,2,2-trifluoro-1-methyl-ethoxy)-benzene (6.74 g) in methanol (80 ml) were hydrogenated at RT over Pd/C (10%, 500 mg) under atmospheric pressure for 12 h. The catalyst was filtered off and filtrate concentrated in vacuo to give the desired (rac)-4-(2,2,2-trifluoro-1-methyl-ethoxy)-phenylamine (5.8 g) as a light yellow oil. MS (ESI): 206.1 (MH+).

Example 5

8-Benzenesulfonyl-2-[4-(2,2,2-trifluoro-1,1-dimethyl-ethoxy)-phenyl]-2,8-diaza-spiro[4.5]decan-1-one

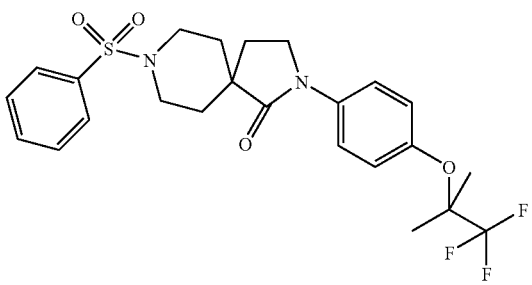

This material was obtained in analogy to example 1 step D) on from 1-benzenesulfonyl-4-(2-methoxy-ethyl)-piperidine-4-carboxylic acid ethyl ester (0.2 g), dimethylaluminium chloride in heptane (0.9 molar, 0.94 ml) and 4-(2,2,2-trifluoro-1,1-dimethyl-ethoxy)-phenylamine (0.148 g) to give the desired 8-benzenesulfonyl-2-[4-(2,2,2-trifluoro-1,1-dimethyl-ethoxy)-phenyl]-2,8-diaza-spiro[4.5]decan-1-one (0.17 g) as a light brown solid. MS (ESI): 497.17 (MH+).

Preparation of the starting material, 4-(2,2,2-trifluoro-1,1-dimethyl-ethoxy)-phenylamine:

i) To a solution of 1-fluoro-4-nitro-benzene (2.82 g) and 1,1,1-trifluoro-2-methyl-propan-2-ol (2.3 ml) in DMF (90 ml) under an argon atmosphere was added under ice cooling NaH (0.914 g, 55% suspension in oil) and the mixture was stirred for 3 h at RT. It was then partitioned between diethyl ether and water, the layers were separated, dried over Na₂SO₄ and the solvent was evaporated off to give 1-nitro-4-(2,2,2-trifluoro-1,1-dimethyl-ethoxy)-benzene as a brown oil (4.9 g) that was used in the next step without further purification.

ii) 1-Nitro-4-(2,2,2-trifluoro-1,1-dimethyl-ethoxy)-benzene (4.9 g) in methanol (30 ml) was hydrogenated over Pd/C (10%, 500 mg) at RT and atmospheric for 12 h. The catalyst was filtered off and the solvent removed in vacuo to give the desired 4-(2,2,2-trifluoro-1,1-dimethyl-ethoxy)-phenylamine (4.2 g) as a brown oil that was used without further purification in the next step.

Example 6

8-Benzenesulfonyl-2-(4-isopropoxy-phenyl)-2,8-diaza-spiro[4.5]decan-1-one

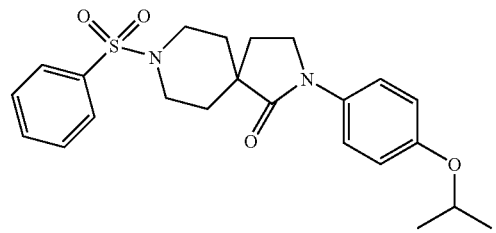

This material was prepared in analogy to example 1 step D) from 1-benzenesulfonyl-4-(2-methoxy-ethyl)-piperidine-4-carboxylic acid ethyl ester (0.2 g), dimethylaluminium chloride in heptane (0.9 molar, 0.94 ml) and 4-isopropoxy-aniline (0.1 g) to give the desired 8-benzenesulfonyl-2-(4-isopropoxy-phenyl)-2,8-diaza-spiro[4.5]decan-1-one (0.14 g) as a yellow solid. MS (ESI): 429.18 (MH+).

Example 7

8-(3,3-Dimethyl-butyryl)-2-(4-trifluoromethoxy-phenyl)-2,8-diaza-spiro[4.5]decan-1-one

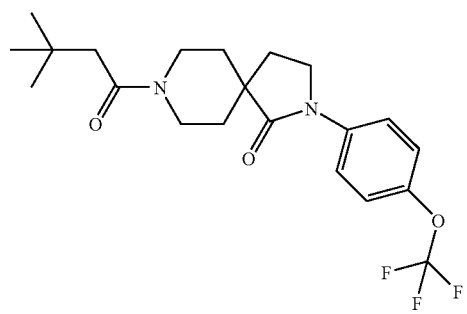

Step A): 1-(3,3-Dimethyl-butyryl)-4-(2-methoxy-ethyl)-piperidine-4-carboxylic acid ethyl ester To a solution of 4-(2-methoxy-ethyl)-piperidine-4-carboxylic acid ethyl ester (0.646 g) under an argon atmosphere were added triethylamine (0.668 g, 0.92 ml) and tert-butyl acetyl chloride (0.44 g, 0.45 ml) under ice cooling. The reaction mixture was stirred at RT for 3 h. It was then partitioned between methylene chloride and aqueous 1M HCl, the layers were separated and the aqueous layer washed with 2M aqueous KHCO₃ and dried over Na₂SO₄. The solvent was evaporated off, the residue purified by flash chromatography (AcOEt/heptane, gradient from 0 to 50%) to give 1-(3,3-Dimethyl-butyryl)-4-(2-methoxy-ethyl)-piperidine-4-carboxylic acid ethyl ester, (0.46 g) as a light yellow solid. MS (ESI): 314 (MH+).

Step B): 8-(3,3-Dimethyl-butyryl)-2-(4-trifluoromethoxy-phenyl)-2,8-diaza-spiro[4.5]decan-1-one This material was obtained in analogy to example 1 step D) on from 1-(3,3-Dimethyl-butyryl)-4-(2-methoxy-ethyl)-piperidine-4-carboxylic acid ethyl ester (0.12 g), dimethylaluminium chloride in heptane (0.9 molar, 0.87 ml) and 4-trifluoromethoxy-aniline (0.083 g) to give the desired 8-(3,3-Dimethyl-butyryl)-2-(4-trifluoromethoxy-phenyl)-2,8-diaza-spiro[4.5]decan-1-one (0.081 g) as a light yellow solid. MS (ESI): 413.20 (MH+).

Example 8

8-(Morpholine-4-sulfonyl)-2-(4-trifluoromethoxy-phenyl)-2,8-diaza-spiro[4.5]decan-1-one

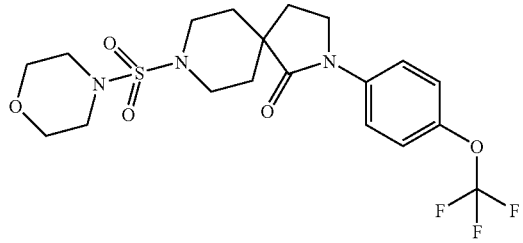

Step A): 4-(2-Methoxy-ethyl)-1-(morpholine-4-sulfonyl)-piperidine-4-carboxylic acid ethyl ester 4-(2-Methoxy-ethyl)-piperidine-4-carboxylic acid ethyl ester (0.646 g) dissolved in methylene chloride (10 ml) under an argon atmosphere were treated with DMAP (0.673 g) at RT, the mixture was cooled to 0° C. and morpholine-4-sulfonylchloride (0613 g) in methylene chloride (2 ml) was added dropwise. The mixture was stirred for 12 h at RT then partitioned between methylen chloride and 1 M HCl. The layers were separated, the organic layer washed with 2M aqueous KHCO₃ then dried over Na₂SO₄. The solvent was evaporated off, the residue purified by flash chromatography (AcOEt/heptane, gradient from 0 to 50%) to give 4-(2-methoxy-ethyl)-1-(morpholine-4-sulfonyl)-piperidine-4-carboxylic acid ethyl ester, (0.68 g) as a light yellow solid. MS (ESI): 365.17 (MH+).

Step B): 8-(Morpholine-4-sulfonyl)-2-(4-trifluoromethoxy-phenyl)-2,8-diaza-spiro[4.5]decan-1-one This material was obtained in analogy to example 1 step D) from 4-(2-methoxy-ethyl)-1-(morpholine-4-sulfonyl)-piperidine-4-carboxylic acid ethyl ester (0.128 g), dimethylaluminium chloride in heptane (0.9 molar, 0.78 ml, and 4-trifluoromethoxy-aniline (0.073 g) to give the desired 8-(morpholine-4-sulfonyl)-2-(4-trifluoromethoxy-phenyl)-2,8-diaza-spiro[4.5]decan-1-one (0.07 g) as an off-white solid. MS (ESI): 464.14 (MH+).

Example 9

9-Benzenesulfonyl-2-(4-trifluoromethoxy-phenyl)-2,9-diaza-spiro[5.5]undecan-1-one

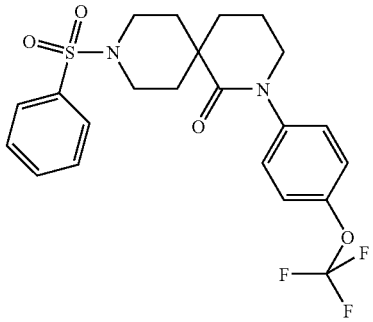

Step A): 4-(3-Methoxy-propyl)-piperidine-1,4-dicarboxylic acid 1-tert-butyl ester 4-ethyl ester To a pre-cooled THF solution (200 ml) under an argon atmosphere was added at –5° C. LDA (2M in THF/heptane/ethylbenzene, 16.24 ml) then dropwise piperidine-1,4-dicarboxylic acid 1-tert-butyl ester 4-ethyl ester (4.4 g, 4.2 ml) in THF (50 ml). The mixture was stirred between –5° C. to 0° C. for 3 hour then 1-bromo-3-methoxypropane (4.97 g) was added slowly at 0° C. The mixture was then stirred overnight at RT, the solvent was evaporated off, the residue taken up in AcOEt and washed with water and brine. The layers were separated, the organic layer dried over sodium sulphate and then evaporated off to give the desired 4-(3-methoxy-propyl)-piperidine-1,4-dicarboxylic acid 1-tert-butyl ester 4-ethyl ester a light brown oil (6.058 g) oil that was used in next reaction step without further purification.

Step B): 4-(3-Methoxy-propyl)-piperidine-4-carboxylic acid ethyl ester 4-(3-Methoxy-propyl)-piperidine-1,4-dicarboxylic acid 1-tert-butyl ester 4-ethyl ester (6 g) was dissolved in methylene chloride (200 ml) under an argon atmosphere, TFA (35.6 ml) was added and the reaction mixture was stirred for 3 hours at RT. The solvent together with most of the TFA was evaporated off, the residue dissolved in methylene chloride (800 ml) and treated with 2M KHCO₃ under ice cooling. The layers were separated, the organic layer was washed with water and brine, dried over sodium sulphate and concentrated in vacuo to give 3.63 g of 4-(3-methoxy-propyl)-piperidine-4-carboxylic acid ethyl ester as a light brown oil which was used in next reaction step without further purification.

Step C): 1-Benzenesulfonyl-4-(3-methoxy-propyl)-piperidine-4-carboxylic acid ethyl ester 4-(3-Methoxy-propyl)-piperidine-4-carboxylic acid ethyl ester (3.36 g) was dissolved under an argon atmosphere in pyridine (80 ml), benzensulfonyl chloride (2.59 g) was added and the mixture was stirred overnight at RT. The pyridine was evaporated off, the residue dissolved in AcOEt and washed with 0.05M HCl and brine. The layers were separated, the organic layer was dried over sodium sulphate, the solvent was then removed in vacuo and the crude oil was purified by flash chromatography over silica gel (AcOEt/heptane gradient from 0 to 25%) to give 1-benzenesulfonyl-4-(3-methoxy-propyl)-piperidine-4-carboxylic acid ethyl ester (4.15 g) as a yellow semi-solid. MS (ESI): 370.16 (MH$^+$).

Step D): 9-Benzenesulfonyl-2-(4-trifluoromethoxy-phenyl)-2,9-diaza-spiro[5.5]undecan-1-one 1-Benzenesulfonyl-4-(3-methoxy-propyl)-piperidine-4-carboxylic acid ethyl ester (0.3 g) was dissolved under an argon atmosphere in toluene (10 ml), 4-(trifluormethoxy)-aniline (0.173 g) was added followed by dimethylaluminium chloride in heptane (1.8 ml, 0.9 molar). The mixture was refluxed 3 hours, more 4-(trifluormethoxy)-aniline (0.173 g) and dimethylaluminium chloride in heptane (1.8 ml) were added and refluxing was continued for further 3 hours. The reaction mixture was then cooled to RT, water (1 ml) was added and the mixture was stirred for 10 minutes. The solvent was evaporated off, the residue absorbed on silica gel and purified by flash-chromatography (AcOEt/heptane, gradient from 0 to 25%) to give the desired 9-benzenesulfonyl-2-(4-trifluoromethoxy-phenyl)-2,9-diaza-spiro[5.5]undecan-1-one (0.215 g) as a white solid. MS (ESI): 469.13 (MH$^+$)

Example 10

8-Benzenesulfonyl-2-(6-isopropyl-pyridin-3-yl)-2,8-diaza-spiro[4.5]decan-1-one

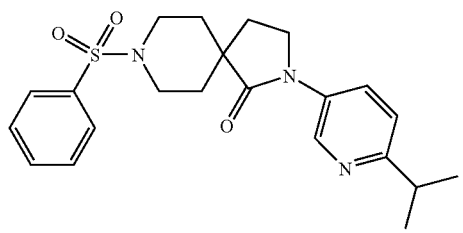

This material was prepared in analogy to example 1 step D) from 1-benzenesulfonyl-4-(2-methoxy-ethyl)-piperidine-4-carboxylic acid ethyl ester (0.15 g), dimethylaluminium chloride in heptane (0.9 molar, 1.22 ml) and 6-(1-methylethyl-3-pyridinamine (0.075 g) to give the desired 8-benzenesulfonyl-2-(6-isopropyl-pyridin-3-yl)-2,8-diaza-spiro[4.5]decan-1-one (0.086 g) as a light-yellow solid. MS (ESI): 414.18 (MH$^+$).

Example 11

8-Benzenesulfonyl-2-(6-chloro-pyridin-3-yl)-2,8-diaza-spiro[4.5]decan-1-one

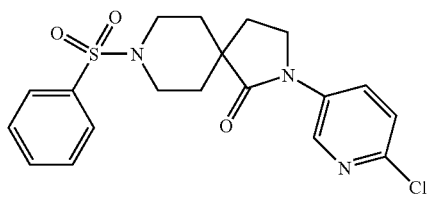

This material was prepared in analogy to example 1 step D) from 1-benzenesulfonyl-4-(2-methoxy-ethyl)-piperidine-4-carboxylic acid ethyl ester (0.2 g), dimethylaluminium chloride in heptane (0.9 molar, 1.88 ml) and 5-amino-2-chloro-pyridine (0.145 g) to give the desired 8-benzenesulfonyl-2-(6-chloro-pyridin-3-yl)-2,8-diaza-spiro[4.5]decan-1-one (0.012 g) as a white solid. MS (ESI): 406.1 (MH$^+$).

Example 12

8-Benzenesulfonyl-2-pyridin-3-yl-2,8-diaza-spiro[4.5]decan-1-one

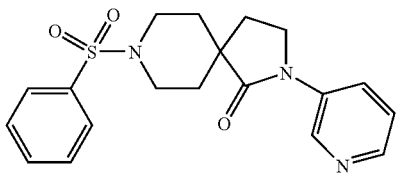

This material was prepared in analogy to example 1 step D) from 1-benzenesulfonyl-4-(2-methoxy-ethyl)-piperidine-4-carboxylic acid ethyl ester (0.2 g), dimethylaluminium chloride in heptane (0.9 molar, 1.88 ml) and 3-amino-pyridine (0.069 g) to give the desired 8-benzenesulfonyl-2-pyridin-3-yl-2,8-diaza-spiro[4.5]decan-1-one (0.055 g) as a white solid. MS (ESI): 372.13 (MH$^+$).

Example 13

8-(3-Cyclopropyl-propionyl)-2-(4-trifluoromethoxy-phenyl)-2,8-diaza-spiro[4.5]decan-1-one

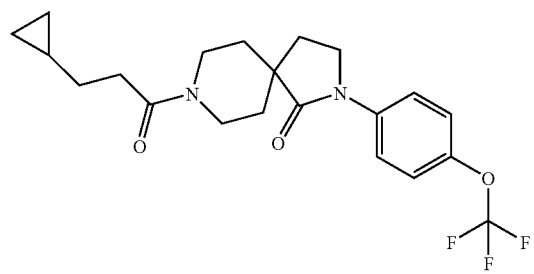

Step A): 1-(3-Cyclopropyl-propionyl)-4-(2-methoxy-ethyl)-piperidine-4-carboxylic acid ethyl ester To a solution of 3-cyclopropyl-propionic acid (0.342 g) in acetonitril (15 ml) were added under an argon atmosphere N-ethyldiisopropylamine (0.775 g, 1.03 ml) and BOP (1.328 g and the mixture was stirred for 50 minutes at RT. Then 4-(2-methoxy-ethyl)-piperidine-4-carboxylic acid ethyl ester (0.646 g) were added and the mixture was stirred for 12 h at RT. The reaction mixture was partitioned between ethyl acetate and aqueous 1M HCl, the layers were separated and the aqueous layer washed with 2M aqueous KHCO$_3$ then dried over Na$_2$SO$_4$. The solvent was evaporated off, the residue purified by flash chromatography (methylene chloride/AcOEt, gradient from 0 to 30%) to give 1-(3-cyclopropyl-propionyl)-4-(2-methoxy-ethyl)-piperidine-4-carboxylic acid ethyl ester, (0.34 g) as a yellow oil that was used in the next step without further purification.

Step B): 8-(3-Cyclopropyl-propionyl)-2-(4-trifluoromethoxy-phenyl)-2,8-diaza-spiro[4.5]decan-1-one This material was prepared in analogy to example 1 step D) from 1-(3-cyclopropyl-propionyl)-4-(2-methoxy-ethyl)-piperidine-4-carboxylic acid ethyl ester (0.1 g), dimethylaluminium chloride in heptane (0.9 molar, 0.71 ml) and 4-trifluoromethoxyanilin (0.057 g) to give the desired 8-(3-cyclopropyl-propionyl)-2-(4-trifluoromethoxy-phenyl)-2,8-diaza-spiro[4.5]decan-1-one (0.021 g) as an off-white solid. MS (ESI): 449.17 (MH$^+$).

Example 14

8-(4,4-Dimethyl-pentanoyl)-2-(4-trifluoromethoxy-phenyl)-2,8-diaza-spiro[4.5]decan-1-one

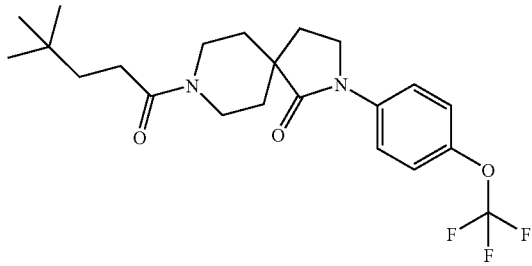

Step A): 1-(4,4-Dimethyl-pentanoyl)-4-(2-methoxy-ethyl)-piperidine-4-carboxylic acid ethyl ester To a solution of 4,4-dimethyl-pentanoic acid (0.351 g) in acetonitril (15 ml) were added under an argon atmosphere N-ethyldiisopropylamin (0.7 g, 0.96 ml) and BOP (1.195 g) and the mixture was stirred for 50 minutes at RT. Then 4-(2-methoxy-ethyl)-piperidine-4-carboxylic acid ethyl ester (0.581 g) was added and the mixture was stirred for further 12 h at RT. The reaction mixture was then partitioned between ethyl acetate and aqueous 1M HCl, the layers were separated and the aqueous layer washed with 2M aqueous KHCO$_3$ then dried over Na$_2$SO$_4$. The solvent was evaporated off, the residue purified by flash chromatography (methylene chloride/AcOEt, gradient from 0 to 30%) to give 1-(4,4-dimethyl-pentanoyl)-4-(2-methoxy-ethyl)-piperidine-4-carboxylic acid ethyl ester (0.466 g) as a yellow semi-solid that was used in the next step without further purification.

Step B): 8-(4,4-Dimethyl-pentanoyl)-2-(4-trifluoromethoxy-phenyl)-2,8-diaza-spiro[4.5]decan-1-one This material was prepared in analogy to example 1 step D) from 1-(4,4-dimethyl-pentanoyl)-4-(2-methoxy-ethyl)-piperidine-4-carboxylic acid ethyl ester (0.115 g), dimethylaluminium chloride in heptane (0.9 molar, 0.78 ml) and 4-trifluoromethoxyanilinin (0.068 g) to give the desired 8-(4,4-dimethyl-pentanoyl)-2-(4-trifluoromethoxy-phenyl)-2,8-diaza-spiro[4.5]decan-1-one (0.06 g) as an off-white solid. MS (ESI): 427.2 (MH$^+$).

Example 15

2-(4-Isopropoxy-phenyl)-8-(morpholine-4-sulfonyl)-2,8-diaza-spiro[4.5]decan-1-one

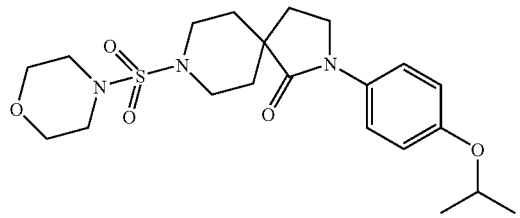

This material was obtained in analogy to example 1 step D) from 4-(2-Methoxy-ethyl)-1-(morpholine-4-sulfonyl)-piperidine-4-carboxylic acid ethyl ester (0.128 g), dimethylaluminium chloride in heptane (0.9 molar, 0.78 ml, and 4-isopropoxyaniline (0.058 g) to give the desired 2-(4-isopropoxy-phenyl)-8-(morpholine-4-sulfonyl)-2,8-diaza-spiro[4.5]decan-1-one (0.056 g) as an off-white solid. MS (ESI): 438.19 (MH$^+$).

Example 16

8-Benzenesulfonyl-2-(6-methoxy-pyridazin-3-yl)-2,8-diaza-spiro[4.5]decan-1-one

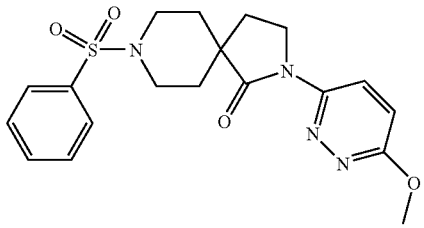

This material was prepared in analogy to example 1 step D) from 1-Benzenesulfonyl-4-(2-methoxy-ethyl)-piperidine-4-carboxylic acid ethyl ester (0.15 g), dimethylaluminium chloride in heptane (0.9 molar, 0.71 ml) and 3-amino-6-methoxy-pyridazine (0.069 g) to give the desired 8-benzenesulfonyl2-(6-methoxy-pyridazin-3-yl)-2,8-diaza-spiro[4.5]decan-1-one (0.024 g) as a white solid. MS (ESI): 403.146 (MH$^+$).

Example 17

8-(2-Chloro-benzenesulfonyl)-2-(4-ethyl-phenyl)-2,8-diaza-spiro[4.5]decan-1-one

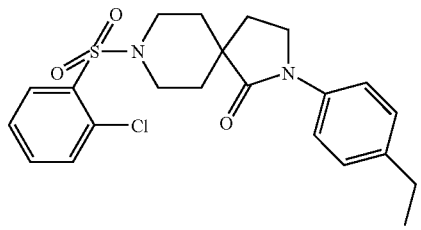

This material was prepared in analogy to example 1 step D) from 1-(2-chloro-benzenesulfonyl)-4-(2-methoxy-ethyl)-piperidine-4-carboxylic acid ethyl ester (0.2 g), dimethylaluminium chloride in heptane (1.0 molar, 0.7 ml) and 4-ethylaniline (0.093 g) to give the desired 8-(2-chloro-benzenesulfonyl)-2-(4-ethyl-phenyl)-2,8-diaza-spiro[4.5]decan-1-one (0.068 g) as a light-brown solid. MS (ESI): 433.136 (MH+).

Example 18

8-(2-Methyl-propane-1-sulfonyl)-2-(4-trifluoromethoxy-phenyl)-2,8-diaza-spiro[4.5]decan-1-one

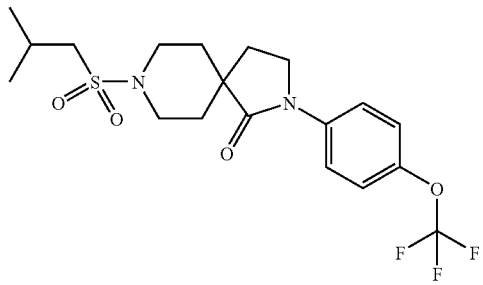

Step A): 4-(2-Methoxy-ethyl)-1-(2-methyl-propane-1-sulfonyl)-piperidine-4-carboxylic acid ethyl ester 4-(2-Methoxy-ethyl)-piperidine-4-carboxylic acid ethyl ester (1 g) was dissolved in pyridine (15 ml) under an argon atmosphere at RT and 2-methyl-propane-1-sulfonyl chloride (0.728 g) was added and the mixture was stirred for 60 h at RT. The pyridine was evaporated off, the residue dissolved in AcOEt, washed with 0.05M HCl and brine. The layers were separated, the organic layer dried over sodium sulphate and concentrated. The crude product was purified by flash chromatography (AcOEt/heptane, gradient from 0 to 25%,) to give the desired 4-(2-methoxy-ethyl)-1-(2-methyl-propane-1-sulfonyl)-piperidine-4-carboxylic acid ethyl ester (0.63 g) as a yellow oil. MS (ESI): 336.18 (MH+).

Step B): 8-(2-Methyl-propane-1-sulfonyl)-2-(4-trifluoromethoxy-phenyl)-2,8-diaza-spiro[4.5]decan-1-one This material was prepared in analogy to example 1 step D) 4-(2-methoxy-ethyl)-1-(2-methyl-propane-1-sulfonyl)-piperidine-4-carboxylic acid ethyl ester (0.134 g), dimethylaluminium chloride in heptane (1.0 molar, 1.2 ml) and 4-(trifluoromethoxy)-aniline (0.106 g) to give the desired 8-(2-methyl-propane-1-sulfonyl)-2-(4-trifluoromethoxy-phenyl)-2,8-diaza-spiro[4.5]decan-1-one (0.134 g) as an off-white solid. MS (ESI): 435.15 (MH+).

Example 19

8-(2,2-Dimethyl-propane-1-sulfonyl)-2-(4-trifluoromethoxy-phenyl)-2,8-diaza-spiro[4.5]decan-1-one

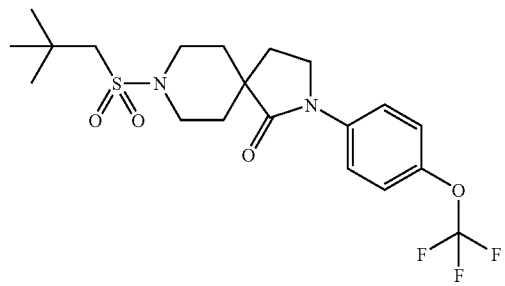

Step A): 1-(2,2-Dimethyl-propane-1-sulfonyl)-4-(2-methoxy-ethyl)-piperidine-4-carboxylic acid ethyl ester To a solution of 4-(2-methoxy-ethyl)-piperidine-4-carboxylic acid ethyl ester (0.72 g) in methylene chloride (40 ml) was added at RT under an argon atmosphere DMAP (0.75 g) and then dropwise 2,2-dimethyl-propane-1-sulfonyl chloride (0.57 ml). The reaction mixture was stirred 12 h at RT then partitioned between AcOEt and aqueous 1M HCl, the layers were separated and the aqueous layer washed with 2M aqueous $KHCO_3$ then dried over $Na_2SO_4$. The solvent was evaporated off, the residue purified by flash chromatography (AcOEt/heptane, gradient from 0 to 40%) to give the desired 1-(2,2-dimethyl-propane-1-sulfonyl)-4-(2-methoxy-ethyl)-piperidine-4-carboxylic acid ethyl ester (0.34 g) as a light yellow viscous oil.

Step B): 8-(2,2-Dimethyl-propane-1-sulfonyl)-2-(4-trifluoromethoxy-phenyl)-2,8-diaza-spiro[4.5]decan-1-one This material was prepared in analogy to example 1 step D) 1-(2,2-dimethyl-propane-1-sulfonyl)-4-(2-methoxy-ethyl)-piperidine-4-carboxylic acid ethyl ester (0.17 g), dimethylaluminium chloride in heptane (1.0 molar, 1.46 ml) and 4-(trifluoromethoxy)-aniline (0.129 g) to give the desired 8-(2,2-dimethyl-propane-1-sulfonyl)-2-(4-trifluoromethoxyphenyl)-2,8-diaza-spiro[4.5]decan-1-one (0.118 g) as an off-white solid. MS (ESI): 449.17 (MH⁺).

Example 20

8-(3,3-Dimethyl-butyryl)-2-(4-ethyl-phenyl)-2,8-diaza-spiro[4.5]decan-1-one

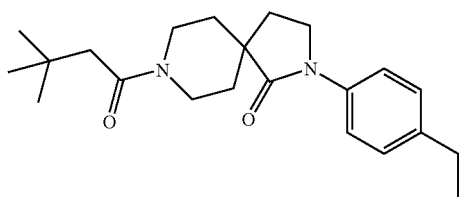

This material was prepared in analogy to example 1 step D) 1-(3,3-Dimethyl-butyryl)-4-(2-methoxy-ethyl)-piperidine-4-carboxylic acid ethyl ester (0.15 g), dimethylaluminium chloride in heptane (1.0 molar, 0.96 ml) and 4-ethylaniline (0.087 g) to give the desired 8-(3,3-dimethyl-butyryl)-2-(4-ethyl-phenyl)-2,8-diaza-spiro[4.5]decan-1-one (0.118 g) as an off-white solid. MS (ESI): 357.25 (MH⁺).

Example 21

2-(4-Ethyl-phenyl)-8-(morpholine-4-sulfonyl)-2,8-diaza-spiro[4.5]decan-1-one

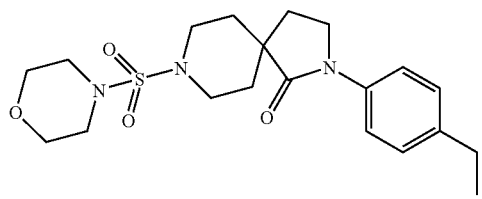

This material was obtained in analogy to example 1 step D) from 4-(2-methoxy-ethyl)-1-(morpholine-4-sulfonyl)-piperidine-4-carboxylic acid ethyl ester (0.128 g), dimethylaluminium chloride in heptane (1 molar, 0.7 ml, and 4-ethylaniline (0.064 g) to give the desired 2-(4-ethyl-phenyl)-8-(morpholine-4-sulfonyl)-2,8-diaza-spiro[4.5]decan-1-one (0.084 g) as an off-white solid. MS (ESI): 408.19 (MH⁺).

Example 22

(rac)-8-(2,2-Dimethyl-propane-1-sulfonyl)-2-[4-(2,2,2-trifluoro-1-methyl-ethoxy)-phenyl]-2,8-diaza-spiro[4.5]decan-1-one

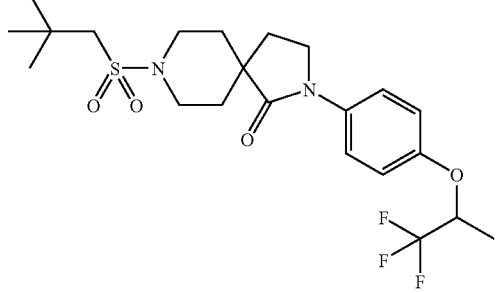

This material was obtained in analogy to example 1 step D) from 1-(2,2-dimethyl-propane-1-sulfonyl)-4-(2-methoxy-ethyl)-piperidine-4-carboxylic acid ethyl ester (0.17 g), dimethylaluminium chloride in heptane (1 molar, 0.97 ml, and (rac)-4-(2,2,2-trifluoro-1-methyl-ethoxy)-phenylamine (0.15 g) to give the desired (rac)-8-(2,2-dimethyl-propane-1-sulfonyl)-2-[4-(2,2,2-trifluoro-1-methyl-ethoxy)-phenyl]-2,8-diaza-spiro[4.5]decan-1-one (0.047 g) as an off-white solid. MS (ESI): 477.20 (MH⁺).

Example 23

2-(4-Isopropoxy-phenyl)-8-(2-methyl-propane-1-sulfonyl)-2,8-diaza-spiro[4.5]decan-1-one

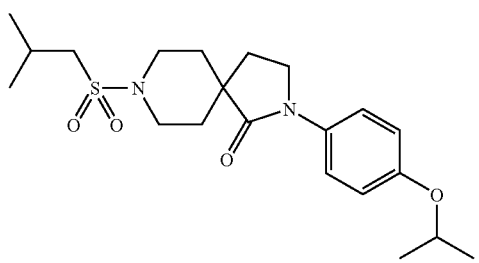

This material was obtained in analogy to example 1 step D) from 4-(2-methoxy-ethyl)-1-(2-methyl-propane-1-sulfonyl)-piperidine-4-carboxylic acid ethyl ester (0.134 g), dimethylaluminium chloride in heptane (1 molar, 0.8 ml) and 4-isopropoxyaniline (0.091 g) to give the desired (2-(4-isopropoxy-phenyl)-8-(2-methyl-propane-1-sulfonyl)-2,8-diaza-spiro[4.5]decan-1-one) (0.05 g) as an light brown solid. MS (ESI): 409.24 (MH⁺).

Example 24

2-(4-Ethyl-phenyl)-8-(2-methyl-propane-1-sulfonyl)-2,8-diaza-spiro[4.5]decan-1-one

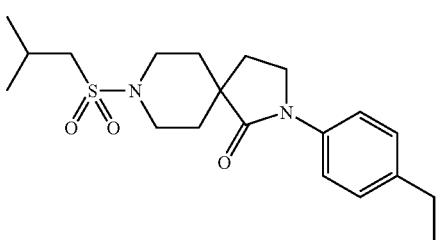

This material was obtained in analogy to example 1 step D) from 4-(2-methoxy-ethyl)-1-(2-methyl-propane-1-sulfonyl)-piperidine-4-carboxylic acid ethyl ester (0.134 g), dimethylaluminium chloride in heptane (1 molar, 0.8 ml, and 4-ethylaniline (0.073 g) to give the desired 2-(4-ethyl-phenyl)-8-(2-methyl-propane-1-sulfonyl)-2,8-diaza-spiro[4.5]decan-1-one (0.075 g) as an off-white solid. MS (ESI): 379.20 (MH⁺).

Example 25

(rac)-8-Benzenesulfonyl-2-[6-(2,2,2-trifluoro-1-methyl-ethoxy)-pyridin-3-yl]-2,8-diaza-spiro[4.5]decan-1-one

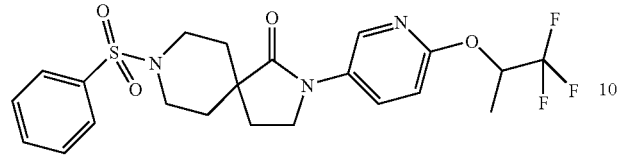

This material was obtained in analogy to example 1 step D) from 1-benzenesulfonyl-4-(2-methoxy-ethyl)-piperidine-4-carboxylic acid ethyl ester. (0.2 g), dimethylaluminium chloride in heptane (1 molar, 1.13 ml), and (rac)-6-(2,2,2-trifluoro-1-methyl-ethoxy)-pyridin-3-ylamine (0.15 g) to give the desired (rac)-8-benzenesulfonyl-2-[6-(2,2,2-trifluoro-1-methyl-ethoxy)-pyridin-3-yl]-2,8-diaza-spiro[4.5]decan-1-one (0.19 g) as an off-white crystalline solid. MS (ESI): 484.3 (MH$^+$).

Preparation of the starting material, (rac)-6-(2,2,2-trifluoro-1-methyl-ethoxy)-pyridin-3-ylamine:

i) To a solution of 2-chloro-5-nitro-pyridine (1.74 g) and 1,1,1-trifluoro-propan-2-ol (1.097 g) in DMF (15 ml) under an argon atmosphere was added under ice cooling NaH (0.528 g 55% suspension in oil). The mixture was stirred for 3 h at RT then partitioned between diethyl ether and water, The layers were separated dried over Na$_2$SO$_4$ and the solvent was evaporated off to give 5-nitro-2-(2,2,2-trifluoro-1-methyl-ethoxy)-pyridine as brown oil (2.28 g) that was used in the next step without further purification.

ii) 5-Nitro-2-(2,2,2-trifluoro-1-methyl-ethoxy)-pyridine (2.23 g) in methanol (30 ml) was hydrogenated over Pd/C (10%, 500 mg) at RT and at atmospheric pressure for 12 h. The catalyst was then filtered off and the solvent removed in vacuo to give the desired (rac)-6-(2,2,2-trifluoro-1-methyl-ethoxy)-pyridin-3-ylamine (1.91 g) as a brown oil. MS (ESI): 270.0 (MH$^+$).

Example 26

8-Benzenesulfonyl-2-[4-(2,2,2-trifluoro-ethoxy)-phenyl]-2,8-diaza-spiro[4.5]decan-1-one

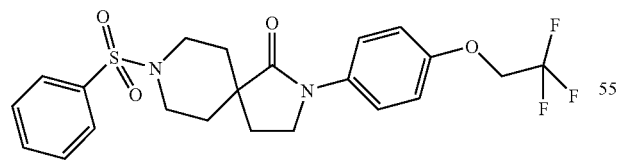

This material was obtained in analogy to example 1 step D) from 1-benzenesulfonyl-4-(2-methoxy-ethyl)-piperidine-4-carboxylic acid ethyl ester. (0.14 g), dimethylaluminium chloride in heptane (1 molar, 1.13 ml), and (4-(2,2,2-trifluoro-ethoxy)-phenylamine (0.14 g) to give the desired 8-benzenesulfonyl-2-[4-(2,2,2-trifluoro-ethoxy)-phenyl]-2,8-diaza-spiro[4.5]decan-1-one (0.088 g) as an off-white crystalline solid. MS (ESI): 469.3 (MH$^+$).

Preparation of the starting material, 4-(2,2,2-trifluoro-ethoxy)-phenylamine:

i) To a solution of 1-fluoro-4-nitro-benzene (10 g) and 2,2,2-trifluoro-ethanol (6.25 ml) in DMF (100 ml) under an argon atmosphere was added under ice cooling NaH (3.74 g, 55% suspension in oil) and the mixture was stirred for 3 h at RT. It was then partitioned between diethyl ether and water, the layers were separated, dried over Na$_2$SO$_4$ and the solvent was evaporated off to give the desired 1-nitro-4-(2,2,2-trifluoro-ethoxy)-benzene as crude oil (16.9 g) that was used in the next step without further purification.

ii) 1-Nitro-4-(2,2,2-trifluoro-ethoxy)-benzene (16.9 g) in methanol (150 ml) was hydrogenated over Pd/C (10%, 500 mg) at RT and at atmospheric pressure for 12 h. The catalyst was then filtered off and the solvent removed in vauo to give the desired 4-(2,2,2-trifluoro-ethoxy)-phenylamine (14 g) as a light yellow oil. MS (ESI): 192.2 (MH$^+$).

Example 27

2-(4-Ethyl-phenyl)-8-(2-methyl-propane-1-sulfonyl)-2,8-diaza-spiro[4.5]decan-1-one

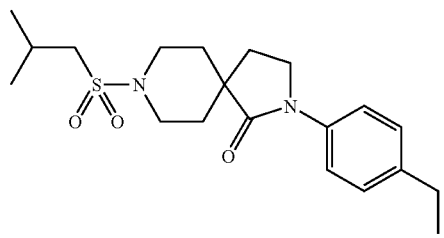

Off-white solid. MS (ESI): 379.20 (MH$^+$). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride and 4-ethylaniline.

Example 28

8-(Thiophene-2-sulfonyl)-2-(4-trifluoromethoxy-phenyl)-2,8-diaza-spiro[4.5]decan-1-one

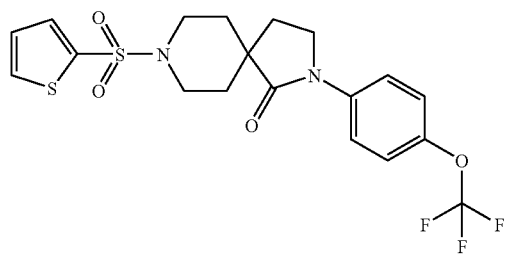

Light yellow solid. MS (ESI): 461.08 (MH$^+$). This example was prepared in analogy to example 1 step C) to D) from 4-(2-methoxy-ethyl)-piperidine-4-carboxylic acid ethyl ester (example 1 step B)), thiophene-2-sulfonyl chloride and 4-(trifluoromethoxy)aniline.

Example 29

2-(4-Ethyl-phenyl)-8-(thiophene-2-sulfonyl)-2,8-diaza-spiro[4.5]decan-1-one

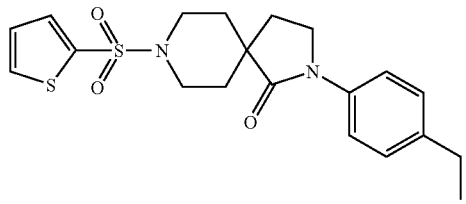

Off-white solid. MS (ESI): 405.12 (MH$^+$). This example was prepared in analogy to example 1 step C) to D) from 4-(2-methoxy-ethyl)-piperidine-4-carboxylic acid ethyl ester (example 1 step B)) thiophene-2-sulfonyl chloride and 4-ethyl-aniline.

Example 30

2-(4-Ethyl-phenyl)-8-(3,3,3-trifluoro-propane-1-sulfonyl)-2,8-diaza-spiro[4.5]decan-1-one

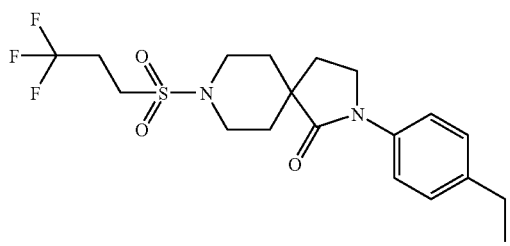

Light yellow solid. MS (ESI): 419.16 (MH$^+$). This example was prepared in analogy to example 1 step C) to D) from 4-(2-methoxy-ethyl)-piperidine-4-carboxylic acid ethyl ester (example 1 step B)), 3,3,3-trifluoro-propane-1-sulfonyl chloride and 4-ethyl-aniline.

Example 31

8-(3,3-Dimethyl-butyryl)-2-(4-propyl-phenyl)-2,8-diaza-spiro[4.5]decan-1-one

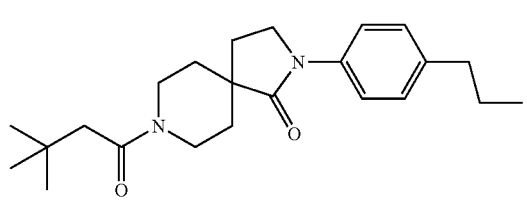

Off-white solid. MS (ESI): 371.26 (MH$^+$). This example was prepared in analogy to example 7 step A) to B) from 4-(2-methoxy-ethyl)-piperidine-4-carboxylic acid ethyl ester (example 1 step B)), 3,3-dimethyl-butyryl chloride and 4-propyl-aniline.

Example 32

8-(2,2-Dimethyl-propane-1-sulfonyl)-2-(4-ethyl-phenyl)-2,8-diaza-spiro[4.5]decan-1-one

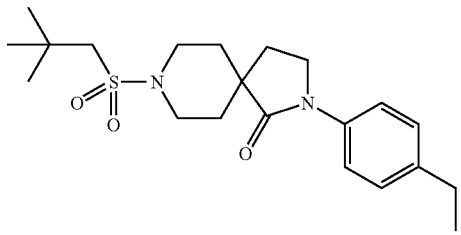

Light brown solid. MS (ESI): 415.2 (MH$^+$). This example was prepared in analogy to example 1 step C) to D) from 4-(2-methoxy-ethyl)-piperidine-4-carboxylic acid ethyl ester (example 1 step B)), 2,2-dimethylpropane-1-sulfonyl chloride and 4-ethyl-aniline.

Example 33

8-(2-Chloro-benzenesulfonyl)-2-(4-cyclopropyl-phenyl)-2,8-diaza-spiro[4.5]decan-1-one

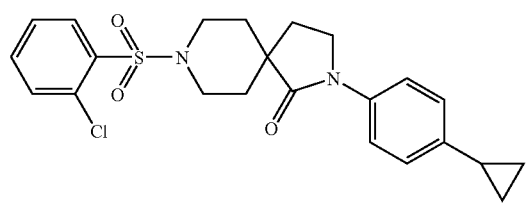

Light brown solid. MS (ESI): 445.11 (MH$^+$). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 4-cyclopropyl-aniline.

Example 34

8-(2-Chloro-benzenesulfonyl)-2-(4-methylsulfanyl-phenyl)-2,8-diaza-spiro[4.5]decan-1-one

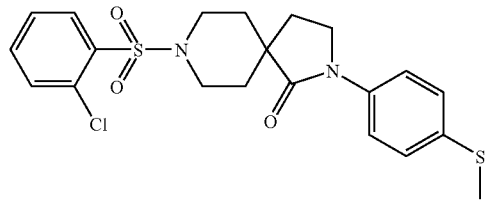

Off-white solid. MS (ESI): 451.09 (MH$^+$). This example was prepared in analogy to example 1 step C) to D)

4-(2-methoxy-ethyl)-piperidine-4-carboxylic acid ethyl ester (example 1 step B)), 2-chlorobenzenesulfonyl chloride and 4-(methylmercapto)-aniline.

Example 35

2-(4-Cyclopropyl-phenyl)-8-(3,3-dimethyl-butyryl)-2,8-diaza-spiro[4.5]decan-1-one

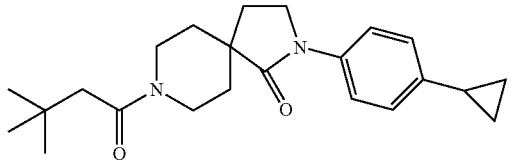

Light yellow solid. MS (ESI): 369.25 (MH⁺). This example was prepared in analogy to example 7 step A) to B) from 4-(2-methoxy-ethyl)-piperidine-4-carboxylic acid ethyl ester (example 1 step B)), tert-butyl acetyl chloride and 4-cyclopropyl-aniline.

Example 36

2-(4-Cyclopropyl-phenyl)-8-(thiophene-2-sulfonyl)-2,8-diaza-spiro[4.5]decan-1-one

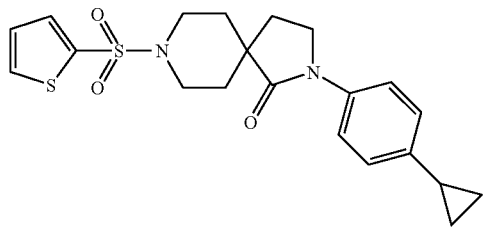

Light brown solid. MS (ESI): 417.13 (MH⁺). This example was prepared in analogy to example 1 step C) to D) from 4-(2-methoxy-ethyl)-piperidine-4-carboxylic acid ethyl ester (example 1 step B)), thiophene-2-sulfonyl chloride and 4-cyclopropyl-aniline.

Example 37

8-(2-Cyclopentyl-acetyl)-2-(4-cyclopropyl-phenyl)-2,8-diaza-spiro[4.5]decan-1-one

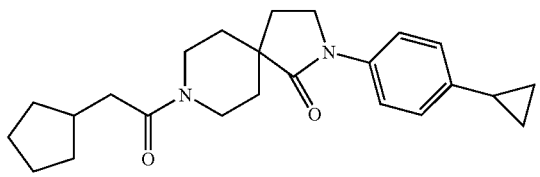

Off-white solid. MS (ESI): 381.25 (MH⁺). This example was prepared in analogy to example 7 step A) to B) from 4-(2-methoxy-ethyl)-piperidine-4-carboxylic acid ethyl ester (example 1 step B)), cyclopentylacetyl chloride and 4-cyclopropyl-aniline.

Example 38

2-(4-Cyclopropyl-phenyl)-8-phenylmethanesulfonyl-2,8-diaza-spiro[4.5]decan-1-one

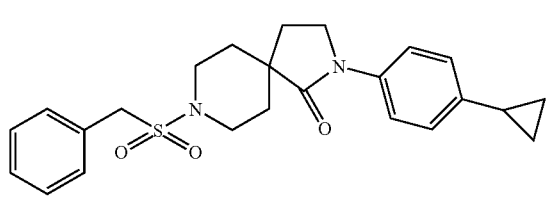

Light brown solid. MS (ESI): 425.19 (MH⁺). This example was prepared in analogy to example 1 step C) to D) from 4-(2-methoxy-ethyl)-piperidine-4-carboxylic acid ethyl ester (example 1 step B)), phenyl-methanesulfonyl chloride and 4-cyclopropyl-aniline.

Example 39

2-(4-Cyclopropyl-phenyl)-8-(propane-1-sulfonyl)-2,8-diaza-spiro[4.5]decan-1-one

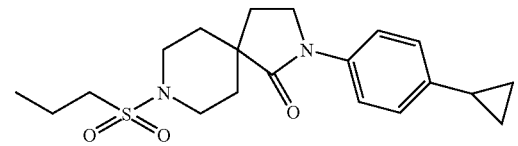

Off-white solid. MS (ESI): 377.19 (MH⁺). This example was prepared in analogy to example 1 step C) to D) from 4-(2-methoxy-ethyl)-piperidine-4-carboxylic acid ethyl ester (example 1 step B)), 1-propanesulfonyl chloride and 4-cyclopropyl-aniline.

Example 40

8-(3,3-Dimethyl-butyryl)-2-[4-(2,2,2-trifluoro-ethyl)-phenyl]-2,8-diaza-spiro[4.5]decan-1-one

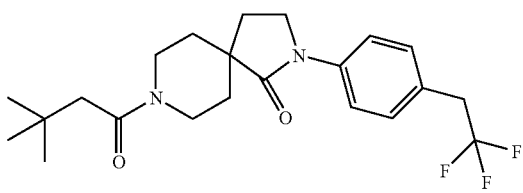

Off-white solid. MS (ESI): 411.22 (MH⁺). This example was prepared in analogy to example 7 step A) to B) from 4-(2-methoxy-ethyl)-piperidine-4-carboxylic acid ethyl ester (example 1 step B)), tert.-butylacetyl chloride and 4-(2,2,2-trifluoroethyl)-aniline.

Example 41

2-(4-Ethyl-phenyl)-8-(5-methyl-thiophene-2-sulfonyl)-2,8-diaza-spiro[4.5]decan-1-one

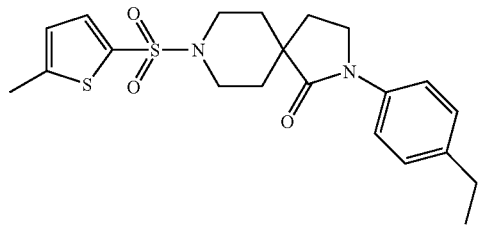

Off-white solid. MS (ESI): 419.14 (MH⁺). This example was prepared in analogy to example 1 step C) to D) from 4-(2-methoxy-ethyl)-piperidine-4-carboxylic acid ethyl ester (example 1 step B)), 5-methylthiophene-2-sulphonyl chloride and 4-ethyl-aniline.

Example 42

8-(5-Methyl-thiophene-2-sulfonyl)-2-(4-trifluoromethoxy-phenyl)-2,8-diaza-spiro[4.5]decan-1-one

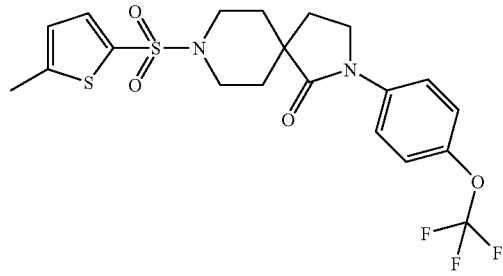

Off-white solid. MS (ESI): 475.07 (MH⁺). This example was prepared in analogy to example 1 step C) to D) from 4-(2-methoxy-ethyl)-piperidine-4-carboxylic acid ethyl ester (example 1 step B)), 5-methylthiophene-2-sulphonyl chloride and 4-(trifluoromethoxy)-aniline.

Example 43

2-(4-sec-Butyl-phenyl)-8-(thiophene-2-sulfonyl)-2,8-diaza-spiro[4.5]decan-1-one

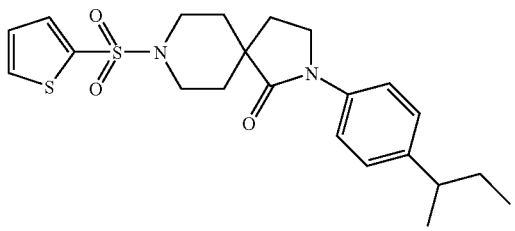

Off-white solid. MS (ESI): 433.16 (MH⁺). This example was prepared in analogy to example 1 step C) to D) from 4-(2-methoxy-ethyl)-piperidine-4-carboxylic acid ethyl ester (example 1 step B)), thiophene-2-sulphonyl chloride and 4-sec-butyl-phenylamine.

Example 44

2-(4-sec-Butyl-phenyl)-8-(morpholine-4-sulfonyl)-2,8-diaza-spiro[4.5]decan-1-one

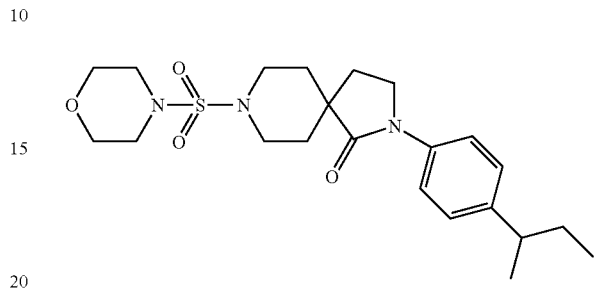

Off-white solid. MS (ESI): 436.22 (MH⁺). This example was prepared in analogy to example 1 step C) to D) from 4-(2-methoxy-ethyl)-piperidine-4-carboxylic acid ethyl ester (example 1 step B)), morpholine-4-sulfonyl chloride and 4-sec-butyl-phenylamine.

Example 45

2-(4-sec-Butyl-phenyl)-8-(5-methyl-thiophene-2-sulfonyl)-2,8-diaza-spiro[4.5]decan-1-one

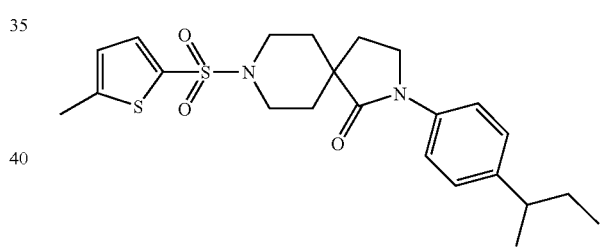

Off-white solid. MS (ESI): 447.17 (MH⁺). This example was prepared in analogy to example 1 step C) to D) from 4-(2-methoxy-ethyl)-piperidine-4-carboxylic acid ethyl ester (example 1 step B)), 5-methylthiophene-2-sulphonyl chloride and 4-sec-butyl-phenylamine.

Example 46

2-(4-sec-Butyl-phenyl)-8-(3,3-dimethyl-butyryl)-2,8-diaza-spiro[4.5]decan-1-one

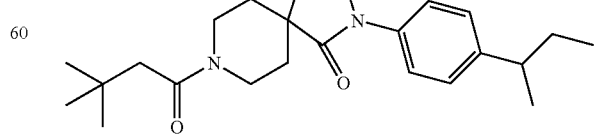

Off-white solid. MS (ESI): 385.5 (MH⁺). This example was prepared in analogy to example 7 step A) to B) from 4-(2-methoxy-ethyl)-piperidine-4-carboxylic acid ethyl ester (example 1 step B)), tert.butylacetyl chloridel and 4-sec-butyl-phenylamine.

Example 47

8-(2-Chloro-benzenesulfonyl)-2-[2-(4-chloro-phenyl)-ethyl]-2,8-diaza-spiro[4.5]decan-1-one

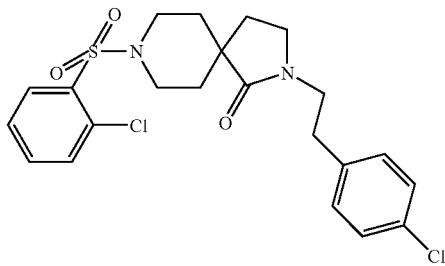

Light yellow crystalline solid. MS (ESI): 467.09 (MH$^+$). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 2-(4-chlorophenyl)-ethylamine.

Example 48

Methanesulfonic acid 4-[8-(2-chloro-benzenesulfonyl)-1-oxo-2,8-diaza-spiro[4.5]dec-2-yl]-phenyl ester

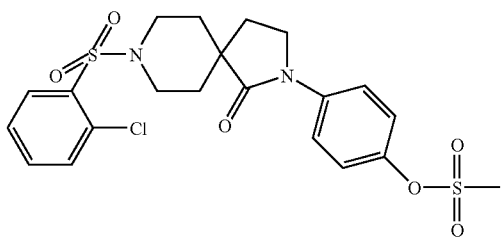

Light brown solid. MS (ESI): 499.07 (MH$^+$). This example was prepared in analogy to example 1 step C) to D) from 4-(2-methoxy-ethyl)-piperidine-4-carboxylic acid ethyl ester (example 1 step B)), 2-chlorobenzenesulfonyl chloride and methanesulfonic acid 4-amino-phenyl ester (synthesis: S. Kobayashi, et al.; Synlett. 2000, p 883).

Example 49

8-(2-Chloro-benzenesulfonyl)-2-(4-trifluoromethoxy-benzyl)-2,8-diaza-spiro[4.5]decan-1-one

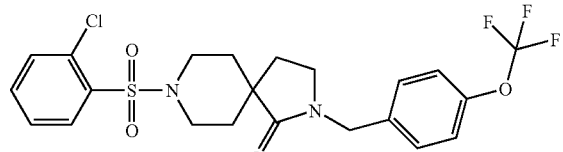

Light yellow viscous oil. MS (ESI): 503.10 (MH$^+$). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 4-(trifluormethoxy)-benzylamine.

Example 50

Methanesulfonic acid 4-[8-(5-methyl-thiophene-2-sulfonyl)-1-oxo-2,8-diaza-spiro[4.5]dec-2-yl]-phenyl ester

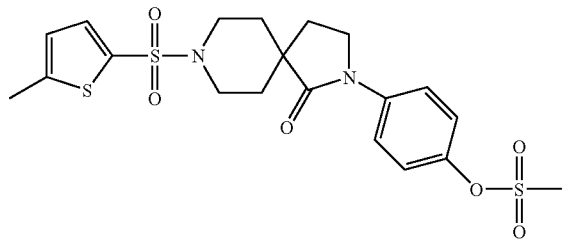

Brown solid. MS (ESI): 485.08 (MH$^+$). This example was prepared in analogy to example 1 step C) to D) from 4-(2-methoxy-ethyl)-piperidine-4-carboxylic acid ethyl ester (example 1 step B)), 5-methylthiophene-2-sulphonyl chloride and methanesulfonic acid 4-amino-phenyl ester.

Example 51

8-(2-Methanesulfonyl-benzenesulfonyl)-2-(4-trifluoromethoxy-phenyl)-2,8-diaza-spiro[4.5]decan-1-one

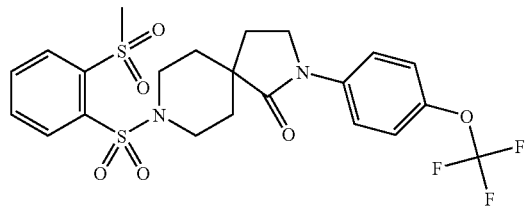

White solid. MS (ESI): 533.10 (MH$^+$). This example was prepared in analogy to example 1 step C) to D) from 4-(2-methoxy-ethyl)-piperidine-4-carboxylic acid ethyl ester (example 1 step B)), 2-methanesulfonyl-benzenesulfonyl chloride and 4-(trifluoromethoxy)-aniline.

Example 52

2-(4-Ethyl-phenyl)-8-(2-methanesulfonyl-benzenesulfonyl)-2,8-diaza-spiro[4.5]decan-1-one

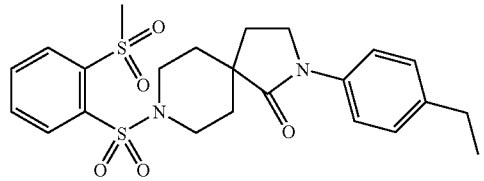

Off-white solid. MS (ESI): 413.20 (MH$^+$). This example was prepared in analogy to example 1 step C) to D) from 4-(2-methoxy-ethyl)-piperidine-4-carboxylic acid ethyl ester (example 1 step B)), 2-methanesulfonyl-benzenesulfonyl chloride and 4-ethylaniline.

Example 53

Methanesulfonic acid 4-[8-(2,2-dimethyl-propane-1-sulfonyl)-1-oxo-2,8-diaza-spiro[4.5]dec-2-yl]-phenyl ester

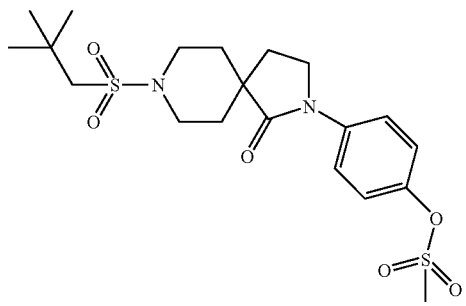

Off-white solid. MS (ESI): 459.16 (MH$^+$). This example was prepared in analogy to example 1 step C) to D) from 4-(2-methoxy-ethyl)-piperidine-4-carboxylic acid ethyl ester (example 1 step B)), 2,2-dimethyl-propane-1-sulfonyl chloride and methanesulfonic acid 4-amino-phenyl ester.

Example 54

2-(4-Ethyl-phenyl)-8-(2-trifluoromethoxy-benzene-sulfonyl)-2,8-diaza-spiro[4.5]decan-1-one

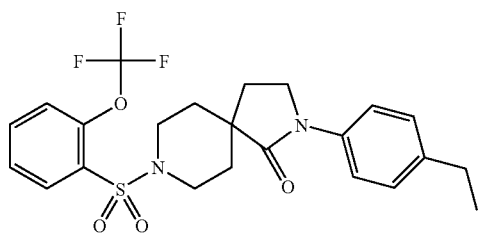

Off-white solid. MS (ESI): 483.15 (MH$^+$). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-ethylaniline.

Example 55

8-(2-Trifluoromethoxy-benzenesulfonyl)-2-(4-trifluoromethoxy-phenyl)-2,8-diaza-spiro[4.5]decan-1-one

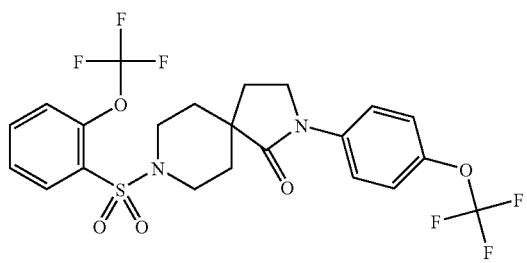

Off-white solid. MS (ESI): 539.10 (MH$^+$). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-(trifluoromethoxy)-aniline.

Example 56

Methanesulfonic acid 4-[1-oxo-8-(2-trifluoromethoxy-benzenesulfonyl)-2,8-diaza-spiro[4.5]dec-2-yl]-phenyl ester

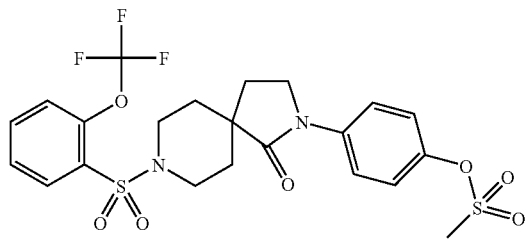

Light brown solid. MS (ESI): 549.09 (MH$^+$). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and methanesulfonic acid 4-amino-phenyl ester.

Example 57

8-(2-Methanesulfonyl-benzenesulfonyl)-2-(4-propyl-phenyl)-2,8-diaza-spiro[4.5]decan-1-one

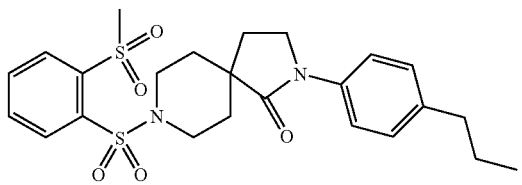

White solid. MS (ESI): 491.16 (MH$^+$). This example was prepared in analogy to example 1 step C) to D) from 4-(2-methoxy-ethyl)-piperidine-4-carboxylic acid ethyl ester (example 1 step B)), 2-methanesulfonyl-benzenesulfonyl chloride and 4-propyl-aniline.

Example 58

2-(4-Propyl-phenyl)-8-(2-trifluoromethoxy-benzene-sulfonyl)-2,8-diaza-spiro[4.5]decan-1-one

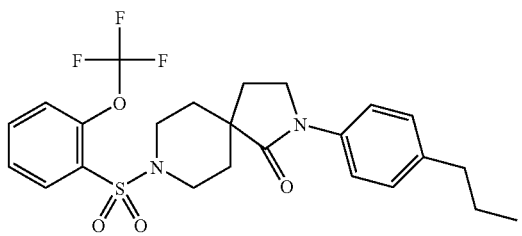

Off-white solid. MS (ESI): 497.17 (MH$^+$). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-propyl-aniline.

Example 59

Methanesulfonic acid 4-[1-oxo-8-(thiophene-2-sulfonyl)-2,8-diaza-spiro[4.5]dec-2-yl]-phenyl ester

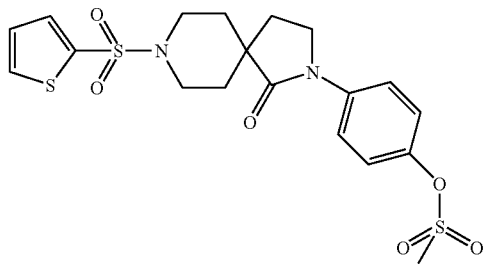

Off-white solid. MS (ESI): 471.07 (MH$^+$). This example was prepared in analogy to example 1 step C) to D) from 4-(2-methoxy-ethyl)-piperidine-4-carboxylic acid ethyl ester (example 1 step B)), thiophene-2-sulphonyl chloride and methanesulfonic acid 4-amino-phenyl ester.

Example 60

8-(2-Methyl-propane-1-sulfonyl)-2-[4-(2,2,2-trifluoro-ethyl)-phenyl]-2,8-diaza-spiro[4.5]decan-1-one

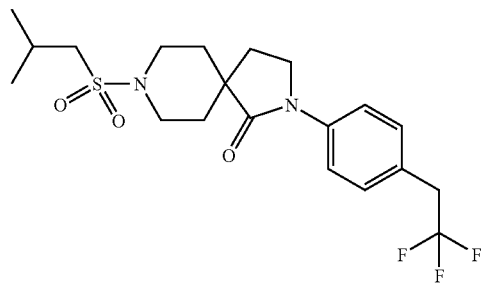

White crystalline solid. MS (ESI): 433.19 (MH$^+$). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride and 4-(2,2,2-trifluoro-ethyl)-phenylamine.

Example 61

2-(4-sec-Butyl-phenyl)-8-(2-methyl-propane-1-sulfonyl)-2,8-diaza-spiro[4.5]decan-1-one

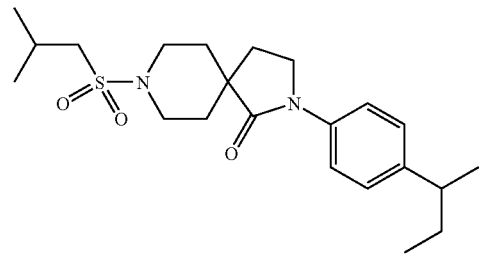

White solid. MS (ESI): 407.23 (MH$^+$). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride and 4-sec-butyl-phenylamine.

Example 62

Methanesulfonic acid 4-[8-(2-methyl-propane-1-sulfonyl)-1-oxo-2,8-diaza-spiro[4.5]dec-2-yl]-phenyl ester

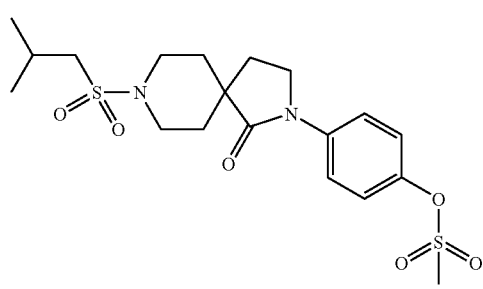

Light brown solid. MS (ESI): 445.14 (MH$^+$). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride and methanesulfonic acid 4-amino-phenyl ester.

Example 63

8-(2-Methyl-propane-1-sulfonyl)-2-[4-(2,2,2-trifluoro-ethoxy)-phenyl]-2,8-diaza-spiro[4.5]decan-1-one

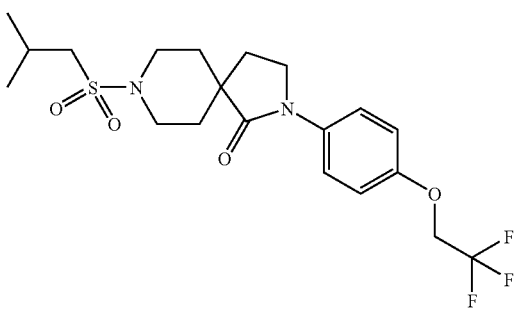

Light brown solid. MS (ESI): 449.17 (MH$^+$). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride and methanesulfonic acid 4-amino-phenyl ester.

Example 64

Cyclopropanesulfonic acid 4-[8-(2-methyl-propane-1-sulfonyl)-1-oxo-2,8-diaza-spiro[4.5]dec-2-yl]-phenyl ester

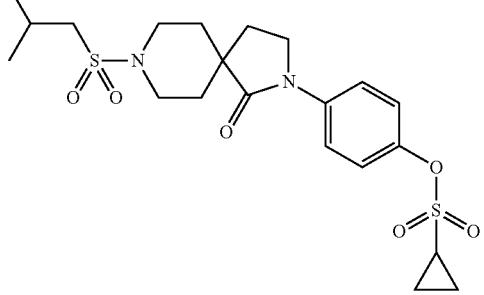

Off-white solid. MS (ESI): 471.16 (MH+). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride and cyclopropanesulfonic acid 4-amino-phenyl ester.

Preparation of cyclopropanesulfonic acid 4-amino-phenyl ester used above:

This material was prepared from cyclopropanesulfonic acid 4-nitro-phenyl ester (J. F. King et al; Phosphorus, Sulfur and Silicon and the Related Elements; 1-4; 1993; p 445) (1.096 g) by hydrogenation over 10% Pd/C with ethanol/AcOEt as solvent (10 ml/15 ml) in analogy to example 4 step ii). Yellow oil (0.55 g). MS (ESI): 214.2 (MH+).

Example 65

2-(4-Cyclopropyl-phenyl)-8-(2-methyl-propane-1-sulfonyl)-2,8-diaza-spiro[4.5]decan-1-one

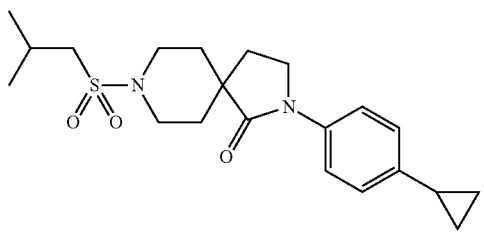

Off-white solid. MS (ESI): 391.2 (MH+). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride and 4-cylopropyl-aniline.

Example 66

2-(4-Cyclopentyloxy-phenyl)-8-(2-methyl-propane-1-sulfonyl)-2,8-diaza-spiro[4.5]decan-1-one

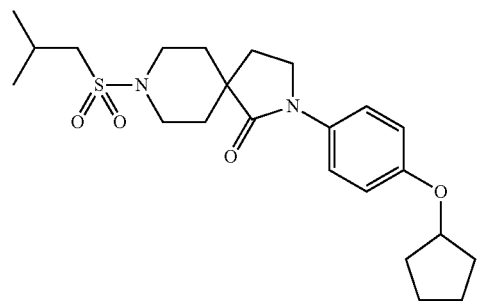

Pink solid. MS (ESI): 435.23 (MH+). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride and 4-(cylopentyloxy)-aniline.

Example 67

2-(4-Ethyl-phenyl)-8-(2-trifluoromethyl-benzenesulfonyl)-2,8-diaza-spiro[4.5]decan-1-one

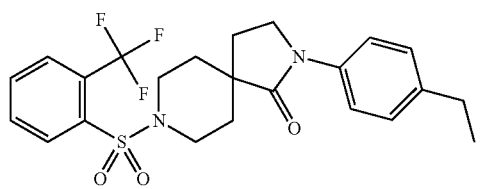

Off white solid. MS (ESI): 467.16 (MH+). This example was prepared in analogy to example 1 step C) to D) from 4-(2-methoxy-ethyl)-piperidine-4-carboxylic acid ethyl ester (example 1 step B)), 2-trifluoromethyl-benzenesulfonyl chloride and 4-ethyl-aniline.

Example 67

2-(4-Ethyl-phenyl)-8-(2-trifluoromethyl-benzenesulfonyl)-2,8-diaza-spiro[4.5]decan-1-one

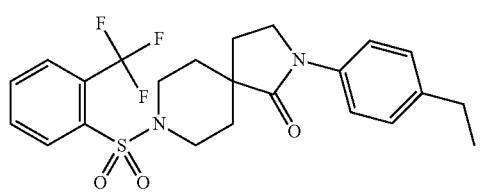

Off white solid. MS (ESI): 467.16 (MH+). This example was prepared in analogy to example 1 step C) to D) from 4-(2-methoxy-ethyl)-piperidine-4-carboxylic acid ethyl ester (example 1 step B)), 2-trifluoromethyl-benzenesulfonyl chloride and 4-ethyl-aniline.

Example 68

2-(4-Trifluoromethoxy-phenyl)-8-(2-trifluoromethyl-benzenesulfonyl)-2,8-diaza-spiro[4.5]decan-1-one

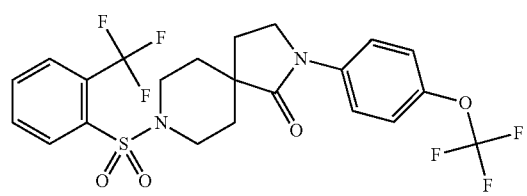

Off white solid. MS (ESI): 523.11 (MH⁺). This example was prepared in analogy to example 1 step C) to D) from 4-(2-methoxy-ethyl)-piperidine-4-carboxylic acid ethyl ester (example 1 step B)), 2-trifluoromethyl-benzenesulfonyl chloride and 4-(trifluoromethoxy)-aniline.

Example 69

8-(2-Chloro-4-trifluoromethyl-benzenesulfonyl)-2-(4-ethyl-phenyl)-2,8-diaza-spiro[4.5]decan-1-one

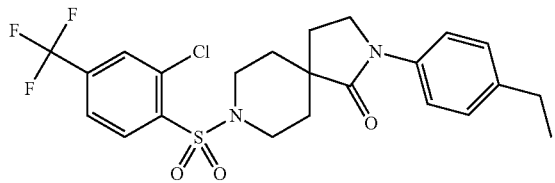

Light brown solid. MS (ESI): 501.12 (MH⁺). This example was prepared in analogy to example 1 step C) to D) from 4-(2-methoxy-ethyl)-piperidine-4-carboxylic acid ethyl ester (example 1 step B)), 2-chloro-4-trifluoromethyl-benzenesulfonyl chloride and 4-ethyl-aniline.

Example 70

8-(2-Chloro-4-trifluoromethyl-benzenesulfonyl)-2-(4-trifluoromethoxy-phenyl)-2,8-diaza-spiro[4.5]decan-1-one

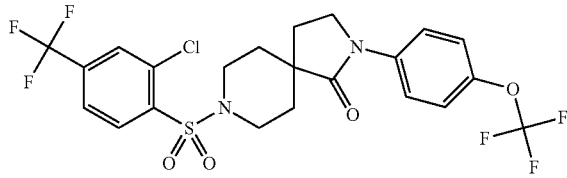

White solid. MS (ESI): 557.07 (MH⁺). This example was prepared in analogy to example 1 step C) to D) from 4-(2-methoxy-ethyl)-piperidine-4-carboxylic acid ethyl ester (example 1 step B)), 2-chloro-4-trifluoromethyl-benzenesulfonyl chloride and 4-(trifluoromethoxy)-aniline.

Example 71

2-(4-Cyclopropyl-phenyl)-8-(2-trifluoromethyl-benzenesulfonyl)-2,8-diaza-spiro[4.5]decan-1-one

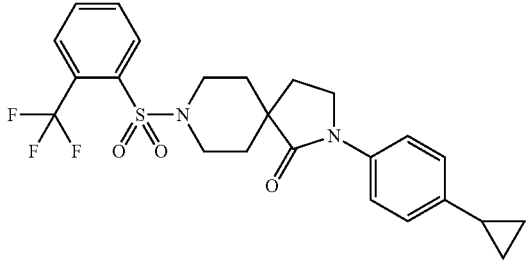

Off-white solid. MS (ESI): 479.16 (MH⁺). This example was prepared in analogy to example 1 step C) to D) from 4-(2-methoxy-ethyl)-piperidine-4-carboxylic acid ethyl ester (example 1 step B)), 2-trifluoromethyl-benzenesulfonyl chloride and 4-cyclopropyl-aniline.

Example 72

2-(4-Cyclopropyl-phenyl)-8-(4-fluoro-2-trifluoromethyl-benzenesulfonyl)-2,8-diaza-spiro[4.5]decan-1-one

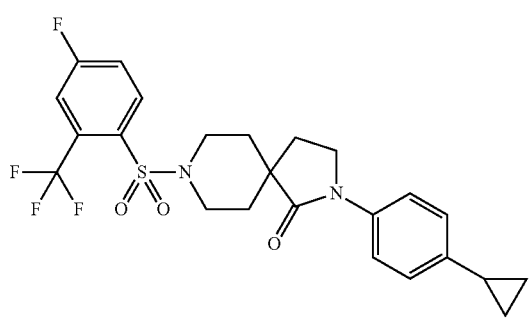

Light brown solid. MS (ESI): 497.15 (MH⁺). This example was prepared in analogy to example 1 step C) to D) from 4-(2-methoxy-ethyl)-piperidine-4-carboxylic acid ethyl ester (example 1 step B)), 4-fluoro-2-trifluoromethyl-benzenesulfonyl chloride and 4-cyclopropyl-aniline.

Example 73

2-[4-(2,2,2-Trifluoro-ethyl)-phenyl]-8-(2-trifluoromethyl-benzenesulfonyl)-2,8-diaza-spiro[4.5]decan-1-one

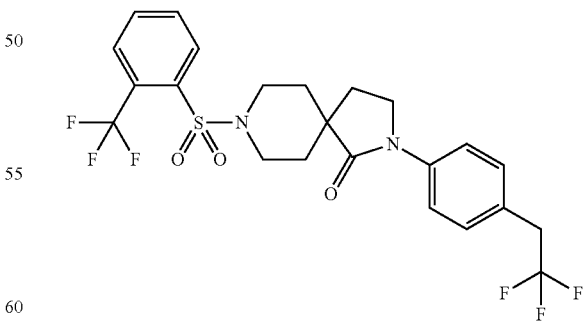

Off-white solid. MS (ESI): 521.13 (MH⁺). This example was prepared in analogy to example 1 step C) to D) from 4-(2-methoxy-ethyl)-piperidine-4-carboxylic acid ethyl ester (example 1 step B)), 2-trifluoromethyl-benzenesulfonyl chloride and 4-(2,2,2-trifluoroethyl)-aniline.

Example 74

2-(4-Ethyl-phenyl)-8-(2-iodo-benzenesulfonyl)-2,8-diaza-spiro[4.5]decan-1-one

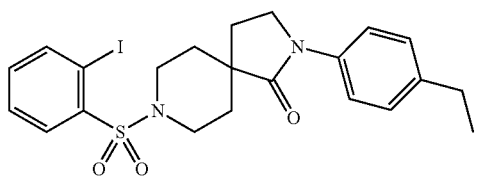

Amorphous brown solid. MS (ESI) 525.07 (MH+). This example was prepared in analogy to example 1 step C) to D) from 4-(2-methoxy-ethyl)-piperidine-4-carboxylic acid ethyl ester (example 1 step B)), 2-Iodo-benzenesulfonyl chloride and 4-(ethyl)-aniline.

Example 75

2-(4-Ethyl-phenyl)-8-(4-fluoro-2-trifluoromethyl-benzenesulfonyl)-2,8-diaza-spiro[4.5]decan-1-one

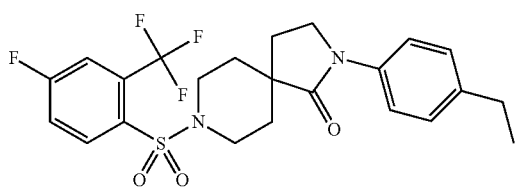

Off-white solid. MS (ESI): 485.15 (MH+). This example was prepared in analogy to example 1 step C) to D) from 4-(2-methoxy-ethyl)-piperidine-4-carboxylic acid ethyl ester (example 1 step B)), 4-fluoro-2-trifluoromethyl-benzenesulfonyl chloride and 4-ethyl-aniline.

Example 76

8-(4-Fluoro-2-trifluoromethyl-benzenesulfonyl)-2-(4-trifluoromethoxy-phenyl)-2,8-diaza-spiro[4.5]decan-1-one

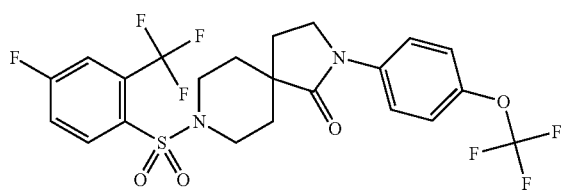

Off-white solid. MS (ESI): 541.10 (MH+). This example was prepared in analogy to example 1 step C) to D) from 4-(2-methoxy-ethyl)-piperidine-4-carboxylic acid ethyl ester (example 1 step B)), 4-fluoro-2-trifluoromethyl-benzenesulfonyl chloride and 4-(2,2,2-trifluoroethyl)-aniline.

Example 77

8-(2-Chloro-4-trifluoromethyl-benzenesulfonyl)-2-(4-cyclopropyl-phenyl)-2,8-diaza-spiro[4.5]decan-1-one

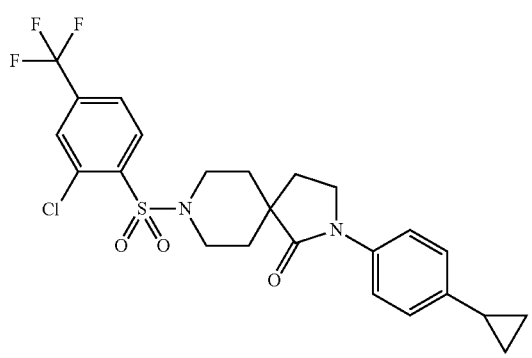

Off-white solid. MS (ESI): 513.12 (MH+). This example was prepared in analogy to example 1 step C) to D) from 4-(2-methoxy-ethyl)-piperidine-4-carboxylic acid ethyl ester (example 1 step B)), 4-chloro-4-trifluoromethyl-benzenesulfonyl chloride and 4-cyclopropyl-aniline.

Example 78

2-[4-(2,2,2-Trifluoro-ethyl)-phenyl]-8-(2-trifluoromethoxy-benzenesulfonyl)-2,8-diaza-spiro[4.5]decan-1-one

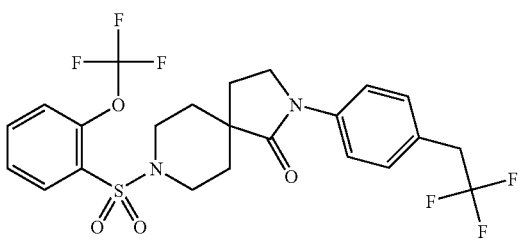

Off-white solid. MS (ESI): 537.12 (MH+). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-(2,2,2-trifluoro-ethyl)-aniline.

Example 79

2-[4-(2,2,2-Trifluoro-ethoxy)-phenyl]-8-(2-trifluoromethoxy-benzenesulfonyl)-2,8-diaza-spiro[4.5]decan-1-one

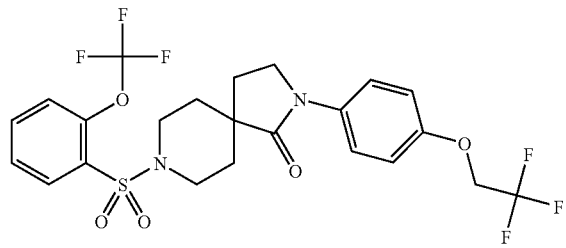

Brown solid. MS (ESI): 553.12 (MH+). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-(2,2,2-trifluoro-ethoxy)-phenylamine.

Example 80

Cyclopropanesulfonic acid 4-[1-oxo-8-(2-trifluoromethoxy-benzenesulfonyl)-2,8-diaza-spiro[4.5]dec-2-yl]-phenyl ester

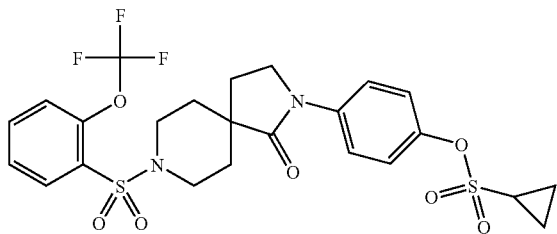

Light brown solid. MS (ESI): 575.11 (MH+). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and cyclopropanesulfonic acid 4-amino-phenyl ester.

Example 81

8-(4-Fluoro-2-trifluoromethyl-benzenesulfonyl)-2-[4-(2,2,2-trifluoro-ethyl)-phenyl]-2,8-diaza-spiro[4.5]decan-1-one

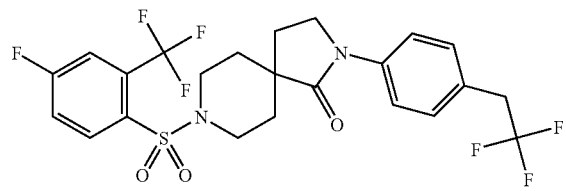

Off-white solid. MS (ESI): 539.12 (MH+). This example was prepared in analogy to example 1 step C) to D) from 4-(2-methoxy-ethyl)-piperidine-4-carboxylic acid ethyl ester (example 1 step B)), 4-fluoro-2-trifluoromethyl-benzenesulfonyl chloride and 4-(2,2,2-trifluoroethyl)-aniline.

Example 82

2-(4-Cyclopropyl-phenyl)-8-(2-trifluoromethoxy-benzenesulfonyl)-2,8-diaza-spiro[4.5]decan-1-one

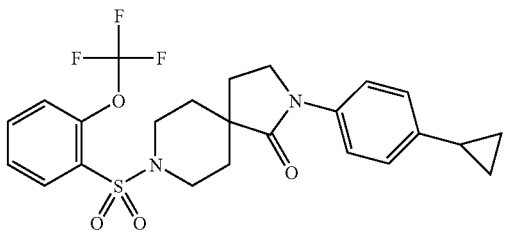

Off-white solid. MS (ESI): 495.15 (MH+). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-(cyclopropyl)-aniline.

Example 83

Methanesulfonic acid 4-[8-(4-fluoro-2-trifluoromethyl-benzenesulfonyl)-1-oxo-2,8-diaza-spiro[4.5]dec-2-yl]-phenyl ester

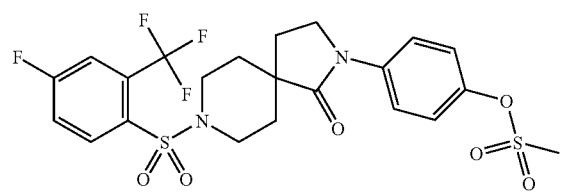

Brown solid. MS (ESI): 551.09 (MH+). This example was prepared in analogy to example 1 step C) to D) from 4-(2-methoxy-ethyl)-piperidine-4-carboxylic acid ethyl ester (example 1 step B)), 4-fluoro-2-trifluoromethyl-benzenesulfonyl chloride and methanesulfonic acid 4-amino-phenyl ester.

Example 84

2-(4-Butoxy-phenyl)-8-(2-methyl-propane-1-sulfonyl)-2,8-diaza-spiro[4.5]decan-1-one

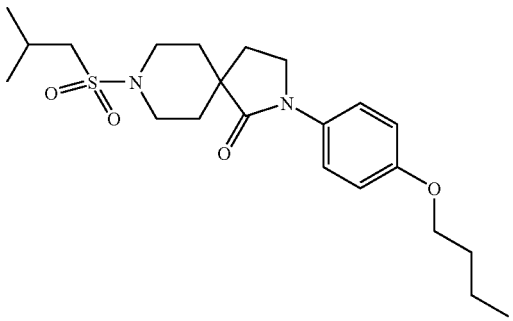

Light brown solid. MS (ESI): 423.23 (MH+). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride and 4-butoxy-aniline.

Example 85

2-(4-sec-Butoxy-phenyl)-8-(2-methyl-propane-1-sulfonyl)-2,8-diaza-spiro[4.5]decan-1-one

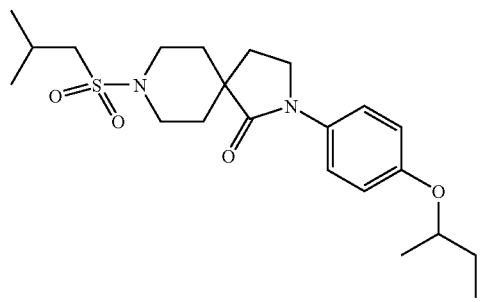

Light brown solid. MS (ESI): 423.23 (MH⁺). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride and 4-sec-butoxy-aniline.

Example 86

8-(2-Methyl-propane-1-sulfonyl)-2-[4-(2,2,2-trifluoro-1-methyl-ethoxy)-phenyl]-2,8-diaza-spiro[4.5]decan-1-one

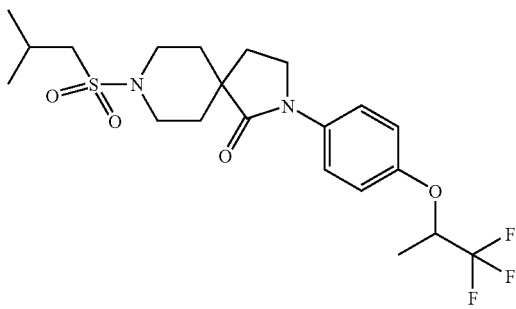

Off-white solid. MS (ESI): 463.18 (MH⁺). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride, 4-(2,2,2-trifluoro-1-methyl-ethoxy)-aniline.

Example 87

2-(4-Isopropoxy-phenyl)-8-(2-trifluoromethoxy-benzenesulfonyl)-2,8-diaza-spiro[4.5]decan-1-one

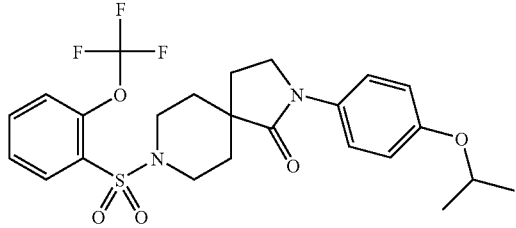

Light brown solid. MS (ESI): 513.16 (MH⁺). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-isopropoxy-aniline.

Example 88

2-(4-Butoxy-phenyl)-8-(2-trifluoromethoxy-benzenesulfonyl)-2,8-diaza-spiro[4.5]decan-1-one

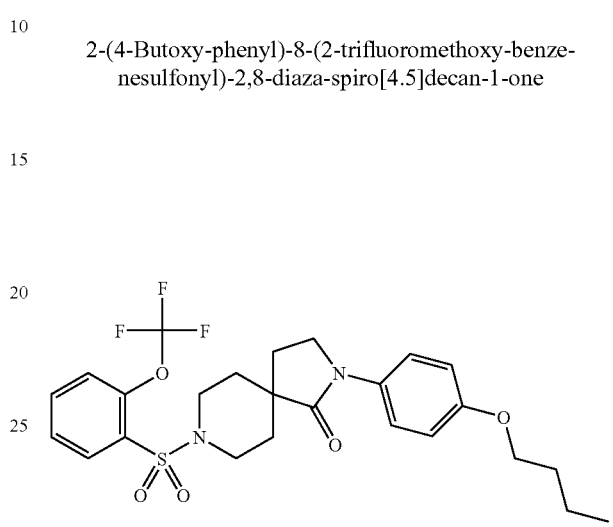

Light brown solid. MS (ESI): 527.18 (MH⁺). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-butoxy-aniline.

Example 89

8-(2-Trifluoromethoxy-benzenesulfonyl)-2-[6-(2,2,2-trifluoro-1-methyl-ethoxy)-pyridin-3-yl]-2,8-diaza-spiro[4.5]decan-1-one

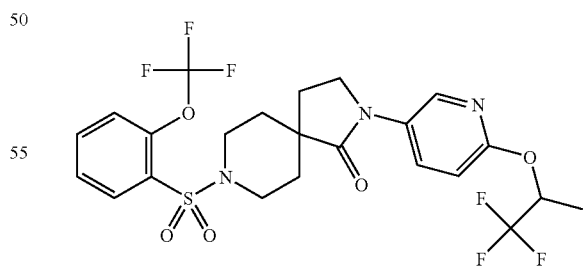

Light brown solid. MS (ESI): 568.13 (MH⁺). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 6-(2,2,2-trifluoro-1-methyl-ethoxy)-pyridin-3-ylamine.

Example 90

2-(4-sec-Butoxy-phenyl)-8-(2-trifluoromethoxy-benzenesulfonyl)-2,8-diaza-spiro[4.5]decan-1-one

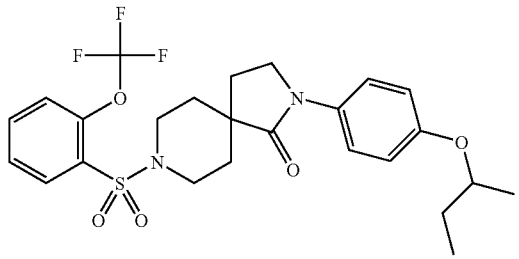

Brown solid. MS (ESI): 527.18 (MH+). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-(sec-buthoxy-aniline.

Example 91

8-(2-Chloro-benzenesulfonyl)-2-(4-vinyl-phenyl)-2,8-diaza-spiro[4.5]decan-1-one

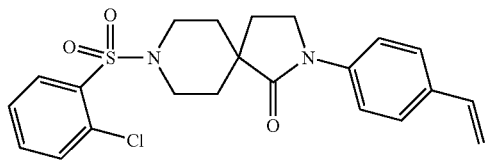

White solid. MS (ESI): 431.3 (MH+). This example was prepared in analogy to example 1 step C) to D) from 4-(2-methoxy-ethyl)-piperidine-4-carboxylic acid ethyl ester (example 1 step B)), 2-chloro-benzenesulfonyl chloride and 4-amino-styrene.

Example 92

8-Cyclobutylmethanesulfonyl-2-(4-isopropoxy-phenyl)-2,8-diaza-spiro[4.5]decan-1-one

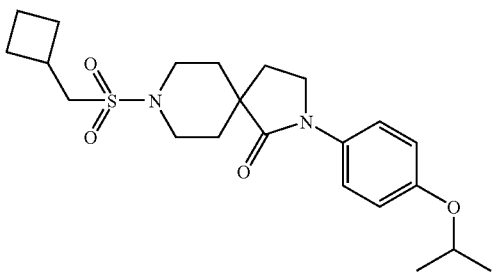

Light brown solid. MS (ESI): 421.21 (MH+). This example was prepared in analogy to example 1 step C) to D) from 4-(2-methoxy-ethyl)-piperidine-4-carboxylic acid ethyl ester (example 1 step B)), cyclobutyl-methanesulfonyl chloride, 4-isopropoxy-aniline.

Example 93

8-Cyclobutylmethanesulfonyl-2-(4-trifluoromethoxy-phenyl)-2,8-diaza-spiro[4.5]decan-1-one

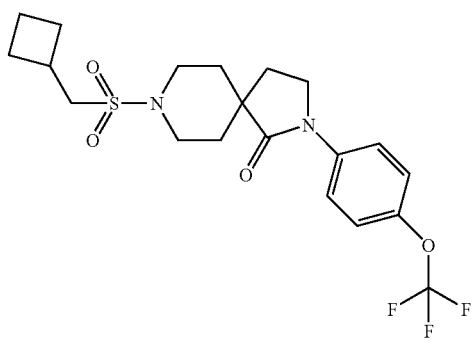

Light brown solid. MS (ESI): 447.15 (MH+). This example was prepared in analogy to example 1 step C) to D) from 4-(2-methoxy-ethyl)-piperidine-4-carboxylic acid ethyl ester (example 1 step B)), cyclobutyl-methanesulfonyl chloride, 4-(trifluoromethoxy)-aniline.

Example 94

2-(4-Cyclopropylmethoxy-phenyl)-8-(2-methyl-propane-1-sulfonyl)-2,8-diaza-spiro[4.5]decan-1-one

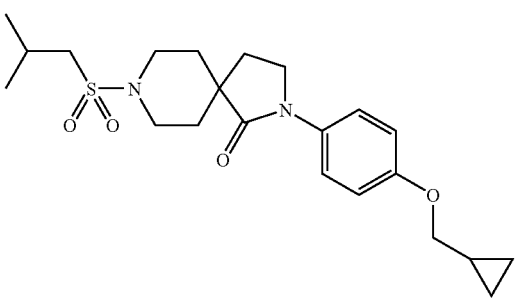

Grey solid. MS (ESI): 421.21 (MH+). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride, 4-cyclopropylmethoxy-aniline.

Example 95

8-Cyclopropanesulfonyl-2-(4-isopropoxy-phenyl)-2,8-diaza-spiro[4.5]decan-1-one

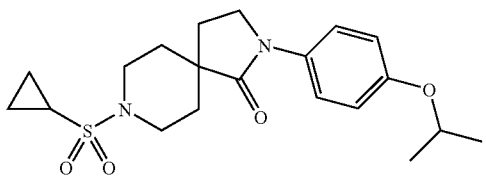

Off-white solid. MS (ESI): 393.18 (MH+). This example was prepared in analogy to example 1 step C) to D) from 4-(2-methoxy-ethyl)-piperidine-4-carboxylic acid ethyl ester (example 1 step B)), cyclopropanesulfonyl chloride, 4-isopropoxy-aniline.

Example 96

8-Cyclopropanesulfonyl-2-(4-trifluoromethoxy-phenyl)-2,8-diaza-spiro[4.5]decan-1-one

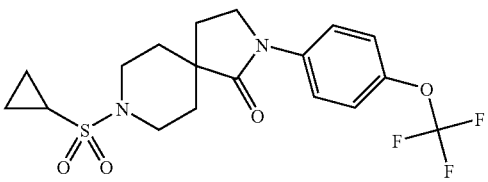

White solid. MS (ESI): 419.12 (MH+). This example was prepared in analogy to example 1 step C) to D) from 4-(2-methoxy-ethyl)-piperidine-4-carboxylic acid ethyl ester (example 1 step B)), cyclopropanesulfonyl chloride, 4-(trifluoromethoxy)-aniline.

Example 97

8-(3,5-Dimethyl-isoxazole-4-sulfonyl)-2-[4-(2,2,2-trifluoro-1-methyl-ethoxy)-phenyl]-2,8-diaza-spiro[4.5]decan-1-one

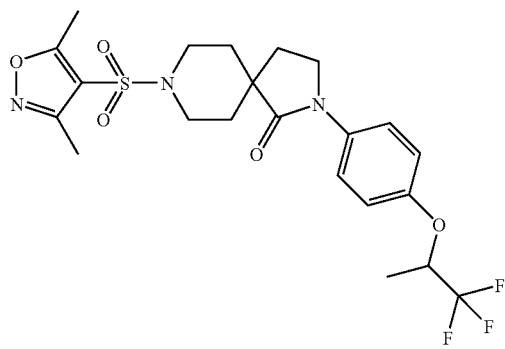

Light brown solid. MS (ESI): 502.16 (MH+). This example was prepared in analogy to example 1 step C) to D) from 4-(2-methoxy-ethyl)-piperidine-4-carboxylic acid ethyl ester (example 1 step B)), 3,5-dimethyl-isoxazole-4-sulfonyl chloride, 4-(2,2,2-trifluoro-1-methyl-ethoxy)-phenylamine.

Example 98

8-Cyclopropanesulfonyl-2-[4-(2,2,2-trifluoro-1-methyl-ethoxy)-phenyl]-2,8-diaza-spiro[4.5]decan-1-one

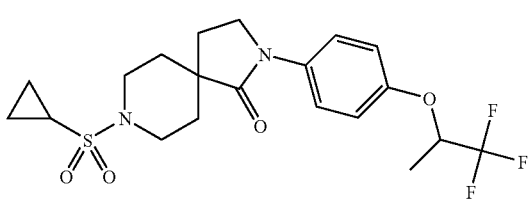

White solid. MS (ESI): 447.15 (MH+). This example was prepared in analogy to example 1 step C) to D) from 4-(2-methoxy-ethyl)-piperidine-4-carboxylic acid ethyl ester (example 1 step B)), cyclopropanesulfonyl chloride, 4-(2,2,2-trifluoro-1-methyl-ethoxy)-phenylamine.

Example 99

8-(2-Trifluoromethoxy-benzenesulfonyl)-2-[4-(2,2,2-trifluoro-1-methyl-ethoxy)-phenyl]-2,8-diaza-spiro[4.5]decan-1-one

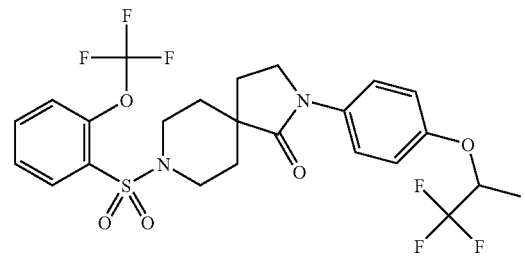

Brown solid. MS (ESI): 567.13 (MH+). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and (4-(2,2,2-trifluoro-1-methyl-ethoxy)-phenylamine.

Example 100

8-(2-Trifluoromethyl-benzenesulfonyl)-2-[4-(2,2,2-trifluoro-1-methyl-ethoxy)-phenyl]-2,8-diaza-spiro[4.5]decan-1-one

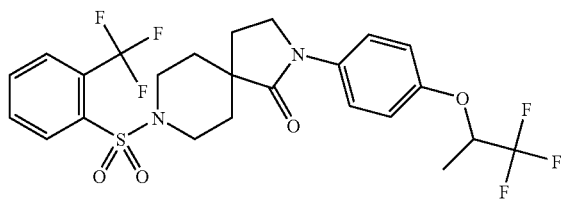

Light brown solid. MS (ESI): 551.14 (MH⁺). This example was prepared in analogy to example 1 step C) to D) from 4-(2-methoxy-ethyl)-piperidine-4-carboxylic acid ethyl ester (example 1 step B)), 2-trifluoromethyl-benzenesulfonyl chloride and 4-(2,2,2-trifluoro-1-methyl-ethoxy)-phenylamine.

Example 101

2-(4-Isopropoxy-phenyl)-8-(2-trifluoromethyl-benzenesulfonyl)-2,8-diaza-spiro[4.5]decan-1-one

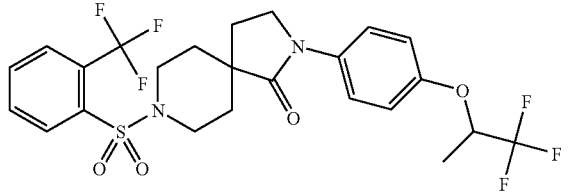

Light brown solid. MS (ESI): 551.14 (MH⁺). This example was prepared in analogy to example 1 step C) to D) from 4-(2-methoxy-ethyl)-piperidine-4-carboxylic acid ethyl ester (example 1 step B)), 2-trifluoromethyl-benzenesulfonyl chloride, 4-(2,2,2-trifluoro-1-methyl-ethoxy)-phenylamine.

Example 102

8-(2-Methyl-propane-1-sulfonyl)-2-[4-(3,3,3-trifluoro-propoxy)-phenyl]-2,8-diaza-spiro[4.5]decan-1-one

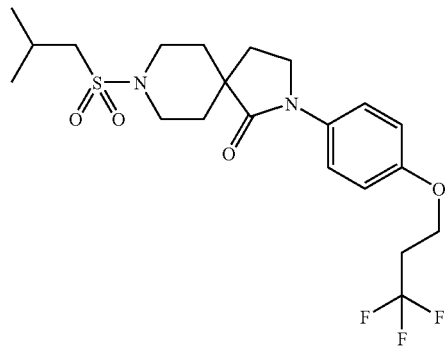

Off-white solid. MS (ESI): 463.2 (MH⁺). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride, 4-(3,3,3-trifluoro-propoxy)-phenylamine.

Preparation of 4-(3,3,3-trifluoro-propoxy)-phenylamine used in the reaction above:

i) To a solution of a 3,3,3-trifluoro-propan-1-ol (6.22 g) in acetonitrile (200 ml) under an argon atmosphere was added was added at RT 1-fluoro-4-nitro-benzene (10.057 g) and Cs₂CO₃ (28.725 g) and the mixture was heated at 100° C. for 18 h. The reaction mixture was cooled to RT, partitioned between AcOEt and ice water, the layers were separated dried over Na₂SO₄, the solvent was evaporated and the residue purified by flash chromatography over silica gel (eluent: AcOEt/heptane: gradient 3 to 5%) to give 1-nitro-4-(3,3,3-trifluoro-propoxy)-benzene as light yellow liquid (3.5 g). MS (EI): 235 (M⁺).

ii) (1-nitro-4-(3,3,3-trifluoro-propoxy)-benzene (1.4 g) in methanol (50 ml) was hydrogenated over Pd/C at RT and at atmospheric pressure for 12 h as usual. The catalyst was filtered off and the solvent removed in vacuo to give the desired 4-(3,3,3-trifluoro-propoxy)-phenylamine (0.45 g) as a light brown solid. MS (ESI): 206.1 (MH⁺).

Example 103

8-(2-Trifluoromethoxy-benzenesulfonyl)-2-[4-(3,3,3-trifluoro-propoxy)-phenyl]-2,8-diaza-spiro[4.5]decan-1-one

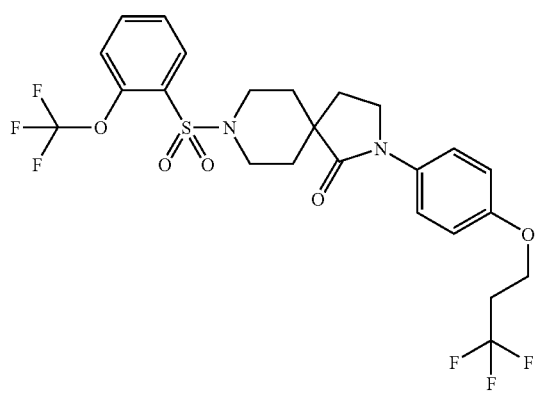

Off-white crystalline solid. MS (ESI): 567.2 (MH⁺). P This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-(3,3,3-trifluoro-propoxy)-phenylamine.

Example 104

2-(4-Iodo-phenyl)-8-(2-trifluoromethoxy-benzene-sulfonyl)-2,8-diaza-spiro[4.5]decan-1-one

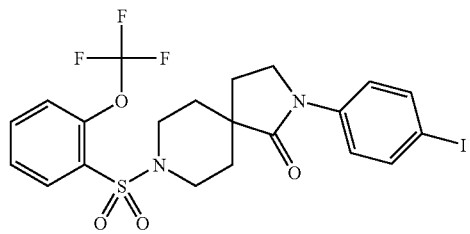

White solid. MS (ESI): 571.0 (MH+). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-iodo-aniline.

Example 105

2-[4-(2-Methoxy-ethyl)-phenyl]-8-(2-trifluoromethoxy-benzenesulfonyl)-2,8-diaza-spiro[4.5]decan-1-one

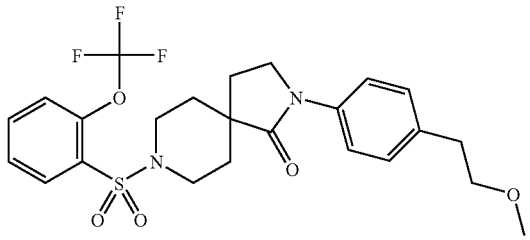

Light yellow solid. MS (ESI): 513.3 (MH+). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-(2-methoxy-ethyl)-phenylamine.

Example 106

2-[4-(2-Methoxy-ethoxy)-phenyl]-8-(2-trifluoromethoxy-benzenesulfonyl)-2,8-diaza-spiro[4.5]decan-1-one

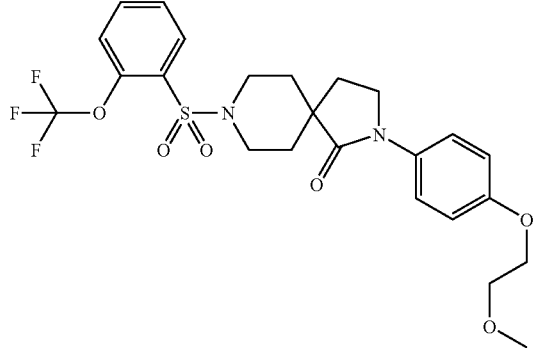

Light brown solid. MS (ESI): 529.16 (MH+). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-(2-methoxy-ethoxy)-phenylamine.

Example 107

2-[4-(3-Methoxy-propoxy)-phenyl]-8-(2-methyl-propane-1-sulfonyl)-2,8-diaza-spiro[4.5]decan-1-one

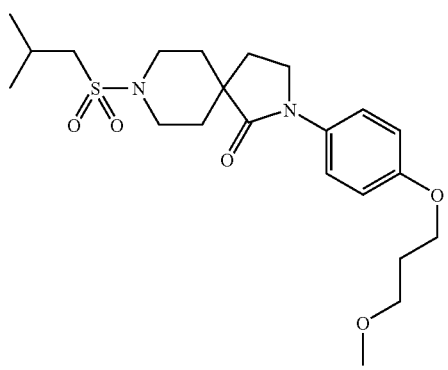

Off-white solid. MS (ESI): 439.22 (MH+). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride, 4-(3-methoxy-propoxy)-phenylamine.

Example 108

2-[4-(2-Methoxy-1,1-dimethyl-ethyl)-phenyl]-8-(2-methyl-propane-1-sulfonyl)-2,8-diaza-spiro[4.5]decan-1-one

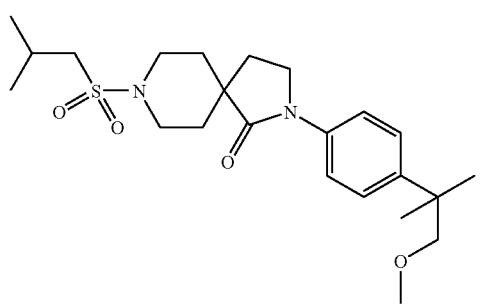

Light yellow solid. MS (ESI): 437.24 (MH$^+$). This example was prepared in analogy to example 1 step C) to D) from 4-(2-methoxy-ethyl)-piperidine-4-carboxylic acid ethyl ester (example 1 step B)), 2-methyl-propane-1-sulfonyl chloride, 4-(2-methoxy-1,1-dimethyl-ethyl)-phenylamine (synthesis: Ch. Tegley et al, WO 2005 021532).

Example 109

2-[4-(3-Methoxy-propoxy)-phenyl]-8-(2-trifluoromethoxy-benzenesulfonyl)-2,8-diaza-spiro[4.5]decan-1-one

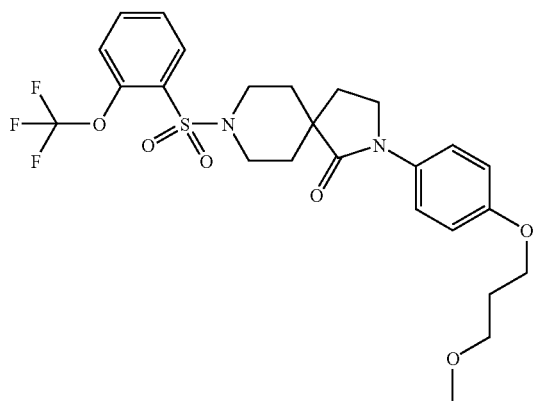

Off-white solid. MS (ESI): 543.17 (MH$^+$). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-(3-methoxy-propoxy)-phenylamine.

Example 110

2-[4-(2-Methoxy-1,1-dimethyl-ethyl)-phenyl]-8-(2-trifluoromethoxy-benzenesulfonyl)-2,8-diaza-spiro[4.5]decan-1-one

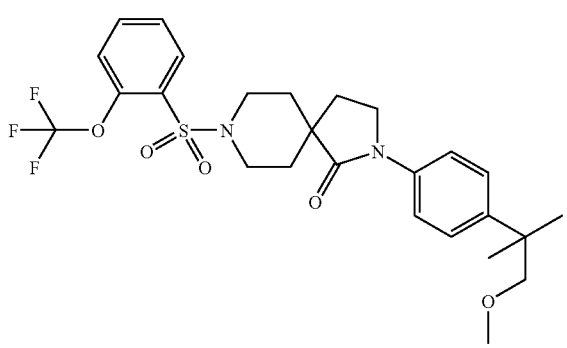

Off-white crystalline solid. MS (ESI): 541.19 (MH$^+$). This example was prepared in analogy to example 1 step C) to D) from 4-(2-methoxy-ethyl)-piperidine-4-carboxylic acid ethyl ester (example 1 step B)), 2-trifluoromethoxy-benzenesulfonyl chloride and 4-(2-methoxy-1,1-dimethyl-ethyl)-phenylamine.

Example 111

8-(3,5-Dimethyl-isoxazole-4-sulfonyl)-2-(4-isopropoxy-phenyl)-2,8-diaza-spiro[4.5]decan-1-one

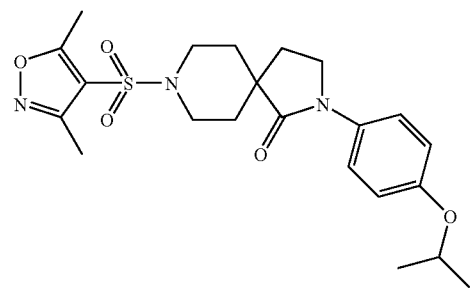

Off-white solid. MS (ESI): 448.19 (MH$^+$). This example was prepared in analogy to example 1 step C) to D) from 4-(2-methoxy-ethyl)-piperidine-4-carboxylic acid ethyl ester (example 1 step B)), 3,5-dimethyl-isoxazole-4-sulfonyl chloride, 4-isopropxy-aniline.

Example 112

8-(3,5-Dimethyl-isoxazole-4-sulfonyl)-2-[4-(2-methoxy-1,1-dimethyl-ethyl)-phenyl]-2,8-diaza-spiro[4.5]decan-1-one

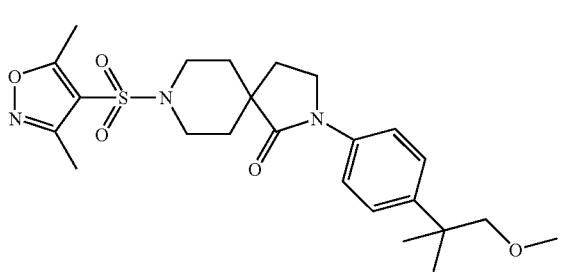

Off-white solid. MS (ESI): 476.22 (MH$^+$). This example was prepared in analogy to example 1 step C) to D) from 4-(2-methoxy-ethyl)-piperidine-4-carboxylic acid ethyl ester (example 1 step B)), 3,5-dimethyl-isoxazole-4-sulfonyl chloride, 4-(2-methoxy-1,1-dimethyl-ethyl)-phenylamine.

Example 113

8-(2,2-Dichloro-1-methyl-cyclopropanecarbonyl)-2-[4-(2,2,2-trifluoro-1-methyl-ethoxy)-phenyl]-2,8-diaza-spiro[4.5]decan-1-one

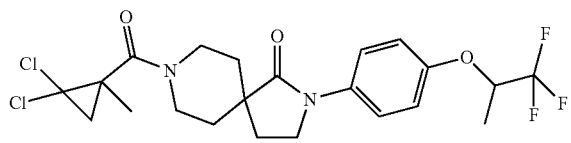

Off-white crystalline solid. MS (ESI): 493.2 (MH+). This example was prepared in analogy to example 13 step A) to B) from 4-(2-methoxy-ethyl)-piperidine-4-carboxylic acid ethyl ester (example 1 step B)), 2,2-dichloro-1-methyl-cyclopropanecarboxylic acid, 4-(2,2,2-trifluoro-1-methyl-ethoxy)-phenylamine.

Example 114

8-(2-Chloro-benzenesulfonyl)-2-[6-(2,2,2-trifluoro-1-methyl-ethoxy)-pyridin-3-yl]-2,8-diaza-spiro[4.5]decan-1-one (rac)

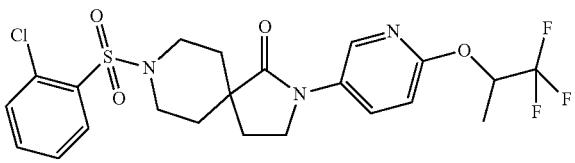

Off-white crystalline solid. MS (ESI): 518.0 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 6-(2,2,2-trifluoro-1-methyl-ethoxy)-pyridin-3-ylamine.

Example 115

8-(2-Chloro-benzenesulfonyl)-2-[4-(2,2,2-trifluoro-ethoxy)-phenyl]-2,8-diaza-spiro[4.5]decan-1-one

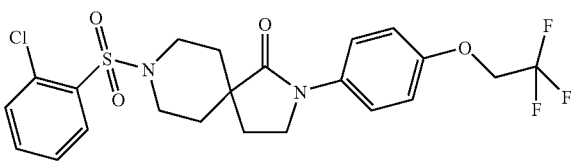

Light brown crystalline solid. MS (ESI): 503.1 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 4-(2,2,2-trifluoro-ethoxy)-phenylamine.

Example 116

8-(2-Chloro-benzenesulfonyl)-2-[6-(3,3,3-trifluoro-propoxy)-pyridin-3-yl]-2,8-diaza-spiro[4.5]decan-1-one

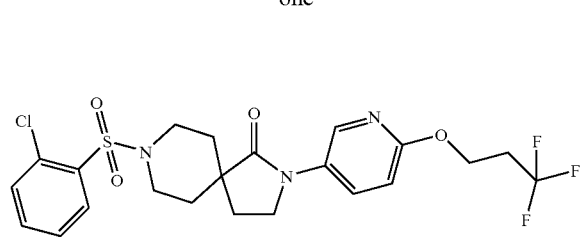

Brown crystalline solid. MS (ESI): 518.1 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 6-(3,3,3-trifluoro-propoxy)-pyridin-3-ylamine.

Preparation of the 6-(3,3,3-trifluoro-propoxy)-pyridin-3-ylamine used in above reaction:

i) To a solution of 2-chloro-5-nitro-pyridine (2.5 g) and 1 3,3,3-trifluoro-propan-1-ol (1.097 g) in DMF (50 ml) under an argon atmosphere was added under ice cooling NaH (0.826 g, 55% suspension in oil). The mixture was stirred for 3 h at RT then partitioned between diethyl ether and water, The layers were separated dried over $Na_2SO_4$ and the solvent was evaporated off to give crude 5-nitro-2-(3,3,3-trifluoro-propoxy)-pyridine as dark brown oil that was used in the next step without further purification.

ii) 5-nitro-2-(3,3,3-trifluoro-propoxy)-pyridine (2.37 g) in methanol (40 ml) was hydrogenated over Pd/C (10%, 350 mg) at RT and at atmospheric pressure for 12 h. The catalyst was then filtered off and the solvent removed in vacuo to give the desired 6-(3,3,3-trifluoro-propoxy)-pyridin-3-ylamine (2.37 g) as a dark brown oil that was directly used without further purification.

Example 117

8-Benzenesulfonyl-2-[6-(2,2,2-trifluoro-ethoxy)-pyridin-3-yl]-2,8-diaza-spiro[4.5]decan-1-one

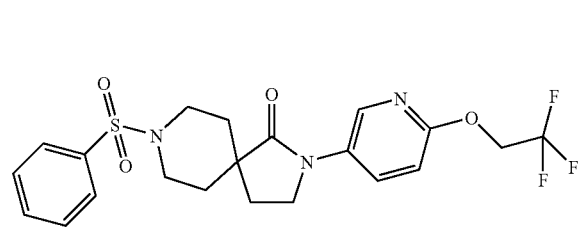

Light brown crystalline solid. MS (ESI): 470.3. (MH+). This example was prepared in analogy to example 1 step C) to D) from 4-(2-methoxy-ethyl)-piperidine-4-carboxylic acid ethyl ester (example 1 step B)), benzenesulfonyl chloride and 6-(2,2,2-trifluoro-ethoxy)-pyridin-3-ylamine.

Example 118

8-Benzenesulfonyl-2-[2-(2,2,2-trifluoro-ethoxy)-pyrimidin-5-yl]-2,8-diaza-spiro[4.5]decan-1-one

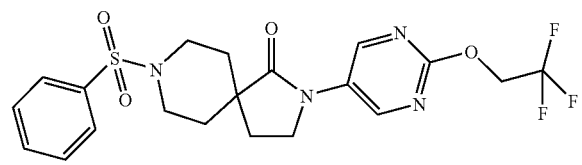

Brown crystalline solid. MS (ESI): 471.3. (MH+). This example was prepared in analogy to example 1 step C) to D) from 4-(2-methoxy-ethyl)-piperidine-4-carboxylic acid ethyl ester (example 1 step B)), benzenesulfonyl chloride and 2-(2,2,2-trifluoro-ethoxy)-pyrimidin-5-ylamine.

2-(2,2,2-trifluoro-ethoxy)-pyrimidin-5-ylamine, used in the reaction above was prepared in analogy to the amine of example 116 steps i) to ii) from 2-chloro-5-nitro-pyrimidine (2 g), 2,2,2-trifluoro-ethanol (1.63 g) and subsequent hydrogenation as a brown oil (2.175 g) which was directly used in the next step.

Example 119

8-(2-Chloro-benzenesulfonyl)-2-[6-(2,2,2-trifluoro-ethoxy)-pyridin-3-yl]-2,8-diaza-spiro[4.5]decan-1-one

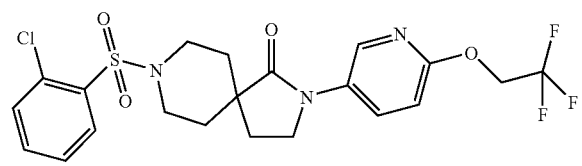

Off-white crystalline solid. MS (ESI): 504.1. (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chlorid and 6-(2,2,2-trifluoro-ethoxy)-pyridin-3-ylamine.

Example 120

8-(3,3-Dimethyl-butyryl)-2-[4-(2,2,2-trifluoro-ethoxy)-phenyl]-2,8-diaza-spiro[4.5]decan-1-one

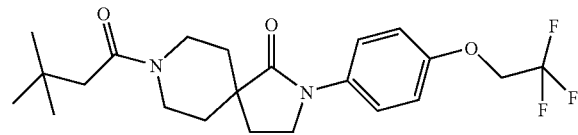

Off-white crystalline solid. MS (ESI): 427.3 (MH+). This example was prepared in analogy to example 7 step A) to B) from 4-(2-methoxy-ethyl)-piperidine-4-carboxylic acid ethyl ester (example 1 step B)), tert-butyl acetyl chloride and 4-(2,2,2-trifluoro-ethoxy)-phenylamine.

Example 121

8-(2,2-Dichloro-1-methyl-cyclopropanecarbonyl)-2-[4-(2,2,2-trifluoro-ethoxy)-phenyl]-2,8-diaza-spiro[4.5]decan-1-one

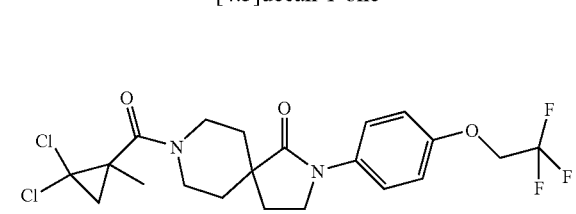

Brown crystalline solid. MS (ESI): 480.2 (MH+). This example was prepared in analogy to example 13 step A) to B) from 4-(2-methoxy-ethyl)-piperidine-4-carboxylic acid ethyl ester (example 1 step B)), 2,2-dichloro-1-methyl-cyclopropanecarboxylic acid, 4-(2,2,2-trifluoro-ethoxy)-phenylamine.

Example 122

8-(3,3-Dimethyl-butyryl)-2-[6-(2,2,2-trifluoro-ethoxy)-pyridin-3-yl]-2,8-diaza-spiro[4.5]decan-1-one

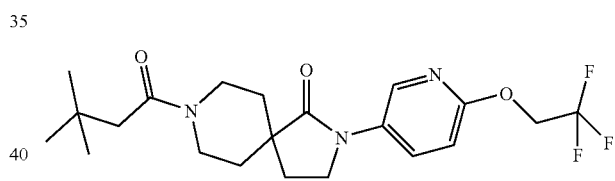

Brown crystalline solid. MS (ESI): 428.4 (MH+). This example was prepared in analogy to example 7 step A) to B) from 4-(2-methoxy-ethyl)-piperidine-4-carboxylic acid ethyl ester (example 1 step B)), tert-butyl acetyl chloride and 6-(2,2,2-trifluoro-ethoxy)-pyridin-3-ylamine.

Example 123

8-(3,3-Dimethyl-butyryl)-2-[4-(2,2,2-trifluoro-1-methyl-ethoxy)-phenyl]-2,8-diaza-spiro[4.5]decan-1-one

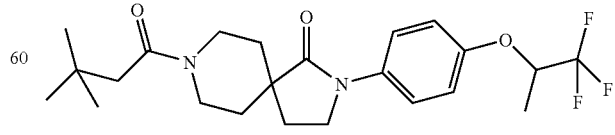

White crystalline solid. MS (ESI): 441.3 (MH+). This example was prepared in analogy to example 7 step A) to B) from 4-(2-methoxy-ethyl)-piperidine-4-carboxylic acid ethyl ester (example 1 step B)), tert-butyl acetyl chloride and 4-(2,2,2-trifluoro-1-methyl-ethoxy)-phenylamine.

Example 124

8-(2-Chloro-benzenesulfonyl)-2-(2-ethyl-2H-indazol-5-yl)-2,8-diaza-spiro[4.5]decan-1-one

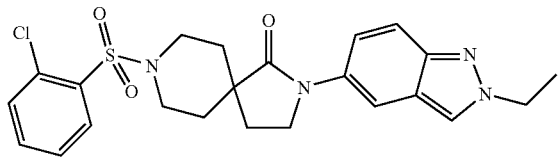

Off-white crystalline solid. MS (ESI): 473.1 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 2-ethyl-2H-indazol-5-ylamine (for synthesis: Kamel et al.; Journal fuer Praktische Chemie, 31; 1966; 100).

Example 125

8-(2-Chloro-benzenesulfonyl)-2-[4-(2,2,2-trifluoro-1-methyl-ethoxy)-phenyl]-2,8-diaza-spiro[4.5]decan-1-one

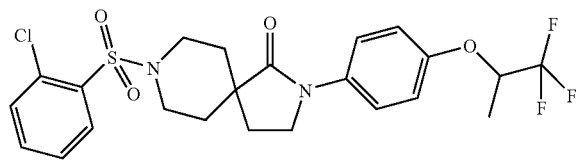

Light brown crystalline solid. MS (ESI): 517.1. (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 4-(2,2,2-trifluoro-1-methyl-ethoxy)-phenylamine.

Example 126

8-(2-Chloro-benzenesulfonyl)-2-(1-ethyl-1H-indazol-5-yl)-2,8-diaza-spiro[4.5]decan-1-one

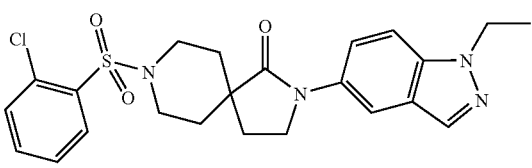

Light brown crystalline solid. MS (ESI): 473.2 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 1-ethyl-1H-indazol-5-ylamine (for synthesis: Chakrabarty et al. Tetrahedron; 64; 2008; 6711).

Example 127

8-(2-Chloro-benzenesulfonyl)-2-(2-methyl-benzothiazol-6-yl)-2,8-diaza-spiro[4.5]decan-1-one

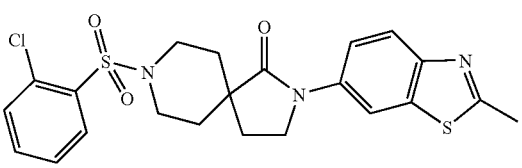

Light yellow crystalline solid. MS (ESI): 476.1 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 2-methyl-benzothiazol-6-ylamine.

Example 128

8-(2-Chloro-benzenesulfonyl)-2-(4-cyclopentyloxy-phenyl)-2,8-diaza-spiro[4.5]decan-1-one

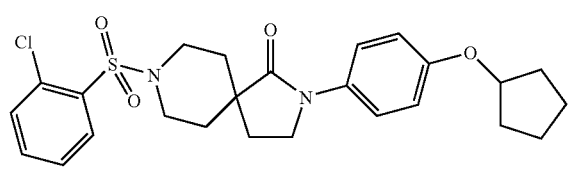

Light brown crystalline solid. MS (ESI): 489.3 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 4-cyclopentyloxy-phenylamine (synthesis: Fortin et al.; Bioorganic and Medicinal Chemistry; 16; 2008; 7477).

Example 129

8-(2-Chloro-benzenesulfonyl)-2-[4-(tetrahydro-furan-3-yloxy)-phenyl]-2,8-diaza-spiro[4.5]decan-1-one

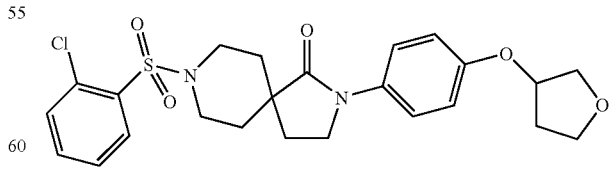

Off-white crystalline solid. MS (ESI): 491.3 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 4-(tetrahydro-furan-3-yloxy)-phenylamine.

Preparation of the starting material, (4-(tetrahydro-furan-3-yloxy)-phenylamine:

i) To a solution of 1-fluoro-4-nitro-benzene (2.82 g) and tetrahydro-furan-3-ol (1.85 g) in DMF: (20 ml) under an argon atmosphere was added under ice cooling NaH (0.916 g, 55% suspension in oil) and the mixture was stirred for 3 h at RT. It was then partitioned between diethyl ether and water, the layers were separated, dried over $Na_2SO_4$ and the solvent was evaporated off to give 3-(4-nitro-phenoxy)-tetrahydro-furan as a brown oil (3.75 g) that was used in the next step without further purification.

ii) 3-(4-nitro-phenoxy)-tetrahydro-furan (3.75 g) in ethanol (30 ml) was hydrogenated over Pd/C (10%, 500 mg) at RT and atmospheric for 12 h. The catalyst was filtered off and the solvent removed in vacuo to give the desired 4-(tetrahydro-furan-3-yloxy)-phenylamine (3.75 g) as a brown oil which was purified by chromatography on silica gel (AcOEt/heptane 1:1) and directly used in the next step.

Example 130

8-(2-Chloro-benzenesulfonyl)-2-(1-methyl-1H-indazol-5-yl)-2,8-diaza-spiro[4.5]decan-1-one

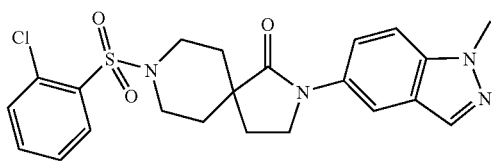

Light brown crystalline solid. MS (ESI): 459.4 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 1-methyl-1H-indazol-5-ylamine (synthesis: Fries et al, Justus Liebigs Annalen der Chemie; 454; 1927; 306).

Example 131

8-(2-Chloro-benzenesulfonyl)-2-(2-methyl-2H-indazol-5-yl)-2,8-diaza-spiro[4.5]decan-1-one

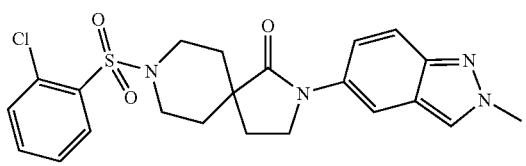

Off-white crystalline solid. MS (ESI): 459.3 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 2-methyl-2H-indazol-5-ylamine (synthesis: Boyer, et al; Journal of Chemical Research, Miniprint; English; 11; 1990; 2601).

Example 132

8-(2-Chloro-benzenesulfonyl)-2-[4-(pyridin-3-yloxy)-phenyl]-2,8-diaza-spiro[4.5]decan-1-one

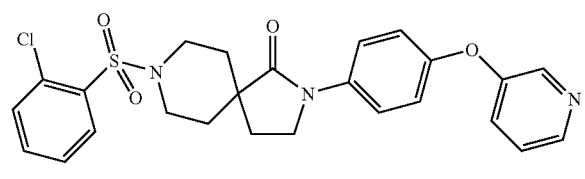

Brown crystalline solid. MS (ESI): 498.2 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 4-(pyridin-3-yloxy)-phenylamine (synthesis: Yoneda et al; Yakugaku Zasshi; 77; 1957; 944; Chem. Abstr.; 1958; 2855).

Example 133

8-(2-Chloro-benzenesulfonyl)-2-(4-cyclopentylmethoxy-phenyl)-2,8-diaza-spiro[4.5]decan-1-one

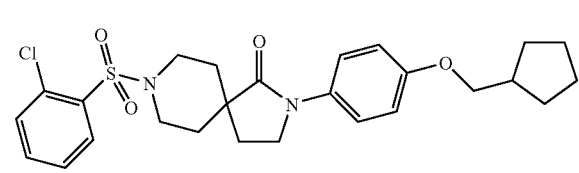

Light Brown crystalline solid. MS (ESI): 503.2 (MH+). This example was prepared in analogy to example 1 step C) to D) from 4-(2-methoxy-ethyl)-piperidine-4-carboxylic acid ethyl ester (example 1 step B)), 2-chlorobenzenesulfonyl chloride and 4-cyclopentylmethoxy-phenylamine.

Example 134

{4-[8-(2-Chloro-benzenesulfonyl)-1-oxo-2,8-diaza-spiro[4.5]dec-2-yl]-phenyl}-acetic acid ethyl ester

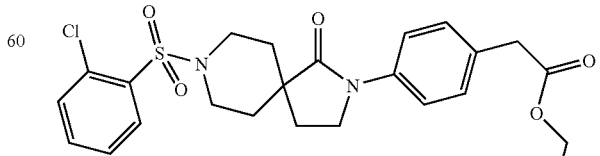

Step A): 1-(2-Chloro-benzenesulfonyl)-4-(2-methoxy-ethyl)-piperidine-4-carboxylic acid

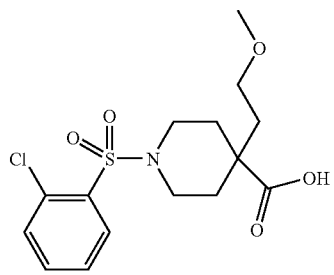

1-(2-Chloro-benzenesulfonyl)-4-(2-methoxy-ethyl)-piperidine-4-carboxylic acid ethyl ester (0.5 g) was dissolved in MeOH (8 ml), 3M aqueous NaOH (6.41 ml) was added and the mixture was stirred at 5 h at 60° C. to complete the reaction. The solvent was evaporated off, the residue was acidified with 3M aqueous HCl and extracted with dichloromethane. The layers were separated, the organic phase was washed with brine, dried over sodium sulphate and concentrated to give the desired 1-(2-chloro-benzenesulfonyl)-4-(2-methoxy-ethyl)-piperidine-4-carboxylic acid (0.519 g) as a light brown solid. MS (ESI): 360.1 (M-H)⁻.

Step B): (4-{[1-(2-Chloro-benzenesulfonyl)-4-(2-methoxy-ethyl)-piperidine-4-carbonyl]-amino}-phenyl)-acetic acid ethyl ester

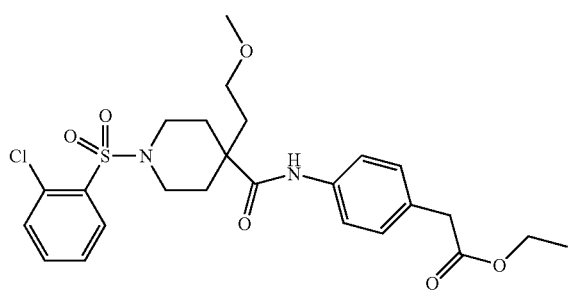

1-(2-Chloro-benzenesulfonyl)-4-(2-methoxy-ethyl)-piperidine-4-carboxylic acid (2.82 g) were dissolved in THF (30 ml) under an argon atmosphere at RT and then sequentially treated with O-(7-azabenzotriazol-1-yl)-N,N,N',N'-tetramethyluronium hexafluorophosphate (HATU) (3.26 g), (4-amino-phenyl)-acetic acid ethyl ester (1.536 g) and N-methyl morpholine (1.04 ml). The reaction mixture was stirred 12 h at RT, and 1 h at reflux to complete the reaction. The mixture was partitioned between AcOEt and 1N HCl/water, the layers were separated; the organic layer was dried over sodium sulphate and then removed in vacuo. The residue was purified by chromatography on silica gel (CH₂Cl₂/AcOEt, 19/1 to 9/1) to give the desired (4-{[1-(2-chloro-benzenesulfonyl)-4-(2-methoxy-ethyl)-piperidine-4-carbonyl]-amino}-phenyl)-acetic acid ethyl ester (2.47 g) which was directly used in the next step.

Step C): {4-[8-(2-Chloro-benzenesulfonyl)-1-oxo-2,8-diaza-spiro[4.5]dec-2-yl]-phenyl}-acetic acid ethyl ester (4-{[1-(2-Chloro-benzenesulfonyl)-4-(2-methoxy-ethyl)-piperidine-4-carbonyl]-amino}-phenyl)-acetic acid ethyl ester (2.47 g) in toluene (50 ml) was treated with dimethylaluminium chloride in heptane (1 molar, 5 ml) under an argon atmosphere at RT, and then refluxed for 3 hours. The reaction was then cooled to RT partitioned between AcOEt and 1N aqueous HCl/water. The layers were separated, the organic layer dried over sodium sulphate and the solvent was removed in vacuo to give the desired {4-[8-(2-chloro-benzenesulfonyl)-1-oxo-2,8-diaza-spiro[4.5]dec-2-yl]-phenyl}-acetic acid ethyl ester as a light brown solid. MS (EI): 491.2 (M⁺).

Example 135

{4-[8-(2-Chloro-benzenesulfonyl)-1-oxo-2,8-diaza-spiro[4.5]dec-2-yl]-phenyl}-acetonitrile

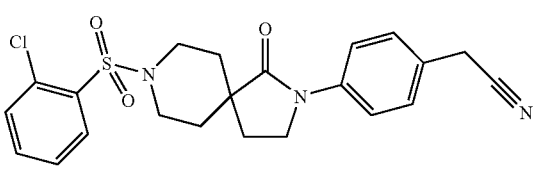

This material was prepared from (4-{[1-(2-Chloro-benzenesulfonyl)-4-(2-methoxy-ethyl)-piperidine-4-carbonyl]-amino}-phenyl)-acetic acid ethyl ester, compound of example 134) in the following way:

First, (4-{[1-(2-chloro-benzenesulfonyl)-4-(2-methoxy-ethyl)-piperidine-4-carbonyl]-amino}-phenyl)-acetic acid ethyl ester (1.94 g) was hydrolysed using standard procedures (THF/MeOH/1M aqueous LiOH, 10 ml each, RT and 2 h reaction time) to the corresponding acid (1.79 g). The acid was then converted to the corresponding amide (1.76 g) using standard procedures: THF (30 ml), CDI (690 mg), reflux for 20 min, then addition of a large excess of ammonium cabamate, 1 h reflux to drive the reaction to completion. The amide (1.76 g) was then dehydrated using standard procedures: treatment with trifluoroacetic anhydride (0.645 ml) in CH₂Cl₂ (30 ml) for 12 h at RT to give the desired {4-[8-(2-chloro-benzenesulfonyl)-1-oxo-2,8-diaza-spiro[4.5]dec-2-yl]-phenyl}-acetonitrile (1.69 g) as a white crystalline solid. MS (ESI): 444.3 (MH⁺).

Example 136

8-(2-Chloro-benzenesulfonyl)-2-[4-(5-methyl-[1,2,4]oxadiazol-3-ylmethyl)-phenyl]-2,8-diaza-spiro[4.5]decan-1-one

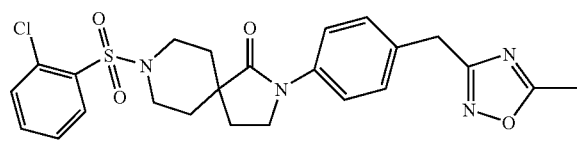

The material was prepared in the following way from {4-[8-(2-chloro-benzenesulfonyl)-1-oxo-2,8-diaza-spiro[4.5]dec-2-yl]-phenyl}-acetonitrile, compound of example 135):

Step A) Conversion of {4-[8-(2-Chloro-benzenesulfonyl)-1-oxo-2,8-diaza-spiro[4.5]dec-2-yl]-phenyl}-acetonitrile to the corresponding N-hydroxy-acatamidine This was achieved using standard literature procedures by heating above nitrile (1 g) in MeOH (20 ml) with hydroxyalamine hydrochloride (695 mg) and NaHCO$_3$ (840 mg) for 6 h to give after aqueous work up the desired 2-{4-[8-(2-chloro-benzenesulfonyl)-1-oxo-2,8-diaza-spiro[4.5]dec-2-yl]-phenyl}-N-hydroxy-acetamidine as a white foam which was directly used in the next step.

Step B) 8-(2-Chloro-benzenesulfonyl)-2-[4-(5-methyl-[1,2,4]oxadiazol-3-ylmethyl)-phenyl]-2,8-diaza-spiro[4.5]decan-1-one Above 2-{4-[8-(2-chloro-benzenesulfonyl)-1-oxo-2,8-diaza-spiro[4.5]dec-2-yl]-phenyl}-N-hydroxy-acetamidine (150 mg) were treated at RT with acetic anhydride (40 ml) and then refluxed for 30 minutes. The reaction mixture was concentrated in vacuo, the residue purified by chromatography on silica gel to give the desired 8-(2-chloro-benzenesulfonyl)-2-[4-(5-methyl-[1,2,4]oxadiazol-3-ylmethyl)-phenyl]-2,8-diaza-spiro[4.5]decan-1-one as a light yellow crystalline solid. MS (ESI): 502.1 (MH$^+$).

Example 137

8-(2-Chloro-benzenesulfonyl)-2-[4-(5-methyl-[1,3,4]oxadiazol-2-ylmethyl)-phenyl]-2,8-diaza-spiro[4.5]decan-1-one

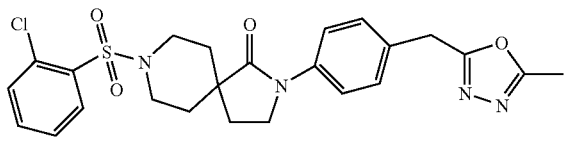

The material was prepared in the following way from {-4-[8-(2-chloro-benzenesulfonyl)-1-oxo-2,8-diaza-spiro[4.5]dec-2-yl]-phenyl}-acetonitrile, compound of example 135):

Step A) Conversion of {4-[8-(2-Chloro-benzenesulfonyl)-1-oxo-2,8-diaza-spiro[4.5]dec-2-yl]-phenyl}-acetonitrile to 8-(2-chloro-benzenesulfonyl)-2-[4-(1H-tetrazol-5-ylmethyl)-phenyl]-2,8-diaza-spiro[4.5]decan-1-one According to established literature procedures (e.g., Peet et al, J. Heterocylic Chem 1989, 23, 713), on treatment of {-4-[8-(2-chloro-benzenesulfonyl)-1-oxo-2,8-diaza-spiro[4.5]dec-2-yl]-phenyl}-acetonitrile (700 mg) with sodium azide (530 mg) and ammonium chloride (650 mg) in MeOH (15 ml), subsequent heating at reflux for 12 h and usual aqueous work up there was obtained the desired tetrazole (403 mg) which was directly used in the next step.

Step B) 8-(2-Chloro-benzenesulfonyl)-2-[4-(5-methyl-[1,3,4]oxadiazol-2-ylmethyl)-phenyl]-2,8-diaza-spiro[4.5]decan-1-one This material was obtained essentially following a procedure described in the literature (Jurisic et al, Synth. Comm. 1994, p 1575) from above 8-(2-chloro-benzenesulfonyl)-2-[4-(1H-tetrazol-5-ylmethyl)-phenyl]-2,8-diaza-spiro[4.5]decan-1-one (135 mg) on treatment with acetic anhydride (2 ml), in CH$_2$Cl$_2$ (2 ml), heating at reflux for 30 minutes and subsequent usual aqueous work-up to give the desired 8-(2-chloro-benzenesulfonyl)-2-[4-(5-methyl-[1,3,4]oxadiazol-2-ylmethyl)-phenyl]-2,8-diaza-spiro[4.5]decan-1-one (133 mg) as a light brown crystalline solid. MS (ESI): 501.1 (MH$^+$).

Example 138

8-(2-Chloro-benzenesulfonyl)-2-[4-(5-trifluoromethyl-[1,3,4]oxadiazol-2-ylmethyl)-phenyl]-2,8-diaza-spiro[4.5]decan-1-one

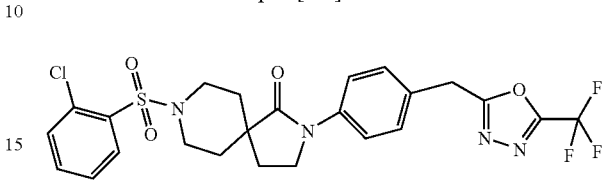

This material was obtained in analogy to example 137 step B) from 8-(2-chloro-benzenesulfonyl)-2-[4-(1H-tetrazol-5-ylmethyl)-phenyl]-2,8-diaza-spiro[4.5]decan-1-one (167 mg), material of example 137 step A) and trifluoroacetic anhydride (2 ml) to give the desired 8-(2-chloro-benzenesulfonyl)-2-[4-(5-trifluoromethyl-[1,3,4]oxadiazol-2-ylmethyl)-phenyl]-2,8-diaza-spiro[4.5]decan-1-one (183 mg) as light brown crystalline solid. MS (ESI): 555.1 (MH$^+$).

Example 139

8-(Neopentylsulfonyl)-2-(4-(3,3,3-trifluoropropoxy)phenyl)-2,8-diazaspiro[4.5]decan-1-one

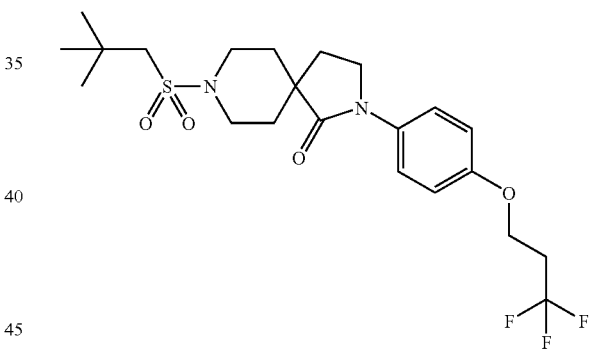

This material was prepared according to example 1 steps C) to D) from 4-(2-methoxy-ethyl)-piperidine-4-carboxylic acid ethyl ester 2,2-dimethyl-propane-1-sulfonyl chloride, 4-(3,3,3-trifluoro-propoxy)-phenylamine as white solid. MS (ESI): 477.2 (MH$^+$).

Example 140

8-(2-Chloro-benzenesulfonyl)-2-(4-methane sulfonyl-phenyl)-2,8-diaza-spiro[4.5]decan-1-one

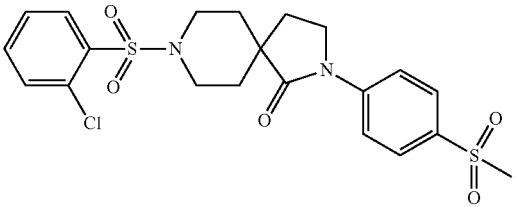

8-(2-Chloro-benzenesulfonyl)-2-(4-methylsulfanyl-phenyl)-2,8-diaza-spiro[4.5]decan-1-one (0.094 g), product of example 34), dissolved in CH₂Cl₂ (10 ml) was treated at RT with 3-chloroperoxybenzoic acid (0.308 g) and stirred for 12 hours until completion of reaction. The reaction mixture was partitioned between CH₂Cl₂ and aqueous 1 M NaOH, the layers were separated, the organic layer washed with water, dried over sodium sulphate. The solvent was then removed in vacuo, the residue triturated with ether then dried in vacuo to give the desired 8-(2-chloro-benzenesulfonyl)-2-(4-methanesulfonyl-phenyl)-2,8-diaza-spiro[4.5]decan-1-one as a white solid. MS (ESI): 635 (MH⁺).

Example 141

8-(2-Chloro-benzenesulfonyl)-2-(4-hydroxymethyl-phenyl)-2,8-diaza-spiro[4.5]decan-1-one

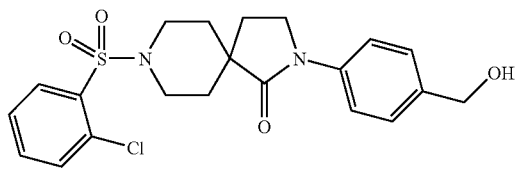

Step A): 4-[8-(2-Chloro-benzenesulfonyl)-1-oxo-2,8-diaza-spiro[4.5]dec-2-yl]-benzoic acid This material was prepared in analogy to example 1 step D) from 1-(2-chloro-benzenesulfonyl)-4-(2-methoxy-ethyl)-piperidine-4-carboxylic acid ethyl ester (3 g), dimethylaluminium chloride in heptane (1.0 molar, 34.62 ml) and 4-aminobenzoic acid (1.58 g) to give the desired 4-[8-(2-chloro-benzenesulfonyl)-1-oxo-2,8-diaza-spiro[4.5]dec-2-yl]-benzoic acid (0.522 g) as a white solid. MS (ESI): 449.1 (MH⁺).

Step B): 8-(2-Chloro-benzenesulfonyl)-2-(4-hydroxymethyl-phenyl)-2,8-diaza-spiro[4.5]decan-1-one 4-[8-(2-Chloro-benzenesulfonyl)-1-oxo-2,8-diaza-spiro[4.5]dec-2-yl]-benzoic acid (0.5 g) was dissolved in THF under an argon atmosphere and then treated at 0° C. with borane THF complex (1 molar, 6.68 ml) and stirred overnight at RT. Then 1M aqueous HCl (1 ml) was added and the mixture was stirred for 10 minutes. The solvent was evaporated off in vacuo, the residue was adsorbed on silica gel and chromatographed over silica gel (AcOEt/heptane, gradient from 0 to 50%) to give the desired 8-(2-chloro-benzenesulfonyl)-2-(4-hydroxymethyl-phenyl)-2,8-diaza-spiro[4.5]decan-1-one as a white solid. MS (ESI): 435.3 (MH⁺).

Example 142

8-(2-Chloro-benzenesulfonyl)-2-(4-methoxymethyl-phenyl)-2,8-diaza-spiro[4.5]decan-1-one

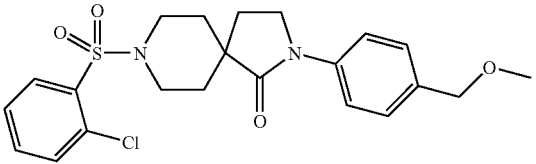

8-(2-Chloro-benzenesulfonyl)-2-(4-hydroxymethyl-phenyl)-2,8-diaza-spiro[4.5]decan-1-one (0.078 g), product of example 141), was dissolved in THF (15 ml), potassium tert-butanolate (0.022 g) was added at RT and the mixture was stirred 5 minutes at RT. Then methyl iodide (0.033 g) was added and stirring was continued for 2 hours. The reaction mixture was made acidic with 3M aqueous HCl, the solvent was removed in vacuo and the residue adsorbed on silica gel and chromatographed over silica gel (AcOEt/heptane, gradient from 0 to 25%,) to give the desired: 8-(2-chloro-benzenesulfonyl)-2-(4-methoxymethyl-phenyl)-2,8-diaza-spiro[4.5]decan-1-one (0.029 mg) as a white solid. MS (ESI): 449.1 (MH⁺).

Example 143

2-(4-Ethyl-phenyl)-8-[2-(2-oxo-pyrrolidin-1-yl)-benzenesulfonyl]-2,8-diaza-spiro[4.5]decan-1-one

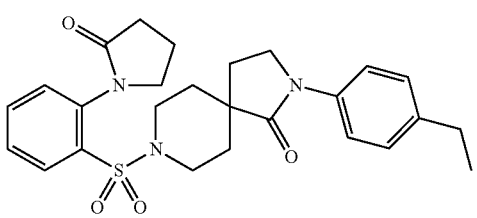

A mixture of 2-(4-ethyl-phenyl)-8-(2-iodo-benzenesulfonyl)-2,8-diaza-spiro[4.5]decan-1-one (0.06 g), compound of example 74), 2-pyrrolidinone (0.015 g), K₂CO₃ (0.055 g) and N,N'-dimethylethylenediamine (0.015 g) was heated in DMF under an argon atmosphere for 24 h at 150° C. The mixture was then cooled to RT and extracted with AcOEt. The extracts were combined, filtered, washed with water and dried over sodium sulphate. The solvent was removed in vacuo. The residue was chromatographed over silica gel (AcOEt/heptane, gradient from 0 to 50%, then MeOH/CH₂Cl₂ from 0 to 7%) to give the desired 2-(4-ethyl-phenyl)-8-[2-(2-oxo-pyrrolidin-1-yl)-benzenesulfonyl]-2,8-diaza-spiro[4.5]decan-1-one as a yellow oil. MS (ESI): 482.21 (MH⁺).

Example 144

2-[4-((E)-3-Methoxy-propenyl)-phenyl]-8-(2-trifluoromethoxy-benzenesulfonyl)-2,8-diaza-spiro[4.5]decan-1-one

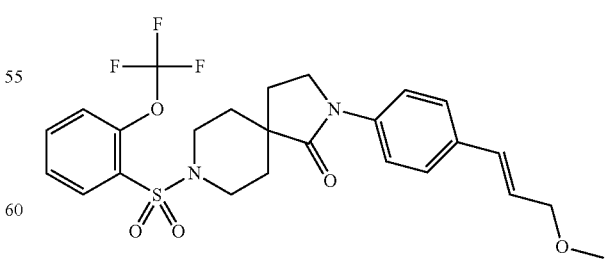

2-(4-Iodo-phenyl)-8-(2-trifluoromethoxy-benzenesulfonyl)-2,8-diaza-spiro[4.5]decan-1-one (0.01 g), product of example 104), was taken up in a mixture of ethanol (1 ml), water (1 ml) and toluene (8 ml), treated with K₂CO₃ (0.071 g)

and (E)-2-(3-methoxypropenyl)-4,4,5,5-tetramethyl-(1,3,2)-dioxaboroane and stirred 30 minutes at RT under an argon atmosphere. Then tetrakis(triphenylphosphine)palladium(0) (0.02 g) was added and the mixture was heated at 85° C. for 4 h. It was then cooled to RT, partitioned between AcOEt and water, the layers were separated, the organic layer was dried over sodium sulphate, the solvent was removed in vacuo and the residue chromatographed over silica gel (AcOEt/heptane, gradient from 0 to 50%) to give the desired 2-[4-((E)-3-methoxy-propenyl)-phenyl]-8-(2-trifluoromethoxy-benzenesulfonyl)-2,8-diaza-spiro[4.5]decan-1-one (0.077 g) as an off white solid. MS (ESI): 525.16 (MH$^+$).

Example 145

2-[4-((E)-2-Cyclopropyl-vinyl)-phenyl]-8-(2-trifluoromethoxy-benzenesulfonyl)-2,8-diaza-spiro[4.5]decan-1-one

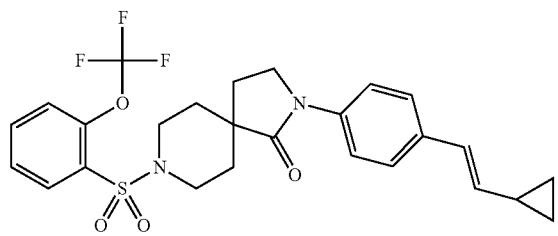

This material was obtained in analogy to example 144) from 2-(4-iodo-phenyl)-8-(2-trifluoromethoxy-benzenesulfonyl)-2,8-diaza-spiro[4.5]decan-1-one and (E)-2-cyclopropylvinylboronic acid pinacol ester. Off white solid. MS (ESI): 521.17 (MH$^+$).

Example 146

2-[4-(3-Methoxy-propyl)-phenyl]-8-(2-trifluoromethoxy-benzenesulfonyl)-2,8-diaza-spiro[4.5]decan-1-one

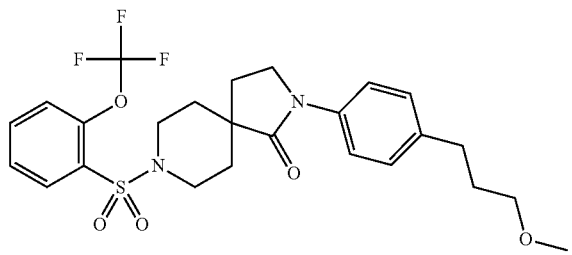

2-[4-((E)-3-Methoxy-propenyl)-phenyl]-8-(2-trifluoromethoxy-benzenesulfonyl)-2,8-diaza-spiro[4.5]decan-1-one (0.07 g), product of example 144), in methanol (10 ml) was hydrogenated over Pd on charcoal (10%) at atmospheric pressure for 12 h. The catalyst was removed by filtration, the solvent evaporated off to give the desired material as white solid. MS (ESI): 527.18 (MH$^+$).

Example 147

2-[4-(2-Cyclopropyl-ethyl)-phenyl]-8-(2-trifluoromethoxy-benzenesulfonyl)-2,8-diaza-spiro[4.5]decan-1-one

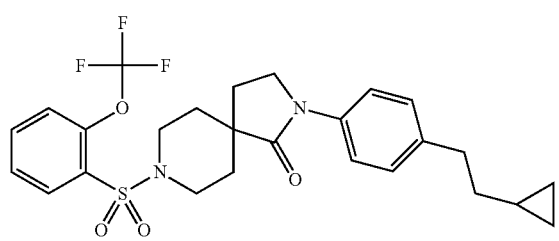

This material was prepared in analogy to example 146) by hydrogenation of 2-[4-((E)-2-cyclopropyl-vinyl)-phenyl]-8-(2-trifluoromethoxy-benzenesulfonyl)-2,8-diaza-spiro[4.5]decan-1-one, product of example 145). White solid. MS (ESI): 523.1 MH$^+$).

Example 148

8-(2-Chloro-benzenesulfonyl)-2-(4-cyclopropyl-methoxymethyl-phenyl)-2,8-diaza-spiro[4.5]decan-1-ones

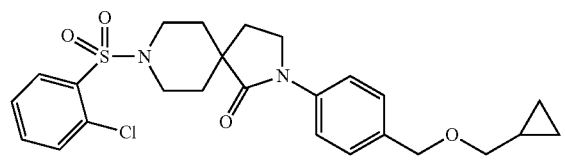

Step A): 4-Cyanomethyl-piperidine-1,4-dicarboxylic acid 1-tert-butyl ester 4-ethyl ester

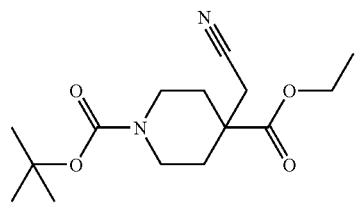

LDA (2M solution in THF/heptane/ethylbenzene, 97.15 ml, 0.194 mol) was added under an argon atmosphere to THF (300 ml) at −5° C., piperidine-1,4-dicarboxylic acid 1-tert-butyl ester 4-ethyl ester (25 g, 0.097 mol) in THF (100 ml) was then added dropwise and the mixture was stirred for 3 hour at −5° C. Then bromoacetonitrile (23.3 g, 0.194 mol) was added at −5° C. and the mixture was stirred overnight at RT. The solvent was evaporated off, the residue partitioned between AcOEt and water. The layers were separated, the organic layer was washed with brine, dried over sodium sulphate and then concentrated to give 4-cyanomethyl-piperidine-1,4-dicarboxylic acid 1-tert-butyl ester 4-ethyl ester (36 g) as a dark brown oil which was essentially pure and used in the next step without further purification. MS (ESI): 197.3 [(M-Boc)H$^+$].

Step B): 4-Cyanomethyl-piperidine-4-carboxylic acid ethyl ester

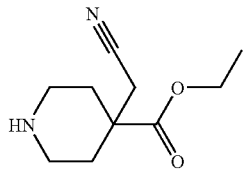

4-Cyanomethyl-piperidine-1,4-dicarboxylic acid 1-tert-butyl ester 4-ethyl ester (36 g) was dissolved in methylene chloride (600 ml), cooled to 0° C. then trifluoroacetic acid (207.8 g, 134.9 ml) was added under an argon atmosphere and the mixture was stirred over night allowing the temperature of the reaction mixture to rise to RT. The reaction mixture was then concentrated in vacuo, the residue taken up in methylene chloride and washed several times with 1M aqueous NaOH (to pH 12). The layers were separated, the organic layer washed with brine, dried over sodium sulphate and concentrated to give 4-cyanomethyl-piperidine-4-carboxylic acid ethyl ester a brown oil (14.2 g) which was essentially pure according to NMR and used in next reaction step without further purification. MS (ESI): 197.2 (MH$^+$).

Step C): 1-(2-Chloro-benzenesulfonyl)-4-cyanomethyl-piperidine-4-carboxylic acid ethyl ester

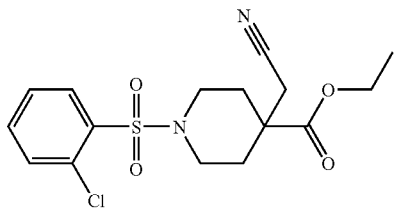

4-Cyanomethyl-piperidine-4-carboxylic acid ethyl ester (14.2 g) was dissolved in pyridine (150 ml), 2-chlorobenzenesulfonyl chloride (16.83 g) was added and the reaction mixture was stirred overnight at RT. Then, most of pyridine was evaporated off in vacuo, the residue was dissolved in AcOEt, washed with 0.5M aqueous HCl and brine. The organic layer was dried over magnesium sulphate and concentrated in vacuo. The residue (crude oil) was chromatographed over silica (AcOEt/Heptanes, gradient from 0 to 25%) to give the desired material (8.5 g) as viscous brown oil. MS (ESI): 388.1 (M+NH4)$^+$.

Step D): 4-(2-Amino-ethyl)-1-(2-chloro-benzenesulfonyl)-piperidine-4-carboxylic acid ethyl ester

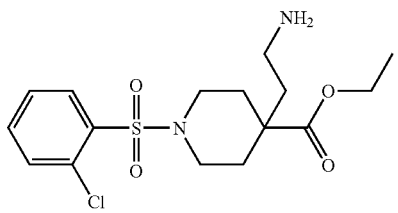

1-(2-Chloro-benzenesulfonyl)-4-cyanomethyl-piperidine-4-carboxylic acid ethyl ester (8.5 g) dissolved in MeOH/AcOH (1:1, 250 ml) was hydrogenated over PtO$_2$ (2.6 g) for 4 h at atmospheric pressure until full conversion (control by thin layer chromatography). The catalyst was filtered off and the filtrate was concentrated in vacuo. The residue was dissolved in AcOEt and washed with 1M aqueous NaOH then with brine. The organic layer was dried over magnesium sulphate, the solvent removed in vacuo to give the desired product, crude light yellow oil (7.09 g), as a mixture together with some already spirocyclised amide. MS (ESI): 375.1 MH$^+$). The crude material was directly used as such in the subsequent ring closure reaction.

Step E): 8-(2-Chloro-benzenesulfonyl)-2,8-diaza-spiro[4.5]decan-1-one

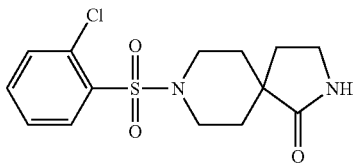

4-(2-Amino-ethyl)-1-(2-chloro-benzenesulfonyl)-piperidine-4-carboxylic acid ethyl ester (7.09 g) was suspended in toluene under an argon atmosphere, dimethylaluminium chloride in heptane (1 molar, 28.39 ml) was added and the mixture was stirred 5 minutes at RT then refluxed for 3 hours. It was then was cooled to RT, MeOH (40 ml) was added and the mixture was stirred for 30 minutes. The solvent was removed, the residue was adsorbed on silica gel and purified by flash chromatography over silica gel (eluents: AcOEt/CH$_2$Cl$_2$ 5 to 50% then acetone/CH$_2$Cl$_2$ 10 to 30%) to give the desired material (4.5 g) as light yellow solid. MS (ESI): 329.0 (MH$^+$).

Step F): 8-(2-Chloro-benzenesulfonyl)-2-(4-cyclopropylmethoxymethyl-phenyl)-2,8-diaza-spiro[4.5]decan-1-one A mixture of 8-(2-chloro-benzenesulfonyl)-2,8-diaza-spiro[4.5]decan-1-one (0.2 g), 1-cyclopropyl-methoxymethyl-4-iodo-benzene (0.351 g), N,N'-dimethylethylenediamine (0.107 g), K$_3$PO$_4$ (0.387 g) and CuI (0.174 g) in DMF (10 ml) under an argon atmosphere was stirred at 145° C. for five hours until conversion was complete. The reaction mixture was cooled to RT, taken up in AcOEt (120 ml) which was then washed twice with water (each 50 ml). The organic layer was dried over magnesium sulphate and the solvent was removed in vacuo. The residue was chromatographed on silica gel (AcOEt/Heptane, gradient from 0 to 25%,) to give the desired 8-(2-chloro-benzenesulfonyl)-2-(4-cyclopropyl-methoxymethyl-phenyl)-2,8-diaza-spiro[4.5]decan-1-one (0.128 g) as a white solid. MS (ESI): 489.3 MH$^+$).

Preparation of the iodide used in the step above:

The iodide 1-cyclopropyl-methoxymethyl-4-iodo-benzene used in the coupling reaction above was prepared by a standard alkylation of 4-iodobenzylalcohol (1 g) with (bromomethyl)cyclopropane (1.154 g) in THF (70 ml) with NaH (0.559 g, 55% suspension in oil) as base, 1 hour reaction time at RT under an argon atmosphere as yellow oil (0.835 g). MS (EI) 288 MH+).

Example 149

8-(2-Chloro-benzenesulfonyl)-2-(4-ethoxymethyl-phenyl)-2,8-diaza-spiro[4.5]decan-1-one

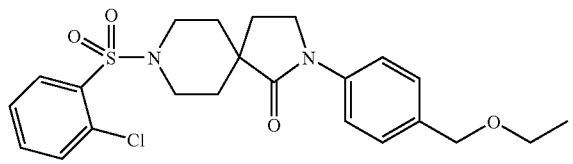

This material was prepared in analogy to example 148 step F) from 8-(2-chloro-benzenesulfonyl)-2,8-diaza-spiro[4.5]decan-1-one and 1-ethoxymethyl-4-iodo-benzene (for synthesis: M. Schamchal et al; J. Gen. Chem. USSR (Engl. Transl.); 34; 1964; 1830). White solid. MS (ESI): 463.2 MH+).

Example 150

8 4-[8-(2-Chloro-benzenesulfonyl)-1-oxo-2,8-diaza-spiro[4.5]dec-2-yl]-benzoic acid methyl ester

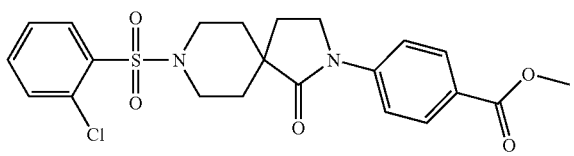

This material was prepared in analogy to example 148 step F) from 8-(2-chloro-benzenesulfonyl)-2,8-diaza-spiro[4.5]decan-1-one and 4-iodo-benzoic acid methyl ester White solid. MS (ESI): 463.1 MH+).

Example 151

2-(4-Acetyl-phenyl)-8-(2-chloro-benzene sulfonyl)-2,8-diaza-spiro[4.5]decan-1-one

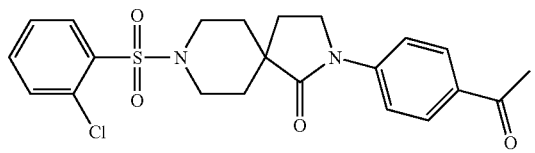

This material was prepared in analogy to example 148 step F) from 8-(2-chloro-benzenesulfonyl)-2,8-diaza-spiro[4.5]decan-1-one and 1-(4-iodo-phenyl)-ethanone. White solid. MS (ESI): 447.1 MH+).

Example 152

8-(2-Chloro-benzenesulfonyl)-2-[4-(2,2,2-trifluoro-1-hydroxy-ethyl)-phenyl]-2,8-diaza-spiro[4.5]decan-1-one

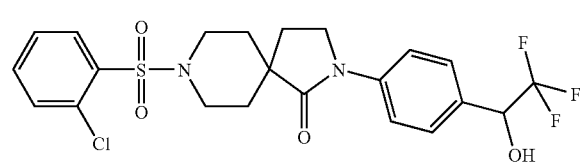

This material was prepared in analogy to example 148 step F) from 8-(2-chloro-benzenesulfonyl)-2,8-diaza-spiro[4.5]decan-1-one and 1-(4-bromo-phenyl)-2,2,2-trifluoro-ethanol White solid. MS (ESI): 503.1 MH+).

Example 153

8-(2-Chloro-benzenesulfonyl)-2-[4-(1-hydroxy-ethyl)-phenyl]-2,8-diaza-spiro[4.5]decan-1-one

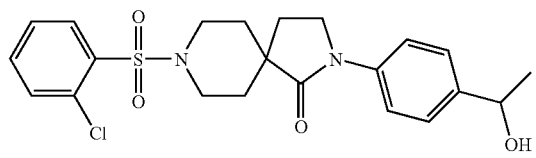

This material was prepared in analogy to example 148 step F) from 8-(2-chloro-benzenesulfonyl)-2,8-diaza-spiro[4.5]decan-1-one and 1-(4-bromo-phenyl)-ethanol. White solid. MS (ESI): 449.1 MH+).

Example 154

8-(2-Chloro-benzenesulfonyl)-2-(2-chloro-5-trifluoromethyl-phenyl)-2,8-diaza-spiro[4.5]decan-1-one

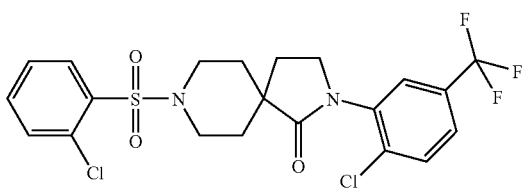

This material was prepared in analogy to example 148 step F) from 8-(2-chloro-benzenesulfonyl)-2,8-diaza-spiro[4.5]

Example 155

8-(2-Chloro-benzenesulfonyl)-2-[4-(2,2,2-trifluoro-1-hydroxy-1-methyl-ethyl)-phenyl]-2,8-diaza-spiro[4.5]decan-1-one

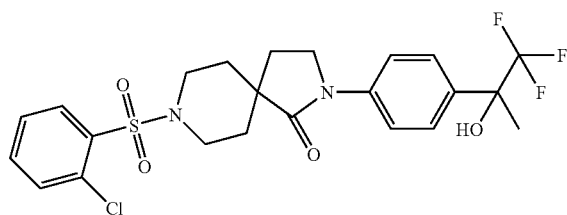

2-(4-Acetyl-phenyl)-8-(2-chloro-benzenesulfonyl)-2,8-diaza-spiro[4.5]decan-1-one (0.13 g), product of example 151), dissolved in THF (12 ml) under an argon atmosphere was treated at RT with (trifluoromethyl)trimethylsilane (0.062 g) then with tetra-n-butylammonium fluoride (1M solution in THF, 0.29 ml) and the reaction mixture was stirred overnight at RT. The mixture was made acidic with 3M aqueous HCl (a few drops) and stirred further 15 minutes. The solvent was removed in vacuo and the residue adsorbed on silica gel and chromatographed over silica gel (AcOEt/heptane, gradient from 0 to 40%) to give the desired product as white solid (0.091 g). MS (ESI): 517.1 MH$^+$.

Example 156

8-(2-Chloro-benzenesulfonyl)-2-(4-ethanesulfonyl-phenyl)-2,8-diaza-spiro[4.5]decan-1-one

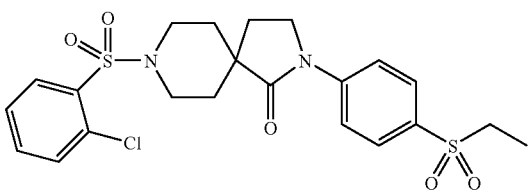

This material was prepared in analogy to example 148 step F) from 8-(2-chloro-benzenesulfonyl)-2,8-diaza-spiro[4.5]decan-1-one and 1-bromo-4-ethanesulfonyl-benzene. White solid. MS (ESI): 497.0 MH$^+$.

Example 157

8-(2-Chloro-benzenesulfonyl)-2-[4-(2,2,2-trifluoro-1-hydroxy-1-trifluoromethyl-ethyl)-phenyl]-2,8-diaza-spiro[4.5]decan-1-one

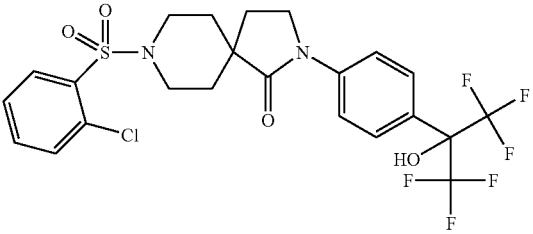

This material was prepared in analogy to example 148 step F) from 8-(2-chloro-benzenesulfonyl)-2,8-diaza-spiro[4.5]decan-1-one and 1-bromo-4-ethanesulfonyl-benzene. Light brown solid. MS (ESI): 571.0 (MH$^+$).

Example 158

9-(2-Chloro-benzenesulfonyl)-2-(4-trifluoromethyl-phenyl)-2,9-diaza-spiro[5.5]undecan-1-one

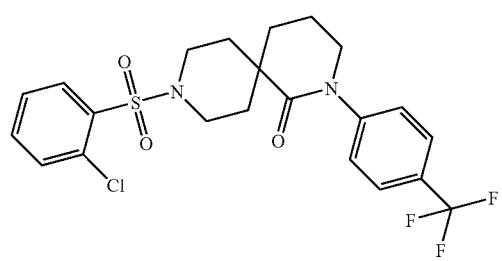

This material was prepared in analogy to example 148 step F) from 9-(2-chloro-benzenesulfonyl)-2,9-diaza-spiro[5.5]undecan-1-one and 1-iodo-4-trifluoromethyl-benzene. White solid. MS (ESI): 487.1 MH$^+$.

Preparation of the starting material, 9-(2-chloro-benzenesulfonyl)-2,9-diaza-spiro[5.5]undecan-1-one:

This material was prepared in analogy to example 148 steps A) to E) from piperidine-1,4-dicarboxylic acid 1-tert-butyl ester 4-ethyl ester and 3-bromopropionitrile (instead of bromoacetonitrile as in example 148). White solid. MS (ESI): 343.0 (MH$^+$).

Example 159

9-(2-Chloro-benzenesulfonyl)-2-(4-ethoxymethyl-phenyl)-2,9-diaza-spiro[5.5]undecan-1-one

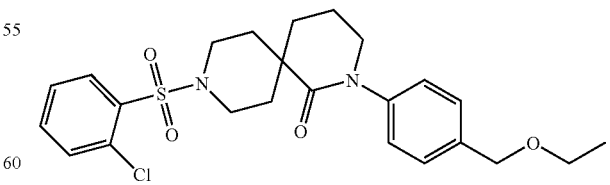

This material was prepared in analogy to example 158) from 9-(2-chloro-benzenesulfonyl)-2,9-diaza-spiro[5.5]undecan-1-one and 1-ethoxymethyl-4-iodo-benzene. White solid. MS (ESI): 477.4 (MH$^+$).

Example 160

4-[8-(2-Chloro-benzenesulfonyl)-1-oxo-2,8-diaza-spiro[4.5]dec-2-yl]-N-isopropyl-benzamide

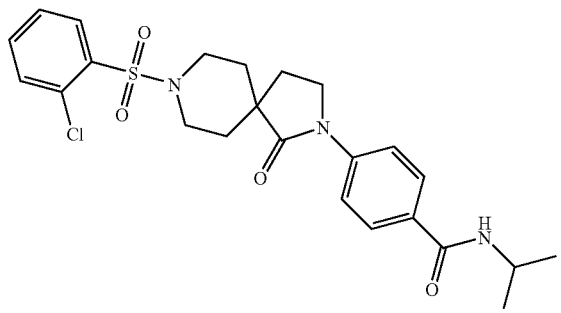

4-[8-(2-Chloro-benzenesulfonyl)-1-oxo-2,8-diaza-spiro[4.5]dec-2-yl]-benzoic acid methyl ester (0.149 g), compound of example 150), was suspended in toluene under an argon atmosphere at RT, isopropylamine (0.057 g) and dimethylaluminium chloride in hexane (1 molar, 1.61 ml) were added and the mixture stirred 10 minutes at 130° than overnight at 95° C. The reaction mixture was cooled to RT, water (0.05 ml) was added, and the mixture was stirred for 10 minutes. Then the solvent was carefully evaporated off in vacuo, the residue was adsorbed on silica gel and chromatographed over silica gel (eluents: AcOEt/heptane, gradient from 0 to 50%) to give the desired compound (0.048 g) as white solid. MS (ESI): 490.15 MH$^+$).

Example 161

4-[8-(2-Chloro-benzenesulfonyl)-1-oxo-2,8-diaza-spiro[4.5]dec-2-yl]-N-isopropyl-N-methyl-benzamide

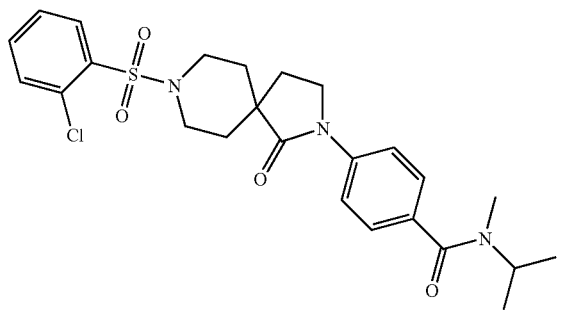

To NaH (0.04 g, 55% suspension in oil, washed with pentane) was added at RT and under an argon atmosphere and at RT 4-[8-(2-chloro-benzenesulfonyl)-1-oxo-2,8-diaza-spiro[4.5]dec-2-yl]-N-isopropyl-benzamide (0.04 g), product of example 160), in THF (4 ml). The reaction mixture was stirred 1 hour at RT, then MeI (0.232 g) was added and stirring was continued overnight at RT until the conversion was complete. The reaction mixture was made acidic with 1M HCl (one drop) and stirred for one minute. The solvent was removed in vacuo, the residue adsorbed on silica gel and chromtographed over silica gel (eluent: AcOEt/CH$_2$Cl$_2$, gradient from 0 to 30%) to give the desired product as off-white solid. MS (ESI): 504.1 MH$^+$).

Example 162

(rac)-8-(3,5-Dimethyl-isoxazole-4-sulfonyl)-2-[4-(2,2,2-trifluoro-1-hydroxy-ethyl)-phenyl]-2,8-diaza-spiro[4.5]decan-1-one

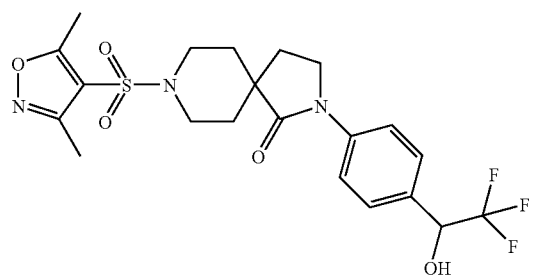

Step A): 8-(3,5-Dimethyl-isoxazole-4-sulfonyl)-2,8-diaza-spiro[4.5]decan-1-one

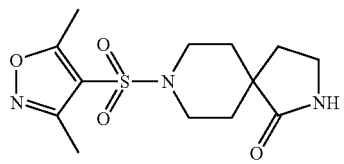

4-Spiro-[3-(2-pyrrolidinone)]piperidine hydrochloride (0.5 g) dissolved in CH$_2$Cl$_2$ (25 ml) was treated under an argon atmosphere with 4-dimethylaminopyridine (DMAP) (0.882 g). The solution was cooled to 0° C., treated dropwise over 15 minutes with 3,5-dimethyl-isoxazolyl-4-sulphonyl chloride (0.564 g in CH$_2$Cl$_2$, 15 ml) and then stirred 20 h at RT to complete the conversion. The reaction mixture was partitioned between CH$_2$Cl$_2$ (150 ml) and 1M aqueous HCl (100 ml), the layers were separated, the organic layer washed with 2M aqueous KHCO$_3$ (200 ml) and brine, dried over Na$_2$SO$_4$, filtered and the solvent was then removed in vacuo to give the desired material as a white solid (0.75 g) which was essentially pure and directly used in the next step. MS (ESI): 314.11 MH$^+$).

Step B): 8-(3,5-Dimethyl-isoxazole-4-sulfonyl)-2-[4-(2,2,2-trifluoro-1-hydroxy-ethyl)-phenyl]-2,8-diaza-spiro[4.5]decan-1-one This material was prepared in analogy to example 148 step F) from 8-(3,5-dimethyl-isoxazole-4-sulfonyl)-2,8-diaza-spiro[4.5]decan-1-one and (rac)-2,2,2-trifluoro-1-(4-iodo-phenyl)-ethanol. Light yellow solid. MS (ESI): 488.14 MH$^+$).

Preparation of the iodide, 2,2,2-trifluoro-1-(4-iodo-phenyl)-ethanol, used above:

4-Iodobenzaldehyde (1 g) was dissolved under an argon atmosphere at RT in THF (25 ml). The solution was cooled to 0° C. and then treated with (trifluoromethyl)trimethylsilane (0.674 g, 0.7 ml) followed by tetra-n-butylammonium fluoride (1M solution in THF, 0.43 ml). This mixture was warmed to RT and stirred overnight. It was then made acidic with 1M aqueous HCl and stirred 15 minutes. AcOEt was added, the layers were separated, the organic layer was washed with brine, dried over magnesium sulphate and concentrated in vacuo. The crude material comprised a mixture of desired product and silylated product at the akohol group and was thus subjected to treatment with acid to cleave off the silyl groupas following: the reaction mixture dissolved in THF (15 ml) was treated with at RT with 3M aqueous HCl (2 ml) and 37% HCl (1 ml) and stirred 4 hours until thin layer chromatography indicated full conversion. AcOEt was added, the layers were separated, washed with brine and dried over magnesium sulphate and concentrated in vacuo to give the desired product as a light brown oil which was essentially pure and directly used in the next step. MS (ESI): 301.1 (M-H)⁻.

Example 163

2-[4-(2,2,2-Trifluoro-1-hydroxy-ethyl)-phenyl]-8-(2-trifluoromethoxy-benzenesulfonyl)-2,8-diaza-spiro[4.5]decan-1-one

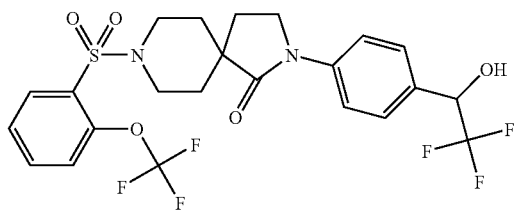

Step A): 2-[4-(2,2,2-Trifluoro-1-hydroxy-ethyl)-phenyl]-2,8-diaza-spiro[4.5]decan-1-one

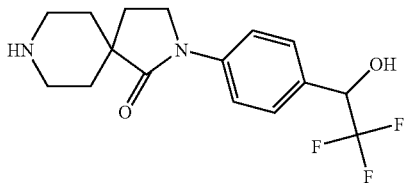

A mixture of 4-spiro-[3-(2-pyrrolidinone)]piperidine hydrochloride (0.15 g), 2,2,2-trifluoro-1-(4-iodo-phenyl)-ethanol (0.588 g), N,N'-dimethylethylenediamine (0.171 g), K₃PO₄ (0.619 g) and CuI (0.278 g) in DMF (9 ml) under an argon atmosphere was stirred at 145° C. for 70 minutes until conversion was complete. The reaction mixture was cooled to RT, taken up in AcOEt (120 ml) which was then washed twice with water (each 50 ml). The organic layer was dried over magnesium sulphate and the solvent was removed in vacuo to give the desired crude product (0.327 g) as a brown solid which was used directly in the next step without further purification. MS (ESI): 329.2 (MH⁺).

Step B): 2-[4-(2,2,2-Trifluoro-1-hydroxy-ethyl)-phenyl]-8-(2-trifluoromethoxy-benzenesulfonyl)-2,8-diaza-spiro[4.5]decan-1-one Crude 2-[4-(2,2,2-trifluoro-1-hydroxy-ethyl)-phenyl]-2,8-diaza-spiro[4.5]decan-1-one from step A) (0.327 g) dissolved in pyridine at RT and under an argon atmosphere was treated with 2-trifluoromethoxy-benzenesulfonyl chloride (0.286 g) and the mixture was then stirred at RT over night. Then the most of pyridine was evaporated off in vacuo, the residue was dissolved in AcOEt which was then washed with 1M aqueous HCl and brine, dried over magnesium sulphate and concentrated in vacuo. The crude product was chromatographed over silica gel (eluent: AcOEt/Heptane, gradient from 0 to 30%) to give the desired product as a light brown solid. MS (ESI): 553.12 (MH⁺).

Example 164

8-(3,5-Dimethyl-isoxazole-4-sulfonyl)-2-(4-trifluoromethyl-phenyl)-2,8-diaza-spiro[4.5]decan-1-one

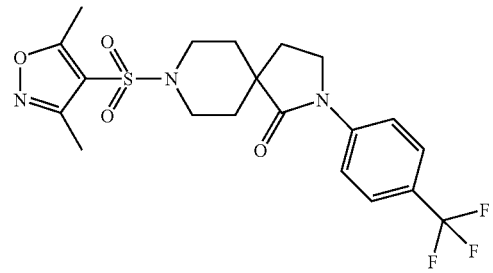

This material was prepared according to example 162 step B) from 8-(3,5-dimethyl-isoxazole-4-sulfonyl)-2,8-diaza-spiro[4.5]decan-1-one and 1-iodo-4-trifluoromethyl-benzene. Off white solid. MS (ESI): 458.13 MH⁺.

Example 165

8-(3,3-Dimethyl-butyryl)-2-[4-(2,2,2-trifluoro-1-hydroxy-ethyl)-phenyl]-2,8-diaza-spiro[4.5]decan-1-one

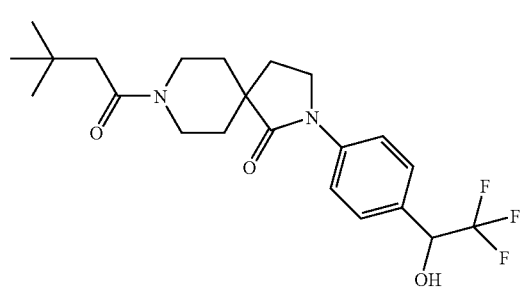

Step A): 8-(3,3-Dimethyl-butyryl)-2,8-diaza-spiro[4.5]decan-1-one

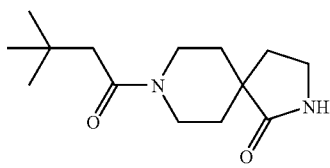

4-Spiro-[3-(2-pyrrolidinone)]piperidine hydrochloride (0.5 g) dissolved in $CH_2Cl_2$ (25 ml) was treated under an argon atmosphere with triethylamine (0.87 g). The solution was cooled to 0° C., treated dropwise with 3,3-dimethyl-butyryl chloride (0.388 g in $CH_2Cl_2$, 5 ml) and then stirred 20 h at RT to complete the conversion. The reaction mixture was partitioned between $CH_2Cl_2$ (150 ml) and 1M aqueous HCl (100 ml), the layers were separated, the organic layer washed with 2M aqueous $KHCO_3$ (200 ml) and brine, dried over $Na_2SO_4$, filtered and the solvent was then removed in vacuo to give the desired material as a white solid (0.553 g) which was essentially pure and directly used in the next step. MS (ESI): 253.19 MH$^+$).

Step B) 8-(3,3-Dimethyl-butyryl)-2-[4-(2,2,2-trifluoro-1-hydroxy-ethyl)-phenyl]-2,8-diaza-spiro[4.5]decan-1-one This material was prepared in analogy to example 148 step F) from 8-(3,3-dimethyl-butyryl)-2,8-diaza-spiro[4.5]decan-1-one and 2,2,2-trifluoro-1-(4-iodo-phenyl)-ethanol. Light yellow crystalline solid. MS (ESI): 427.3 MH$^+$).

Example 166

2-(4-(2,2,2-trifluoro-1-hydroxyethyl)phenyl)-8-(2-(trifluoromethyl)phenylsulfonyl)-2,8-diazaspiro[4.5]decan-1-one

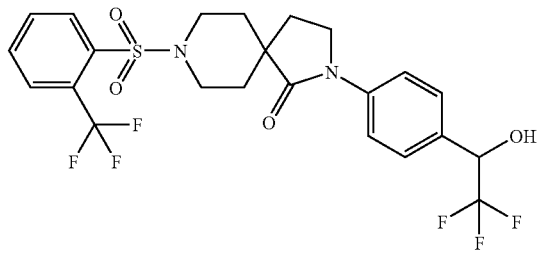

Step A): 8-(2-Trifluoromethyl-benzenesulfonyl)-2,8-diaza-spiro[4.5]decan-1-one

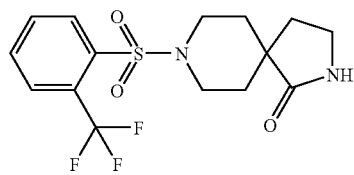

This material was prepared in analogy to example 162 A) from 4-spiro-[3-(2-pyrrolidinone)]piperidine hydrochloride (0.4 g) and 2-trifluoromethylbenzenesulphonyl chloride as off white solid (0.737 g). MS (ESI): 363.09 MH$^+$).

Step B): 2-(4-(2,2,2-trifluoro-1-hydroxyethyl)phenyl)-8-(2-(trifluoromethyl)phenylsulfonyl)-2,8-diazaspiro[4.5]decan-1-one This material was prepared in analogy to example 162 B) from 8-(2-trifluoromethyl-benzenesulfonyl)-2,8-diaza-spiro[4.5]decan-1-one and 2,2,2-trifluoro-1-(4-iodo-phenyl)-ethanol. White solid. MS (ESI): 537.12 MH$^+$).

Example 167

8-(isobutylsulfonyl)-2-(4-(2,2,2-trifluoro-1-hydroxyethyl)phenyl)-2,8-diazaspiro[4.5]decan-1-one

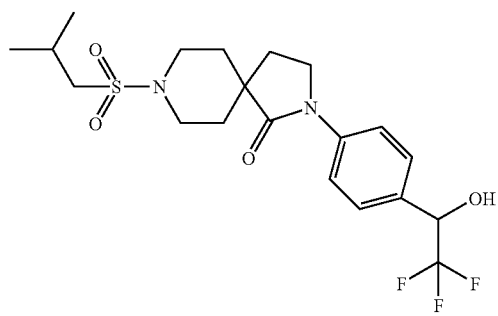

Step A): 8-(Isobutylsulfonyl)-2,8-diazaspiro[4.5]decan-1-one

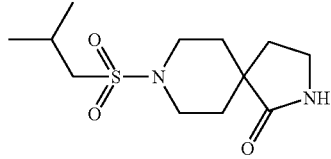

This material was prepared in analogy to example 162 A) from 4-spiro-[3-(2-pyrrolidinone)]piperidine hydrochloride (0.572 g) and 2-methyl-propane-1-sulfonyl chloride (0.517 g) as off-white solid (0.67 g). MS (ESI): 275.14 MH$^+$).

Step B): 8-(isobutylsulfonyl)-2-(4-(2,2,2-trifluoro-1-hydroxyethyl)phenyl)-2,8-diazaspiro[4.5]decan-1-one This material was prepared In analogy to example 162 B) from 8-(isobutylsulfonyl)-2,8-diazaspiro[4.5]decan-1-one and 2,2,2-trifluoro-1-(4-iodo-phenyl)-ethanol. White solid. MS (ESI): 449.17 MH$^+$).

Example 168

8-(isobutylsulfonyl)-2-(4-(1,1,1-trifluoro-2-hydroxypropan-2-yl)phenyl)-2,8-diazaspiro[4.5]decan-1-one

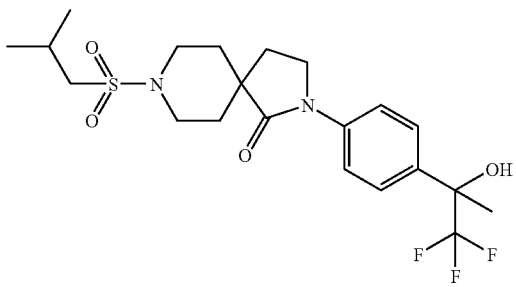

This material was prepared in analogy to example 162 step B) from 8-(isobutylsulfonyl)-2,8-diazaspiro[4.5]decan-1-one, product of example 167 A) and 1,1,1-trifluoro-2-(4-iodo-phenyl)-propan-2-ol (synthesis: H. Urata et al, Tetrahedron Letters; 1991; p 91). White crystalline solid. MS (ESI): 463.2 (MH$^+$).

Example 169

2-(4-(1,1,1-trifluoro-2-hydroxypropan-2-yl)phenyl)-8-(2-(trifluoromethyl)phenylsulfonyl)-2,8-diazaspiro[4.5]decan-1-one

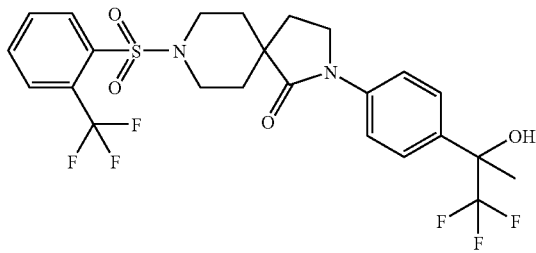

This material was prepared In analogy to example 162 step B) from 8-(2-trifluoromethyl-benzenesulfonyl)-2,8-diazaspiro[4.5]decan-1-one, product of example 166 A) and 1,1,1-trifluoro-2-(4-iodo-phenyl)-propan-2-ol). White crystalline solid. MS (ESI): 551.1 (MH$^+$).

Example 170

8-(Cyclopropylsulfonyl)-2-(4-(2,2,2-trifluoro-1-hydroxyethyl)phenyl)-2,8-diazaspiro[4.5]decan-1-one

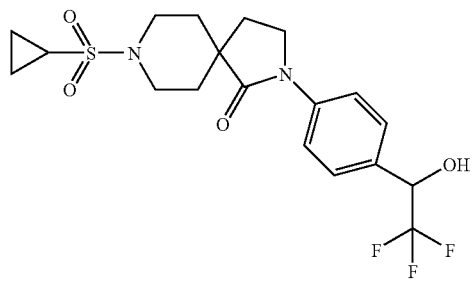

Step A): 8-(Cyclopropylsulfonyl)-2,8-diazaspiro[4.5]decan-1-one

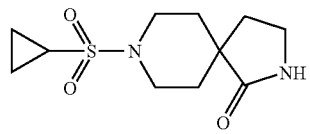

This material was prepared In analogy to example 162 A) from 4-spiro-[3-(2-pyrrolidinone)]piperidine hydrochloride (0.572 g) and cyclopropylsulphonyl chloride (0.464 g) as light yellow solid (0.738 g). MS (ESI): 259.11 MH$^+$).

Step B): 8-(Cyclopropylsulfonyl)-2-(4-(2,2,2-trifluoro-1-hydroxyethyl)phenyl)-2,8-diazaspiro[4.5]decan-1-one This material was prepared In analogy to example 162 step B) from 8-(cyclopropylsulfonyl)-2,8-diazaspiro[4.5]decan-1-one and 2,2,2-trifluoro-1-(4-iodo-phenyl)-ethanol. White solid. MS (ESI): 433.14 MH$^+$).

Example 171

8-(Cyclopropylsulfonyl)-2-(4-(1,1,1-trifluoro-2-hydroxypropan-2-yl)phenyl)-2,8-diazaspiro[4.5]decan-1-one

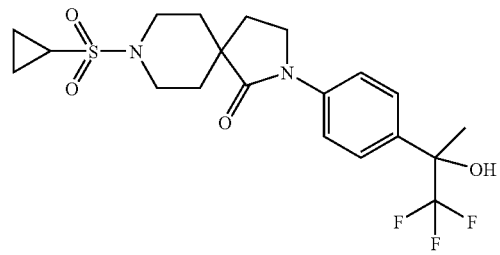

This material was prepared In analogy to example 162 step B) from 8-(cyclopropylsulfonyl)-2,8-diazaspiro[4.5]decan-1-one, product of example 170 A) and 1,1,1-trifluoro-2-(4-iodo-phenyl)-propan-2-ol). Pink crystalline solid. MS (ESI): 447.15 (MH$^+$).

Example 172

8-(2,2-Dimethyl-propane-1-sulfonyl)-2-(4-ethanesulfonyl-phenyl)-2,8-diaza-spiro[4.5]decan-1-one

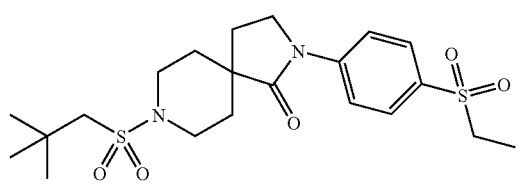

This material was obtained in analogy to example 163 A) to B) from of 4-spiro-[3-(2-pyrrolidinone)]piperidine hydro-

Example 173

2-(4-(2-fluoro-1-hydroxyethyl)phenyl)-8-(2-(trifluoromethyl)phenylsulfonyl)-2,8-diazaspiro[4.5]decan-1-one

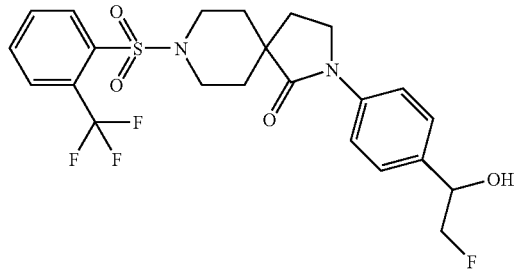

This material was prepared In analogy to example 162 step B) from 8-(2-trifluoromethyl-benzenesulfonyl)-2,8-diazaspiro[4.5]decan-1-one, product of example 166 A) and 2-fluoro-1-(4-iodo-phenyl)-ethanol. White solid. MS (ESI): 501.14 (MH+).

Preparation of the iodide, 2-fluoro-1-(4-iodo-phenyl)-ethanol used in the reaction above:

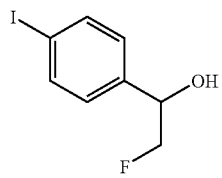

2-Fluoro-1-(4-iodo-phenyl)-ethanone (0.198 g) (for synthesis: Kitano et al.; Kogyo Kagaku Zasshi; 58; 1955; p 54, Chem. Abstr.; 1956; 3293) dissolved in THF (5 ml) under an argon atmosphere was cooled to 0° C., treated with NaBH4 (56.7 mg) and then stirred over night allowing the temperature of the solution to rise to RT. AcOH (1 ml) was then added followed by AcOEt (75 ml) and 1M aqueous HCl (40 ml). The layers were separated, the organic layer washed with 2 M KHCO3 (40 ml), dried over Na2SO4 filtered and the solvent was removed in vacuo to give the desired material as a yellow gum (0.2 g). MS (EI): 266 (M+).

Example 174

2-[4-(1-Hydroxy-1-methyl-ethyl)-phenyl]-8-(2-trifluoromethyl-benzenesulfonyl)-2,8-diaza-spiro[4.5]decan-1-one

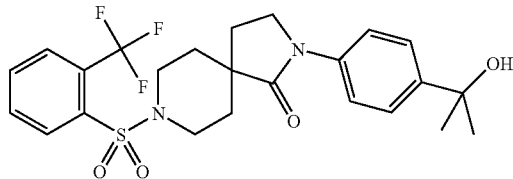

This material was prepared In analogy to example 162 step B) from 8-(2-trifluoromethyl-benzenesulfonyl)-2,8-diazaspiro[4.5]decan-1-one, product of example 166 A) and 2-(4-iodo-phenyl)-propan-2-ol (synthesis: Brown et al.; JACS; 79; 1957, p 1906). Light yellow solid. MS (ESI): 497.17 (MH+).

Example 175

2-(4-(2,2-difluoro-1-hydroxypropyl)phenyl)-8-(3,3-dimethylbutanoyl)-2,8-diazaspiro[4.5]decan-1-one

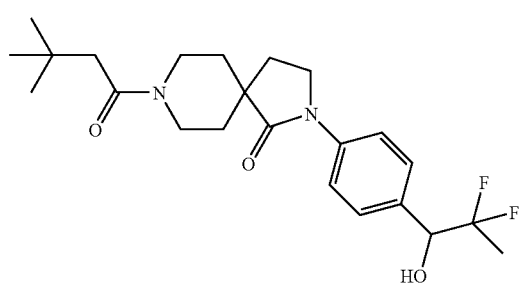

This material was prepared In analogy to example 162 step B) from 8-(3,3-dimethyl-butyryl)-2,8-diaza-spiro[4.5]decan-1-one, product of example 165 A) and 1-(4-bromo-phenyl)-2,2-difluoro-propan-1-ol (synthesis: R. Mogi, et al, Journal of Fluorine Chemistry; 10; 2007; p 1098). White solid. MS (ESI): 423.24 (MH+).

Example 176

(rac)-2-(4-(2,2-difluoro-1-hydroxyethyl)phenyl)-8-(2-(trifluoromethyl)phenylsulfonyl)-2,8-diazaspiro[4.5]decan-1-one

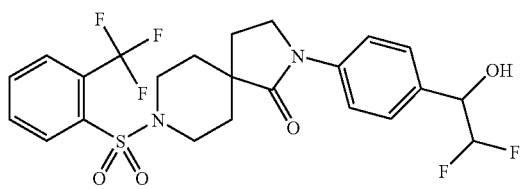

This material was prepared In analogy to example 162 step B) from 8-(2-trifluoromethyl-benzenesulfonyl)-2,8-diazaspiro[4.5]decan-1-one, product of example 166 A) and 1-(4-bromo-phenyl)-2,2-difluoro-ethanol. Off white solid. MS (ESI): 519.13 (MH+).

Preparation of the bromide, 1-(4-bromo-phenyl)-2,2-difluoro-ethanol, used in the reaction above:

This material was prepared from 1-(4-bromo-phenyl)-2,2-difluoro-ethanone (1.6 g) (for synthesis, e.g.: G. K. Prakash et al; Journal of Fluorine Chemistry; 112; 2001; p 357) by reduction with NaBH4 (0.515 g) in THF (20 ml) at RT and 2 h reaction time (analogues to the reduction of 2-fluoro-1-(4-iodo-phenyl)-ethanone, described in example 173). Colorless oil (1.23 g). MS (EI): 236 (M+).

Example 177

2-(4-(2,2-difluoro-1-hydroxyethyl)phenyl)-8-(isobutylsulfonyl)-2,8-diazaspiro[4.5]decan-1-one

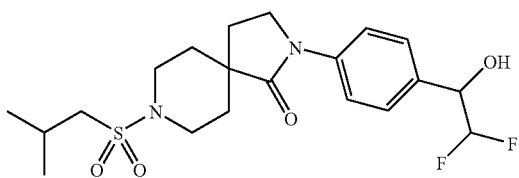

This material was prepared In analogy to example 162 step B) from 8-(isobutylsulfonyl)-2,8-diazaspiro[4.5]decan-1-one, product of example 167 A) and 1-(4-bromo-phenyl)-2,2-difluoro-ethanol, described in example 176). Light yellow solid. MS (ESI): 431.18 (MH+).

Example 178

2-(4-(2,2-difluoro-1-hydroxyethyl)phenyl)-8-(3,3-dimethylbutanoyl)-2,8-diazaspiro[4.5]decan-1-one

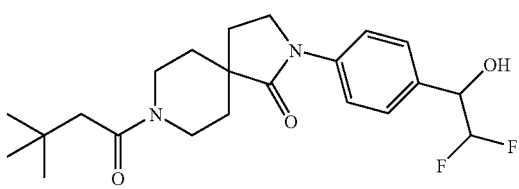

This material was prepared In analogy to example 162 step B) from 8-(3,3-dimethyl-butyryl)-2,8-diaza-spiro[4.5]decan-1-one, product of example 165 A) and 1-(4-bromo-phenyl)-2,2-difluoro-ethanol, described in example 176). Yellow solid. MS (ESI): 408.22 (MH+).

Example 179

8-(2-Chloro-benzenesulfonyl)-2-(4-trifluoromethyl-phenyl)-2,8-diaza-spiro[4.5]decan-1-one

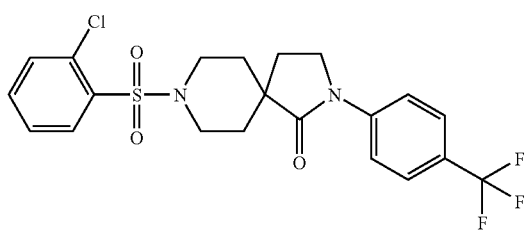

Step A) Preparation of 8-(2-Chloro-benzenesulfonyl)-2,8-diaza-spiro[4.5]decan-1-one As an alternative to the preparation described in example 148 steps A) to E) the material was prepared in analogy to example 162 A) from 4-spiro-[3-(2-pyrrolidinone)]piperidine hydrochloride (0.6 g), 2-chloro-benzenesulfonyl chloride (0.732 g) as a white solid (0.67 g). MS (ESI): 329.3 (MH+)

Step B) 8-(2-Chloro-benzenesulfonyl)-2-(4-trifluoromethyl-phenyl)-2,8-diaza-spiro[4.5]decan-1-one As an alternative, this material was prepared through a palladium-catalyzed coupling in analogy to a procedure described in literature: W. E Shakespeare, Tetrahedron Lett. 1999, 40 p 2035): A mixture of 8-(2-chloro-benzenesulfonyl)-2,8-diaza-spiro[4.5]decan-1-one (0.085 g), palladium (II) acetate (0.012 g), 1,1'-bis(diphenylphosphino)-ferrocene (0.021 g) was treated under an argon atmosphere at RT with 4-iodobenzotrifluoride (0.211 g in toluene, 5 ml) and sodium tert-butoxide (0.142 g). More toluene (5 ml) was added and the mixture was then heated at 120° C. for 23 h. It was then cooled to RT, diluted with AcOEt and filtered through Celite. The filtrate was washed with aqueous NH$_4$Cl, brine, dried over Na$_2$SO$_4$ and concentrated onto silica gel. Flash chromatography (eluent; MeOH/CH$_2$Cl$_2$ 0 to 5%) gave the desired compound as a light brown solid (0.029 g). 473.1 (MH+)

Example 180

2-(4-Trifluoromethoxy-phenyl)-8-(1,3,5-trimethyl-1H-pyrazole-4-sulfonyl)-2,8-diaza-spiro[4.5]decan-1-one

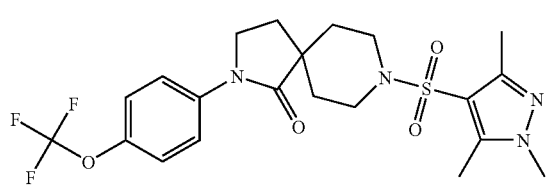

Step A: 1-Benzyl-4-(2-methoxy-ethyl)-piperidine-4-carboxylic acid ethyl ester

To a solution of diisopropylamine (5.68 ml, 0.040 mol) in 100 ml THF at −78° C. was added nBuli (1.6M solution in hexane, 25.9 ml, 0.041 mol) drop-wise. The reaction mixture was warmed to −5° C. and stirring was continued for 30 mins. A solution of 1-benzylpiperidine-4-carboxylic acid ethyl ester (5.00 g, 0.020 mol) in THF (20 ml) was added drop wise and stirring was continued for a further 3 hr followed by the addition of a solution of 1-bromo-2-methoxy-ethane (3.82 g, 0.040 mol) in THF (20 ml) at −5° C. The reaction mixture was then allowed to warm to room temperature and stirring was continued overnight. The reaction mixture was quenched with water and concentrated in vacuo to give a brown residue which was diluted with ethyl acetate and extracted 1N HCl. The aqueous layers were then combined, made basic (with 1N NaOH) and extracted with ethyl acetate. The organic layers were combined, washed with brine, dried (Na$_2$SO$_4$), filtered and concentrated in vacuo to give a crude residue which was purified by flash column chromatography (1:1 AcOEt/heptane) to give 1-benzyl-4-(2-methoxyethyl)-piperidine-4-carboxylic acid ethyl ester (5.2 g, 84%) as a brown oil. MS (ESI): 306.3 (MH+).

Step B: 8-Benzyl-2-(4-trifluoromethoxy-phenyl)-2,8-diaza-spiro[4.5]decan-1-one To a solution of 1-benzyl-4-(2-methoxyethyl)-piperidine-4-carboxylic acid ethyl ester (5.2 g, 0.017 mol) and 4-(trifluormethoxy)aniline (4.57 ml, 0.034 mol) in toluene (200 ml) under an argon atmosphere at room temperature, was added dimethylaluminium chloride (0.9M solution in heptane, 37 ml, 0.034 mol) and the mixture was refluxed for 4 hours. The reaction mixture was cooled to room temperature and quenched was sat. $Na_2SO_{4\ (aq)}$ solution and the mixture was filtered through Celite® and evaporated under reduced pressure. The crude residue was purified by flash column chromatography (1:3 AcOEt/heptane) to give 8-benzyl-2-(4-trifluoromethoxy-phenyl)-2,8-diaza-spiro[4.5]decan-1-one as a white solid. MS (ESI): 405.4 (MH+).

Step C: 2-(4-Trifluoromethoxy-phenyl)-2,8-diaza-spiro[4.5]decan-1-one

A mixture of 8-benzyl-2-(4-trifluoromethoxy-phenyl)-2,8-diaza-spiro[4.5]decan-1-one (3.14 g, 0.007 mol), acetic acid (5 ml) and Pearlman's catalyst (0.43 mg) in MeOH (40 ml) was stirred at room temperature under an atmospheric pressure of $H_2$ for 3 h. The catalyst was removed by filtration and the filtrate was evaporated to give a crude residue which was triturated with diethyl ether (50 ml) to give 2-(4-trifluoromethoxy-phenyl)-2,8-diaza-spiro[4.5]decan-1-one; acetic acid salt as a white solid (1.43 g, 49%). MS (ESI): 315.1 (MH+).

The acetic acid salt could be liberated in the following manner: The resulting residue was dissolved in water and the solution was made basic with 1N NaOH and extracted with ethyl acetate. The combined organic extracts were dried ($Na_2SO_4$), filtered and evaporated under reduced pressure to yield 2-(4-trifluoromethoxy-phenyl)-2,8-diaza-spiro[4.5]decan-1-one as an off white solid. MS (ESI): 315.1 (MH+).

Step D: 2-(4-Trifluoromethoxy-phenyl)-8-(1,3,5-trimethyl-1H-pyrazole-4-sulfonyl)-2,8-diaza-spiro[4.5]decan-1-one 2-(4-Trifluoromethoxy-phenyl)-2,8-diaza-spiro[4.5]decan-1-one acetic acid salt (0.02 g, 0.05 mmol) was dissolved in pyridine (0.5 ml) at room temperature and 1,3,5-trimethyl-1H-pyrazole-4-sulfonyl chloride (0.013 g, 0.06 mmol) was added and the mixture was stirred overnight at room temperature. The reaction mixture was concentrated in vacuo and the resulting residue was dissolved in AcOEt and washed with 0.1M HCl and brine. The organic layer was dried ($Na_2SO_4$), filtered and evaporated under reduced pressure to give a crude residue which was purified by flash column chromatography (4:1 AcOEt/heptane) to yield 2-(4-trifluoromethoxy-phenyl)-8-(1,3,5-trimethyl-1H-pyrazole-4-sulfonyl)-2,8-diaza-spiro[4.5]decan-1-one]-2,8-diaza-spiro[4.5]decan-1-one as an off-white solid (0.09 g, 31%). MS (ESI): 487.3 (MH+)

This procedure could also be followed using the corresponding free base (prepared as described in example 180 step C) instead of the acetic acid salt.

Example 181

8-(1-Methyl-1H-imidazole-4-sulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diaza-spiro[4.5]decan-1-one acetic acid salt (described in example 180 step C) and 1-methyl-1H-imidazole-4-sulfonyl chloride. Off-white solid. MS (ESI): 459.3 (MH+)

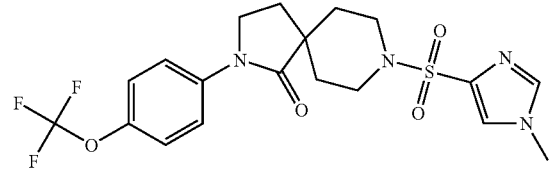

Example 182

8-(Pyrrolidine-1-sulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diaza-spiro[4.5]decan-1-one acetic acid salt (described in example 180 step C) and pyrrolidine-1-sulfonyl chloride. Off-white solid. MS (ESI): 448.2 (MH+).

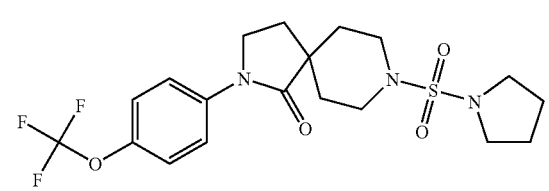

Example 183

8-(2-Methyl-2H-pyrazole-3-sulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diaza-spiro[4.5]decan-1-one acetic acid salt (described in example 180 step C) and 2-methyl-2H-pyrazole-3-sulfonyl chloride. Off-white solid. MS (ESI): 459.3 (MH+)

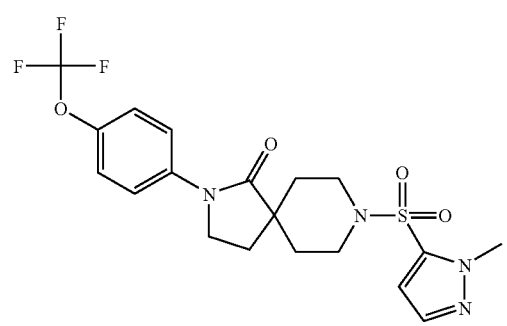

Example 184

8-(1-Methyl-1H-pyrazole-3-sulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diazaspiro[4.5]decan-1-one acetic acid salt (described in example 180 step C) and 1-methyl-1H-pyrazole-3-sulfonyl chloride Off-white solid. MS (ESI): 459.3 (MH+)

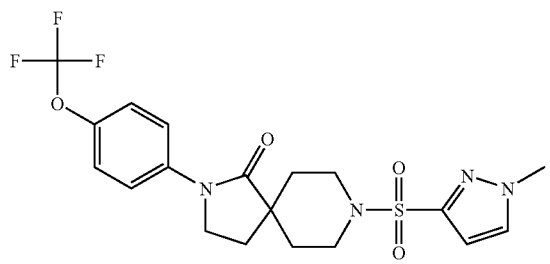

Example 185

8-(5-Methyl-isoxazole-4-sulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diaza-spiro[4.5]decan-1-one acetic acid salt (described in example 180 step C) and 5-methyl-isoxazole-4-sulfonyl chloride. White solid. MS (ESI): 460.3 (MH+).

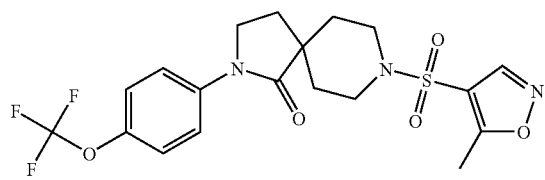

Example 186

8-(3,5-Dimethyl-isoxazole-4-sulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diaza-spiro[4.5]decan-1-one acetic acid salt (described in example 180 step C) and 3,5-dimethyl-isoxazole-4-sulfonyl chloride. White solid. MS (ESI): 474.2 (MH+)

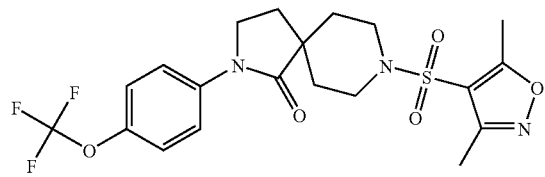

Example 187

8-(Pyridine-3-sulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diaza-spiro[4.5]decan-1-one acetic acid salt (described in example 180 step C) and pyridine-3-sulfonyl chloride; hydrochloride. White solid. MS (ESI): 456.2 (MH+).

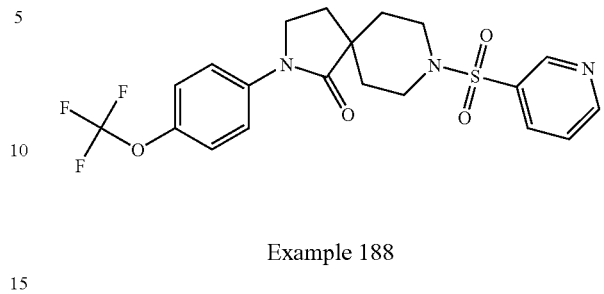

Example 188

8-(2-Chloro-pyridine-3-sulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diaza-spiro[4.5]decan-1-one (described in example 180 step C) and 2-chloro-pyridine-3-sulfonyl chloride. White solid. MS (ESI): 490.2 (MH+)

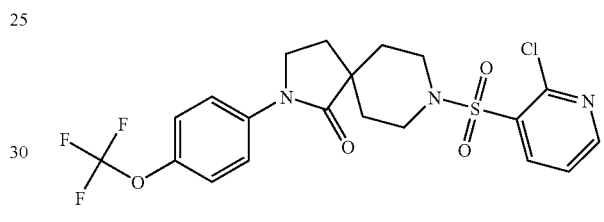

Example 189

8-(2-Methylamino-pyridine-3-sulfonyl)-2-(4-trifluoromethoxy-phenyl)-2,8-diaza-spiro[4.5]decan-1-one A mixture of 8-(2-chloro-pyridine-3-sulfonyl)-2-(4-trifluoromethoxy-phenyl)-2,8-diaza-spiro[4.5]decan-1-one (described in example 188, 40 mg, 0.08 mmol) and 8M methyl amine solution in ethanol (408 uL, 3.26 mmol) and was heated to 90° C. in a sealed tube for 48 h. The reaction mixture was transferred to a round bottom flask and concentrated in vacuo to give a crude residue which was diluted with ethyl acetate and washed with water, sat. NaHCO$_3$ and brine. The organic layer was dried (Na$_2$SO$_4$), filtered and evaporated under reduced pressure to give a crude residue which was purified by flash column chromatography using Amine-Silica to yield the desired product as a white solid (39 mg, 98%). MS (ESI): 485.2 (MH+).

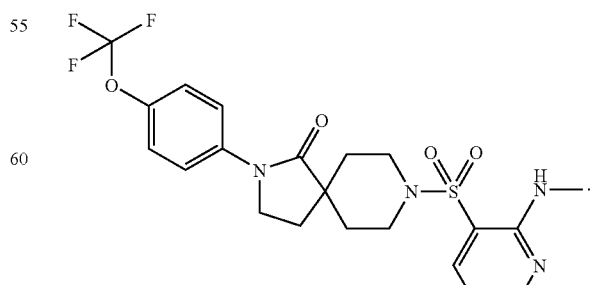

Example 190

8-(2-Dimethylamino-pyridine-3-sulfonyl)-2-(4-trifluoromethoxy-phenyl)-2,8-diaza-spiro[4.5]decan-1-one The title compound was prepared in analogy to example 189 from 8-(2-chloro-pyridine-3-sulfonyl)-2-(4-trifluoromethoxy-phenyl)-2,8-diaza-spiro[4.5]decan-1-one (described in example 188) and dimethyl amine (7.9M in H$_2$O). Off-white solid. MS (ESI): 499.3 (MH$^+$).

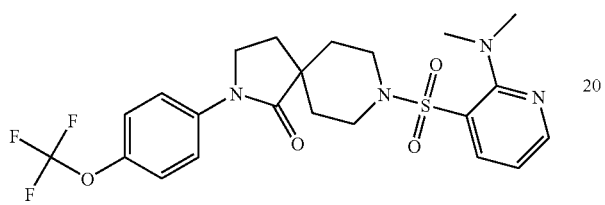

Example 191

8-(2-Cyclopropylamino-pyridine-3-sulfonyl)-2-(4-trifluoromethoxy-phenyl)-2,8-diaza-spiro[4.5]decan-1-one The title compound was prepared in analogy to example 189 from 8-(2-chloro-pyridine-3-sulfonyl)-2-(4-trifluoromethoxy-phenyl)-2,8-diaza-spiro[4.5]decan-1-one (described in example 188) and cyclopropyl amine. Light yellow oil. MS (ESI): 511.2 (MH$^+$).

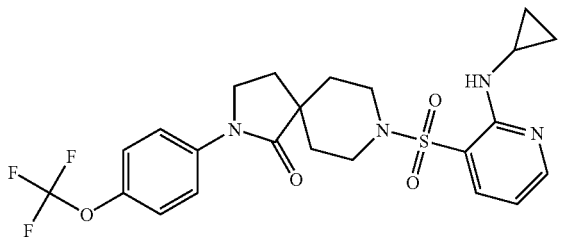

Example 192

8-[2-(2-Hydroxy-ethylamino)-pyridine-3-sulfonyl]-2-(4-trifluoromethoxy-phenyl)-2,8-diaza-spiro[4.5]decan-1-one The title compound was prepared in analogy to example 189 from 8-(2-chloro-pyridine-3-sulfonyl)-2-(4-trifluoromethoxy-phenyl)-2,8-diaza-spiro[4.5]decan-1-one (described in example 188) and ethanolamine. White gum. MS (ESI): 515.3 (MH$^+$).

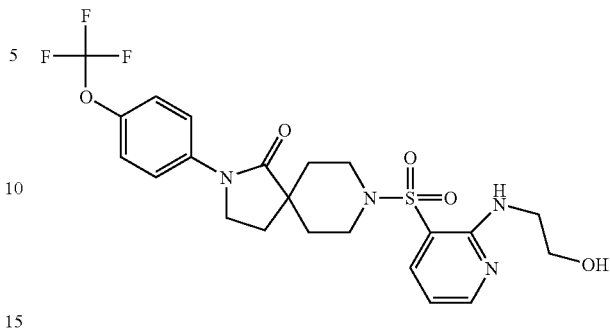

Example 193

8-[2-(2-Hydroxy-1-methyl-ethylamino)-pyridine-3-sulfonyl]-2-(4-trifluoromethoxy-phenyl)-2,8-diaza-spiro[4.5]decan-1-one The title compound was prepared in analogy to example 189 from 8-(2-chloro-pyridine-3-sulfonyl)-2-(4-trifluoromethoxy-phenyl)-2,8-diaza-spiro[4.5]decan-1-one (described in example 188) and DL-2-amino-1-propanol. White solid. MS (ESI): 529.3 (MH$^+$).

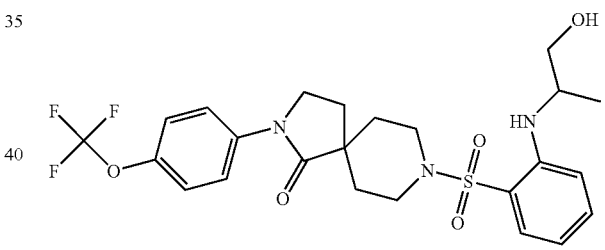

Example 194

8-(2-Methoxy-pyridine-3-sulfonyl)-2-(4-trifluoromethoxy-phenyl)-2,8-diaza-spiro[4.5]decan-1-one To a solution of 8-(2-chloro-pyridine-3-sulfonyl)-2-(4-trifluoromethoxy-phenyl)-2,8-diaza-spiro[4.5]decan-1-one (described in example 188, 15 mg, 0.03 mmol) in methanol (1 mL) was added sodium methoxide solution (5.4M solution in methanol, 11 uL, 0.06 mmol) and the reaction mixture was then stirred at 90° C. for 16 h. The reaction mixture was concentrated in vacuo to give a crude residue which was diluted with ethyl acetate and washed with water, sat. NaHCO$_3$ and brine. The organic layer was dried (Na$_2$SO$_4$), filtered and evaporated under reduced pressure to give a crude residue which was purified by flash column chromatography to yield the desired product as a white solid (14 mg, 94%). MS (ESI): 486.3 (MH$^+$).

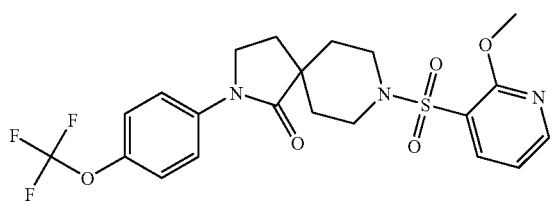

Example 195

8-(2-Benzyloxy-pyridine-3-sulfonyl)-2-(4-trifluoromethoxy-phenyl)-2,8-diaza-spiro[4.5]decan-1-one To a suspension of NaH (12 mg, 0.31 mmol) in DMF (2 mL) at 0° C. was added benzyl alcohol (25 uL, 0.25 mmol) and the mixture was stirred for 30 min at 0° C. A solution of 8-(2-chloro-pyridine-3-sulfonyl)-2-(4-trifluoromethoxy-phenyl)-2,8-diaza-spiro[4.5]decan-1-one (described in example 188, 100 mg, 0.20 mmol) in DMF (500 uL) was added drop-wise and the reaction mixture was allowed to warm to room temperature and stirred for 16 h. The reaction mixture was diluted with ethyl acetate and washed with brine. The organic phase was dried ($Na_2SO_4$), filtered and concentrated in vacuo to give the crude residue which was purified by flash column chromatography (1:2 AcOEt/heptane) which afforded the desired product as a colourless solid (100 mg, 87%). MS (ESI): 562.3 ($MH^+$).

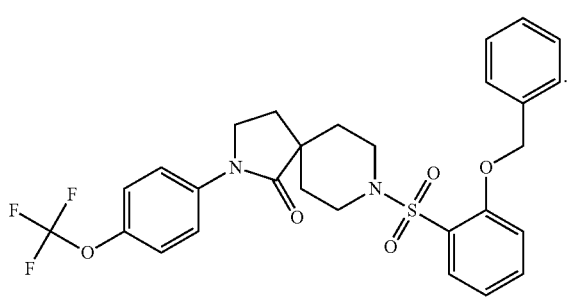

Example 196

8-(2-Hydroxy-pyridine-3-sulfonyl)-2-(4-trifluoromethoxy-phenyl)-2,8-diaza-spiro[4.5]decan-1-one The title compound was prepared in analogy to example 189 from 8-(2-chloro-pyridine-3-sulfonyl)-2-(4-trifluoromethoxy-phenyl)-2,8-diaza-spiro[4.5]decan-1-one (described in example 188) and 6N NaOH. White solid. MS (ESI): 472.2 ($MH^+$).

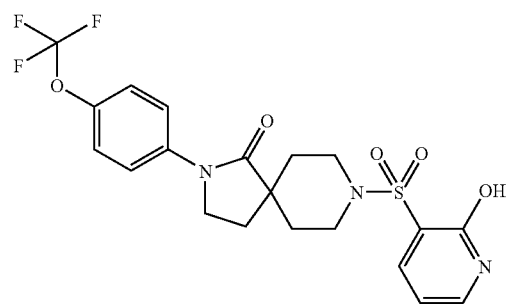

Example 197

8-(2-Amino-pyridine-3-sulfonyl)-2-(4-trifluoromethoxy-phenyl)-2,8-diaza-spiro[4.5]decan-1-one A mixture of 8-(2-chloro-pyridine-3-sulfonyl)-2-(4-trifluoromethoxy-phenyl)-2,8-diaza-spiro[4.5]decan-1-one (example 188, 40 mg, 0.08 mmol) and ammonium hydroxide (2M solution in water, 8 mL) was heated in an autoclave at 150° C. for 16 h. The reaction mixture was concentrated in vacuo to give a crude residue which was purified by flash column chromatography (5% methanol in chloroform) to yield the desired product as a white solid (36 mg, 98%). MS (ESI): 471.2 ($MH^+$).

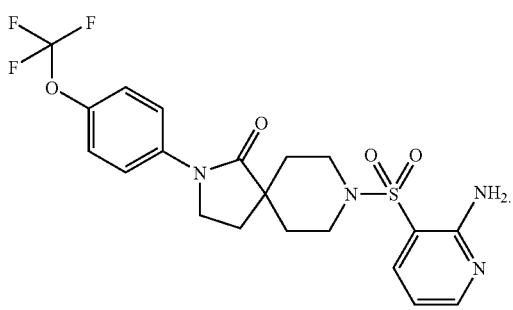

Example 198

8-(6-Chloro-pyridine-3-sulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diaza-spiro[4.5]decan-1-one acetic acid salt (described in example 180 step C) and 6-chloro-pyridine-3-sulfonyl chloride. White solid. MS (ESI): 490.2 ($MH^+$).

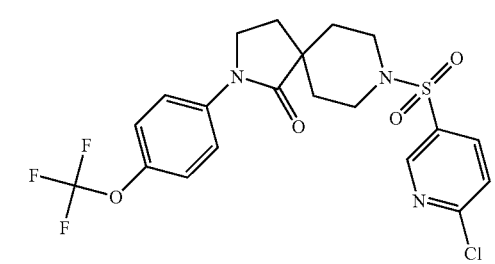

Example 199

8-(4-Chloro-pyridine-3-sulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diaza-spiro[4.5]decan-1-one (described in example 180 step C) and 4-chloro-pyridine-3-sulfonyl chloride. Off-white solid. MS (ESI): 490.2 (MH+).

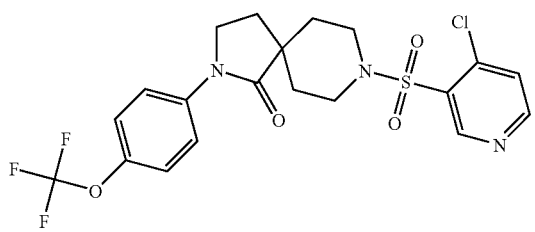

Example 200

8-(4-Methoxy-pyridine-3-sulfonyl)-2-(4-trifluoromethoxy-phenyl)-2,8-diaza-spiro[4.5]decan-1-one The title compound was prepared in analogy to example 194 from 8-(4-chloro-pyridine-3-sulfonyl)-2-(4-trifluoromethoxy-phenyl)-2,8-diaza-spiro[4.5]decan-1-one (described in 199) and sodium methoxide. Off-white solid. MS (ESI): 486.3 (MH+).

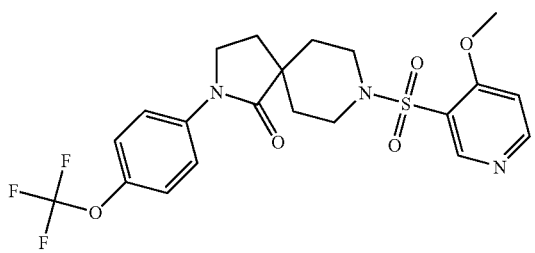

Example 201

8-(Pyridine-2-sulfonyl)-2-(4-trifluoromethoxy-phenyl)-2,8-diaza-spiro[4.5]decan-1-one Pyridine-2-thiol (5.4 mg, 0.05 mmol) was stirred in a mixture of 1 mL of CH$_2$Cl$_2$ and 1 mL of 1 M HCl for 10 min at −10 to −5° C. Cold sodium hypochlorite (1.68M solution, 95 uL, 0.16 mmol) was added drop-wise with and the reaction mixture was stirred at −10 to −5° C. for 15 min. The mixture was transferred to a separatory funnel (pre-cooled with ice water) and an additional 15 mL of cold CH$_2$Cl$_2$ was added. The organic phase was rapidly separated and collected in a pre-cooled Erlenmeyer flask. A pre-cooled mixture of 2-(4-trifluoromethoxy-phenyl)-2,8-diaza-spiro[4.5]decan-1-one acetic acid salt (described in example 180 step C, 20 mg, 0.05 mmol) and triethylamine (8 uL, 0.06 mmol) in 1 ml of DCM was added drop-wise. Then the flask was warmed to 0° C. and stirring was continued for 10 min. The reaction mixture was washed with water, sat. NaHCO$_3$ and brine. The organic phase was dried (Na$_2$SO$_4$), filtered and concentrated in vacuo to give a crude residue which was purified by flash column chromatography (1:4 AcOEt/heptane) which afforded the desired product as a white solid (14 mg, 63%). MS (ESI): 456.2 (MH+).

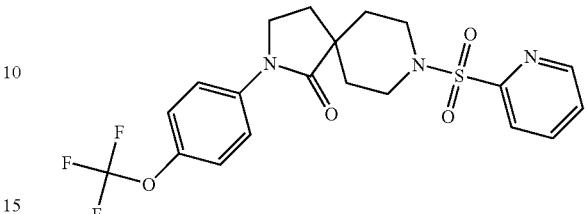

Example 202

8-(Pyrimidine-2-sulfonyl)-2-(4-trifluoromethoxy-phenyl)-2,8-diaza-spiro[4.5]decan-1-one Pyrimidine-2-thiol (15.3 mg, 0.14 mmol) was stirred in a mixture of 2 mL of CH$_2$Cl$_2$ and 2 mL of 1M HCl (25 w % CaCl$_2$) for 10 min at −30 to −25° C. A cold mixture of sodium hypochlorite (1.68M solution, 268 uL, 0.45 mmol) and calcium chloride (272 mg, 2.46 mmol, in 200 uL of water) was added dropwise −30 to −25° C. and stirring was continued for 15 min. The mixture was transferred to a separatory funnel (pre-cooled with ice water) and an additional 15 mL of cold CH$_2$Cl$_2$ was added. The organic phase was rapidly separated and collected in a pre-cooled Erlenmeyer flask. A pre-cooled mixture of 2-(4-trifluoromethoxy-phenyl)-2,8-diaza-spiro[4.5]decan-1-one acetic acid salt (described in example 180 step C, 28 mg, 0.08 mmol) and triethylamine (11 uL, 0.08 mmol) in 1 ml of DCM was added dropwise. Then the flask was warmed to 0° C. and stirring was continued for 1 h. The reaction mixture was washed with water, sat. NaHCO$_3$ and brine. The organic phase was dried (Na$_2$SO$_4$), filtered and concentrated in vacuo to give the crude residue which was purified by flash column chromatography (1:4 AcOEt/heptane) which afforded the desired product as an off-white solid (20.6 mg, 33%). MS (ESI): 457.2 (MH+).

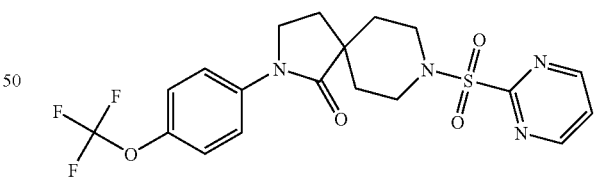

Example 203

8-(Pyridine-4-sulfonyl)-2-(4-trifluoromethoxy-phenyl)-2,8-diaza-spiro[4.5]decan-1-one The title compound was prepared in analogy to example 202 from 2-(4-trifluoromethoxy-phenyl)-2,8-diaza-spiro[4.5]decan-1-one acetic acid salt (described in example 180 step C) and pyridine-4-thiol. Off-white solid. MS (ESI): 456.2 (MH+).

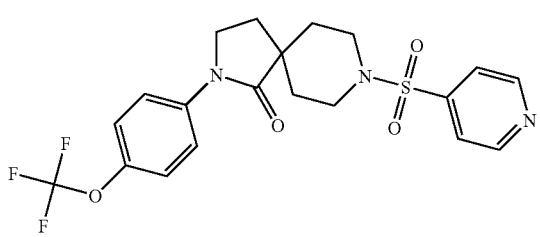

Example 204

8-(6-Methyl-pyridazine-3-sulfonyl)-2-(4-trifluoromethoxy-phenyl)-2,8-diaza-spiro[4.5]decan-1-one The title compound was prepared in analogy to example 202 from 2-(4-trifluoromethoxy-phenyl)-2,8-diaza-spiro[4.5]decan-1-one acetic acid salt (described in example 180 step C) and 6-methyl-pyridazine-3-thiol. Off-white solid. MS (ESI): 471.2 (MH$^+$).

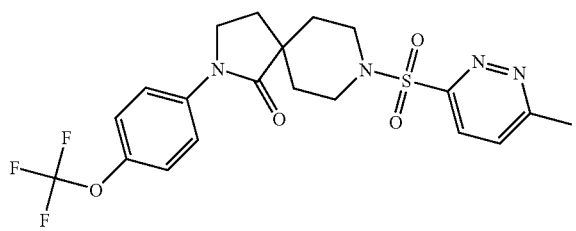

Example 205

8-(Pyridine-3-sulfonyl)-2-[4-(2,2,2-trifluoroethoxy)-phenyl]-2,8-diaza-spiro[4.5]decan-1-one The title compound was prepared in analogy to example 180 step D from 2-[4-(2,2,2-trifluoro-ethoxy)-phenyl]-2,8-diaza-spiro[4.5]decan-1-one (prepared in analogy to example 180 step B-D using 1-benzyl-4-(2-methoxyethyl)-piperidine-4-carboxylic acid ethyl ester and 4-(2,2,2-trifluoro-ethoxy) aniline) and pyridine-3-sulfonyl chloride; hydrochloride. White solid. MS (ESI): 470.1 (MH$^+$).

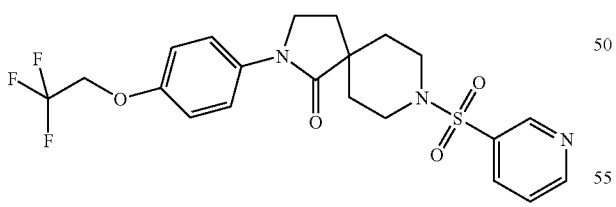

Example 206

8-(2-Chloro-pyridine-3-sulfonyl)-2-[4-(2,2,2-trifluoro-ethoxy)-phenyl]-2,8-diaza-spiro[4.5]decan-1-one The title compound was prepared in analogy to example 180 step D from 2-[4-(2,2,2-trifluoro-ethoxy)-phenyl]-2,8-diaza-spiro[4.5]decan-1-one (prepared in analogy to example 180 step B-D using 1-benzyl-4-(2-methoxyethyl)-piperidine-4-carboxylic acid ethyl ester and 4-(2,2,2-trifluoro-ethoxy) aniline) and 2-chloro-pyridine-3-sulfonyl chloride. White solid. MS (ESI): 504.1 (MH$^+$).

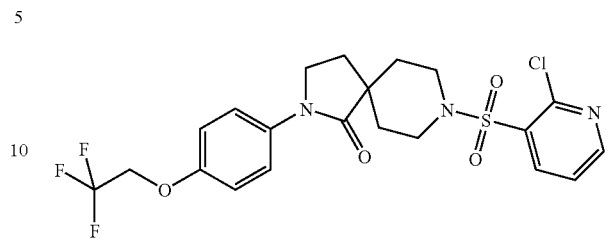

Example 207

8-(2-Methylamino-pyridine-3-sulfonyl)-2-[4-(2,2,2-trifluoro-ethoxy)-phenyl]-2,8-diaza-spiro[4.5]decan-1-one The title compound was prepared in analogy to example 189 from 8-(2-Chloro-pyridine-3-sulfonyl)-2-[4-(2,2,2-trifluoro-ethoxy)-phenyl]-2,8-diaza-spiro[4.5]decan-1-one (described in example 206) and methyl amine. Off-white solid. MS (ESI): 499.3 (MH$^+$).

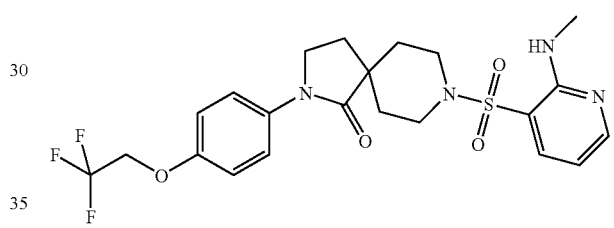

Example 208

8-(2-Cyclopropyl-2-hydroxy-ethanesulfonyl)-2-(4-trifluoromethoxy-phenyl)-2,8-diaza-spiro[4.5]decan-1-one Step A: 8-Methanesulfonyl-2-(4-trifluoromethoxy-phenyl)-2,8-diaza-spiro[4.5]decan-1-one

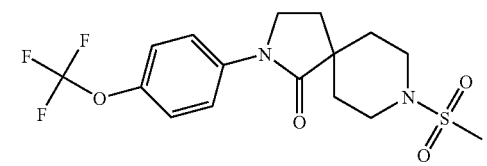

The title compound was prepared in analogy to example 180 step D from 2-(4-trifluoromethoxy-phenyl)-2,8-diaza-spiro[4.5]decan-1-one (described in example 180 step C) and methanesulfonyl chloride. White solid. MS (ESI): 393.2 (MH$^+$).

Step B: 8-(2-Cyclopropyl-2-hydroxy-ethanesulfonyl)-2-(4-trifluoromethoxy-phenyl)-2,8-diaza-spiro[4.5]decan-1-one To a solution of 8-methanesulfonyl-2-(4-trifluoromethoxy-phenyl)-2,8-diaza-spiro[4.5]decan-1-one (76 mg, 0.19 mmol) in THF at −78° C. was added n-BuLi (1.6M, 145 uL, 0.23 mmol) dropwise. The reaction mixture was stirred for 5 min followed by the addition of a solution of cyclopropanecarbaldehyde (54 mg, 0.78 mmol) in THF (500 uL) at −78° C. The dry ice bath was removed and the reaction mixture was warmed to 0° C. and stirring was continued for a further 30 min. The reaction mixture was quenched with AcOH (20 uL) and was then concentrated to dryness under reduced pressure. The crude residue was partitioned between ethyl acetate and water and the organic layer was then washed with brine, dried with $Na_2SO_4$, filtered and concentrated in vacuo to give a crude residue which was purified by flash column chromatography to afford 8-(2-cyclopropyl-2-hydroxy-ethanesulfonyl)-2-(4-trifluoromethoxy-phenyl)-2,8-diaza-spiro[4.5]decan-1-one (42 mg, 47%) as a white solid. MS (ESI): 463.2 (MH+)

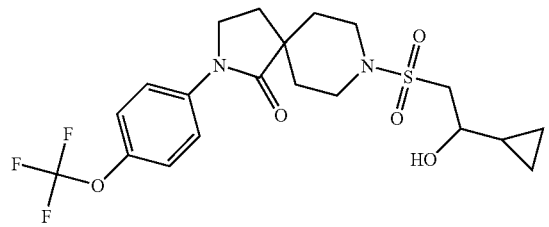

Example 209

8-(2-Cyclopropyl-2-methoxy-ethanesulfonyl)-2-(4-trifluoromethoxy-phenyl)-2,8-diaza-spiro[4.5]decan-1-one A mixture of 8-(2-cyclopropyl-2-hydroxy-ethanesulfonyl)-2-(4-trifluoromethoxy-phenyl)-2,8-diaza-spiro[4.5]decan-1-one (described in example 208, 30 mg, 0.07 mmol), dry calcium sulfate (33 mg, 0.26 mmol) and silver oxide (60 mg, 0.26 mmol) in methyl iodide (1 mL) was stirred at room temperature for 48 h. The reaction mixture was filtered through Celite® and washed with methylene chloride. The filtrate was concentrated to dryness under reduced pressure to give the crude residue which was purified by flash column chromatography (1:1 AcOEt/heptane) which afforded the desired product as a white solid (12.5 mg, 40%). MS (ESI): 477.2 (MH+).

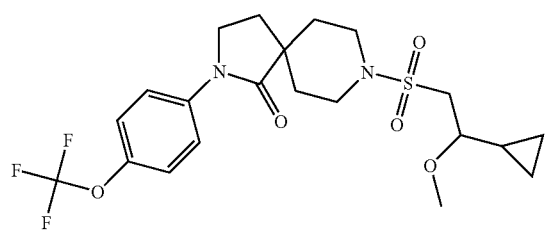

Example 210

8-(1-Hydroxy-cyclopentylmethanesulfonyl)-2-(4-trifluoromethoxy-phenyl)-2,8-diaza-spiro[4.5]decan-1-one The title compound was prepared in analogy to example 208 step B from 8-methanesulfonyl-2-(4-trifluoromethoxy-phenyl)-2,8-diaza-spiro[4.5]decan-1-one (described in example 208, step A) and cyclopentanone. White solid. MS (ESI): 477.2 (MH+).

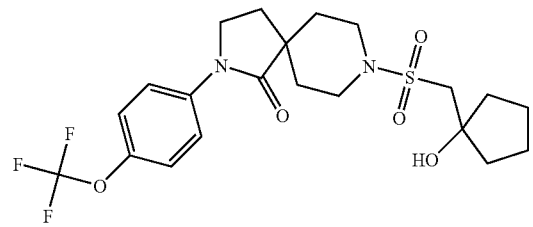

Example 211

8-(1-Methoxy-cyclopentylmethanesulfonyl)-2-(4-trifluoromethoxy-phenyl)-2,8-diaza-spiro[4.5]decan-1-one The title compound was prepared in analogy to example 209 from 8-(1-hydroxy-cyclopentylmethanesulfonyl)-2-(4-trifluoromethoxy-phenyl)-2,8-diaza-spiro[4.5]decan-1-one (described in example 210) and methyl iodide. Off-white solid. MS (ESI): 491.2 (MH+).

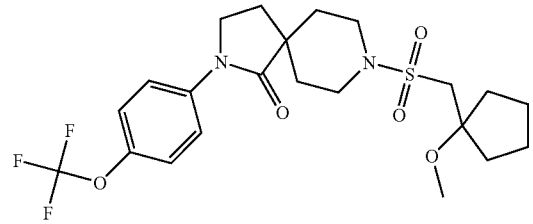

Example 212

8-(2-Hydroxy-2-methyl-propane-1-sulfonyl)-2-(4-trifluoromethoxy-phenyl)-2,8-diaza-spiro[4.5]decan-1-one The title compound was prepared in analogy to example 208 step B from 8-methanesulfonyl-2-(4-trifluoromethoxy-phenyl)-2,8-diaza-spiro[4.5]decan-1-one (described in example 208, step A) and propan-2-one. White solid. MS (ESI): 451.2 (MH+).

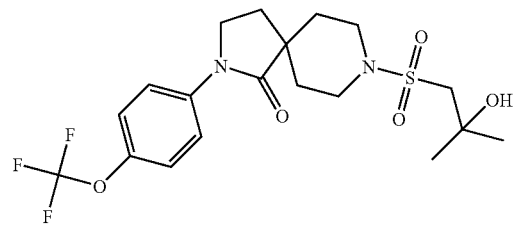

Example 213

8-[Dihydro-furan-(2Z)-ylidenemethanesulfonyl]-2-(4-trifluoromethoxy-phenyl)-2,8-diaza-spiro[4.5]decan-1-one To a solution of 8-methanesulfonyl-2-(4-trifluoromethoxy-phenyl)-2,8-diaza-spiro[4.5]decan-1-one (described in example 208, step A) (50 mg, 13 mmol) in THF (3 mL) at −78° C. was added nBuLi (1.6M solution in heptane, 80 uL, 13 mmol), and the reaction mixture was stirred at −78° C. for 10 mins. Then a solution of 4-bromo-butyryl chloride (15 uL 0.13 mmol) in THF (1 mL) was added and the reaction mixture was stirred for a further 30 mins at −78° C. and then another 2 equivalents of nBuLi were added and the reaction mixture was warmed to room temperature. The reaction was quenched with water and extracted with ethyl acetate. The organic phases were combined, dried ($Na_2SO_4$), filtered and concentrated in vacuo to give a crude residue was purified by flash column chromatography (4:1 AcOEt/heptane) to yield 8-[dihydro-furan-(2Z)-ylidenemethanesulfonyl]-2-(4-trifluoromethoxy-phenyl)-2,8-diaza-spiro[4.5]decan-1-one (15 mg, 26%) as a white solid. MS (ESI): 461.4 ($MH^+$).

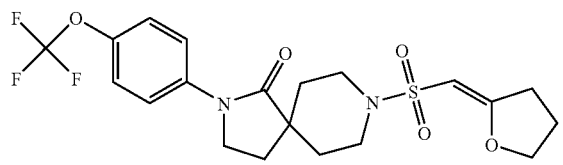

Example 214

8-(Tetrahydro-furan-2-ylmethanesulfonyl)-2-(4-trifluoromethoxy-phenyl)-2,8-diaza-spiro[4.5]decan-1-one 8-[Dihydro-furan-(2Z)-ylidenemethanesulfonyl]-2-(4-trifluoromethoxy-phenyl)-2,8-diaza-spiro[4.5]decan-1-one (described in example 213, 15 mg, 0.03 mmol) was dissolved in MeOH (2 mL). The flask was evacuated and then purged with argon. Pd/C (2 mg) was added in one portion and the flask was evacuated, then purged with hydrogen three times. The reaction mixture was then stirred at room temperature for 16 h. The mixture was filtered through Celite® and the filtrate was then concentrated in vacuo and purified by flash column chromatography (3:2 AcOEt/heptane) to give 8-(tetrahydro-furan-2-ylmethanesulfonyl)-2-(4-trifluoromethoxy-phenyl)-2,8-diaza-spiro[4.5]decan-1-one (5 mg, 33%) as a white solid. MS (ESI): 463.3 ($MH^+$).

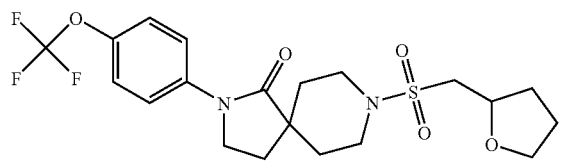

Example 215

8-(3-Hydroxy-3-methyl-pentanoyl)-2-(4-trifluoromethoxy-phenyl)-2,8-diaza-spiro[4.5]decan-1-one

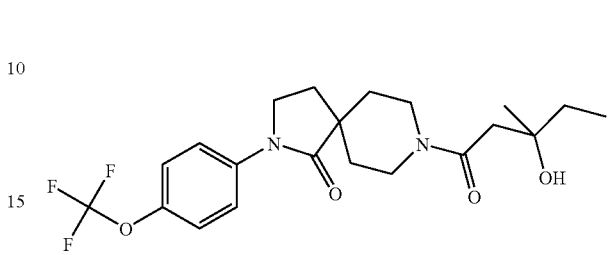

The title compound was prepared in analogy to example 13 step A (using TBTU instead of BOP as the coupling reagent) from 2-(4-trifluoromethoxy-phenyl)-2,8-diaza-spiro[4.5]decan-1-one acetic acid salt (described in example 180 step C) and 3-hydroxy-3-methyl-pentanoic acid. Light brown oil. MS (ESI): 429.2 ($MH^+$).

Example 216

8-(2-Cyclobutyl-acetyl)-2-(4-trifluoromethoxy-phenyl)-2,8-diaza-spiro[4.5]decan-1-one The title compound was prepared in analogy to example 13 step A (using TBTU instead of BOP as the coupling reagent) from 2-(4-trifluoromethoxy-phenyl)-2,8-diaza-spiro[4.5]decan-1-one acetic acid salt (described in example 180 step C) and cyclobutyl-acetic acid. Off-white solid. MS (ESI): 411.3 ($MH^+$).

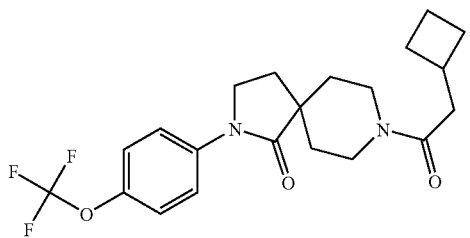

Example 217

8-(2-Isopropoxy-acetyl)-2-(4-trifluoromethoxy-phenyl)-2,8-diaza-spiro[4.5]decan-1-one The title compound was prepared in analogy to example 13 step A (using TBTU instead of BOP as the coupling reagent) from 2-(4-trifluoromethoxy-phenyl)-2,8-diaza-spiro[4.5]decan-1-one acetic acid salt (described in example 180 step C) and isopropoxy-acetic acid. Off-white solid. MS (ESI): 415.3 ($MH^+$).

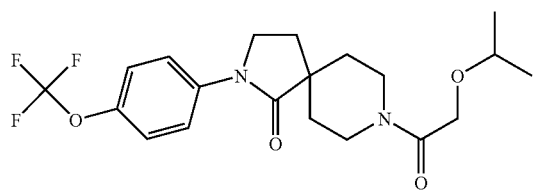

Example 218

8-(2-tert-Butoxy-acetyl)-2-(4-trifluoromethoxy-phenyl)-2,8-diaza-spiro[4.5]decan-1-one The title compound was prepared in analogy to example 13 step A (using TBTU instead of BOP as the coupling reagent) from 2-(4-trifluoromethoxy-phenyl)-2,8-diaza-spiro[4.5]decan-1-one acetic acid salt (described in example 180 step C) and tert-butoxy-acetic acid. White solid. MS (ESI): 429.3 (MH$^+$).

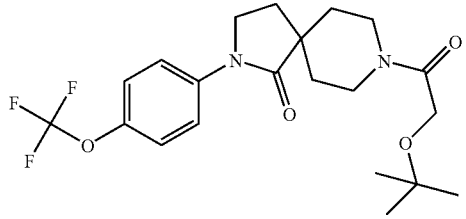

Example 219

8-(1-Hydroxy-cyclopropanecarbonyl)-2-(4-trifluoromethoxy-phenyl)-2,8-diaza-spiro[4.5]decan-1-one The title compound was prepared in analogy to example 13 step A (using TBTU instead of BOP as the coupling reagent) from 2-(4-trifluoromethoxy-phenyl)-2,8-diaza-spiro[4.5]decan-1-one acetic acid salt (described in example 180 step C) and 1-hydroxy-cyclopropanecarboxylic acid. White solid. MS (ESI): 399.1 (MH$^+$).

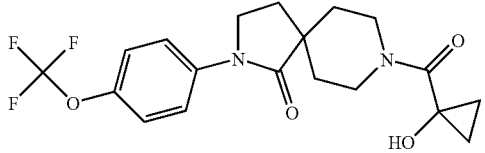

Example 220

8-(2-Benzyloxy-acetyl)-2-(4-trifluoromethoxy-phenyl)-2,8-diaza-spiro[4.5]decan-1-one The title compound was prepared in analogy to example 7 step A from 2-(4-trifluoromethoxy-phenyl)-2,8-diaza-spiro[4.5]decan-1-one acetic acid salt (described in example 180 step C) and benzyloxy-acetyl chloride. Off-white solid. MS (ESI): 463.3 (MH$^+$).

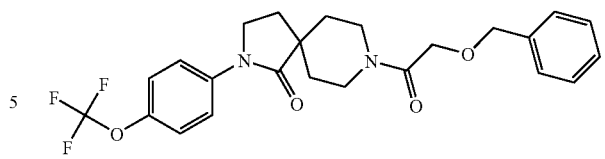

Example 221

8-(2-Phenoxy-acetyl)-2-(4-trifluoromethoxy-phenyl)-2,8-diaza-spiro[4.5]decan-1-one The title compound was prepared in analogy to example 7 step A from 2-(4-trifluoromethoxy-phenyl)-2,8-diaza-spiro[4.5]decan-1-one acetic acid salt (described in example 180 step C) and phenoxy-acetyl chloride. White solid. MS (ESI): 449.2 (MH$^+$).

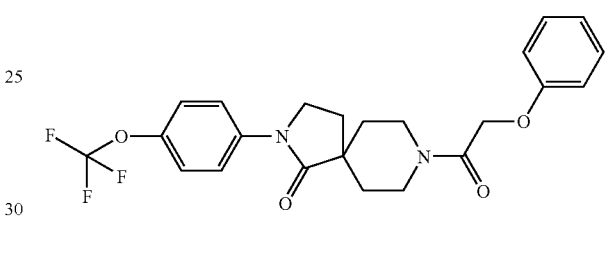

Example 222

8-(2-Phenyl-propionyl)-2-(4-trifluoromethoxy-phenyl)-2,8-diaza-spiro[4.5]decan-1-one The title compound was prepared in analogy to example 7 step A from 2-(4-trifluoromethoxy-phenyl)-2,8-diaza-spiro[4.5]decan-1-one acetic acid salt (described in example 180 step C) and 2-phenyl-propionyl chloride. Off-white solid. MS (ESI): 447.3 (MH$^+$).

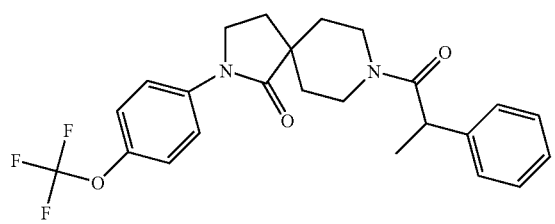

Example 223

8-(2-Phenyl-butyryl)-2-(4-trifluoromethoxy-phenyl)-2,8-diaza-spiro[4.5]decan-1-one The title compound was prepared in analogy to example 7 step A from 2-(4-trifluoromethoxy-phenyl)-2,8-diaza-spiro[4.5]decan-1-one acetic acid salt (described in example 180 step C) and 2-phenyl-butyryl chloride. Off-white solid. MS (ESI): 461.4 (MH$^+$).

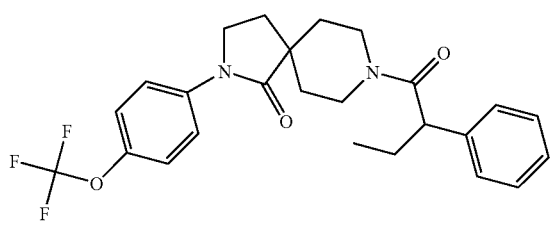

Example 224

8-(2-Methyl-thiazole-4-carbonyl)-2-(4-trifluoromethoxy-phenyl)-2,8-diaza-spiro[4.5]decan-1-one The title compound was prepared in analogy to example 7 step A from 2-(4-trifluoromethoxy-phenyl)-2,8-diaza-spiro[4.5]decan-1-one acetic acid salt (described in example 180 step C) and 2-methyl-thiazole-4-carbonyl chloride; hydrochloride. Off-white solid. MS (ESI): 440.2 (MH$^+$).

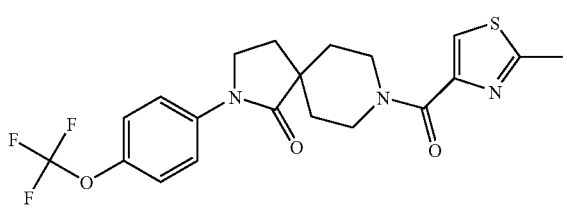

Example 225

8-(2-Chloro-acetyl)-2-(4-trifluoromethoxy-phenyl)-2,8-diaza-spiro[4.5]decan-1-one The title compound was prepared in analogy to example 7 step A from 2-(4-trifluoromethoxy-phenyl)-2,8-diaza-spiro[4.5]decan-1-one (described in example 180 step C) and chloroacetyl chloride. White solid. MS (ESI): 391.1 (MH$^+$).

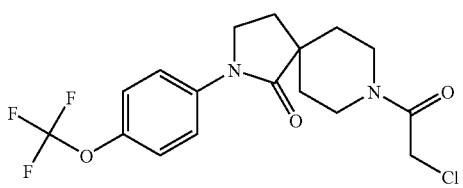

Example 226

8-(2-Cyclopentyloxy-acetyl)-2-(4-trifluoromethoxy-phenyl)-2,8-diaza-spiro[4.5]decan-1-one To a suspension of NaH (5 mg, 0.13 mmol) in THF (2 mL) at 0° C. was added cyclopentanol (10 uL, 0.11 mmol) and the mixture was stirred for 30 min at 0° C. A solution of 8-(2-chloro-acetyl)-2-(4-trifluoromethoxy-phenyl)-2,8-diaza-spiro[4.5]decan-1-one (example 225, 42 mg, 0.11 mmol) in THF (500 uL) was added drop-wise and the reaction mixture was allowed to warm to room temperature and stirred for 16 h. The reaction mixture was diluted with chloroform and the resultant precipitate was filtered off and the filtrate was concentrated in vacuo to give the crude residue which was purified by flash column chromatography (7:3 AcOEt/heptane) which afforded the desired product as a white solid (16 mg, 34%). MS (ESI): 441.3 (MH$^+$).

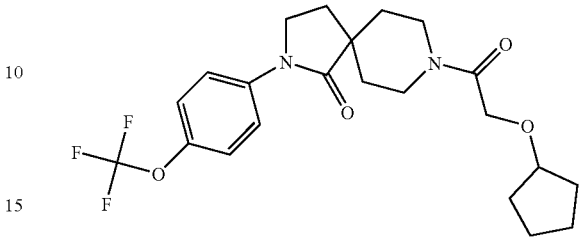

Example 227

8-(2-Chloro-benzenesulfonyl)-2-(3-chloro-4-trifluoromethyl-phenyl)-2,8-diaza-spiro[4.5]decan-1-one The title compound was prepared in analogy to example 148 step F) from 8-(2-chloro-benzenesulfonyl)-2,8-diaza-spiro[4.5]decan-1-one (described in example 148 step E or example 179 step A for an alternative synthesis) and 4-bromo-2-chloro-1-trifluoromethyl-benzene. Off-white solid. MS (ESI): 507.1 (MH$^+$).

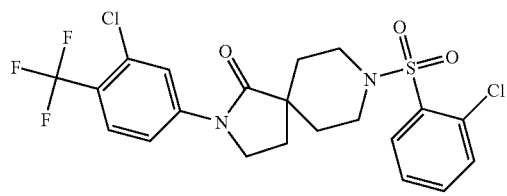

Example 228

8-(2-Chloro-benzenesulfonyl)-2-(2,2-difluoro-benzo[1,3]-dioxol-5-yl)-2,8-diaza-spiro[4.5]decan-1-one The title compound was prepared in analogy to example 148 step F) from 8-(2-chloro-benzenesulfonyl)-2,8-diaza-spiro[4.5]decan-1-one (described in example 148 step E or example 179 step A for an alternative synthesis) and 5-bromo-2,2-difluoro-benzo[1,3]dioxole. Off-white solid. MS (ESI): 485.1 (MH$^+$).

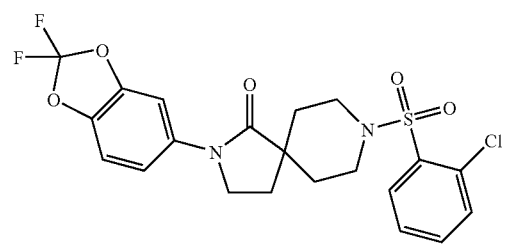

Example 229

8-(2-Chloro-benzenesulfonyl)-2-[4-(3-hydroxy-oxetan-3-yl)-phenyl]-2,8-diaza-spiro[4.5]decan-1-one The title compound was prepared in analogy to example 148 step F) from 8-(2-chloro-benzenesulfonyl)-2,8-diaza-spiro[4.5]decan-1-one (described in example 148 step E or example 179 step A for an alternative synthesis) and 3-(4-bromo-phenyl)-oxetan-3-ol (prepared as described in WO 2008/156726). White solid. MS (ESI): 477.1 (MH$^+$).

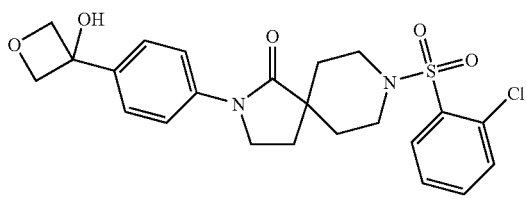

Example 230

8-(2-Chloro-benzenesulfonyl)-2-[4-(3-fluoro-oxetan-3-yl)-phenyl]-2,8-diaza-spiro[4.5]decan-1-one To a solution of 8-(2-chloro-benzenesulfonyl)-2-[4-(3-hydroxy-oxetan-3-yl)-phenyl]-2,8-diaza-spiro[4.5]decan-1-one (described in example 229, 35 mg, 0.07 mmol) in DCM was added DAST (11 uL, 0.08 mmol) at −78° C. The reaction mixture was stirred at −78° C. for 3 hr and then quenched with sat. NaHCO3. The reaction mixture was diluted with DCM and washed with brine, dried (Na2SO4), filtered and concentrated in vacuo to give a crude residue which was purified by flash column chromatography (1:1 AcOEt/heptane) to give 8-(2-chloro-benzenesulfonyl)-2-[4-(3-fluoro-oxetan-3-yl)-phenyl]-2,8-diaza-spiro[4.5]decan-1-one (14 mg, 40%) as a white solid. MS (ESI): 479.1 (MH$^+$).

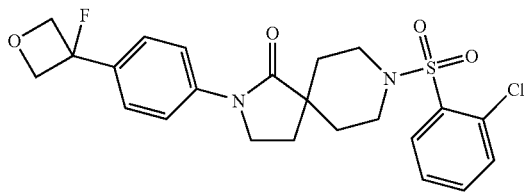

Example 231

8-(2-Chloro-benzenesulfonyl)-2-[4-(1-hydroxy-cyclobutyl)-phenyl]-2,8-diaza-spiro[4.5]decan-1-one The title compound was prepared in analogy to example 148 step F) from 8-(2-chloro-benzenesulfonyl)-2,8-diaza-spiro[4.5]decan-1-one (described in example 148 step E or example 179 step A for an alternative synthesis) and 1-(4-bromo-phenyl)-cyclobutanol (prepared as described in SYNLETT 2004, No. 8, pp 1440-1442). White solid. MS (ESI): 475.0 (MH$^+$).

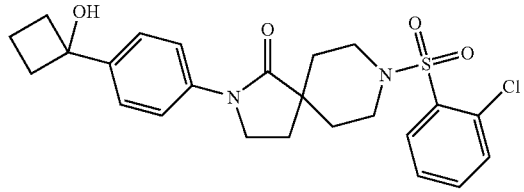

Example 232

8-(5-Methyl-isoxazol-3-ylmethanesulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diaza-spiro[4.5]decan-1-one acetic acid salt (described in example 180 step C) and (5-Methyl-isoxazol-3-yl)-methanesulfonyl chloride. Light yellow solid. MS (ESI): 474.13 (MH$^+$)

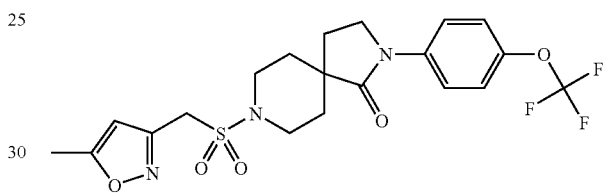

Example 233

8-(3-Isopropyl-isoxazol-5-ylmethanesulfonyl)-2-(4-trifluoromethoxy-phenyl)-2,8-diaza-spiro[4.5]decan-1-one The title compound was prepared in analogy to example 180 step D from 2-(4-trifluoromethoxy-phenyl)-2,8-diaza-spiro[4.5]decan-1-one acetic acid salt (described in example 180 step C) and (3-isopropyl-isoxazol-5-yl)-methanesulfonyl chloride. Light yellow solid. MS (ESI): 502.16 (MH$^+$)

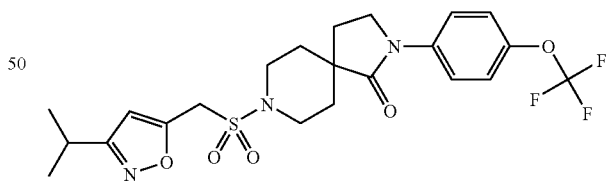

Preparation of the sulfonyl chloride, (3-isopropyl-isoxazol-5-yl)-methanesulfonyl chloride, used in the reaction above:

5-Chloromethyl-3-isopropyl-isoxazole (1.3 g) dissolved in acetone/water (50 ml/25 ml) was treated at RT with Na$_2$SO$_3$ (1.334 g) and then heated at 85° C. over night. The solvent was removed in vacuo and the white crystals obtained were carefully dried in a high vacuum for 24 h then suspended in POCl$_3$ (18.732 ml) and heated at 150° C. for 2.5 h. The reaction mixture was then concentrated in vacuo, the residue taken up in CH$_2$Cl$_2$ which was washed with water, dried over Na$_2$SO$_4$ and filtered. Removal of the solvent in vacuo gave then the desired product as brown oil (2.047 g). MS (EI): 223 (M$^+$)

Example 234

3-Methyl-2-[1-oxo-2-(4-trifluoromethoxy-phenyl)-2,8-diaza-spiro[4.5]decane-8-sulfonyl]-benzoic acid methyl ester The title compound was prepared in analogy to example 180 step D from 2-(4-trifluoromethoxy-phenyl)-2,8-diaza-spiro[4.5]decan-1-one acetic acid salt (described in example 180 step C) and 2-Chlorosulfonyl-3-methyl-benzoic acid methyl ester. White solid. MS (ESI): 527.14 (MH$^+$)

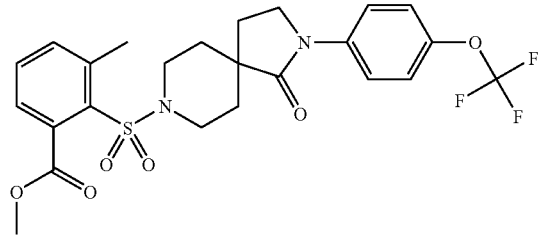

Example 235

8-(2-Chloro-benzenesulfonyl)-2-(3-chloro-benzyl)-2,8-diaza-spiro[4.5]decan-1-one

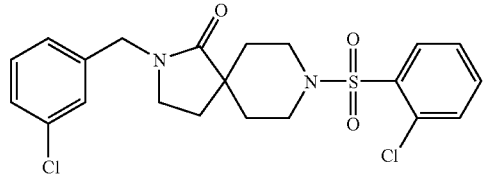

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 3-chloro-benzylamine. MS (ESI): 453.1 (MH$^+$).

Example 236

8-(2-Chloro-benzenesulfonyl)-2-phenethyl-2,8-diaza-spiro[4.5]decan-1-one

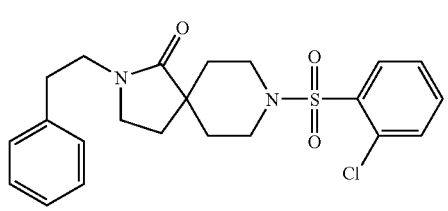

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and phenethylamine. MS (ESI): 433.3 (MH$^+$).

Example 237

8-(2-Chloro-benzenesulfonyl)-2-[2-(4-ethyl-phenyl)-ethyl]-2,8-diaza-spiro[4.5]decan-1-one

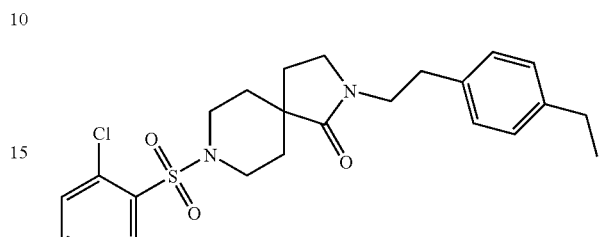

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 2-(4-Ethyl-phenyl)-ethylamine. MS (ESI): 461.4 (MH$^+$).

Example 238

2-[2-(4-tert-Butyl-phenyl)-ethyl]-8-(2-chloro-benzenesulfonyl)-2,8-diaza-spiro[4.5]decan-1-one

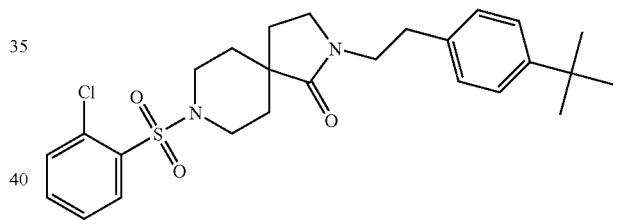

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 2-(4-tert-Butyl-phenyl)-ethylamine. MS (ESI): 489.4 (MH$^+$).

Example 239

8-(2-Chloro-benzenesulfonyl)-2-[2-(4-fluoro-phenyl)-ethyl]-2,8-diaza-spiro[4.5]decan-1-one

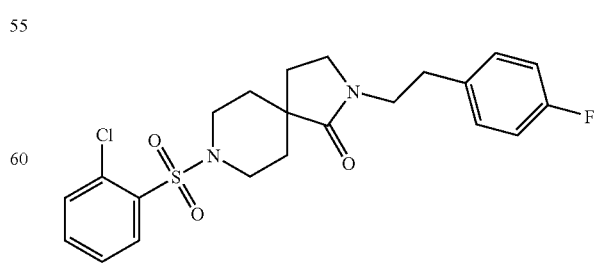

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 2-(4-Fluoro-phenyl)-ethylamine. MS (ESI): 451.3 (MH+).

Example 240

8-(2-Chloro-benzenesulfonyl)-2-[2-(4-methoxy-phenyl)-ethyl]-2,8-diaza-spiro[4.5]decan-1-one

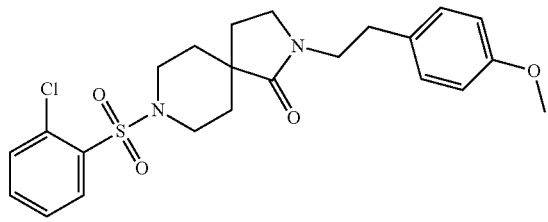

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 2-(4-Methoxy-phenyl)-ethylamine. MS (ESI): 463.4 (MH+).

Example 241

8-(2-Chloro-benzenesulfonyl)-2-(3-phenyl-propyl)-2,8-diaza-spiro[4.5]decan-1-one

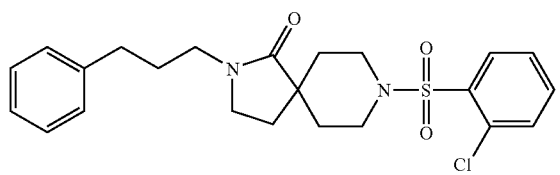

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 3-Phenyl-propylamine. MS (ESI): 447.4 (MH+).

Example 242

8-(2-Chloro-benzenesulfonyl)-2-[2-(2-chloro-phenyl)-ethyl]-2,8-diaza-spiro[4.5]decan-1-one

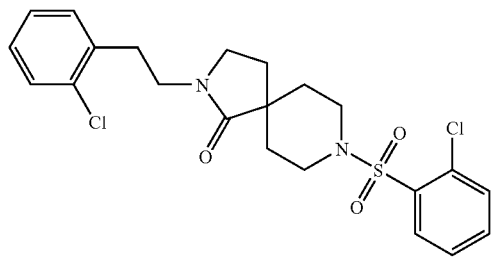

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 2-(2-Chloro-phenyl)-ethylamine. MS (ESI): 467.3 (MH+).

Example 243

8-(2-Chloro-benzenesulfonyl)-2-[2-(3-fluoro-phenyl)-ethyl]-2,8-diaza-spiro[4.5]decan-1-one

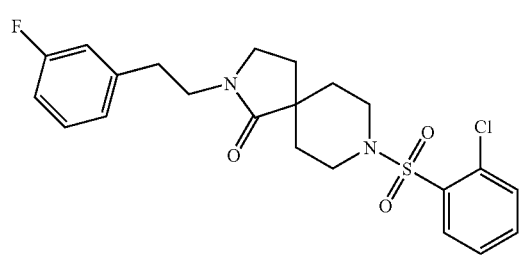

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 2-(3-Fluoro-phenyl)-ethylamine. MS (ESI): 451.4 (MH+).

Example 244

8-(2-Chloro-benzenesulfonyl)-2-[2-(3-methoxy-phenyl)-ethyl]-2,8-diaza-spiro[4.5]decan-1-one

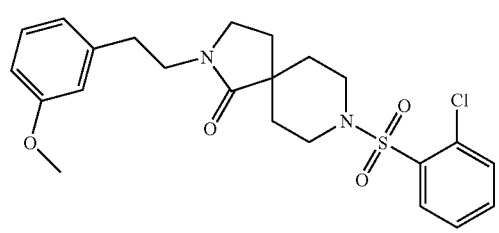

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 2-(3-Methoxy-phenyl)-ethylamine. MS (ESI): 463.4 (MH+).

Example 245

8-(2-Chloro-benzenesulfonyl)-2-[2-(3-trifluoromethyl-phenyl)-ethyl]-2,8-diaza-spiro[4.5]decan-1-one

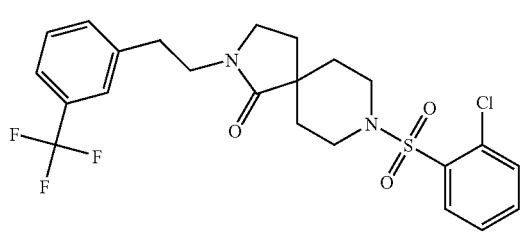

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 2-(3-Trifluoromethyl-phenyl)-ethylamine. MS (ESI): 501.4 (MH+).

Example 246

8-(2-Chloro-benzenesulfonyl)-2-(4-phenyl-butyl)-2,8-diaza-spiro[4.5]decan-1-one

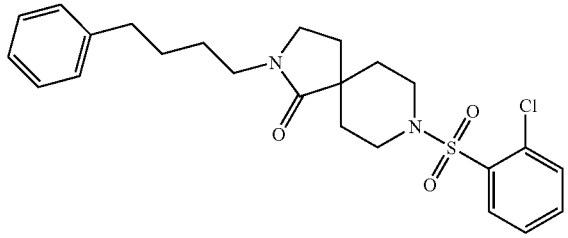

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 4-Phenyl-butylamine. MS (ESI): 461.4 (MH+).

Example 247

8-(2-Chloro-benzenesulfonyl)-2-[2-(3-chloro-phenyl)-ethyl]-2,8-diaza-spiro[4.5]decan-1-one

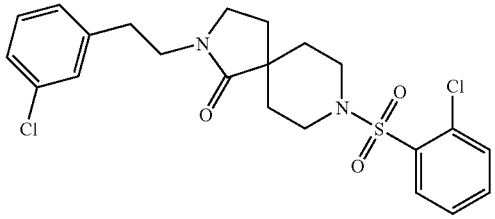

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 2-(3-Chloro-phenyl)-ethylamine. MS (ESI): 467.2 (MH+).

Example 248

8-(2-Chloro-benzenesulfonyl)-2-[2-(3,4-dichloro-phenyl)-ethyl]-2,8-diaza-spiro[4.5]decan-1-one

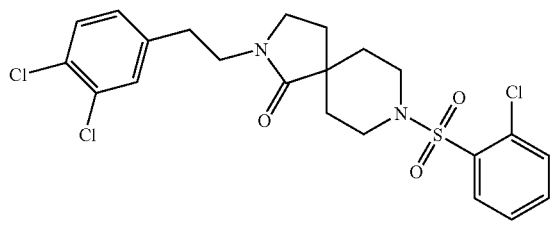

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 2-(3,4-Dichloro-phenyl)-ethylamine. MS (ESI): 503.1 (MH+).

Example 249

8-(2-Chloro-benzenesulfonyl)-2-[2-(4-fluoro-phenyl)-1-methyl-ethyl]-2,8-diaza-spiro[4.5]decan-1-one

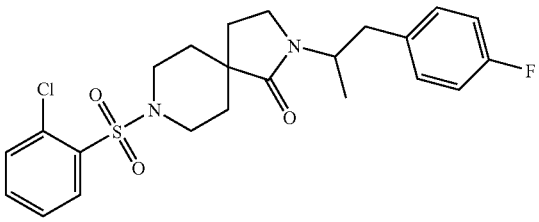

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in toluene and 2-(4-Fluoro-phenyl)-1-methyl-ethylamine. MS (ESI): 465.3 (MH+).

Example 250

8-(2-Chloro-benzenesulfonyl)-2-(6-ethyl-pyridin-3-yl)-2,8-diaza-spiro[4.5]decan-1-one

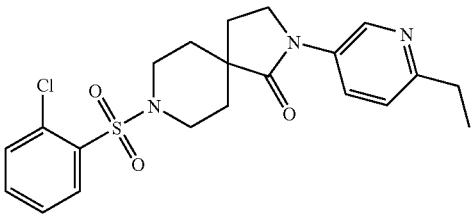

This material was prepared in analogy to example 1 step D) from 1-(2-chloro-benzenesulfonyl)-4-(2-methoxy-ethyl)-piperidine-4-carboxylic acid ethyl ester, dimethylaluminium chloride in heptane and 6-Ethyl-pyridin-3-ylamine. MS (ESI): 434.3 (MH+).

Example 251

1-Oxo-2-(4-trifluoromethoxy-phenyl)-2,8-diaza-spiro[4.5]decane-8-carboxylic acid propylamide

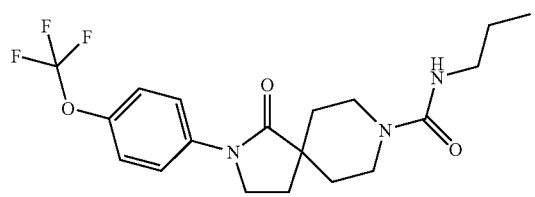

Step A): 2-(4-Trifluoromethoxy-phenyl)-2,8-diaza-spiro[4.5]decan-1-one

This material was prepared in analogy to example 1 step D) from 4-(2-methoxy-ethyl)-piperidine-1,4-dicarboxylic acid 1-tert-butyl ester 4-ethyl ester, dimethylaluminium chloride in hexane and 4-trifluoromethoxy-phenylamine, with concomitant cleavage of the Boc protecting group at the reaction conditions applied. MS (ESI): 315.2 (MH$^+$).

(This presents an alternative reaction sequence to prepare this compound besides the reaction sequence described in example 180 steps A to C).

Step B): 1-Oxo-2-(4-trifluoromethoxy-phenyl)-2,8-diaza-spiro[4.5]decane-8-carboxylic acid propylamide To a mixture of 13.7 mg (0.06 mmol) 2-(4-Trifluoromethoxy-phenyl)-2,8-diaza-spiro[4.5]decan-1-one and 24.2 mg (0.24 mmol) NEt$_3$ in 2 mL CH$_2$Cl$_2$ at 0° C. was added 13 mg (0.066 mmol) diphosgene and stirred for 10 min. After addition of 10.6 mg (0.18 mmol) propylamine the mixture was stirred for 16 h at room temperature, evaporated to dryness and purified by preparative HPLC on reversed phase eluting with a gradient formed from acetonitrile, water and NEt$_3$. The product containing fractions were evaporated to yield 1.1 mg (5%) the title compound. MS (ESI): 400.3 (MH$^+$).

Example 252

2-(4-Ethyl-phenyl)-1-oxo-2,8-diaza-spiro[4.5]decane-8-carboxylic acid methyl-propyl-amide

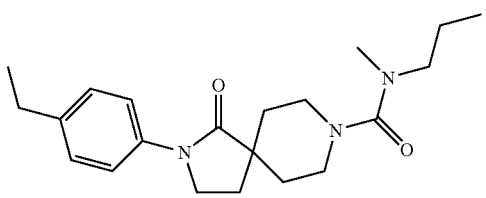

step A): 2-(4-Ethyl-phenyl)-2,8-diaza-spiro[4.5]decan-1-one

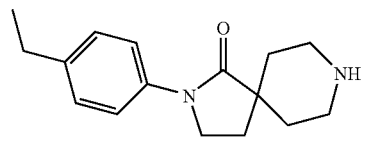

This material was prepared in analogy to example 251 step A) from 4-(2-methoxy-ethyl)-piperidine-1,4-dicarboxylic acid 1-tert-butyl ester 4-ethyl ester, dimethylaluminium chloride in hexane and 4-ethyl-phenylamine, with concomitant cleavage of the Boc protecting group under the conditions. MS (ESI): 259.1 (MH$^+$).

step B): 2-(4-Ethyl-phenyl)-1-oxo-2,8-diaza-spiro[4.5]decane-8-carboxylic acid methyl-propyl-amide This material was prepared in analogy to example 251 step B) from 2-(4-Ethyl-phenyl)-2,8-diaza-spiro[4.5]decan-1-one, diphosgene and methyl-propyl-amine. MS (ESI): 358.4 (MH$^+$).

Example 253

1-Oxo-2-(4-trifluoromethoxy-phenyl)-2,8-diaza-spiro[4.5]decane-8-carboxylic acid methyl-propyl-amide

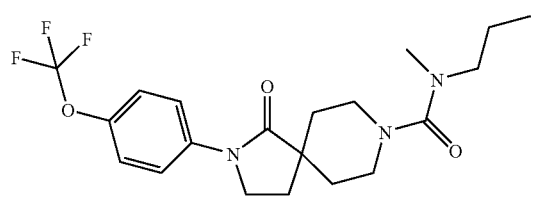

This material was prepared in analogy to example 251 step B) from 2-(4-trifluoromethoxy-phenyl)-2,8-diaza-spiro[4.5]decan-1-one, diphosgene and methyl-propyl-amine. MS (ESI): 414.3 (MH$^+$).

Example 254

1-Oxo-2-(4-trifluoromethoxy-phenyl)-2,8-diaza-spiro[4.5]decane-8-carboxylic acid isopropylamide

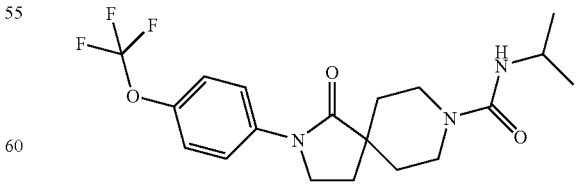

This material was prepared in analogy to example 251 step B) from 2-(4-trifluoromethoxy-phenyl)-2,8-diaza-spiro[4.5]decan-1-one, diphosgene and isopropylamine. MS (ESI): 400.3 (MH$^+$).

Example 255

2-(4-Ethyl-phenyl)-8-(piperidine-1-carbonyl)-2,8-diaza-spiro[4.5]decan-1-one

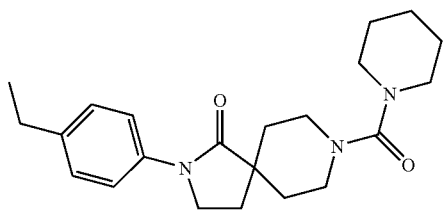

This material was prepared in analogy to example 251 step B) from 2-(4-Ethyl-phenyl)-2,8-diaza-spiro[4.5]decan-1-one, diphosgene and piperidine. MS (ESI): 370.3 (MH$^+$).

Example 256

8-(Piperidine-1-carbonyl)-2-(4-trifluoromethoxy-phenyl)-2,8-diaza-spiro[4.5]decan-1-one

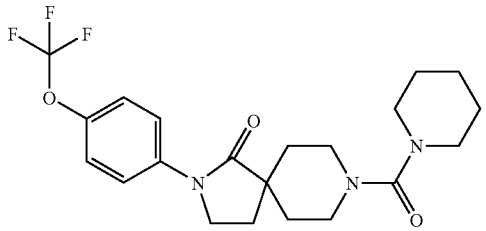

This material was prepared in analogy to example 251 step B) from 2-(4-trifluoromethoxy-phenyl)-2,8-diaza-spiro[4.5]decan-1-one, diphosgene and piperidine. MS (ESI): 426.3 (MH$^+$).

Example 257

8-(Morpholine-4-carbonyl)-2-(4-trifluoromethoxy-phenyl)-2,8-diaza-spiro[4,5]decan-1-one

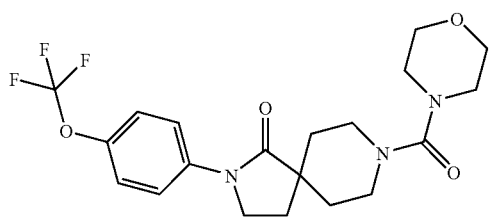

This material was prepared in analogy to example 251 step B) from 2-(4-trifluoromethoxy-phenyl)-2,8-diaza-spiro[4.5]decan-1-one, diphosgene and morpholine. MS (ESI): 428.3 (MH$^+$).

Example 258

2-(4-Ethyl-phenyl)-1-oxo-2,8-diaza-spiro[4.5]decane-8-carboxylic acid (4-fluoro-phenyl)-amide

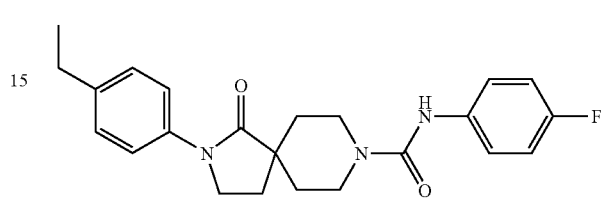

This material was prepared in analogy to example 251 step B) from 2-(4-Ethyl-phenyl)-2,8-diaza-spiro[4.5]decan-1-one, diphosgene and 4-Fluoro-phenylamine. MS (ESI): 396.3 (MH$^+$).

Example 259

1-Oxo-2-(4-trifluoromethoxy-phenyl)-2,8-diaza-spiro[4.5]decane-8-carboxylic acid (4-fluoro-phenyl)-amide

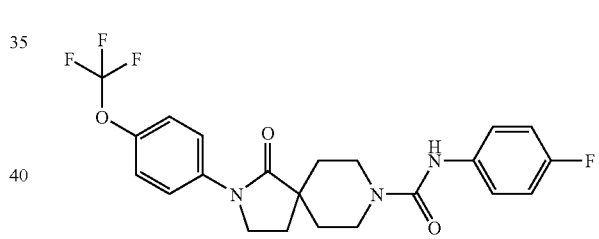

This material was prepared in analogy to example 251 step B) from 2-(4-trifluoromethoxy-phenyl)-2,8-diaza-spiro[4.5]decan-1-one, diphosgene and 4-Fluoro-phenylamine. MS (ESI): 452.3 (MH$^+$).

Example 260

2-(4-Ethyl-phenyl)-1-oxo-2,8-diaza-spiro[4.5]decane-8-carboxylic acid 4-fluoro-benzylamide

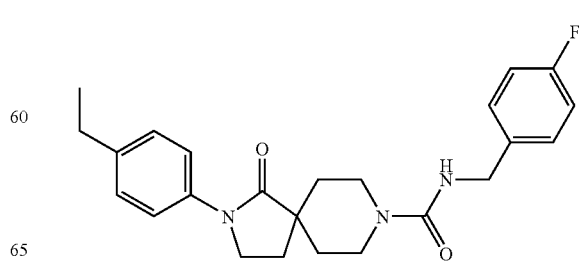

This material was prepared in analogy to example 251 step B) from 2-(4-Ethyl-phenyl)-2,8-diaza-spiro[4.5]decan-1-one, diphosgene and 4-Fluoro-benzylamine. MS (ESI): 410.4 (MH⁺).

Example 261

1-Oxo-2-(4-trifluoromethoxy-phenyl)-2,8-diaza-spiro[4.5]decane-8-carboxylic acid 4-fluoro-benzylamide

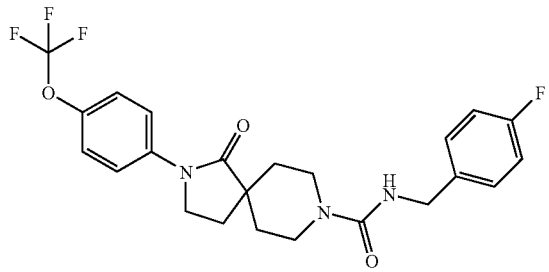

This material was prepared in analogy to example 251 step B) from 2-(4-trifluoromethoxy-phenyl)-2,8-diaza-spiro[4.5]decan-1-one, diphosgene and 4-Fluoro-benzylamine. MS (ESI): 466.4 (MH⁺).

Example 262

1-Oxo-2-(4-trifluoromethoxy-phenyl)-2,8-diaza-spiro[4.5]decane-8-carboxylic acid 2-chloro-benzylamide

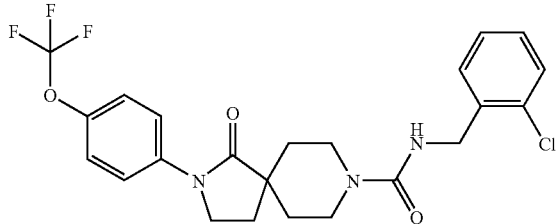

This material was prepared in analogy to example 251 step B) from 2-(4-trifluoromethoxy-phenyl)-2,8-diaza-spiro[4.5]decan-1-one, diphosgene and 2-Chloro-benzylamine. MS (ESI): 482.3 (MH⁺).

Example 263

2-(4-Ethyl-phenyl)-1-oxo-2,8-diaza-spiro[4.5]decane-8-carboxylic acid phenethyl-amide

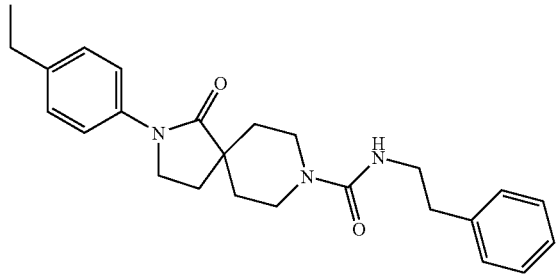

This material was prepared in analogy to example 251 step B) from 2-(4-Ethyl-phenyl)-2,8-diaza-spiro[4.5]decan-1-one, diphosgene and phenethylamine. MS (ESI): 406.4 (MH⁺).

Example 264

1-Oxo-2-(4-trifluoromethoxy-phenyl)-2,8-diaza-spiro[4.5]decane-8-carboxylic acid phenethyl-amide

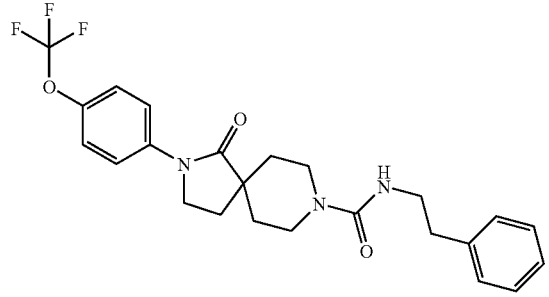

This material was prepared in analogy to example 251 step B) from 2-(4-trifluoromethoxy-phenyl)-2,8-diaza-spiro[4.5]decan-1-one, diphosgene and phenethylamine. MS (ESI): 462.4 (MH⁺).

Example 265

8-(Pyrrolidine-1-carbonyl)-2-(4-trifluoromethoxy-phenyl)-2,8-diaza-spiro[4.5]decan-1-one

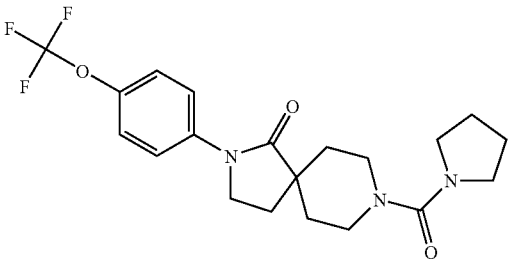

This material was prepared in analogy to example 251 step B) from 2-(4-trifluoromethoxy-phenyl)-2,8-diaza-spiro[4.5]decan-1-one, diphosgene and pyrrolidine MS (ESI): 412.3 (MH⁺).

Example 266

1-Oxo-2-(4-trifluoromethoxy-phenyl)-2,8-diaza-spiro[4.5]decane-8-carboxylic acid diethylamide

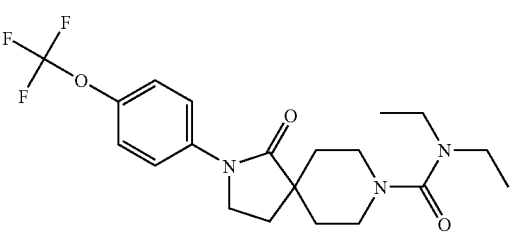

This material was prepared in analogy to example 251 step B) from 2-(4-trifluoromethoxy-phenyl)-2,8-diaza-spiro[4.5]decan-1-one, diphosgene and diethylamine. MS (ESI): 414.3 (MH⁺).

Example 267

8-(2-Methyl-pyrrolidine-1-carbonyl)-2-(4-trifluoromethoxy-phenyl)-2,8-diaza-spiro[4.5]decan-1-one

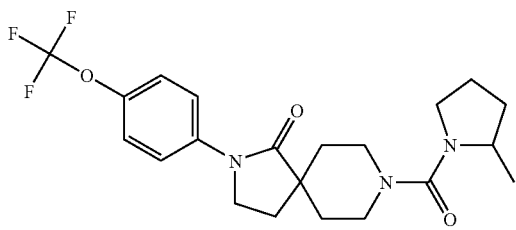

This material was prepared in analogy to example 251 step B) from 2-(4-trifluoromethoxy-phenyl)-2,8-diaza-spiro[4.5]decan-1-one, diphosgene and 2-methyl-pyrrolidine. MS (ESI): 426.3 (MH⁺).

Example 268

1-Oxo-2-(4-trifluoromethoxy-phenyl)-2,8-diaza-spiro[4.5]decane-8-carboxylic acid ethyl-propyl-amide

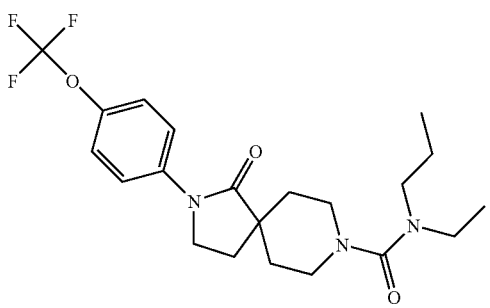

This material was prepared in analogy to example 251 step B) from 2-(4-trifluoromethoxy-phenyl)-2,8-diaza-spiro[4.5]decan-1-one, diphosgene and ethyl-propyl-amine. MS (ESI): 428.3 (MH⁺).

Example 269

1-Oxo-2-(4-trifluoromethoxy-phenyl)-2,8-diaza-spiro[4.5]decane-8-carboxylic acid butyl-methyl-amide

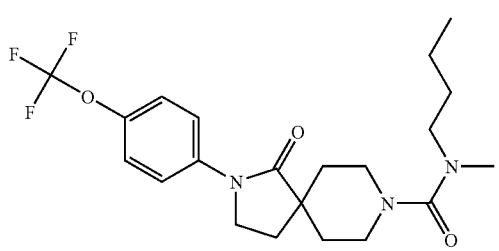

This material was prepared in analogy to example 251 step B) from 2-(4-trifluoromethoxy-phenyl)-2,8-diaza-spiro[4.5]decan-1-one, diphosgene and butyl-methyl-amine. MS (ESI): 428.4 (MH⁺).

Example 270

1-Oxo-2-(4-trifluoromethoxy-phenyl)-2,8-diaza-spiro[4.5]decane-8-carboxylic acid isobutyl-methyl-amide

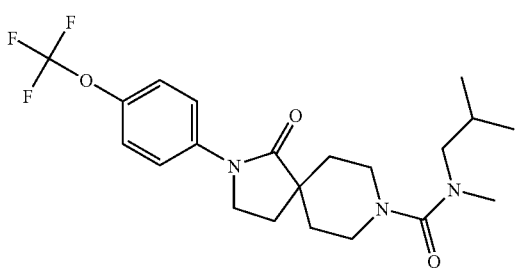

This material was prepared in analogy to example 251 step B) from 2-(4-trifluoromethoxy-phenyl)-2,8-diaza-spiro[4.5]decan-1-one, diphosgene and Isobutyl-methyl-amine. MS (ESI): 428.4 (MH⁺).

Example 271

8-(Azepane-1-carbonyl)-2-(4-trifluoromethoxy-phenyl)-2,8-diaza-spiro[4.5]decan-1-one

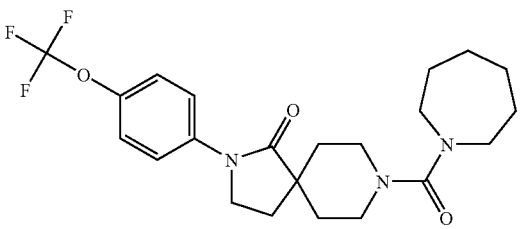

This material was prepared in analogy to example 251 step B) from 2-(4-trifluoromethoxy-phenyl)-2,8-diaza-spiro[4.5]decan-1-one, diphosgene and azepane. MS (ESI): 440.4 (MH⁺).

Example 272

8-(2-Methyl-piperidine-1-carbonyl)-2-(4-trifluoromethoxy-phenyl)-2,8-diaza-spiro[4.5]decan-1-one

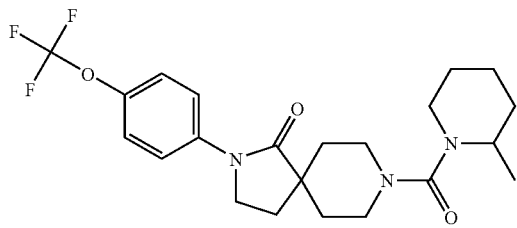

This material was prepared in analogy to example 251 step B) from 2-(4-trifluoromethoxy-phenyl)-2,8-diaza-spiro[4.5]decan-1-one, diphosgene and 2-methyl-piperidine. MS (ESI): 440.4 (MH+).

Example 273

1-Oxo-2-(4-trifluoromethoxy-phenyl)-2,8-diaza-spiro[4.5]decane-8-carboxylic acid methyl-pentyl-amide

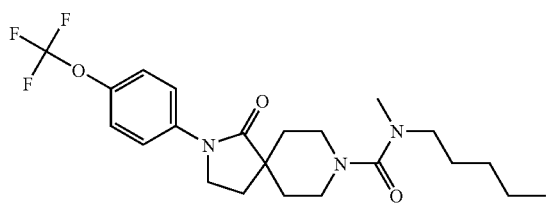

This material was prepared in analogy to example 251 step B) from 2-(4-trifluoromethoxy-phenyl)-2,8-diaza-spiro[4.5]decan-1-one, diphosgene and methyl-pentyl-amine. MS (ESI): 442.4 (MH+).

Example 274

1-Oxo-2-(4-trifluoromethoxy-phenyl)-2,8-diaza-spiro[4.5]decane-8-carboxylic acid ethyl-(2-methoxy-ethyl)-amide

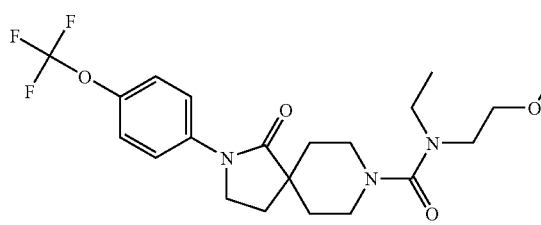

This material was prepared in analogy to example 251 step B) from 2-(4-Trifluoromethoxy-phenyl)-2,8-diaza-spiro[4.5]decan-1-one, diphosgene and methyl-propyl-amine. MS (ESI): 444.4 (MH+).

Example 275

1-Oxo-2-(4-trifluoromethoxy-phenyl)-2,8-diaza-spiro[4.5]decane-8-carboxylic acid methyl-phenyl-amide

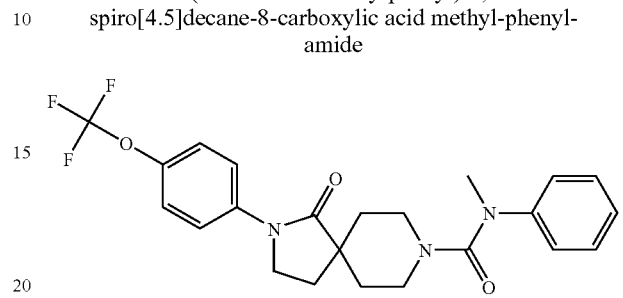

This material was prepared in analogy to example 251 step B) from 2-(4-trifluoromethoxy-phenyl)-2,8-diaza-spiro[4.5]decan-1-one, diphosgene and methyl-phenyl-amine. MS (ESI): 448.3 (MH+).

Example 276

1-Oxo-2-(4-trifluoromethoxy-phenyl)-2,8-diaza-spiro[4.5]decane-8-carboxylic acid cyclohexyl-methyl-amide

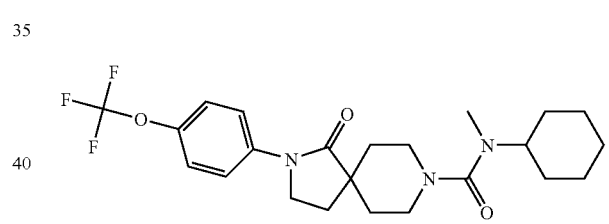

This material was prepared in analogy to example 251 step B) from 2-(4-trifluoromethoxy-phenyl)-2,8-diaza-spiro[4.5]decan-1-one, diphosgene and cyclohexyl-methyl-amine. MS (ESI): 454.4 (MH+).

Example 277

8-(1,3-Dihydro-isoindole-2-carbonyl)-2-(4-trifluoromethoxy-phenyl)-2,8-diaza-spiro[4.5]decan-1-one

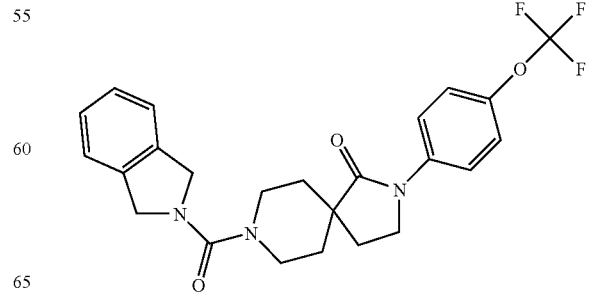

This material was prepared in analogy to example 251 step B) from 2-(4-trifluoromethoxy-phenyl)-2,8-diaza-spiro[4.5]decan-1-one, diphosgene and 2,3-dihydro-1H-isoindole. MS (ESI): 460.4 (MH+).

Example 278

1-Oxo-2-(4-trifluoromethoxy-phenyl)-2,8-diaza-spiro[4.5]decane-8-carboxylic acid benzyl-methyl-amide

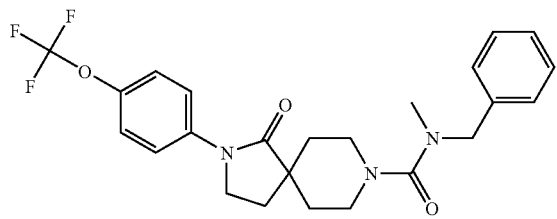

This material was prepared in analogy to example 251 step B) from 2-(4-trifluoromethoxy-phenyl)-2,8-diaza-spiro[4.5]decan-1-one, diphosgene and benzyl-methyl-amine. MS (ESI): 462.4 (MH+).

Example 279

1-Oxo-2-(4-trifluoromethoxy-phenyl)-2,8-diaza-spiro[4.5]decane-8-carboxylic acid ethyl-phenyl-amide

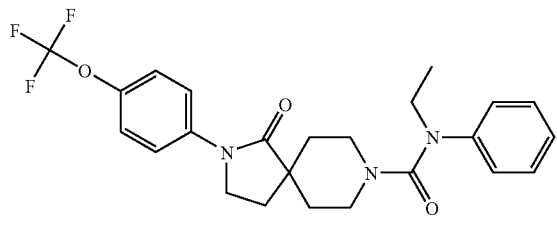

This material was prepared in analogy to example 251 step B) from 2-(4-trifluoromethoxy-phenyl)-2,8-diaza-spiro[4.5]decan-1-one, diphosgene and ethyl-phenyl-amine. MS (ESI): 462.4 (MH+).

Example 280

1-Oxo-2-(4-trifluoromethoxy-phenyl)-2,8-diaza-spiro[4.5]decane-8-carboxylic acid (3-fluoro-phenyl)-methyl-amide

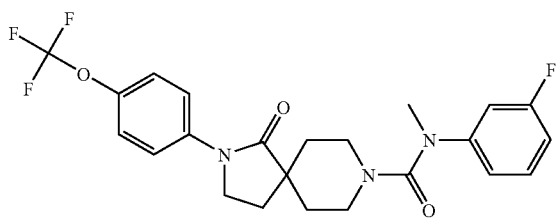

This material was prepared in analogy to example 251 step B) from 2-(4-trifluoromethoxy-phenyl)-2,8-diaza-spiro[4.5]decan-1-one, diphosgene and (3-Fluoro-phenyl)-methyl-amine. MS (ESI): 466.4 (MH+).

Example 281

8-(3,4-Dihydro-2H-quinoline-1-carbonyl)-2-(4-trifluoromethoxy-phenyl)-2,8-diaza-spiro[4.5]decan-1-one

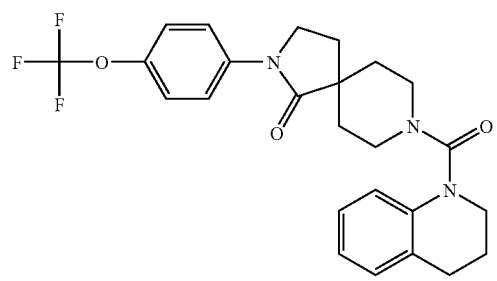

This material was prepared in analogy to example 251 step B) from 2-(4-trifluoromethoxy-phenyl)-2,8-diaza-spiro[4.5]decan-1-one, diphosgene and 1,2,3,4-tetrahydro-quinoline. MS (ESI): 474.4 (MH+).

Example 282

1-Oxo-2-(4-trifluoromethoxy-phenyl)-2,8-diaza-spiro[4.5]decane-8-carboxylic acid methyl-phenethyl-amide

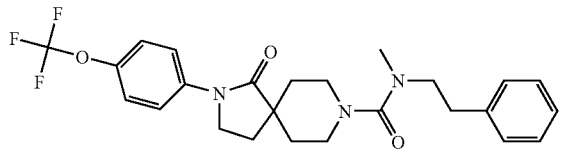

This material was prepared in analogy to example 251 step B) from 2-(4-trifluoromethoxy-phenyl)-2,8-diaza-spiro[4.5]decan-1-one, diphosgene and Methyl-phenethyl-amine. MS (ESI): 476.4 (MH+).

Example 283

1-Oxo-2-(4-trifluoromethoxy-phenyl)-2,8-diaza-spiro[4.5]decane-8-carboxylic acid methyl-(2-pyridin-2-yl-ethyl)-amide

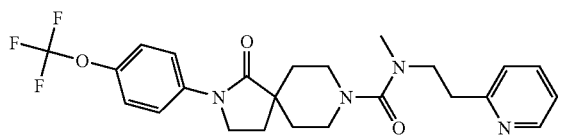

This material was prepared in analogy to example 251 step B) from 2-(4-trifluoromethoxy-phenyl)-2,8-diaza-spiro[4.5]

Example 284

1-Oxo-2-(4-trifluoromethoxy-phenyl)-2,8-diaza-spiro[4.5]decane-8-carboxylic acid ethyl-(2-pyridin-2-yl-ethyl)-amide

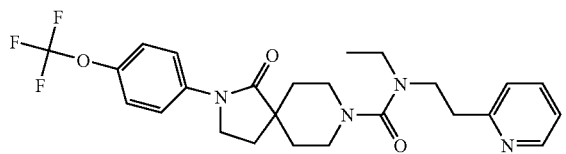

This material was prepared in analogy to example 251 step B) from 2-(4-trifluoromethoxy-phenyl)-2,8-diaza-spiro[4.5]decan-1-one, diphosgene and ethyl-(2-pyridin-2-yl-ethyl)-amine. MS (ESI): 491.4 (MH+).

Example 285

1-Oxo-2-(4-trifluoromethoxy-phenyl)-2,8-diaza-spiro[4.5]decane-8-sulfonic acid isopropylamide

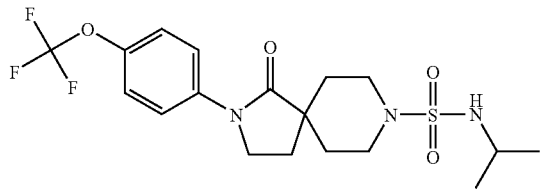

Step A): 1-Oxo-2-(4-trifluoromethoxy-phenyl)-2,8-diaza-spiro[4.5]decane-8-sulfonyl chloride To a solution of 405 mg (2.91 mmol) sulfuryl chloride in 15 mL anhydrous CHCl$_3$ at 0° C. was slowly added a mixture of 915 mg (2.91 mmol) 2-(4-(trifluoromethoxy)phenyl)-2,8-diazaspiro[4.5]decan-1-one and 295 mg (2.91 mmol) NEt$_3$ over a period of 30 min and stirred at 0° C. for 1 h. the mixture was allowed to warm to room temperature stirred for 1 h and 405 mg (2.91 mmol) sulfuryl chloride was added. The mixture was stirred for 5 h at room temperature, evaporated to dryness and used without further purification in the consecutive step. MS (ESI): 315.2 (M-SO$_2$Cl)H+.

Step B): 1-Oxo-2-(4-trifluoromethoxy-phenyl)-2,8-diaza-spiro[4.5]decane-8-sulfonic acid isopropylamide A mixture of 74 mg (0.18 mmol) 1-Oxo-2-(4-trifluoromethoxy-phenyl)-2,8-diaza-spiro[4.5]decane-8-sulfonyl chloride, 73 mg (0.72 mmol) NEt$_3$ and 14.8 mg (0.252 mmol) isopropylamine in 2 mL CH$_2$Cl$_2$ was stirred for 16 h at 50° C. The mixture was evaporated to dryness and the residue was subjected to purification by preparative HPLC on reversed phase eluting with a gradient formed from acetonitrile, water and formic acid. The product containing fractions were evaporated to yield 12.5 mg (16%) of the title compound. MS (ESI): 436.4 (MH+).

Example 286

1-Oxo-2-(4-trifluoromethoxy-phenyl)-2,8-diaza-spiro[4.5]decane-8-sulfonic acid phenylamide

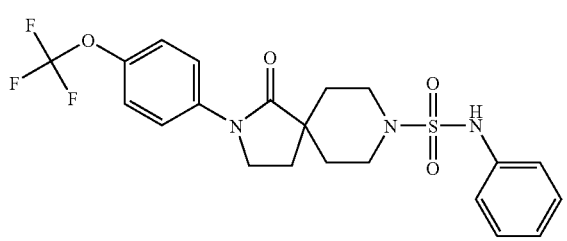

This material was prepared in analogy to example 285 step B) from 1-Oxo-2-(4-trifluoromethoxy-phenyl)-2,8-diaza-spiro[4.5]decane-8-sulfonyl chloride and phenylamine. MS (ESI): 440.4 (MH+).

Example 287

1-Oxo-2-(4-trifluoromethoxy-phenyl)-2,8-diaza-spiro[4.5]decane-8-sulfonic acid benzylamide

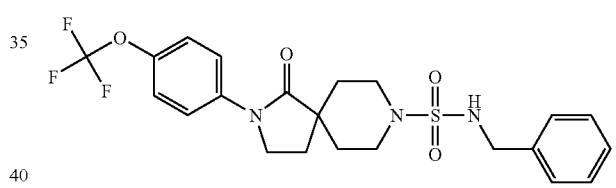

This material was prepared in analogy to example 285 step B) from 1-Oxo-2-(4-trifluoromethoxy-phenyl)-2,8-diaza-spiro[4.5]decane-8-sulfonyl chloride and ethyl-(2-pyridin-2-yl-ethyl)-amine. MS (ESI): 484.4 (MH+).

Example 288

1-Oxo-2-(4-trifluoromethoxy-phenyl)-2,8-diaza-spiro[4.5]decane-8-sulfonic acid (2-phenyl-propyl)-amide

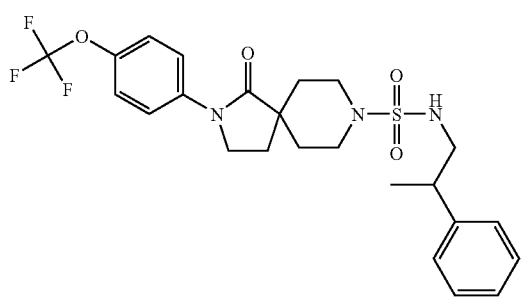

This material was prepared in analogy to example 285 step B) from 1-Oxo-2-(4-trifluoromethoxy-phenyl)-2,8-diazaspiro[4.5]decane-8-sulfonyl chloride and 2-phenyl-propylamine. MS (ESI): 512.5 (MH+).

Example 289

1-Oxo-2-(4-trifluoromethoxy-phenyl)-2,8-diazaspiro[4.5]decane-8-sulfonic acid (2-methoxy-ethyl)-amide

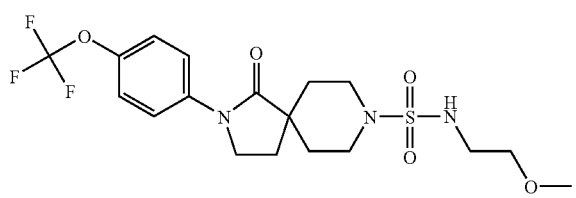

This material was prepared in analogy to example 285 step B) from 1-Oxo-2-(4-trifluoromethoxy-phenyl)-2,8-diazaspiro[4.5]decane-8-sulfonyl chloride and 2-methoxy-ethylamine. MS (ESI): 452.4 (MH+).

Example 290

1-Oxo-2-(4-trifluoromethoxy-phenyl)-2,8-diazaspiro[4.5]decane-8-sulfonic acid ethylamide

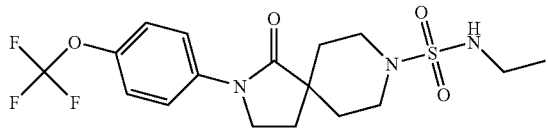

This material was prepared in analogy to example 285 step B) from 1-Oxo-2-(4-trifluoromethoxy-phenyl)-2,8-diazaspiro[4.5]decane-8-sulfonyl chloride and ethylamine. MS (ESI): 422.3 (MH+).

Example 291

1-Oxo-2-(4-trifluoromethoxy-phenyl)-2,8-diazaspiro[4.5]decane-8-sulfonic acid diethylamide

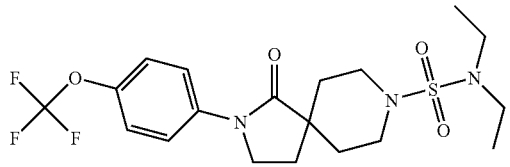

This material was prepared in analogy to example 285 step B) from 1-Oxo-2-(4-trifluoromethoxy-phenyl)-2,8-diazaspiro[4.5]decane-8-sulfonyl chloride and diethylamine. The reaction was subjected to work-up and purification after stirring for 2 h at room temperature. MS (ESI): 450.4 (MH+).

Example 292

1-Oxo-2-(4-trifluoromethoxy-phenyl)-2,8-diazaspiro[4.5]decane-8-sulfonic acid (2-hydroxy-ethyl)-methyl-amide

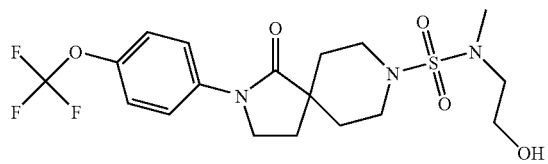

This material was prepared in analogy to example 285 step B) from 1-Oxo-2-(4-trifluoromethoxy-phenyl)-2,8-diazaspiro[4.5]decane-8-sulfonyl chloride and 2-methylamino-ethanol. The reaction was subjected to work-up and purification after stirring for 2 h at room temperature. MS (ESI): 452.4 (MH+).

Example 293

1-Oxo-2-(4-trifluoromethoxy-phenyl)-2,8-diazaspiro[4.5]decane-8-sulfonic acid isobutyl-methyl-amide

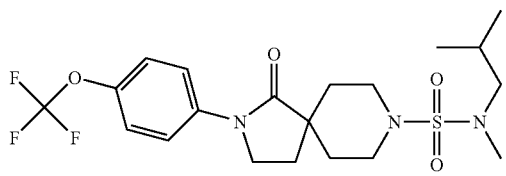

This material was prepared in analogy to example 285 step B) from 1-Oxo-2-(4-trifluoromethoxy-phenyl)-2,8-diazaspiro[4.5]decane-8-sulfonyl chloride and isobutyl-methyl-amine. The reaction was subjected to work-up and purification after stirring for 2 h at room temperature. MS (ESI): 464.4 (MH+).

Example 294

1-Oxo-2-(4-trifluoromethoxy-phenyl)-2,8-diazaspiro[4.5]decane-8-sulfonic acid ethyl-(2-methoxy-ethyl)-amide

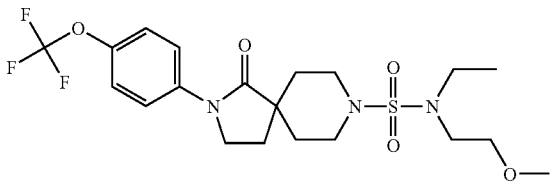

This material was prepared in analogy to example 285 step B) from 1-Oxo-2-(4-trifluoromethoxy-phenyl)-2,8-diazaspiro[4.5]decane-8-sulfonyl chloride and ethyl-(2-methoxy-ethyl)-amine. The reaction was subjected to work-up and purification after stirring for 2 h at room temperature. MS (ESI): 480.4 (MH⁺).

Example 295

1-Oxo-2-(4-trifluoromethoxy-phenyl)-2,8-diaza-spiro[4.5]decane-8-sulfonic acid methyl-phenyl-amide

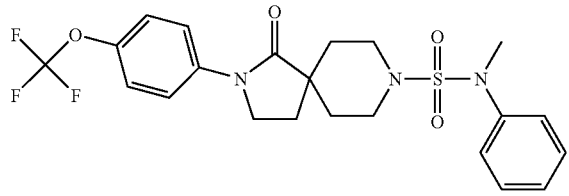

This material was prepared in analogy to example 285 step B) from 1-Oxo-2-(4-trifluoromethoxy-phenyl)-2,8-diaza-spiro[4.5]decane-8-sulfonyl chloride and methyl-phenyl-amine. The reaction was subjected to work-up and purification after stirring for 2 h at room temperature. MS (ESI): 484.4 (MH⁺).

Example 296

1-Oxo-2-(4-trifluoromethoxy-phenyl)-2,8-diaza-spiro[4.5]decane-8-sulfonic acid benzyl-methyl-amide

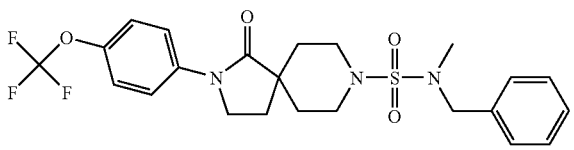

This material was prepared in analogy to example 285 step B) from 1-Oxo-2-(4-trifluoromethoxy-phenyl)-2,8-diaza-spiro[4.5]decane-8-sulfonyl chloride and diethylamine. The reaction was subjected to work-up and purification after stirring for 2 h at room temperature. MS (ESI): 498.5 (MH⁺).

Example 297

1-Oxo-2-(4-trifluoromethoxy-phenyl)-2,8-diaza-spiro[4.5]decane-8-sulfonic acid methyl-phenethyl-amide

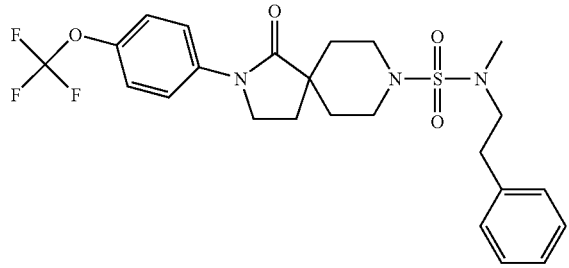

This material was prepared in analogy to example 285 step B) from 1-Oxo-2-(4-trifluoromethoxy-phenyl)-2,8-diaza-spiro[4.5]decane-8-sulfonyl chloride and methyl-phenethyl-amine. The reaction was subjected to work-up and purification after stirring for 2 h at room temperature. MS (ESI): 512.5 (MH⁺).

Example 298

1-Oxo-2-(4-trifluoromethoxy-phenyl)-2,8-diaza-spiro[4.5]decane-8-sulfonic acid methyl-(2-pyridin-2-yl-ethyl)-amide

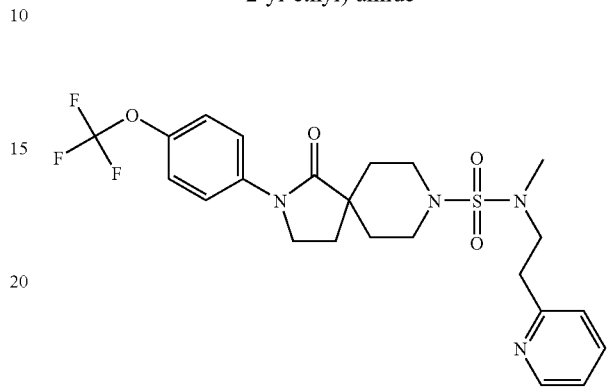

This material was prepared in analogy to example 285 step B) from 1-Oxo-2-(4-trifluoromethoxy-phenyl)-2,8-diaza-spiro[4.5]decane-8-sulfonyl chloride and methyl-(2-pyridin-2-yl-ethyl)-amine. The reaction was subjected to work-up and purification after stirring for 2 h at room temperature. MS (ESI): 513.5 (MH⁺).

Example 299

1-Oxo-2-(4-trifluoromethoxy-phenyl)-2,8-diaza-spiro[4.5]decane-8-carboxylic acid methyl-(4-trifluoromethyl-phenyl)-amide

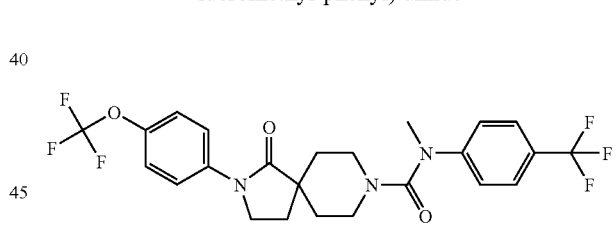

This material was prepared in analogy to example 251 step B) from 2-(4-trifluoromethoxy-phenyl)-2,8-diaza-spiro[4.5]decan-1-one, diphosgene and methyl-(4-trifluoromethyl-phenyl)-amine. The reaction mixture was stirred for 1 h at room temperature, 2 h at 50° C. and 1 h at 80° C. before subjecting to work-up and purification. MS (ESI): 516.5 (MH⁺).

Example 300

1-Oxo-2-(4-trifluoromethoxy-phenyl)-2,8-diaza-spiro[4.5]decane-8-carboxylic acid (4-chloro-phenyl)-methyl-amide

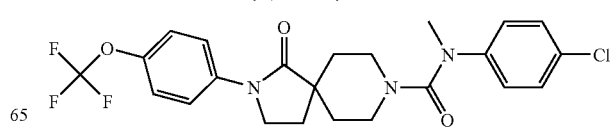

This material was prepared in analogy to example 251 step B) from 2-(4-trifluoromethoxy-phenyl)-2,8-diaza-spiro[4.5]decan-1-one, diphosgene and (4-chloro-phenyl)-methyl-amine. The reaction mixture was stirred for 1 h at room temperature, 2 h at 50° C. and 1 h at 80° C. before subjecting to work-up and purification. MS (ESI): 482.4 (MH$^+$).

Example 301

1-Oxo-2-(4-trifluoromethoxy-phenyl)-2,8-diaza-spiro[4.5]decane-8-carboxylic acid (3,4-dichloro-phenyl)-methyl-amide

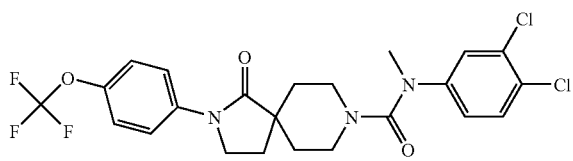

This material was prepared in analogy to example 251 step B) from 2-(4-trifluoromethoxy-phenyl)-2,8-diaza-spiro[4.5]decan-1-one, diphosgene and (3,4-dichloro-phenyl)-methyl-amine. The reaction mixture was stirred for 1 h at room temperature, 2 h at 50° C. and 1 h at 80° C. before subjecting to work-up and purification. MS (ESI): 516.4 (MH$^+$).

Example 302

1-Oxo-2-(4-trifluoromethoxy-phenyl)-2,8-diaza-spiro[4.5]decane-8-carboxylic acid (3-chloro-phenyl)-methyl-amide

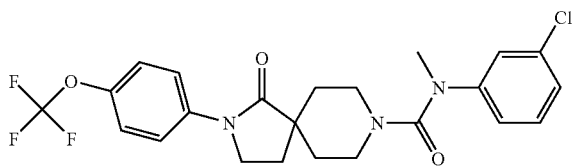

This material was prepared in analogy to example 251 step B) from 2-(4-trifluoromethoxy-phenyl)-2,8-diaza-spiro[4.5]decan-1-one, diphosgene and (3-chloro-phenyl)-methyl-amine. The reaction mixture was stirred for 1 h at room temperature, 2 h at 50° C. and 1 h at 80° C. before subjecting to work-up and purification. MS (ESI): 482.4 (MH$^+$).

Example 303

1-Oxo-2-(4-trifluoromethoxy-phenyl)-2,8-diaza-spiro[4.5]decane-8-carboxylic acid butyl-ethyl-amide

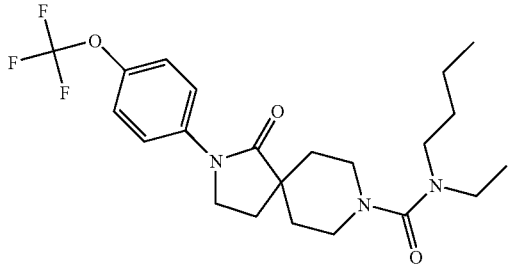

This material was prepared in analogy to example 251 step B) from 2-(4-trifluoromethoxy-phenyl)-2,8-diaza-spiro[4.5]decan-1-one, diphosgene and butyl-ethyl-amine. The reaction mixture was stirred for 1 h at room temperature, 2 h at 50° C. and 1 h at 80° C. before subjecting to work-up and purification. MS (ESI): 442.4 (MH$^+$).

Example 304

1-Oxo-2-(4-trifluoromethoxy-phenyl)-2,8-diaza-spiro[4.5]decane-8-carboxylic acid ethyl-isopropyl-amide

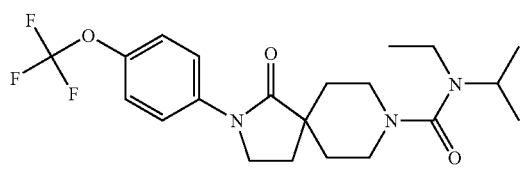

This material was prepared in analogy to example 251 step B) from 2-(4-trifluoromethoxy-phenyl)-2,8-diaza-spiro[4.5]decan-1-one, diphosgene and ethyl-isopropyl-amine. The reaction mixture was stirred for 1 h at room temperature, 2 h at 50° C. and 1 h at 80° C. before subjecting to work-up and purification. MS (ESI): 428.4 (MH$^+$).

Example 305

1-Oxo-2-(4-trifluoromethoxy-phenyl)-2,8-diaza-spiro[4.5]decane-8-carboxylic acid cyclohexyl-ethyl-amide

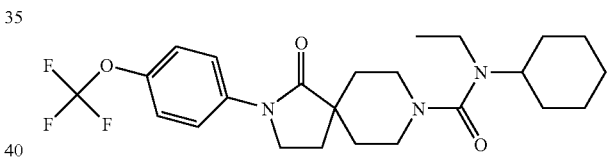

This material was prepared in analogy to example 251 step B) from 2-(4-trifluoromethoxy-phenyl)-2,8-diaza-spiro[4.5]decan-1-one, diphosgene and cyclohexyl-ethyl-amine. The reaction mixture was stirred for 1 h at room temperature, 2 h at 50° C. and 1 h at 80° C. before subjecting to work-up and purification. MS (ESI): 468.5 (MH$^+$).

Example 306

1-Oxo-2-(4-trifluoromethoxy-phenyl)-2,8-diaza-spiro[4.5]decane-8-carboxylic acid ethyl-(2-fluoro-benzyl)-amide

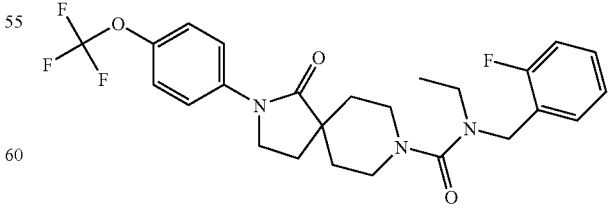

This material was prepared in analogy to example 251 step B) from 2-(4-trifluoromethoxy-phenyl)-2,8-diaza-spiro[4.5]decan-1-one, diphosgene and ethyl-(2-fluoro-benzyl)-amine. The reaction mixture was stirred for 1 h at room temperature, 2 h at 50° C. and 1 h at 80° C. before subjecting to work-up and purification. MS (ESI): 494.5 (MH⁺).

Example 307

1-Oxo-2-(4-trifluoromethoxy-phenyl)-2,8-diaza-spiro[4.5]decane-8-carboxylic acid ethyl-pyridin-4-ylmethyl-amide

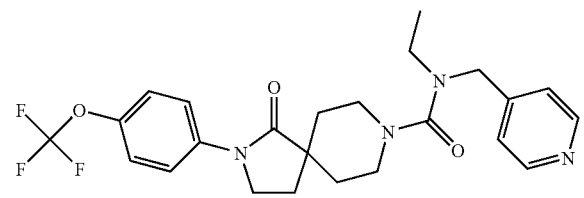

This material was prepared in analogy to example 251 step B) from 2-(4-trifluoromethoxy-phenyl)-2,8-diaza-spiro[4.5]decan-1-one, diphosgene and ethyl-pyridin-4-ylmethyl-amine. The reaction mixture was stirred for 1 h at room temperature, 2 h at 50° C. and 1 h at 80° C. before subjecting to work-up and purification. MS (ESI): 477.5 (MH⁺).

Example 308

1-Oxo-2-(4-trifluoromethoxy-phenyl)-2,8-diaza-spiro[4.5]decane-8-carboxylic acid ethyl-m-tolyl-amide

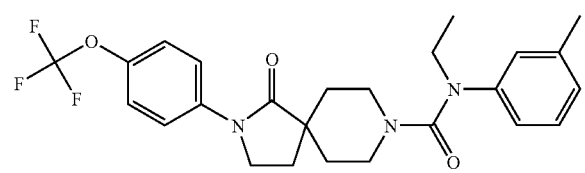

This material was prepared in analogy to example 251 step B) from 2-(4-trifluoromethoxy-phenyl)-2,8-diaza-spiro[4.5]decan-1-one, diphosgene and ethyl-m-tolyl-amine. The reaction mixture was stirred for 1 h at room temperature, 2 h at 50° C. and 1 h at 80° C. before subjecting to work-up and purification. MS (ESI): 467.4 (MH⁺).

Example 309

1-Oxo-2-(4-trifluoromethoxy-phenyl)-2,8-diaza-spiro[4.5]decane-8-carboxylic acid (4-chloro-phenyl)-ethyl-amide

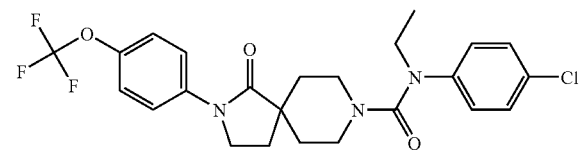

This material was prepared in analogy to example 251 step B) from 2-(4-trifluoromethoxy-phenyl)-2,8-diaza-spiro[4.5]decan-1-one, diphosgene and (4-chloro-phenyl)-ethyl-amine. The reaction mixture was stirred for 1 h at room temperature, 2 h at 50° C. and 1 h at 80° C. before subjecting to work-up and purification. MS (ESI): 496.4 (MH⁺).

Example 310

1-Oxo-2-(4-trifluoromethoxy-phenyl)-2,8-diaza-spiro[4.5]decane-8-carboxylic acid benzyl-ethyl-amide

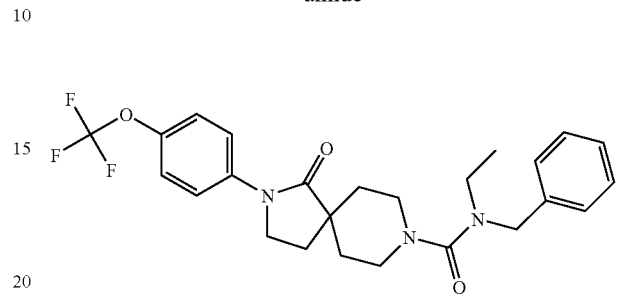

This material was prepared in analogy to example 251 step B) from 2-(4-trifluoromethoxy-phenyl)-2,8-diaza-spiro[4.5]decan-1-one, diphosgene and benzyl-ethyl-amine. The reaction mixture was stirred for 1 h at room temperature, 2 h at 50° C. and 1 h at 80° C. before subjecting to work-up and purification. MS (ESI): 476.5 (MH⁺).

Example 311

1-Oxo-2-(4-trifluoromethoxy-phenyl)-2,8-diaza-spiro[4.5]decane-8-carboxylic acid ethyl-(4-trifluoromethoxy-phenyl)-amide

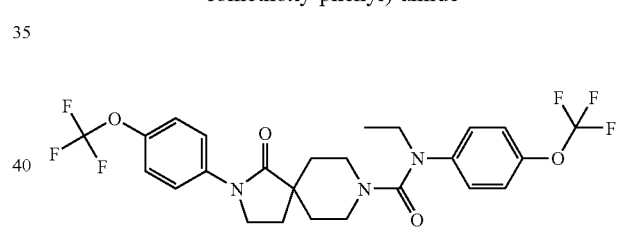

This material was prepared in analogy to example 251 step B) from 2-(4-trifluoromethoxy-phenyl)-2,8-diaza-spiro[4.5]decan-1-one, diphosgene and ethyl-(4-trifluoromethoxy-phenyl)-amine. The reaction mixture was stirred for 1 h at room temperature, 2 h at 50° C. and 1 h at 80° C. before subjecting to work-up and purification. MS (ESI): 546.5 (MH⁺).

Example 312

8-(2-Chloro-6-methyl-benzenesulfonyl)-2-(4-trifluoromethoxy-phenyl)-2,8-diaza-spiro[4.5]decan-1-one

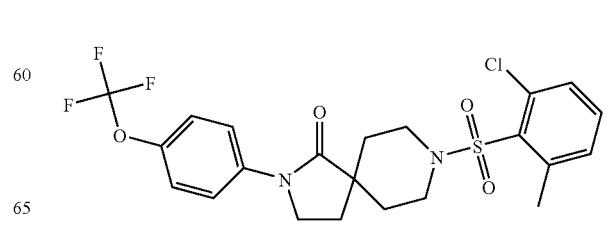

A mixture of 37.7 mg (0.12 mmol) 2-(4-Trifluoromethoxy-phenyl)-2,8-diaza-spiro[4.5]decan-1-one, 29.7 mg (example 251, step A), 0.132 mmol), 2-chloro-6-methylbenzene-1-sulfonyl chloride and 36.4 mg (0.36 mmol) NEt3 in 2 mL DCM was stirred for 16 h at room temperature. The mixture was evaporated to dryness and the residue was subjected to purification by preparative HPLC on reversed phase eluting with a gradient formed from acetonitrile, water and formic acid. The product containing fractions were evaporated to yield 14.7 mg (24%) of the title compound. MS (ESI): 503.4 (MH$^+$).

Example 313

2-(4-Cyclopropyl-phenyl)-1-oxo-2,8-diaza-spiro[4.5] decane-8-carboxylic acid isobutyl-methyl-amide

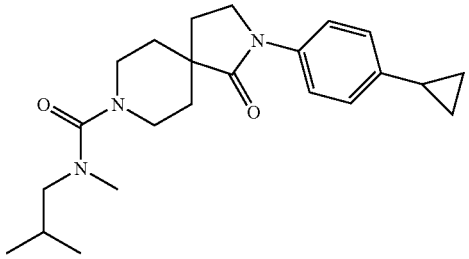

Step A): 2-(4-Cyclopropyl-phenyl)-2,8-diaza-spiro [4.5]decan-1-one

This material was prepared in analogy to example 1 step D) from 4-(2-Methoxy-ethyl)-piperidine-1,4-dicarboxylic acid 1-tert-butyl ester 4-ethyl ester, dimethylaluminium chloride in hexane and 4-cyclopropyl-phenylamine, with concomitant cleavage of the Boc protecting group under the reaction conditions. MS (ESI): 271.2 (MH$^+$).

Step B): 2-(4-Cyclopropyl-phenyl)-1-oxo-2,8-diaza-spiro[4.5]decane-8-carboxylic acid isobutyl-methyl-amide This material was prepared in analogy to example 251 step B) from 2-(4-Cyclopropyl-phenyl)-2,8-diaza-spiro[4.5]decan-1-one, diphosgene and isobutyl-methyl-amine. MS (ESI): 384.3 (MH$^+$).

Example 314

2-(4-Cyclopropyl-phenyl)-1-oxo-2,8-diaza-spiro[4.5] decane-8-carboxylic acid butyl-methyl-amide

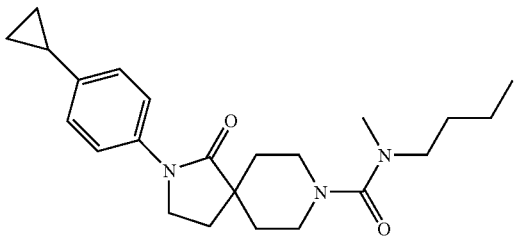

This material was prepared in analogy to example 251 step B) from 2-(4-Cyclopropyl-phenyl)-2,8-diaza-spiro[4.5]decan-1-one, diphosgene and butyl-methyl-amine. MS (ESI): 384.4 (MH$^+$).

Example A

A compound of formula (I) can be used in a manner known per se as the active ingredient for the production of tablets of the following composition:

|  | tablet |
| --- | --- |
| Active ingredient | 0 mg |
| Microcrystalline cellulose | 55 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound of formula (I)

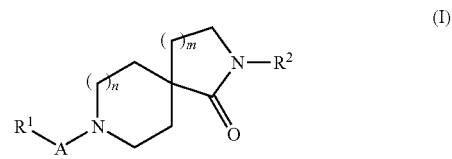

wherein
m is 1;
n is 1;
A is —S(O)$_2$— or carbonyl;
R$^1$ is selected from the group consisting of alkyl, aminoalkyl, cycloalkyl, cycloalkylalkyl, haloalkyl, haloalkylcycloalkyl, hydroxycycloalkylalkyl, (cycloalkyl)(hydroxy)alkyl, (cycloalkyl)(alkoxy)alkyl, alkoxycycloalkylalkyl, hydroxycycloalkyl, cycloalkoxyalkyl, hydroxyalkyl, alkoxyalkyl, benzyloxyalkyl, phenyloxyalkyl, dihydro-furanylidenemethyl, tetrahydro-furanylmethyl, dihydro-isoindolyl, dihydro-quinolinyl, —NR$^4$R$^5$, azepanyl, morpholinyl, piperidinyl, pyrrolidinyl, pyrazolyl, imidazolyl, isoxazolyl, oxazolyl, thiophenyl, thiazolyl, pyridinyl, pyridinylalkyl, pyridazinyl, pyridazinylalkyl, pyrazinyl, pyrazinylalkyl, pyrimidyl, pyrimidylalkyl, phenyl, phenylalkyl, substituted piperidinyl, substituted pyrrolidinyl, substituted pyrazolyl, substituted imidazolyl, substituted isoxazolyl, substituted oxazolyl, substituted thiophenyl, substituted thiazolyl, substituted pyridinyl, substituted pyridinylalkyl, substituted pyridazinyl, substituted pyridazinylalkyl, substituted pyrazinyl, substituted pyrazinylalkyl, substituted pyrimidyl, substituted pyrimidylalkyl, substituted phenyl and substituted phenylalkyl, wherein said substituted piperidinyl, substituted pyrrolidinyl, substituted pyrazolyl, substituted imidazolyl, substituted isoxazolyl, substituted oxazolyl, substituted thiophenyl, substituted thiazolyl, substituted pyridinyl, substituted pyridinylalkyl, substituted pyridazinyl, substituted pyridazinylalkyl, substituted pyrazinyl, substituted pyrazinylalkyl, substituted pyrimidyl, substituted pyrimidylalkyl, substituted phenyl or substituted phenylalkyl is substituted with one to three substituents independently selected from the group consisting of: alkyl, haloalkyl, halogen, hydroxy, alkoxy, haloalkoxy, phenyloxy, alkylphenyloxy, alkylsulfonyl, oxopyrrolidinyl, alkoxycarbonyl, benzyloxy and —NR$^6$R$^7$;

$R^2$ is selected from the group consisting of imidazolyl, imidazolylalkyl, phenyl, phenylalkyl, pyridinyl, pyridinylalkyl, pyridazinyl, pyridazinylalkyl, pyrazolyl, pyrazolylalkyl, alkylindazolyl, alkylbenzothiazolyl, difluorobenzo[1,3]dioxolyl, pyrimidyl, pyrimidylalkyl, pyrazinyl, pyrazinylalkyl, substituted imidazolyl, substituted imidazolylalkyl, substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted pyrimidyl, substituted pyrimidylalkyl, substituted pyrazinyl and substituted pyrazinylalkyl, wherein said substituted imidazolyl, substituted imidazolylalkyl, substituted phenyl, substituted phenylalkyl, substituted pyridinyl, substituted pyridinylalkyl, substituted pyridazinyl, substituted pyridazinylalkyl, substituted pyrazolyl substituted pyrazolylalkyl, substituted pyrimidyl, substituted pyrimidylalkyl, substituted pyrazinyl or substituted pyrazinylalkyl is substituted with one to three substituents independently selected from the group consisting of: alkyl, haloalkyl, cycloalkyl, cycloalkylalkyl, halogen, haloalkoxy, alkoxy, hydroxy, alkoxyalkyl, hydroxyalkyl, alkylsulfonyl, alkylsulfonyloxy, alkylsulfanyl, cycloalkylsulfonyloxy, cycloalkoxy, alkenyl, cycloalkylalkoxy, alkoxyalkoxy, tetrahydrofuranyloxy, pyridinyloxy, alkoxycarbonylalkyl, cyanoalkyl, alkyloxazodiazolylalkyl, haloalkyloxazodiazolylalkyl, alkoxyalkenyl, cycloalkylalkenyl, cycloalkylalkoxyalkyl, alkoxycarbonyl, alkylcarbonyl, haloalkylhydroxyalkyl, alkylaminocarbonyl, dialkylaminocarbonyl, hydroxyoxetanyl, fluorooxetanyl and hydroxycycloalkyl;

one of $R^4$ and $R^5$ is hydrogen or alkyl and the other is selected from the group consisting of hydrogen, alkyl, hydroxyalkyl, alkoxyalkyl, cycloalkyl, phenyl, alkylphenyl, haloalkoxyphenyl, phenylalkyl, halophenyl, halophenylalkyl, haloalkylphenyl and pyridinylalkyl; and one of $R^6$ and $R^7$ is selected from the group consisting of hydrogen, alkyl, cycloalkyl or hydroxyalkyl and the other is selected from the group consisting of hydrogen, alkyl, cycloalkyl or hydroxyalkyl;

or a pharmaceutically acceptable salt thereof.

2. A compound according to claim 1, wherein $R^1$ is selected from the group consisting of alkyl, cycloalkyl, cycloalkylalkyl, haloalkyl, haloalkylcycloalkyl, hydroxycycloalkylalkyl, (cycloalkyl)(hydroxy)alkyl, (cycloalkyl)(alkoxy)alkyl, alkoxycycloalkylalkyl, hydroxycycloalkyl, cycloalkoxyalkyl, hydroxyalkyl, alkoxyalkyl, benzyloxyalkyl, phenyloxyalkyl, dihydro-furanylidenemethyl, tetrahydro-furanylmethyl, dihydro-isoindolyl, dihydro-quinolinyl, —NR$^4$R$^5$, azepanyl, morpholinyl, piperidinyl, pyrrolidinyl, thiophenyl, pyridinyl, alkoxypyridinyl, pyrimidyl, phenyl, phenylalkyl, substituted piperidinyl, substituted pyrrolidinyl, substituted pyrazolyl, substituted imidazolyl, substituted isoxazolyl, substituted thiophenyl, substituted thiazolyl, substituted pyridinyl, substituted pyridazinyl, substituted phenyl and substituted phenylalkyl, wherein said substituted piperidinyl, substituted pyrrolidinyl, substituted pyrazolyl, substituted imidazolyl, substituted isoxazolyl, substituted thiophenyl, substituted thiazolyl, substituted pyridinyl, substituted pyridazinyl, substituted phenyl or substituted phenylalkyl is substituted with one to three substituents independently selected from the group consisting of: alkyl, haloalkyl, halogen, hydroxy, haloalkoxy, alkylsulfonyl, oxopyrrolidinyl, alkoxycarbonyl, benzyloxy and —NR$^6$R$^7$.

3. A compound according to claim 1, wherein $R^2$ is selected from the group consisting of phenylalkyl, alkylindazolyl, alkylbenzothiazolyl, difluorobenzo[1,3]dioxolyl, substituted phenyl, substituted phenylalkyl, substituted pyridinyl, substituted pyridazinyl and substituted pyrimidyl, wherein said substituted phenyl, substituted phenylalkyl, substituted pyridinyl, substituted pyridazinyl or substituted pyrimidyl is substituted with one to three substituents independently selected from the group consisting of: alkyl, haloalkyl, cycloalkyl, cycloalkylalkyl, halogen, haloalkoxy, alkoxy, alkoxyalkyl, hydroxyalkyl, alkylsulfonyl, alkylsulfonyloxy, alkylsulfanyl, cycloalkylsulfonyloxy, cycloalkoxy, alkenyl, cycloalkylalkoxy, alkoxyalkoxy, tetrahydrofuranyloxy, pyridinyloxy, alkoxycarbonylalkyl, cyanoalkyl, alkyloxazodiazolylalkyl, haloalkyloxazodiazolylalkyl, alkoxyalkenyl, cycloalkylalkenyl, cycloalkylalkoxyalkyl, alkoxycarbonyl, alkylcarbonyl, haloalkylhydroxyalkyl, alkylaminocarbonyl, dialkylaminocarbonyl, hydroxyoxetanyl, fluorooxetanyl and hydroxycycloalkyl.

4. A compound according to claim 1, wherein
m is 1;
n is 1;
A is —S(O)$_2$— or carbonyl;
$R^1$ is selected from the group consisting of alkyl, aminoalkyl, alkylamino, cycloalkyl, cycloalkylalkyl, haloalkyl, morpholinyl, piperidinyl, pyrrolidinyl, pyrazolyl, imidazolyl, oxazolyl, thiophenyl, thiazolyl, pyridinyl, pyridinylalkyl, pyridazinyl, pyrazinyl, phenyl, phenylalkyl, substituted phenyl and substituted phenylalkyl, wherein said substituted phenyl or substituted phenylalkyl is substituted with one to three substituents independently selected from the group consisting of: alkyl, haloalkyl, halogen, hydroxy, alkoxy, haloalkoxy, phenyloxy and alkylphenyloxy; and
$R^2$ is selected from the group consisting of phenyl, phenylalkyl, pyridinyl, pyridinylalkyl, pyridazinyl, pyridazinylalkyl, pyrazolyl, pyrazolylalkyl, substituted phenyl, substituted phenylalkyl, substituted pyridinyl, substituted pyridinylalkyl, substituted pyridazinyl, substituted pyridazinylalkyl, substituted pyrazolyl and substituted pyrazolylalkyl, wherein said substituted phenyl, substituted phenylalkyl, substituted pyridinyl, substituted pyridinylalkyl, substituted pyridazinyl, substituted pyridazinylalkyl, substituted pyrazolyl or substituted pyrazolylalkyl is substituted with one to three substituents independently selected from the group consisting of: alkyl, haloalkyl, cycloalkyl, cycloalkylalkyl, halogen, haloalkoxy, alkoxy, hydroxy, alkoxyalkyl, hydroxyalkyl, alkylsulfonyl and al kylsulfonyloxy;

or a pharmaceutically acceptable salt thereof.

5. A compound according to claim 1, wherein $R^1$ is selected from the group consisting of alkyl, cycloalkylalkyl, haloalkyl, morpholinyl, phenyl and substituted phenyl, wherein said substituted phenyl is substituted with one to three substituents independently selected from the group consisting of: alkyl, haloalkyl, halogen, hydroxy, alkoxy and haloalkoxy.

6. A compound according to claim 1, wherein $R^1$ is selected from the group consisting of alkyl, phenyl, substituted pyrazolyl, substituted isoxazolyl, substituted pyridinyl and substituted phenyl, wherein said substituted pyrazolyl, substituted isoxazolyl, substituted pyridinyl or substituted phenyl is substituted with one to three substituents independently selected from the group consisting of: alkyl, haloalkyl, halogen, hydroxy and haloalkoxy.

7. A compound according to claim 1, wherein $R^2$ is selected from the group consisting of: phenyl, pyridinyl, pyridazinyl, pyrazolyl, substituted phenyl, substituted pyridinyl, substituted pyridazinyl and substituted pyrazolyl, wherein said substituted phenyl, substituted pyridinyl, substituted pyridazinyl or substituted pyrazolyl is substituted with one to three substituents independently selected from the group consisting of: alkyl, haloalkyl, cycloalkyl, cycloalkylalkyl, halogen, haloalkoxy, alkoxy, hydroxy, alkoxyalkyl and hydroxyalkyl.

8. A compound according to claim 1, wherein $R^2$ is substituted phenyl or substituted pydridinyl, wherein said substituted phenyl and substituted pydridinyl are substituted with one to three substituents independently selected from the group consisting of: alkyl, haloalkyl, cycloalkyl, haloalkoxy, alkoxy, haloalkylhydroxyalkyl and hydroxycycloalkyl.

9. A compound according to claim 1, wherein $R^2$ is phenyl substituted with one to three substituents independently selected from alkyl, haloalkoxy and alkoxy.

10. A compound according to claim 1, selected from the group consisting of:
- 8-(2-Chloro-benzenesulfonyl)-2-(4-trifluoromethoxy-phenyl)-2,8-diaza-spiro[4.5]decan-1-one;
- 8-Benzenesulfonyl-2-(4-trifluoromethoxy-phenyl)-2,8-diaza-spiro[4.5]decan-1-one;
- 8-Benzenesulfonyl-2-(4-tert-butyl-phenyl)-2,8-diaza-spiro[4.5]decan-1-one;
- (rac)-8-Benzenesulfonyl-2-[4-(2,2,2-trifluoro-1-methyl-ethoxy)-phenyl]-2,8-diaza-spiro[4.5]decan-1-one;
- 8-Benzenesulfonyl-2-[4-(2,2,2-trifluoro-1,1-dimethyl-ethoxy)-phenyl]-2,8-diaza-spiro[4.5]decan-1-one;
- 8-Benzenesulfonyl-2-(4-isopropoxy-phenyl)-2,8-diaza-spiro[4.5]decan-1-one;
- 8-(3,3-Dimethyl-butyryl)-2-(4-trifluoromethoxy-phenyl)-2,8-diaza-spiro[4.5]decan-1-one;
- 8-(Morpholine-4-sulfonyl)-2-(4-trifluoromethoxy-phenyl)-2,8-diaza-spiro[4.5]decan-1-one;
- 8-Benzenesulfonyl-2-(6-isopropyl-pyridin-3-yl)-2,8-diaza-spiro[4.5]decan-1-one;
- 8-Benzenesulfonyl-2-(6-chloro-pyridin-3-yl)-2,8-diaza-spiro[4.5]decan-1-one;
- 8-Benzenesulfonyl-2-pyridin-3-yl-2,8-diaza-spiro[4.5]decan-1-one;
- 8-(3-Cyclopropyl-propionyl)-2-(4-trifluoromethoxy-phenyl)-2,8-diaza-spiro[4.5]decan-1-one;
- 8-(4,4-Dimethyl-pentanoyl)-2-(4-trifluoromethoxy-phenyl)-2,8-diaza-spiro[4.5]decan-1-one;
- 2-(4-Isopropoxy-phenyl)-8-(morpholine-4-sulfonyl)-2,8-diaza-spiro[4.5]decan-1-one;
- 8-Benzenesulfonyl-2-(6-methoxy-pyridazin-3-yl)-2,8-diaza-spiro[4.5]decan-1-one;
- 8-(2-Chloro-benzenesulfonyl)-2-(4-ethyl-phenyl)-2,8-diaza-spiro[4.5]decan-1-one;
- 8-(2-Methyl-propane-1-sulfonyl)-2-(4-trifluoromethoxy-phenyl)-2,8-diaza-spiro[4.5]decan-1-one;
- 8-(2,2-Dimethyl-propane-1-sulfonyl)-2-(4-trifluoromethoxy-phenyl)-2,8-diaza-spiro[4.5]decan-1 -one;
- 8-(3,3-Dimethyl-butyryl)-2-(4-ethyl-phenyl)-2,8-diaza-spiro[4.5]decan-1-one;
- 2-(4-Ethyl-phenyl)-8-(morpholine-4-sulfonyl)-2,8-diaza-spiro[4.5]decan-1-one;
- (rac)-8-(2,2-Dimethyl-propane-1-sulfonyl)-2-[4-(2,2,2-trifluoro-1-methyl-ethoxy)-phenyl]-2,8-diaza-spiro[4.5]decan-1-one;
- 2-(4-Isopropoxy-phenyl)-8-(2-methyl-propane-1-sulfonyl)-2,8-diaza-spiro[4.5]decan-1-one;
- 2-(4-Ethyl-phenyl)-8-(2-methyl-propane-1-sulfonyl)-2,8-diaza-spiro[4.5]decan-1-one;
- (rac)-8-Benzenesulfonyl-2-[6-(2,2,2-trifluoro-1-methyl-ethoxy)-pyridin-3-yl]-2,8-diaza-spiro[4.5]decan-1-one; and
- 8-Benzenesulfonyl-2-[4-(2,2,2-trifluoro-ethoxy)-phenyl]-2,8-diaza-spiro[4.5]decan-1-one.

11. A pharmaceutical composition comprising a compound according to claim 1 and a therapeutically inert carrier.

* * * * *